(12) United States Patent
Buscaglia et al.

(10) Patent No.: US 10,548,648 B2
(45) Date of Patent: Feb. 4, 2020

(54) INTRAMEDULLARY FRACTURE FIXATION DEVICES AND METHODS

(71) Applicant: Arthrex, Inc., Naples, FL (US)

(72) Inventors: Alexander Carlo Buscaglia, Chicago, IL (US); Brian Bradford Carpenter, Decatur, TX (US); Kyle Edward Lappin, Lake Zurich, IL (US); Stephen Riddle McDaniel, San Rafael, CA (US); Selene Gunvant Parekh, Cary, NC (US); Terrence Michael Philbin, Westerville, OH (US); Robert Dean Tonks, San Diego, CA (US); Daryll Leonard Charles Fletcher, Santa Rosa, CA (US)

(73) Assignee: ARTHREX, INC., Naples, FL (US)

( * ) Notice: Subject to any disclaimer, the term of this patent is extended or adjusted under 35 U.S.C. 154(b) by 74 days.

(21) Appl. No.: 15/805,798

(22) Filed: Nov. 7, 2017

(65) Prior Publication Data
US 2018/0125545 A1 May 10, 2018

Related U.S. Application Data

(62) Division of application No. 14/861,355, filed on Sep. 22, 2015, now Pat. No. 9,814,499.
(Continued)

(51) Int. Cl.
*A61B 17/72* (2006.01)
*A61B 17/84* (2006.01)
(Continued)

(52) U.S. Cl.
CPC ...... *A61B 17/7233* (2013.01); *A61B 17/1725* (2013.01); *A61B 17/683* (2013.01);
(Continued)

(58) Field of Classification Search
CPC . A61B 17/7233; A61B 17/1725; A61B 17/56; A61B 17/88; A61B 2017/564
See application file for complete search history.

(56) References Cited

U.S. PATENT DOCUMENTS

| 958,127 A | 5/1910 | Hufrud |
|---|---|---|
| 1,169,635 A | 1/1916 | Grimes |

(Continued)

FOREIGN PATENT DOCUMENTS

| CA | 2561552 A1 | 11/2005 |
|---|---|---|
| EP | 1582163 A1 | 10/2005 |

(Continued)

OTHER PUBLICATIONS

US 6,030,385 A, 02/2000, Faccioli et al. (withdrawn)
(Continued)

*Primary Examiner* — Ellen C Hammond
(74) *Attorney, Agent, or Firm* — Carlson, Gaskey & Olds, P.C.

(57) ABSTRACT

An intramedullary bone fixation device is provided with an elongate body having a longitudinal axis and an actuator to deploy at least one gripper to engage an inner surface of the intramedullary space to anchor the fixation device to the bone. Methods of repairing a fracture of a bone are also disclosed. One such method comprises inserting a fixation device into an intramedullary space of the bone to place at least a portion of the fixation device on one side of the fracture, providing rigidity across the fracture, and operating an actuator to deploy at least one gripper to engage an inner surface of the intramedullary space to anchor the fixation device to the bone. Various configurations allow a segmented device body to lock in the intramedullary space before and/or after fixation of the bone.

19 Claims, 101 Drawing Sheets

Related U.S. Application Data

(60) Provisional application No. 62/057,913, filed on Sep. 30, 2014.

(51) Int. Cl.
  *A61B 17/86* (2006.01)
  *A61B 17/17* (2006.01)
  *A61B 17/68* (2006.01)
  *A61B 90/00* (2016.01)

(52) U.S. Cl.
  CPC ...... *A61B 17/7208* (2013.01); *A61B 17/7266* (2013.01); *A61B 17/848* (2013.01); *A61B 17/86* (2013.01); *A61B 2090/031* (2016.02)

(56) References Cited

U.S. PATENT DOCUMENTS

| | | |
|---|---|---|
| 1,790,841 A | 2/1931 | Rosen |
| 2,502,267 A | 3/1950 | Mcpherson |
| 2,685,877 A | 8/1954 | Dobelle |
| 2,998,007 A | 8/1961 | Herzog |
| 3,118,444 A | 1/1964 | Serrato, Jr. |
| 3,441,017 A | 4/1969 | Kaessmann |
| 3,626,935 A | 12/1971 | Pollock et al. |
| 3,710,789 A | 1/1973 | Ersek |
| 3,759,257 A | 9/1973 | Fischer et al. |
| 3,760,802 A | 9/1973 | Fischer et al. |
| 3,779,239 A | 12/1973 | Fischer et al. |
| 3,791,380 A | 2/1974 | Dawidowski |
| 3,846,846 A | 11/1974 | Fischer |
| 3,955,565 A | 5/1976 | Johnson, Jr. |
| 3,978,528 A | 9/1976 | Crep |
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,050,646 A | 9/1977 | Burchette, Jr. |
| 4,064,567 A | 12/1977 | Burstein et al. |
| 4,065,816 A | 1/1978 | Sawyer |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |
| 4,227,518 A | 10/1980 | Aginsky |
| 4,236,512 A | 12/1980 | Aginsky |
| 4,237,875 A | 12/1980 | Termanini |
| 4,246,662 A | 1/1981 | Pastrick |
| 4,262,665 A | 4/1981 | Roalstad et al. |
| 4,275,717 A | 6/1981 | Bolesky |
| 4,293,962 A | 10/1981 | Fuson |
| 4,294,251 A | 10/1981 | Greenwald et al. |
| 4,312,336 A | 1/1982 | Danieletto et al. |
| 4,313,434 A | 2/1982 | Segal |
| 4,338,926 A | 7/1982 | Kummer et al. |
| 4,351,069 A | 9/1982 | Ballintyn et al. |
| 4,352,212 A | 10/1982 | Greene et al. |
| 4,353,358 A | 10/1982 | Emerson |
| 4,379,451 A | 4/1983 | Getscher |
| 4,409,974 A | 10/1983 | Freedland |
| 4,453,539 A | 6/1984 | Raftopoulos et al. |
| 4,457,301 A | 7/1984 | Walker |
| 4,459,708 A | 7/1984 | Buttazzoni |
| 4,462,394 A | 7/1984 | Jacobs |
| 4,467,794 A | 8/1984 | Maffei et al. |
| RE31,809 E | 1/1985 | Danieletto et al. |
| 4,492,226 A | 1/1985 | Belykh et al. |
| 4,503,847 A | 3/1985 | Mouradian |
| 4,519,100 A | 5/1985 | Wills et al. |
| 4,520,511 A | 6/1985 | Gianezio et al. |
| 4,522,200 A | 6/1985 | Stednitz |
| 4,541,423 A | 9/1985 | Barber |
| 4,552,136 A | 11/1985 | Kenna |
| 4,589,883 A | 5/1986 | Kenna |
| 4,590,930 A | 5/1986 | Kurth et al. |
| 4,604,997 A | 8/1986 | De Bastiani et al. |
| 4,621,627 A | 11/1986 | DeBastiani et al. |
| 4,622,959 A | 11/1986 | Marcus |
| 4,624,673 A | 11/1986 | Meyer |
| 4,628,920 A | 12/1986 | Mathys, Jr. et al. |
| 4,632,101 A | 12/1986 | Freedland |
| 4,643,177 A | 2/1987 | Sheppard et al. |
| 4,651,724 A | 3/1987 | Berentey et al. |
| 4,653,487 A | 3/1987 | Maale |
| 4,662,887 A | 5/1987 | Turner et al. |
| 4,667,663 A | 5/1987 | Miyata |
| D290,399 S | 6/1987 | Kitchens |
| 4,681,590 A | 7/1987 | Tansey |
| 4,697,585 A | 10/1987 | Williams |
| 4,705,027 A | 11/1987 | Klaue |
| 4,705,032 A | 11/1987 | Keller |
| 4,721,103 A | 1/1988 | Freedland |
| 4,735,625 A | 4/1988 | Davidson |
| 4,753,657 A | 6/1988 | Lee et al. |
| 4,776,330 A | 10/1988 | Chapman et al. |
| 4,781,181 A | 11/1988 | Tanguy |
| 4,805,595 A | 2/1989 | Kanbara |
| 4,805,607 A | 2/1989 | Engelhardt et al. |
| 4,813,963 A | 3/1989 | Hori et al. |
| 4,817,591 A | 4/1989 | Klaue et al. |
| 4,827,919 A | 5/1989 | Barbarito et al. |
| 4,828,277 A | 5/1989 | De Bastiani et al. |
| 4,854,312 A | 8/1989 | Raftopoulos et al. |
| 4,858,602 A | 8/1989 | Seidel et al. |
| 4,862,883 A | 9/1989 | Freeland |
| 4,871,369 A | 10/1989 | Muller |
| 4,875,474 A | 10/1989 | Border |
| 4,875,475 A | 10/1989 | Comte et al. |
| 4,896,662 A | 1/1990 | Noble |
| 4,921,499 A | 5/1990 | Hoffman et al. |
| 4,927,424 A | 5/1990 | McConnell et al. |
| 4,932,969 A | 6/1990 | Frey et al. |
| 4,943,291 A | 7/1990 | Tanguy |
| 4,946,179 A | 8/1990 | De Bastiani et al. |
| 4,959,066 A | 9/1990 | Dunn et al. |
| 4,969,889 A | 11/1990 | Greig |
| 4,976,258 A | 12/1990 | Richter et al. |
| 4,978,349 A | 12/1990 | Frigg |
| 4,978,358 A | 12/1990 | Bobyn |
| 4,988,349 A | 1/1991 | Pennig |
| 5,002,547 A | 3/1991 | Poggie et al. |
| 5,002,580 A | 3/1991 | Noble et al. |
| 5,006,120 A | 4/1991 | Carter et al. |
| 5,013,314 A | 5/1991 | Firica et al. |
| 5,019,077 A | 5/1991 | De Bastiani et al. |
| 5,026,374 A | 6/1991 | Dezza et al. |
| 5,027,799 A | 7/1991 | Laico et al. |
| 5,030,222 A | 7/1991 | Calandruccio et al. |
| 5,034,012 A | 7/1991 | Frigg |
| 5,034,013 A | 7/1991 | Kyle et al. |
| 5,035,697 A | 7/1991 | Frigg |
| 5,037,423 A | 8/1991 | Kenna |
| 5,041,114 A | 8/1991 | Chapman et al. |
| 5,041,115 A | 8/1991 | Frigg et al. |
| 5,053,035 A | 10/1991 | McLaren |
| 5,057,103 A | 10/1991 | Davis |
| 5,062,854 A | 11/1991 | Noble et al. |
| 5,066,296 A | 11/1991 | Chapman et al. |
| 5,084,050 A | 1/1992 | Draenert |
| 5,092,892 A | 3/1992 | Ashby |
| 5,098,433 A | 3/1992 | Freedland |
| 5,100,404 A | 3/1992 | Hayes |
| 5,102,413 A | 4/1992 | Poddar |
| 5,108,404 A | 4/1992 | Scholten et al. |
| 5,112,333 A | 5/1992 | Fixel |
| 5,116,335 A | 5/1992 | Hannon et al. |
| 5,116,380 A | 5/1992 | Hewka et al. |
| 5,122,141 A | 6/1992 | Simpson et al. |
| 5,122,146 A | 6/1992 | Chapman et al. |
| 5,124,106 A | 6/1992 | Morr et al. |
| 5,147,408 A | 9/1992 | Noble et al. |
| 5,152,766 A | 10/1992 | Kirkley |

(56) References Cited

U.S. PATENT DOCUMENTS

| | | | |
|---|---|---|---|
| 5,163,963 | A | 11/1992 | Hewka et al. |
| 5,171,324 | A | 12/1992 | Campana et al. |
| 5,176,681 | A | 1/1993 | Lawes et al. |
| 5,178,621 | A | 1/1993 | Cook et al. |
| 5,190,544 | A | 3/1993 | Chapman et al. |
| 5,190,546 | A | 3/1993 | Jervis |
| 5,192,281 | A | 3/1993 | de la Caffiniere |
| 5,197,966 | A | 3/1993 | Sommerkamp |
| 5,197,990 | A | 3/1993 | Lawes et al. |
| 5,201,735 | A | 4/1993 | Chapman et al. |
| 5,201,767 | A | 4/1993 | Caldarise et al. |
| 5,211,664 | A | 5/1993 | Tepic et al. |
| 5,217,049 | A | 6/1993 | Forsyth |
| 5,263,955 | A | 11/1993 | Baumgart et al. |
| 5,268,000 | A | 12/1993 | Ottieri et al. |
| 5,281,224 | A | 1/1994 | Faccioli et al. |
| 5,281,225 | A | 1/1994 | Vicenzi |
| 5,292,322 | A | 3/1994 | Faccioli et al. |
| 5,295,991 | A | 3/1994 | Frigg |
| 5,303,718 | A | 4/1994 | Krajicek |
| 5,314,489 | A | 5/1994 | Hoffman et al. |
| 5,320,622 | A | 6/1994 | Faccioli et al. |
| 5,320,623 | A | 6/1994 | Pennig |
| 5,326,376 | A | 7/1994 | Warner et al. |
| 5,334,184 | A | 8/1994 | Bimman |
| 5,342,360 | A | 8/1994 | Faccioli et al. |
| 5,342,362 | A | 8/1994 | Kenyon et al. |
| 5,346,496 | A | 9/1994 | Pennig |
| 5,350,379 | A | 9/1994 | Spievack |
| 5,352,227 | A | 10/1994 | OHara |
| 5,358,534 | A | 10/1994 | Dudasik et al. |
| 5,364,398 | A | 11/1994 | Chapman et al. |
| 5,368,594 | A | 11/1994 | Martin et al. |
| 5,376,090 | A | 12/1994 | Pennig |
| 5,376,123 | A | 12/1994 | Klaue et al. |
| 5,380,328 | A | 1/1995 | Morgan |
| 5,383,932 | A | 1/1995 | Wilson et al. |
| 5,387,243 | A | 2/1995 | Devanathan |
| 5,397,328 | A | 3/1995 | Behrens et al. |
| 5,403,321 | A | 4/1995 | DiMarco |
| 5,411,503 | A | 5/1995 | Hollstien et al. |
| 5,415,660 | A | 5/1995 | Campbell et al. |
| 5,417,695 | A | 5/1995 | Axelson, Jr. |
| RE34,985 | E | 6/1995 | Pennig |
| 5,423,848 | A | 6/1995 | Washizuka et al. |
| 5,423,850 | A | 6/1995 | Berger |
| 5,433,718 | A | 7/1995 | Brinker |
| 5,433,720 | A | 7/1995 | Faccioli et al. |
| 5,441,500 | A | 8/1995 | Seidel et al. |
| 5,443,477 | A | 8/1995 | Marin et al. |
| 5,445,642 | A | 8/1995 | McNulty et al. |
| 5,454,813 | A | 10/1995 | Lawes |
| 5,454,816 | A | 10/1995 | Ashby |
| 5,458,599 | A | 10/1995 | Adobbati |
| 5,458,651 | A | 10/1995 | Lawes |
| 5,458,653 | A | 10/1995 | Davidson |
| 5,468,242 | A | 11/1995 | Reisberg |
| 5,472,444 | A | 12/1995 | Huebner et al. |
| 5,478,341 | A | 12/1995 | Cook et al. |
| 5,480,400 | A | 1/1996 | Berger |
| 5,484,438 | A | 1/1996 | Pennig |
| 5,484,446 | A | 1/1996 | Burke et al. |
| 5,488,761 | A | 2/1996 | Leone |
| 5,490,852 | A | 2/1996 | Azer et al. |
| 5,505,734 | A | 4/1996 | Caniggia et al. |
| 5,514,137 | A | 5/1996 | Coutts |
| 5,516,335 | A | 5/1996 | Kummer et al. |
| 5,520,695 | A | 5/1996 | Luckman |
| 5,527,316 | A | 6/1996 | Stone et al. |
| 5,531,748 | A | 7/1996 | de la Caffiniere |
| 5,534,004 | A | 7/1996 | Santangelo |
| 5,545,162 | A | 8/1996 | Huebner |
| 5,549,610 | A | 8/1996 | Russell et al. |
| 5,549,706 | A | 8/1996 | McCarthy |
| 5,554,192 | A | 9/1996 | Crowninshield |
| 5,556,433 | A | 9/1996 | Gabriel et al. |
| 5,562,667 | A | 10/1996 | Shuler et al. |
| 5,562,673 | A | 10/1996 | Koblish et al. |
| 5,562,674 | A | 10/1996 | Stalcup et al. |
| 5,562,675 | A | 10/1996 | McNulty et al. |
| 5,569,249 | A | 10/1996 | James et al. |
| 5,571,189 | A | 11/1996 | Kuslich |
| 5,571,204 | A | 11/1996 | Nies |
| 5,573,536 | A | 11/1996 | Grosse et al. |
| 5,578,035 | A | 11/1996 | Lin |
| 5,586,985 | A | 12/1996 | Putnam et al. |
| 5,591,169 | A | 1/1997 | Benoist |
| 5,591,196 | A | 1/1997 | Marin et al. |
| 5,593,451 | A | 1/1997 | Averill et al. |
| 5,593,452 | A | 1/1997 | Higham et al. |
| 5,605,713 | A | 2/1997 | Boltong |
| 5,607,431 | A | 3/1997 | Dudasik et al. |
| 5,613,970 | A | 3/1997 | Houston et al. |
| 5,618,286 | A | 4/1997 | Brinker |
| 5,618,300 | A | 4/1997 | Marin et al. |
| 5,620,449 | A | 4/1997 | Faccioli et al. |
| 5,624,440 | A | 4/1997 | Huebner |
| 5,624,447 | A | 4/1997 | Myers |
| 5,626,580 | A | 5/1997 | Brosnahan |
| 5,643,258 | A | 7/1997 | Robioneck et al. |
| 5,645,545 | A | 7/1997 | Bryant |
| 5,645,599 | A | 7/1997 | Samani |
| 5,658,283 | A | 8/1997 | Huebner |
| 5,658,287 | A | 8/1997 | Hofmann et al. |
| 5,658,292 | A | 8/1997 | Axelson, Jr. |
| 5,658,293 | A | 8/1997 | Vanlaningham |
| 5,658,351 | A | 8/1997 | Dudasik et al. |
| 5,662,648 | A | 9/1997 | Faccioli |
| 5,662,649 | A | 9/1997 | Huebner |
| 5,662,712 | A | 9/1997 | Pathak et al. |
| 5,665,090 | A | 9/1997 | Rockwood et al. |
| 5,665,091 | A | 9/1997 | Noble et al. |
| 5,681,289 | A | 10/1997 | Wilcox et al. |
| 5,681,316 | A | 10/1997 | DeOrio et al. |
| 5,681,318 | A | 10/1997 | Pennig et al. |
| 5,683,389 | A | 11/1997 | Orsak |
| 5,683,460 | A | 11/1997 | Persoons |
| 5,688,271 | A | 11/1997 | Faccioli et al. |
| 5,688,279 | A | 11/1997 | McNulty et al. |
| 5,690,634 | A | 11/1997 | Muller et al. |
| 5,693,047 | A | 12/1997 | Meyers et al. |
| 5,693,048 | A | 12/1997 | Stalcup et al. |
| 5,695,729 | A | 12/1997 | Chow et al. |
| 5,697,930 | A | 12/1997 | Itoman et al. |
| 5,702,215 | A | 12/1997 | Li |
| 5,702,481 | A | 12/1997 | Lin |
| 5,702,487 | A | 12/1997 | Averill et al. |
| 5,707,370 | A | 1/1998 | Berki et al. |
| 5,718,704 | A | 2/1998 | Medoff |
| 5,725,595 | A | 3/1998 | Gustilo |
| 5,728,096 | A | 3/1998 | Faccioli et al. |
| 5,741,256 | A | 4/1998 | Bresina |
| 5,741,266 | A | 4/1998 | Moran et al. |
| 5,749,872 | A | 5/1998 | Kyle et al. |
| 5,749,880 | A | 5/1998 | Banas et al. |
| 5,759,184 | A | 6/1998 | Santangelo |
| 5,766,174 | A | 6/1998 | Perry |
| 5,766,176 | A | 6/1998 | Duncan |
| 5,766,178 | A | 6/1998 | Michielli et al. |
| 5,766,179 | A | 6/1998 | Faccioli et al. |
| 5,766,180 | A | 6/1998 | Winquist |
| 5,772,662 | A | 6/1998 | Chapman et al. |
| 5,772,663 | A | 6/1998 | Whiteside et al. |
| 5,776,194 | A | 7/1998 | Mikol et al. |
| 5,776,204 | A | 7/1998 | Noble et al. |
| 5,779,703 | A | 7/1998 | Benoist |
| 5,779,705 | A | 7/1998 | Matthews |
| 5,782,921 | A | 7/1998 | Colleran et al. |
| 5,785,057 | A | 7/1998 | Fischer |
| 5,788,703 | A | 8/1998 | Mittelmeier et al. |
| 5,807,241 | A | 9/1998 | Heimberger |
| 5,810,750 | A | 9/1998 | Buser |
| 5,810,820 | A | 9/1998 | Santori et al. |
| 5,810,826 | A | 9/1998 | Akerfeldt et al. |

(56) References Cited

U.S. PATENT DOCUMENTS

| | | |
|---|---|---|
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,827,289 A | 10/1998 | Reiley et al. |
| 5,829,081 A | 11/1998 | Pearce |
| 5,836,949 A | 11/1998 | Campbell, Jr. et al. |
| 5,837,909 A | 11/1998 | Bill et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,858,020 A | 1/1999 | Johnson et al. |
| 5,863,295 A | 1/1999 | Averill et al. |
| 5,876,459 A | 3/1999 | Powell |
| 5,879,352 A | 3/1999 | Filoso et al. |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,906,210 A | 5/1999 | Herbert |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,951,561 A | 9/1999 | Pepper et al. |
| 5,954,722 A | 9/1999 | Bono |
| 5,954,728 A | 9/1999 | Heller et al. |
| 5,961,553 A | 10/1999 | Coty et al. |
| 5,964,770 A | 10/1999 | Flomenblit et al. |
| 5,968,047 A | 10/1999 | Reed |
| 5,971,986 A | 10/1999 | Santori et al. |
| 5,976,134 A | 11/1999 | Huebner |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,018,094 A | 1/2000 | Fox |
| 6,019,761 A | 2/2000 | Gustilo |
| 6,019,762 A | 2/2000 | Cole |
| 6,020,396 A | 2/2000 | Jacobs |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A | 4/2000 | Krause et al. |
| 6,056,756 A | 5/2000 | Eng et al. |
| 6,074,392 A | 6/2000 | Durham |
| 6,077,264 A | 6/2000 | Chemello |
| 6,080,159 A | 6/2000 | Vichard |
| 6,083,522 A | 7/2000 | Chu et al. |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo, Jr. et al. |
| 6,168,595 B1 | 1/2001 | Durham et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotorno et al. |
| 6,183,470 B1 | 2/2001 | Booth, Jr. et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,258,093 B1 | 7/2001 | Edwards et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,456 B1 | 8/2001 | Scribner et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,309,396 B1 | 10/2001 | Ritland |
| 6,319,253 B1 | 11/2001 | Ackeret et al. |
| 6,325,830 B1 | 12/2001 | Mastrorio et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,044 B1 | 3/2002 | Hair |
| 6,355,069 B1 | 3/2002 | DeCarlo, Jr. et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,364,909 B1 | 4/2002 | McGee |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,083 B2 | 7/2002 | Reiley et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |

(56) References Cited

U.S. PATENT DOCUMENTS

| | | |
|---|---|---|
| 6,447,515 B1 | 9/2002 | Meldrum |
| 6,447,518 B1 | 9/2002 | Krause et al. |
| 6,461,358 B1 | 10/2002 | Faccioli et al. |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,544,265 B2 | 4/2003 | Lieberman |
| 6,551,319 B2 | 4/2003 | Lieberman |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 | 5/2003 | Bartsch et al. |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Mann et al. |
| 6,582,453 B1 | 6/2003 | Tran et al. |
| 6,592,578 B2 | 7/2003 | Henniges et al. |
| 6,607,531 B2 | 8/2003 | Frigg |
| 6,613,052 B1 | 9/2003 | Kinnett |
| 6,616,667 B1 | 9/2003 | Steiger et al. |
| 6,616,742 B2 | 9/2003 | Lin et al. |
| 6,620,197 B2 | 9/2003 | Maroney et al. |
| 6,623,487 B1 | 9/2003 | Goshert |
| 6,629,976 B1 | 10/2003 | Gnos et al. |
| 6,632,224 B2 | 10/2003 | Cachia et al. |
| 6,632,235 B2 | 10/2003 | Weikel et al. |
| 6,641,596 B1 | 11/2003 | Lizardi |
| 6,648,889 B2 | 11/2003 | Bramlet et al. |
| 6,648,890 B2 | 11/2003 | Culbert et al. |
| 6,648,893 B2 | 11/2003 | Dudasik |
| 6,652,529 B2 | 11/2003 | Swanson |
| 6,652,591 B2 | 11/2003 | Serbousek et al. |
| 6,656,189 B1 | 12/2003 | Wilson et al. |
| 6,663,647 B2 | 12/2003 | Reiley et al. |
| 6,679,890 B2 | 1/2004 | Margulies et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,692,530 B2 | 2/2004 | Doubler et al. |
| 6,694,667 B2 | 2/2004 | Davis |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,719,793 B2 | 4/2004 | McGee |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,749,614 B2 | 6/2004 | Teitelbaum et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,790,210 B1 | 9/2004 | Cragg et al. |
| 6,793,655 B2 | 9/2004 | Orsak |
| 6,793,659 B2 | 9/2004 | Putnam |
| 6,808,527 B2 | 10/2004 | Lower et al. |
| 6,821,277 B2 | 11/2004 | Teitelbaum |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,875,212 B2 | 4/2005 | Shaolian et al. |
| 6,887,243 B2 | 5/2005 | Culbert |
| 6,887,271 B2 | 5/2005 | Justin et al. |
| 6,887,276 B2 | 5/2005 | Gerbec et al. |
| 6,890,333 B2 | 5/2005 | von Hoffmann et al. |
| 6,893,444 B2 | 5/2005 | Orbay |
| 6,899,713 B2 | 5/2005 | Shaolian et al. |
| 6,899,719 B2 | 5/2005 | Reiley et al. |
| 6,902,583 B2 | 6/2005 | Gerbec et al. |
| 6,908,465 B2 | 6/2005 | von Hoffmann et al. |
| 6,916,323 B2 | 7/2005 | Kitchens |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,981,981 B2 | 1/2006 | Reiley et al. |
| 6,986,771 B2 | 1/2006 | Paul et al. |
| 6,999,819 B2 | 2/2006 | Swoyer et al. |
| 7,001,386 B2 | 2/2006 | Sohngen et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |

(56) References Cited

U.S. PATENT DOCUMENTS

| | | |
|---|---|---|
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |
| 7,963,966 B2 * | 6/2011 | Cole ............... A61B 17/683 606/62 |
| 8,287,541 B2 * | 10/2012 | Nelson ............... A61B 17/1717 606/62 |
| 2001/0011174 A1 | 8/2001 | Reiley et al. |
| 2001/0034526 A1 | 10/2001 | Kuslich et al. |
| 2001/0049531 A1 | 12/2001 | Reiley et al. |
| 2002/0004685 A1 | 1/2002 | White |
| 2002/0029041 A1 | 3/2002 | Hover et al. |
| 2002/0032444 A1 | 3/2002 | Mische |
| 2002/0041896 A1 | 4/2002 | Straub et al. |
| 2002/0068939 A1 | 6/2002 | Levy et al. |
| 2002/0068981 A1 | 6/2002 | Hajianpour |
| 2002/0095214 A1 | 7/2002 | Hyde, Jr. |
| 2002/0099385 A1 | 7/2002 | Ralph et al. |
| 2002/0103488 A1 | 8/2002 | Lower et al. |
| 2002/0143344 A1 | 10/2002 | Taylor |
| 2002/0161369 A1 | 10/2002 | Bramlet et al. |
| 2002/0165544 A1 | 11/2002 | Perren et al. |
| 2002/0173792 A1 | 11/2002 | Severns et al. |
| 2002/0177866 A1 | 11/2002 | Weikel et al. |
| 2002/0188297 A1 | 12/2002 | Dakin et al. |
| 2002/0198526 A1 | 12/2002 | Shaolian et al. |
| 2003/0032960 A1 | 2/2003 | Dudasik |
| 2003/0040752 A1 | 2/2003 | Kitchens |
| 2003/0045919 A1 | 3/2003 | Swoyer et al. |
| 2003/0073999 A1 | 4/2003 | Putnam |
| 2003/0074075 A1 | 4/2003 | Thomas, Jr. et al. |
| 2003/0078669 A1 | 4/2003 | Martin et al. |
| 2003/0097136 A1 | 5/2003 | Hajianpour |
| 2003/0109932 A1 | 6/2003 | Keynan |
| 2003/0130660 A1 | 7/2003 | Levy et al. |
| 2003/0130664 A1 | 7/2003 | Boucher et al. |
| 2003/0139802 A1 | 7/2003 | Wulfman et al. |
| 2003/0181918 A1 | 9/2003 | Smothers et al. |
| 2003/0216738 A1 | 11/2003 | Azar |
| 2003/0236529 A1 | 12/2003 | Shluzas et al. |
| 2004/0006341 A1 | 1/2004 | Shaolian et al. |
| 2004/0010263 A1 | 1/2004 | Boucher et al. |
| 2004/0098017 A1 | 5/2004 | Saab et al. |
| 2004/0098134 A1 | 5/2004 | Meulink |
| 2004/0133204 A1 | 7/2004 | Davies |
| 2004/0133280 A1 | 7/2004 | Trieu |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0193255 A1 | 9/2004 | Shanley et al. |
| 2004/0193267 A1 | 9/2004 | Jones et al. |
| 2004/0213825 A1 | 10/2004 | Levy |
| 2004/0214311 A1 | 10/2004 | Levy |
| 2004/0215193 A1 | 10/2004 | Shaolian et al. |
| 2004/0230193 A1 | 11/2004 | Cheung et al. |
| 2004/0236327 A1 | 11/2004 | Paul et al. |
| 2004/0260398 A1 | 12/2004 | Kelman |
| 2004/0267269 A1 | 12/2004 | Middleton et al. |
| 2004/0267271 A9 | 12/2004 | Scribner et al. |
| 2005/0015154 A1 | 1/2005 | Lindsey et al. |
| 2005/0027294 A1 | 2/2005 | Woll |
| 2005/0027301 A1 | 2/2005 | Stihl |
| 2005/0043737 A1 | 2/2005 | Reiley et al. |
| 2005/0043757 A1 | 2/2005 | Arad et al. |
| 2005/0047892 A1 | 3/2005 | Bremner |
| 2005/0055023 A1 | 3/2005 | Sohngen et al. |
| 2005/0055024 A1 | 3/2005 | James et al. |
| 2005/0080425 A1 | 4/2005 | Bhatnagar et al. |
| 2005/0090852 A1 | 4/2005 | Layne et al. |
| 2005/0107883 A1 | 5/2005 | Goodfried et al. |
| 2005/0119662 A1 | 6/2005 | Reiley et al. |
| 2005/0131386 A1 | 6/2005 | Freeman et al. |
| 2005/0143827 A1 | 6/2005 | Globerman et al. |
| 2005/0149022 A1 | 7/2005 | Shaolian et al. |
| 2005/0149024 A1 | 7/2005 | Ferrante et al. |
| 2005/0149025 A1 | 7/2005 | Ferrante et al. |
| 2005/0159749 A1 | 7/2005 | Levy et al. |
| 2005/0165395 A1 | 7/2005 | Orbay et al. |
| 2005/0171552 A1 | 8/2005 | Johnson et al. |
| 2005/0171563 A1 | 8/2005 | Heinrich et al. |
| 2005/0177158 A1 | 8/2005 | Doubler et al. |
| 2005/0203510 A1 | 9/2005 | Sohngen |
| 2005/0209595 A1 | 9/2005 | Karmon |
| 2005/0216007 A1 | 9/2005 | Woll et al. |
| 2005/0228391 A1 | 10/2005 | Levy et al. |
| 2005/0234453 A1 | 10/2005 | Shaolian et al. |
| 2005/0234559 A1 | 10/2005 | Fernandez et al. |
| 2005/0251140 A1 | 11/2005 | Shaolian et al. |
| 2005/0261781 A1 | 11/2005 | Sennett et al. |
| 2005/0267481 A1 | 12/2005 | Carl et al. |
| 2005/0267483 A1 | 12/2005 | Middleton |
| 2005/0267586 A1 | 12/2005 | Sidebotham |
| 2005/0283250 A1 | 12/2005 | Coon et al. |
| 2005/0288678 A1 | 12/2005 | Reiley et al. |
| 2006/0004465 A1 | 1/2006 | Bergin et al. |
| 2006/0015101 A1 | 1/2006 | Warburton et al. |
| 2006/0015123 A1 | 1/2006 | Fencl et al. |
| 2006/0030945 A1 | 2/2006 | Wright |
| 2006/0036248 A1 | 2/2006 | Ferrante et al. |
| 2006/0052788 A1 | 3/2006 | Thelen et al. |
| 2006/0064094 A1 | 3/2006 | Levy et al. |
| 2006/0084997 A1 | 4/2006 | Dejardin |
| 2006/0084998 A1 | 4/2006 | Levy et al. |
| 2006/0122601 A1 | 6/2006 | Tandon |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264951 A1 | 11/2006 | Nelson et al. |
| 2007/0123876 A1 | 5/2007 | Czartoski et al. |
| 2007/0123878 A1 | 5/2007 | Shaver et al. |
| 2007/0142916 A1 | 6/2007 | Olson et al. |
| 2007/0260257 A1 | 11/2007 | Phan |
| 2008/0077154 A1 | 3/2008 | Edwards et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0221620 A1 | 9/2008 | Krause |
| 2008/0234678 A1 | 9/2008 | Gutierrez et al. |
| 2008/0243132 A1 | 10/2008 | Tipimeni et al. |
| 2008/0255560 A1 | 10/2008 | Myers et al. |
| 2008/0262495 A1 | 10/2008 | Coati et al. |
| 2008/0269751 A1 | 10/2008 | Matityahu |
| 2008/0269776 A1 | 10/2008 | Justin et al. |
| 2008/0287949 A1 * | 11/2008 | Keith ............... A61B 17/7233 606/62 |
| 2008/0287951 A1 | 11/2008 | Stoneburner et al. |
| 2009/0018542 A1 | 1/2009 | Saravia et al. |
| 2009/0182336 A1 | 7/2009 | Brenzel et al. |
| 2009/0187116 A1 | 7/2009 | Noishiki et al. |
| 2009/0228007 A1 | 9/2009 | Justin et al. |
| 2009/0228008 A1 | 9/2009 | Justin et al. |
| 2010/0023010 A1 | 1/2010 | Nelson et al. |
| 2010/0094347 A1 | 4/2010 | Nelson et al. |
| 2011/0087227 A1 | 4/2011 | Mazur et al. |
| 2011/0144645 A1 | 6/2011 | Saravia et al. |
| 2011/0178520 A1 | 7/2011 | Taylor et al. |
| 2011/0190832 A1 | 8/2011 | Taylor et al. |
| 2011/0218585 A1 | 9/2011 | Krinke et al. |
| 2011/0218626 A1 | 9/2011 | Krinke et al. |
| 2011/0282346 A1 | 11/2011 | Pham et al. |
| 2011/0282347 A1 | 11/2011 | Gordon et al. |

(56) References Cited

U.S. PATENT DOCUMENTS

| | | | |
|---|---|---|---|
| 2013/0012942 A1 | 1/2013 | Nelson et al. | |
| 2013/0116693 A1* | 5/2013 | Nelson | A61B 17/7233 606/64 |
| 2015/0038966 A1* | 2/2015 | Zandona | A61B 17/64 606/59 |
| 2016/0030064 A1* | 2/2016 | Dacosta | A61B 17/1717 606/64 |

FOREIGN PATENT DOCUMENTS

| | | |
|---|---|---|
| EP | 1815813 A2 | 8/2007 |
| EP | 1753354 | 9/2010 |
| WO | 1997018769 | 5/1997 |
| WO | 1998027876 | 7/1998 |
| WO | 199856301 | 12/1998 |
| WO | 1999020195 | 4/1999 |
| WO | 2000028906 | 5/2000 |
| WO | 0128443 A1 | 4/2001 |
| WO | 2002000270 | 1/2002 |
| WO | 2002000275 | 1/2002 |
| WO | 2002002158 | 1/2002 |
| WO | 2005112804 A1 | 12/2005 |
| WO | 2006053210 A1 | 5/2006 |
| WO | 2007009123 A2 | 1/2007 |
| WO | 2011112619 | 9/2011 |

OTHER PUBLICATIONS

Andermahr et al., "Anatomy of the clavicle and the intramedullary nailing of midclavicular fractures," Clinical Anatomy, vol. 20; pp. 48-56; 2007.
The Titanium Flexible Humeral Nail System (Quick reference for surgical technique), Synthes, 1999.
The Titanium Flexible Humeral Nail System (Technique Guide), Synthes, 1999.
Extended European Serach Report for European Application No. 15187485.6, dated Feb. 10, 2016 in 6 pages.

\* cited by examiner

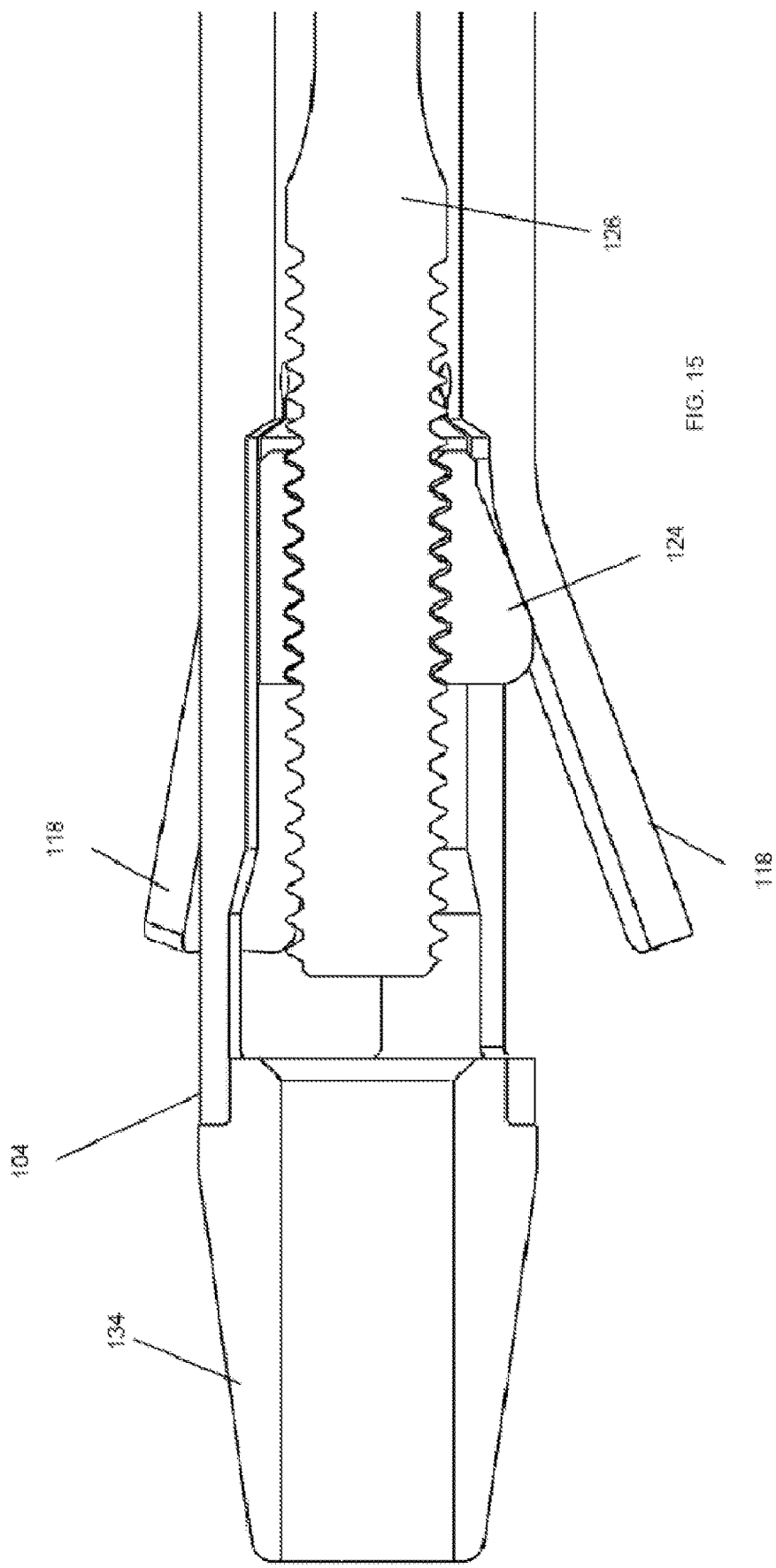

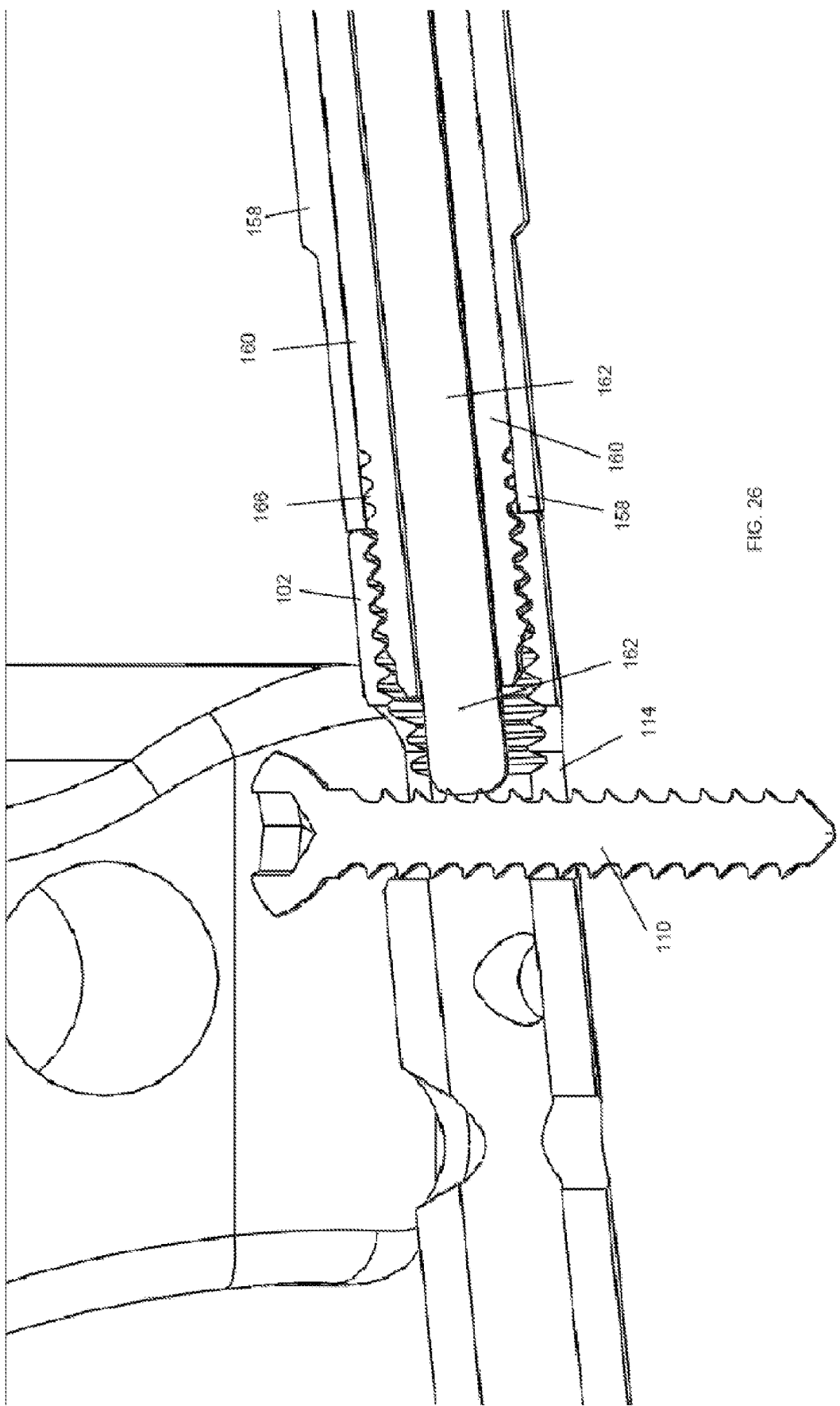

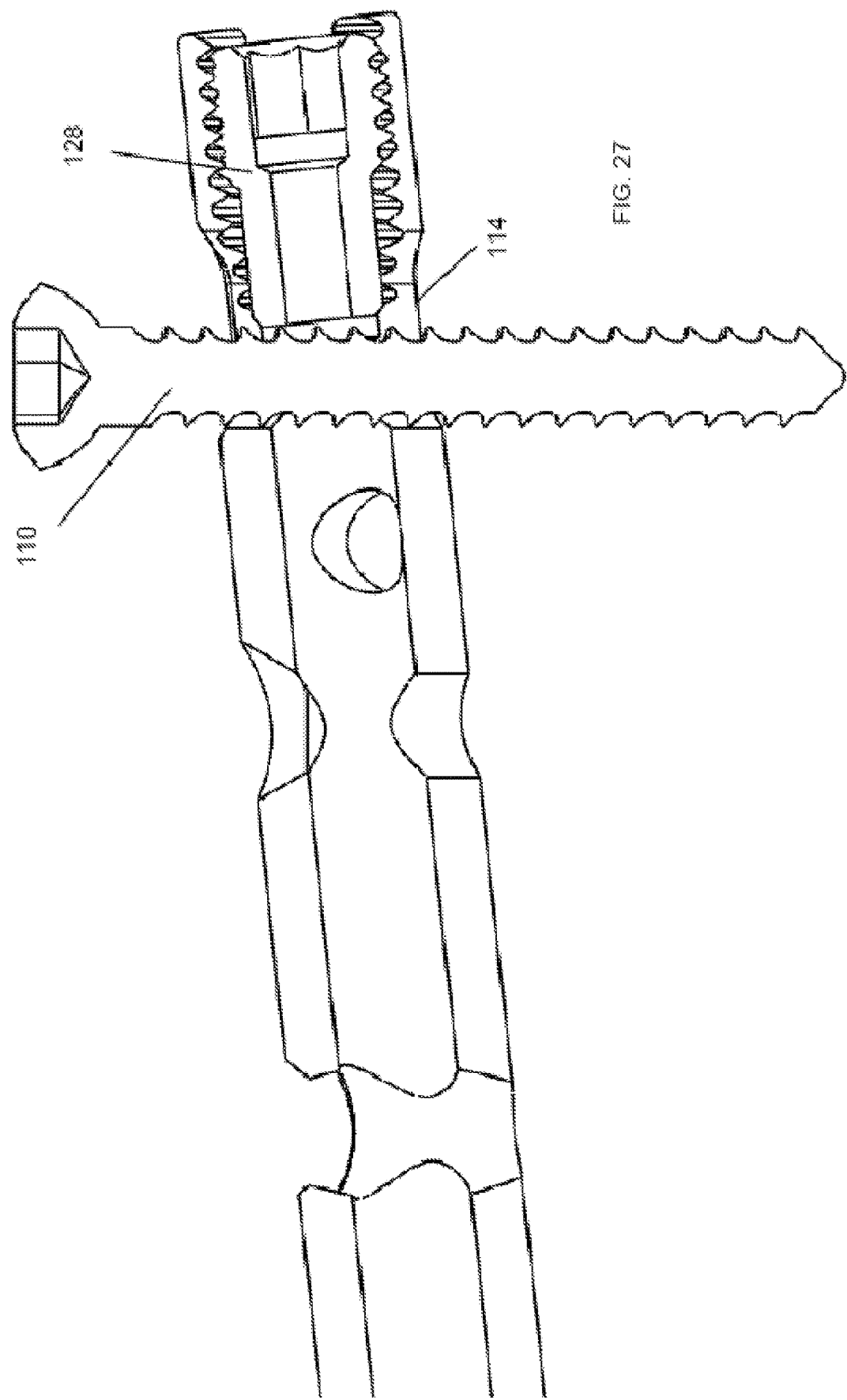

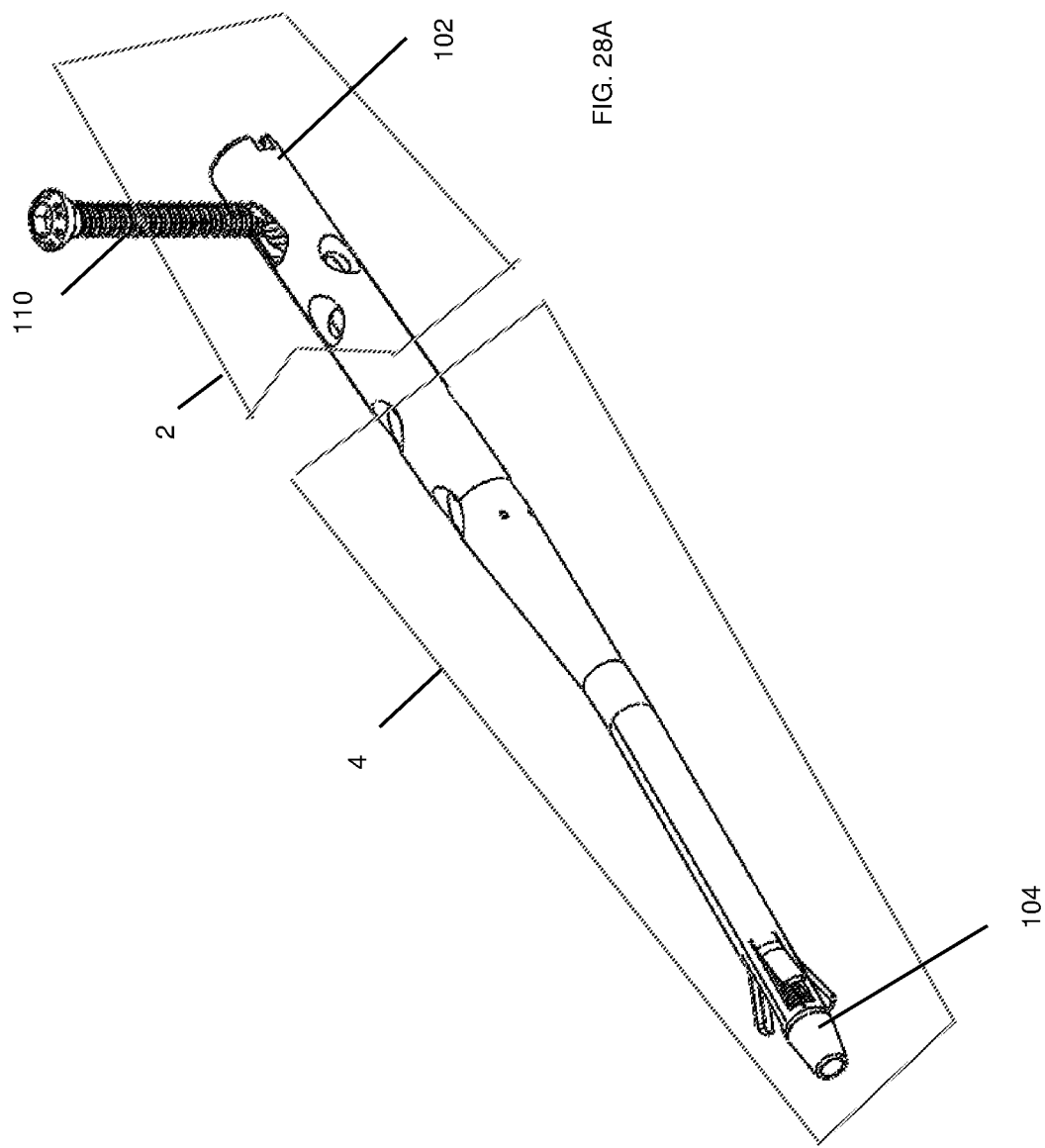

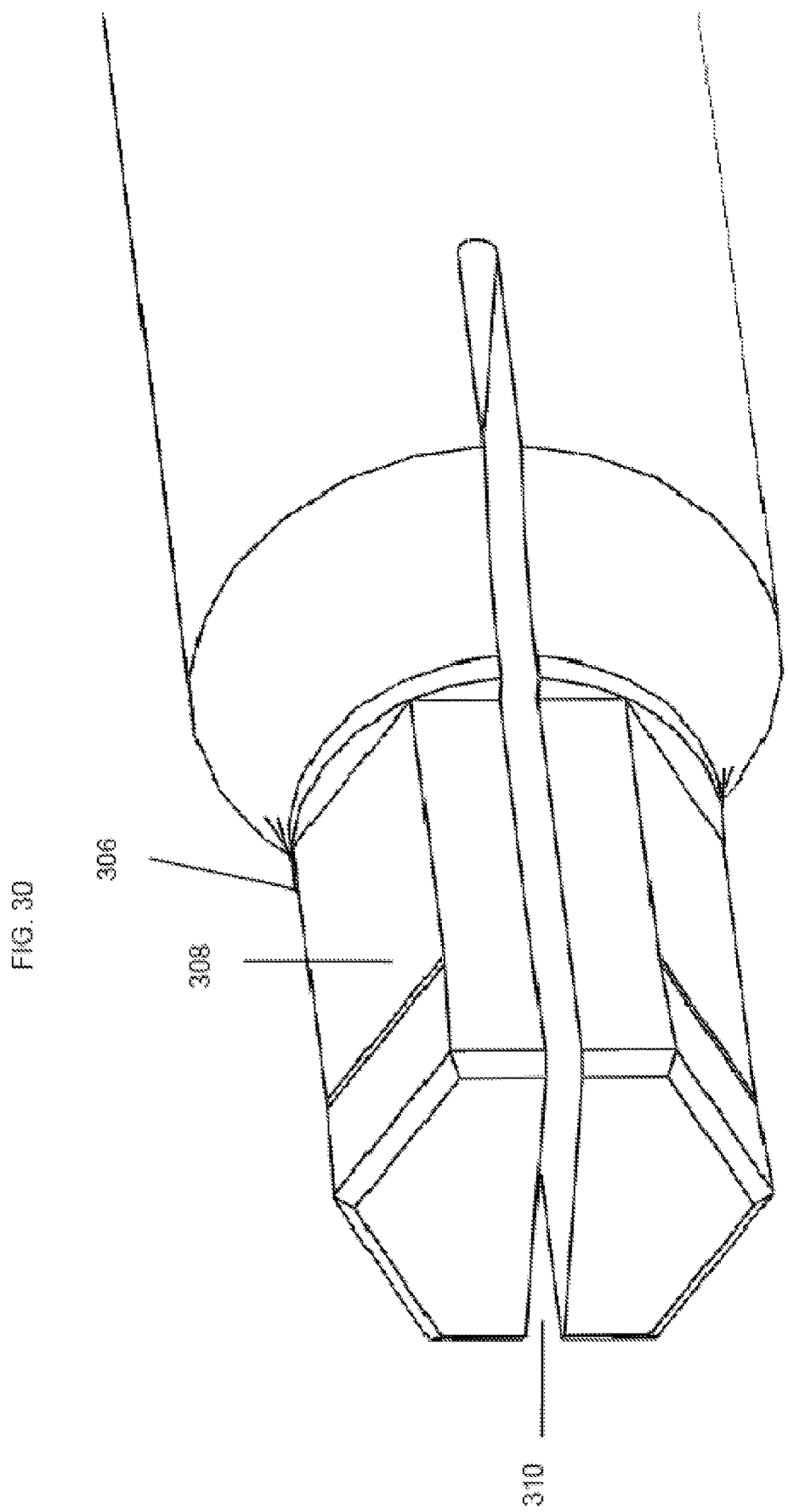

FIG. 31B

FIG. 31C
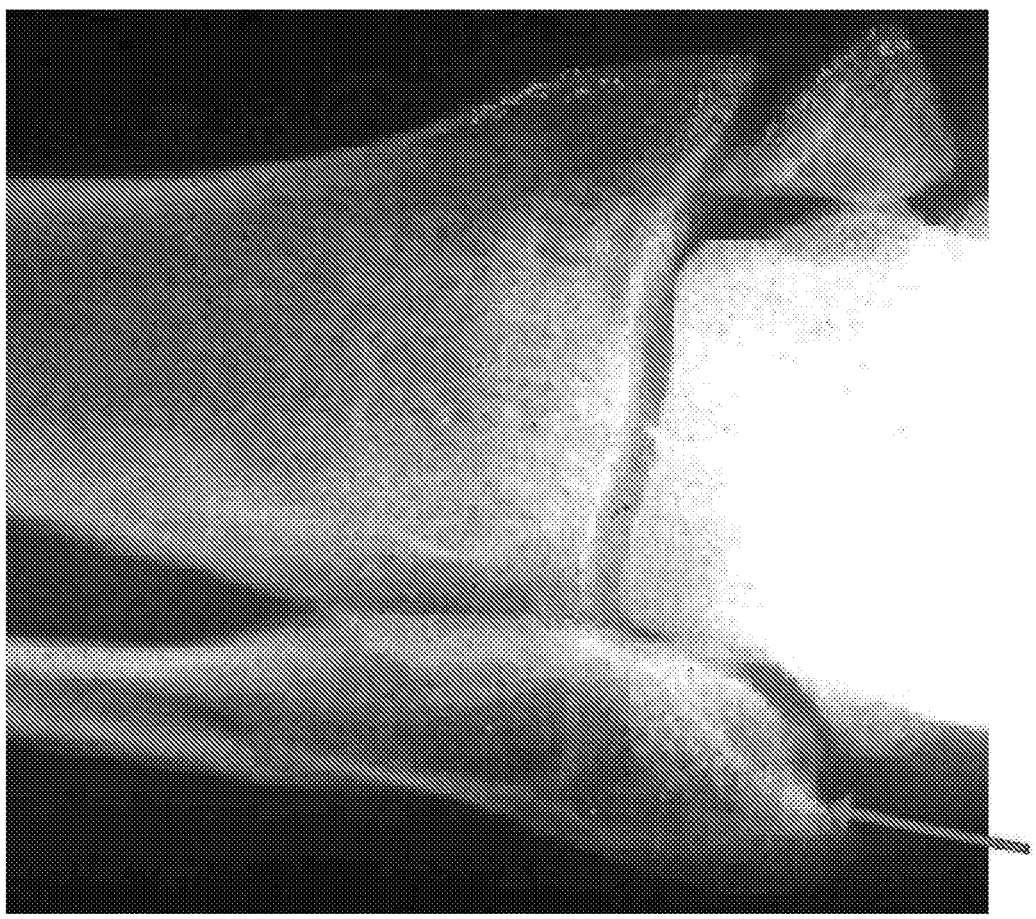
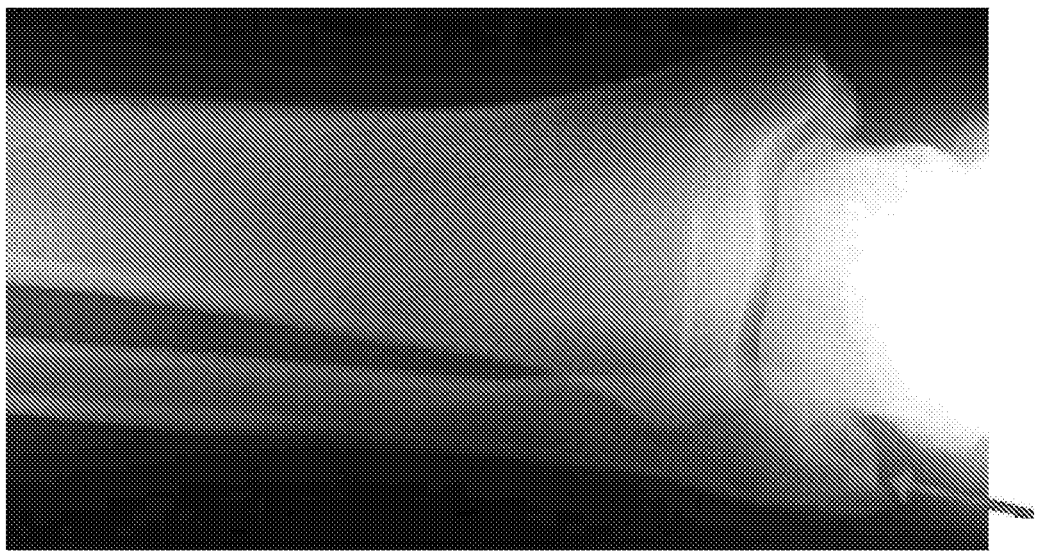

FIG. 31O
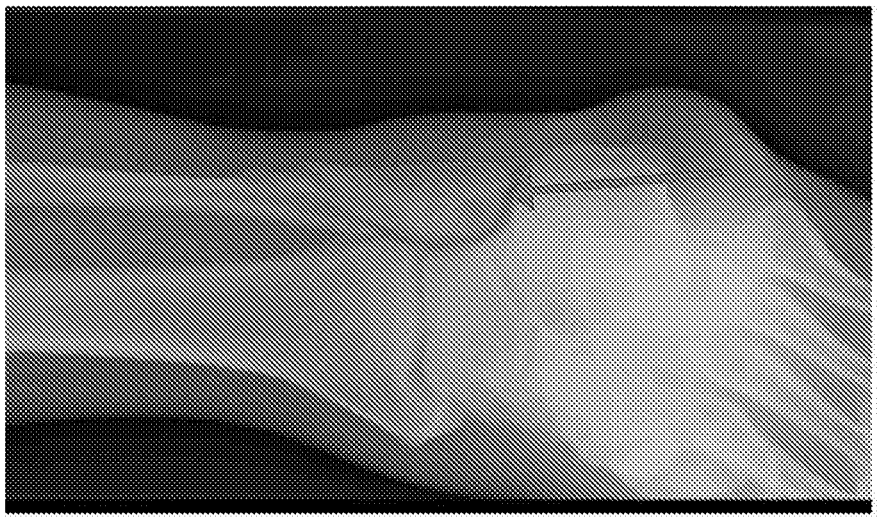

FIG. 31E

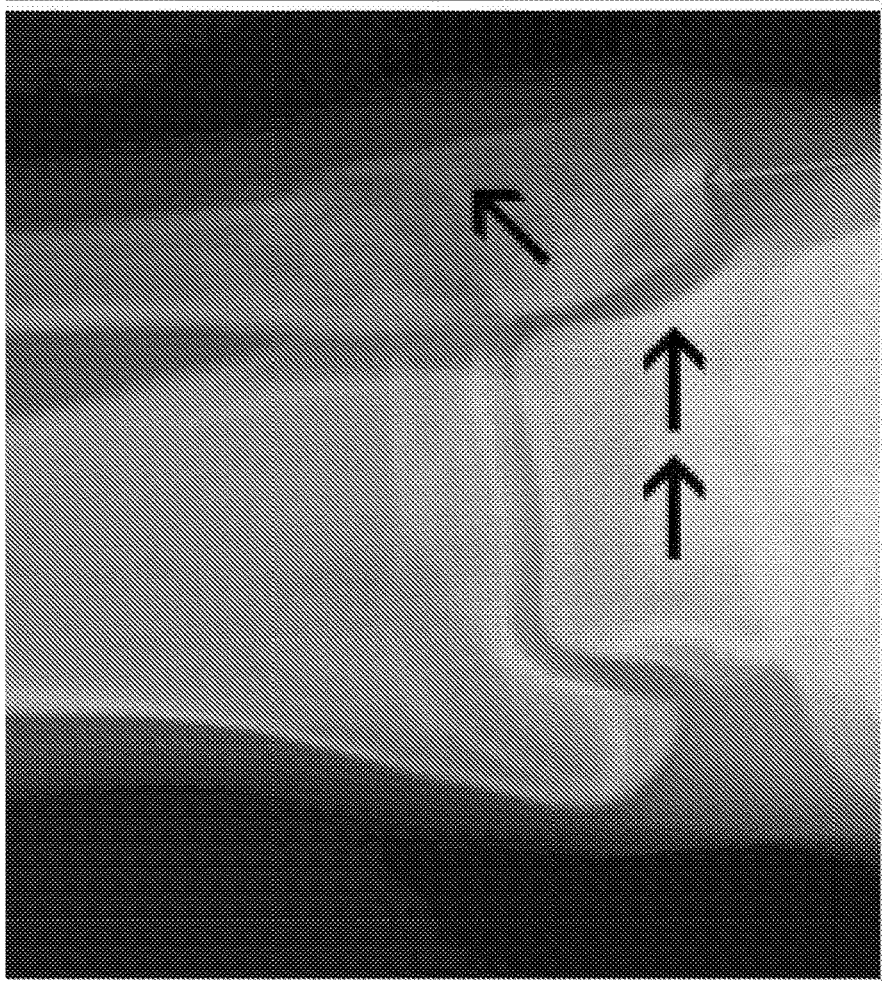
FIG. 31F

FIG. 31G
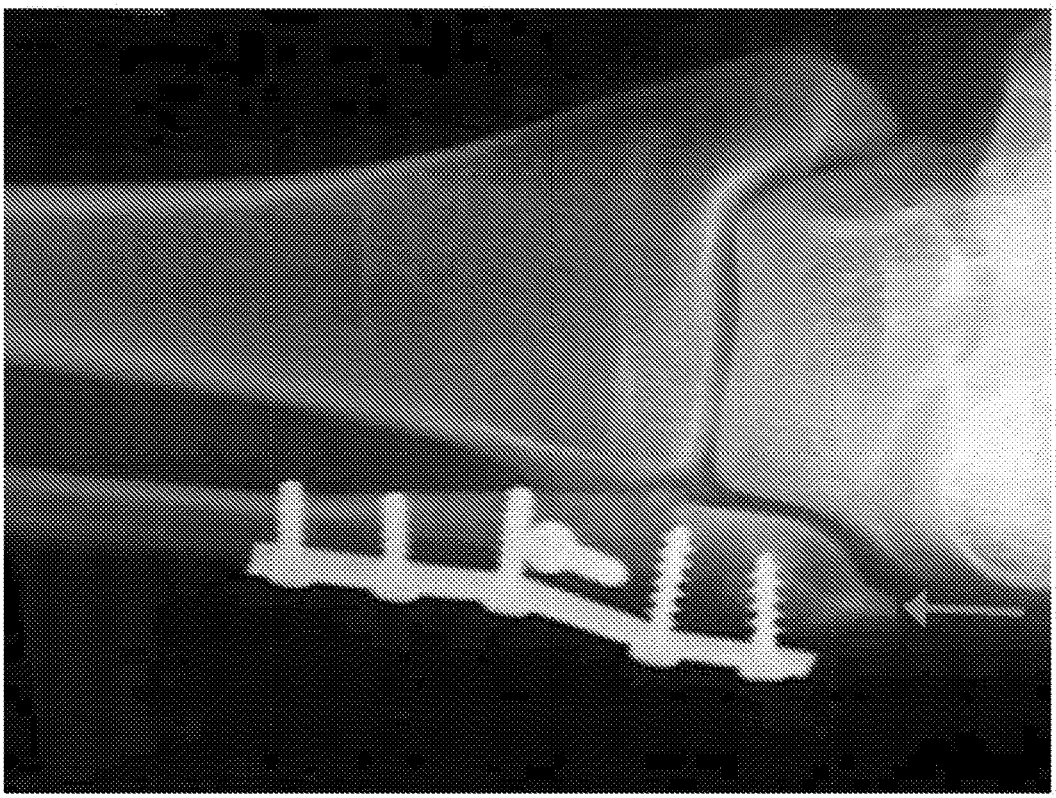

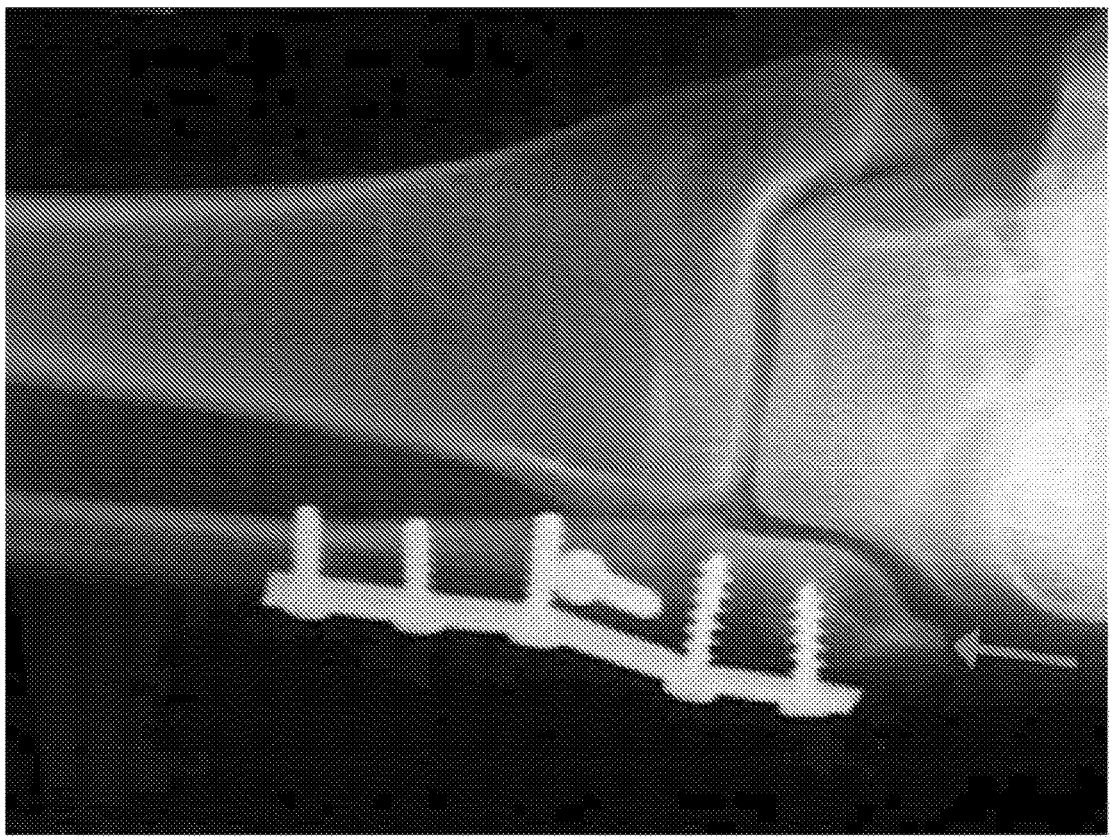
FIG. 31H

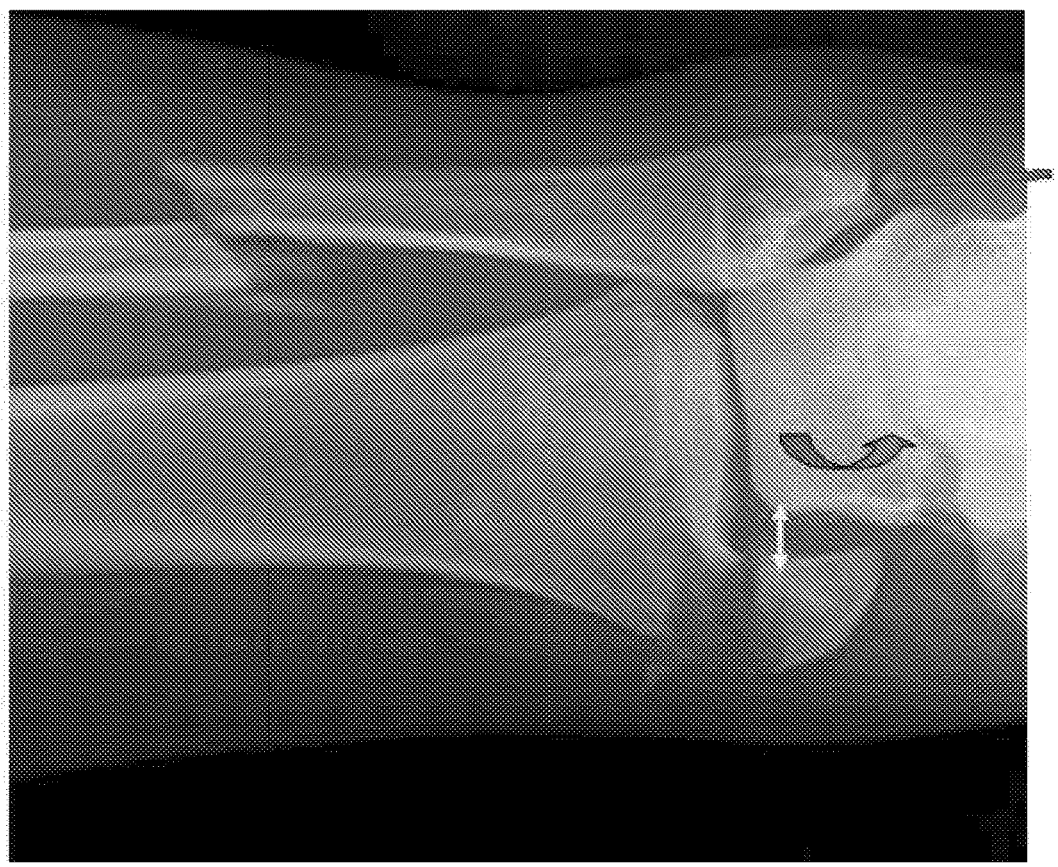
FIG. 311

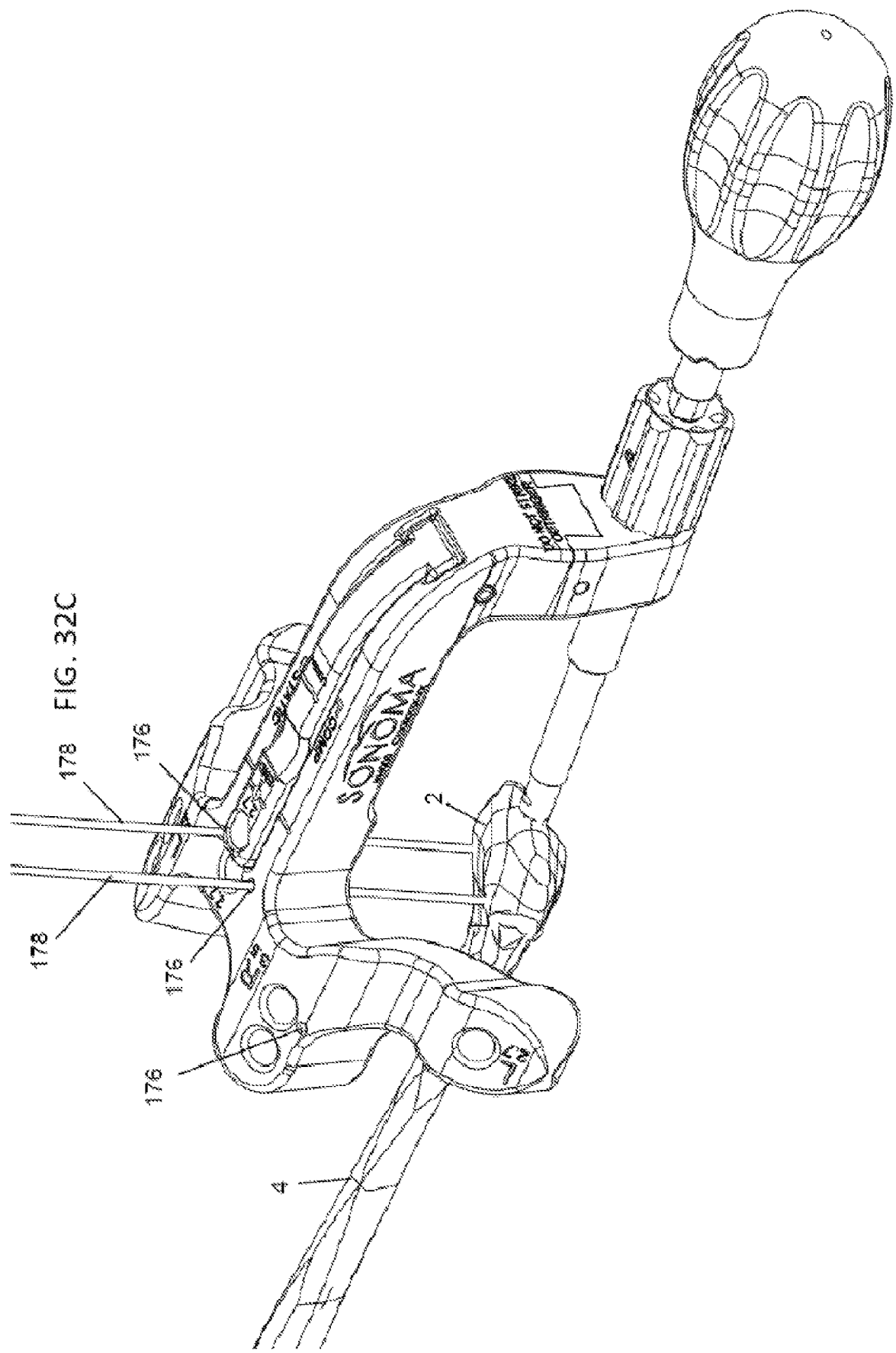

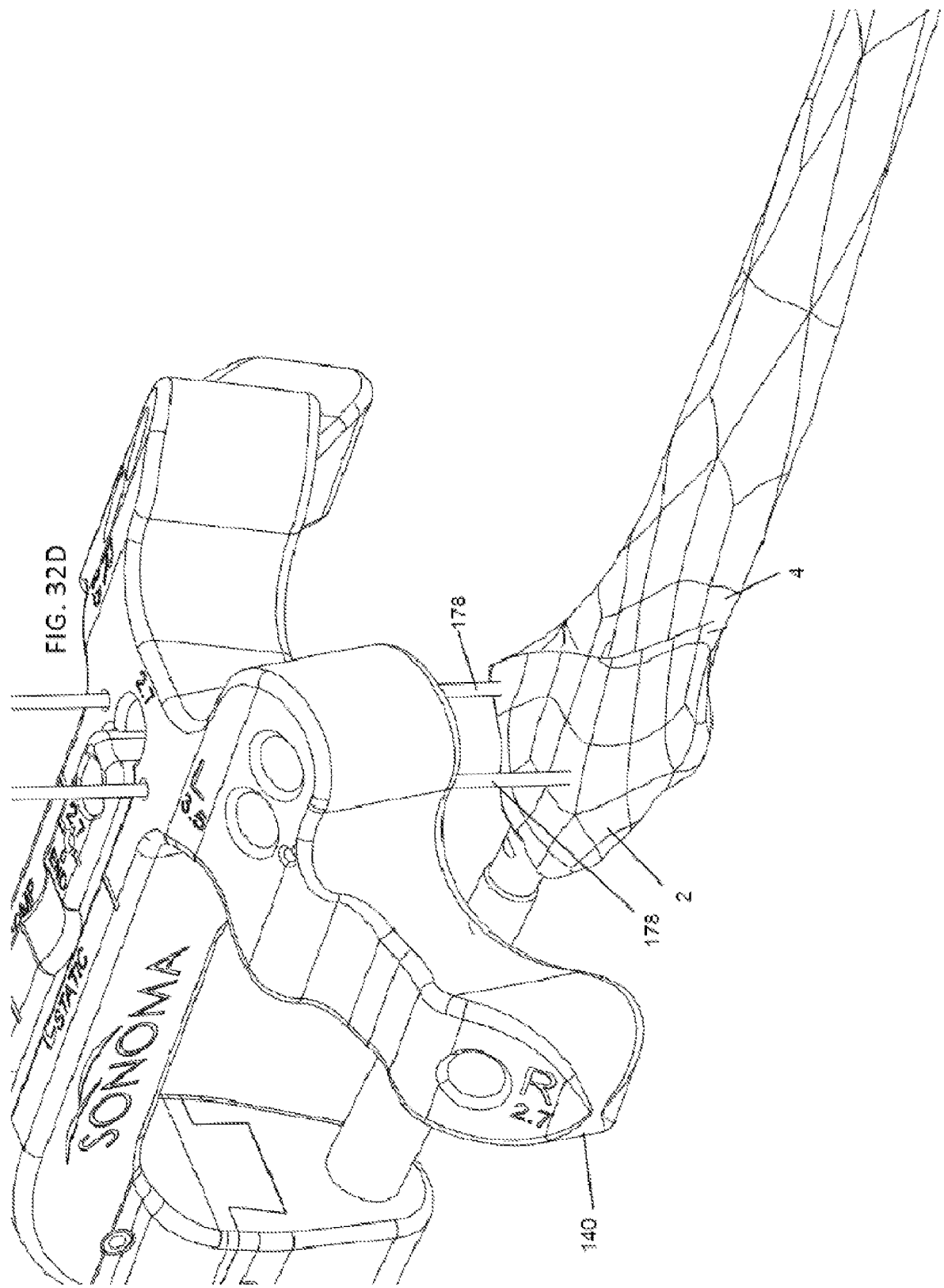

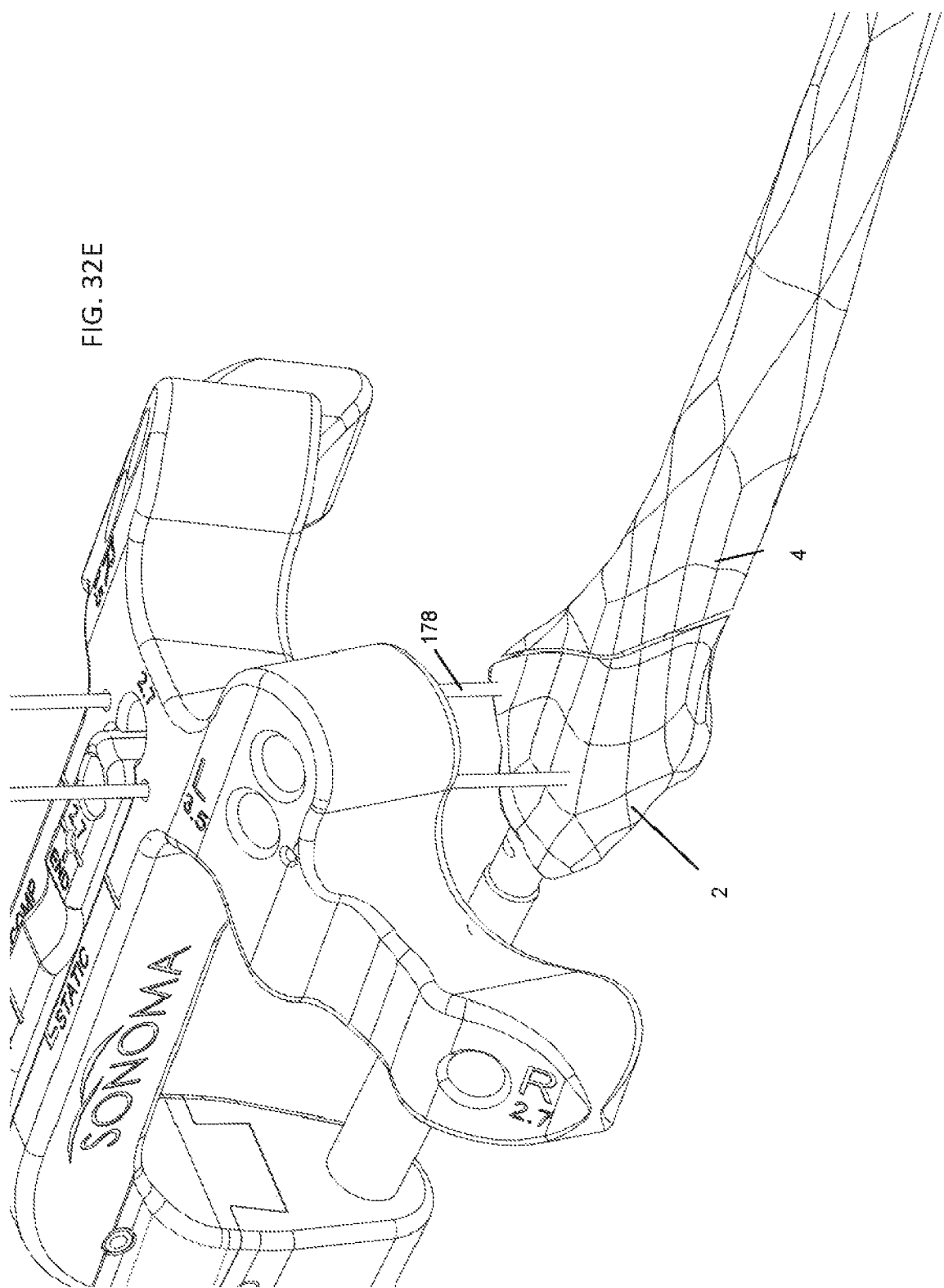

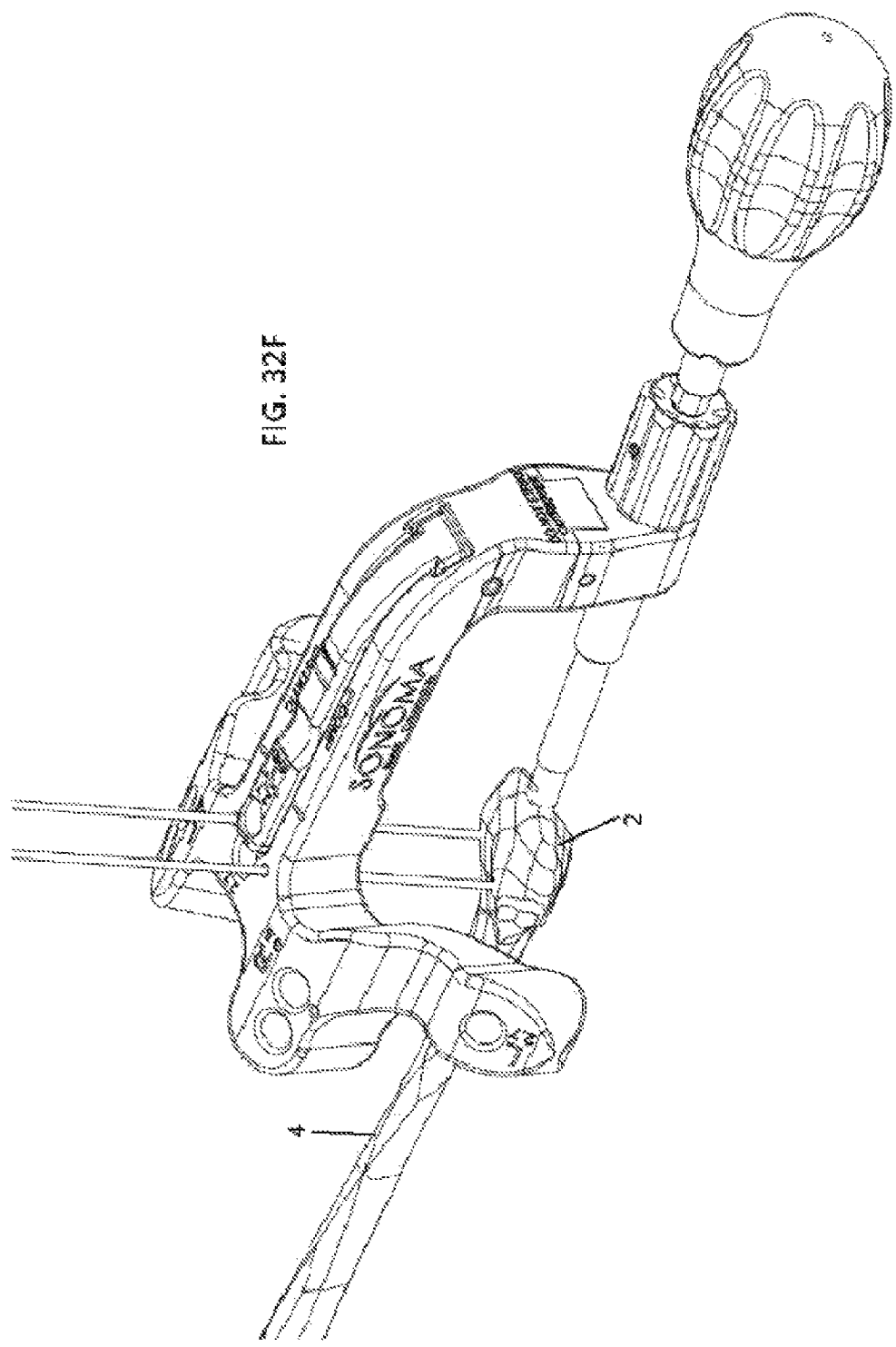

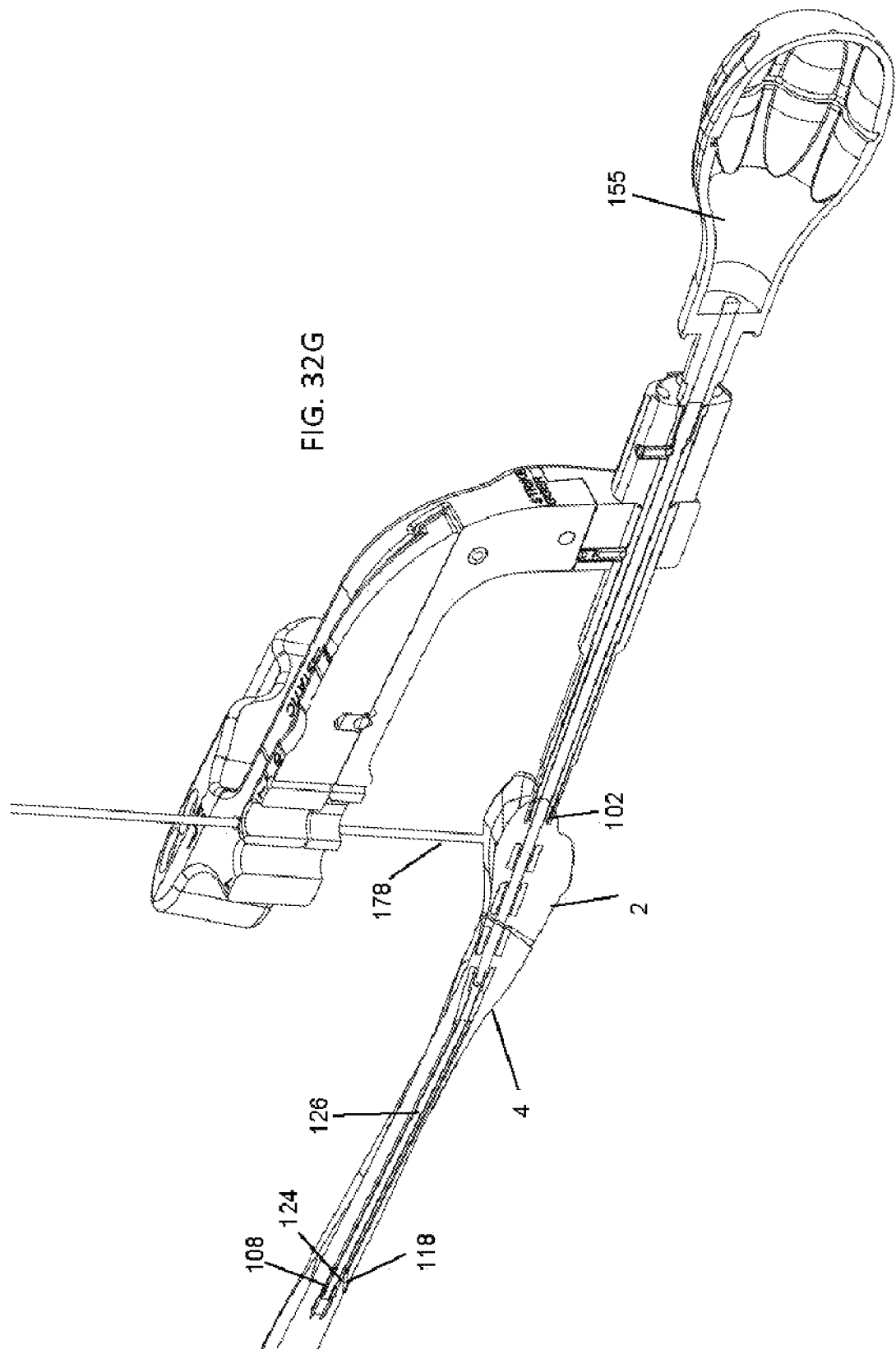

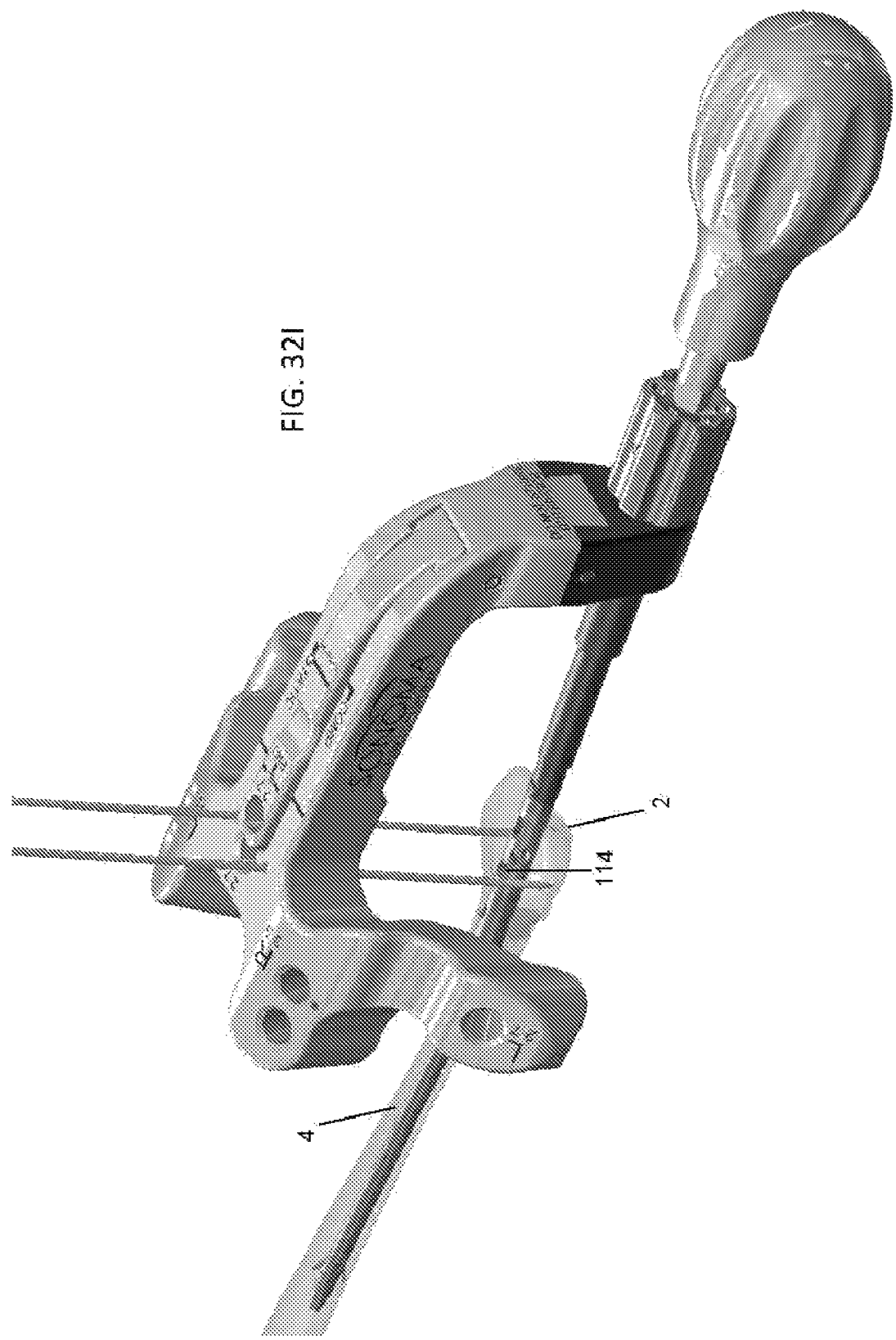

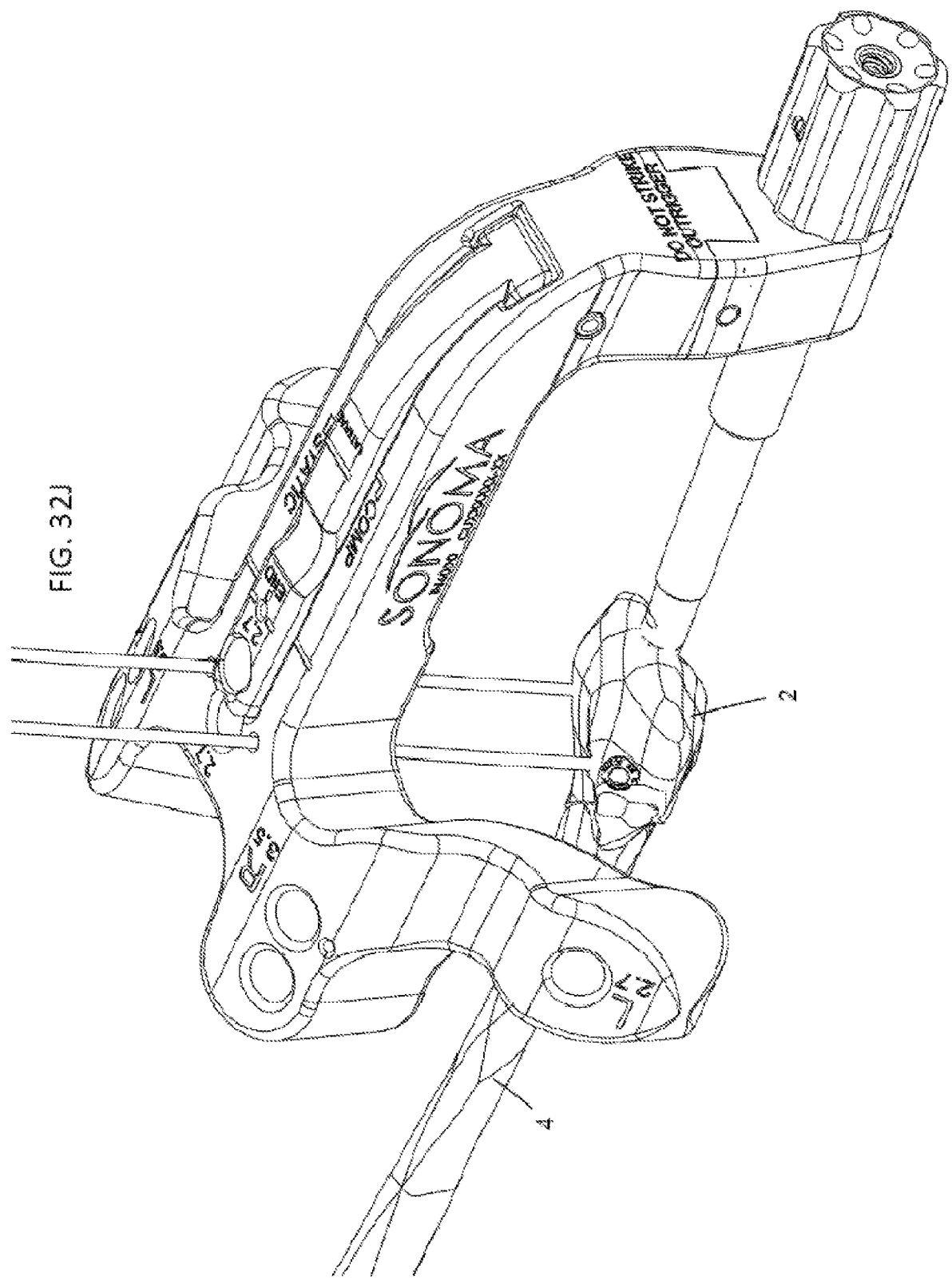

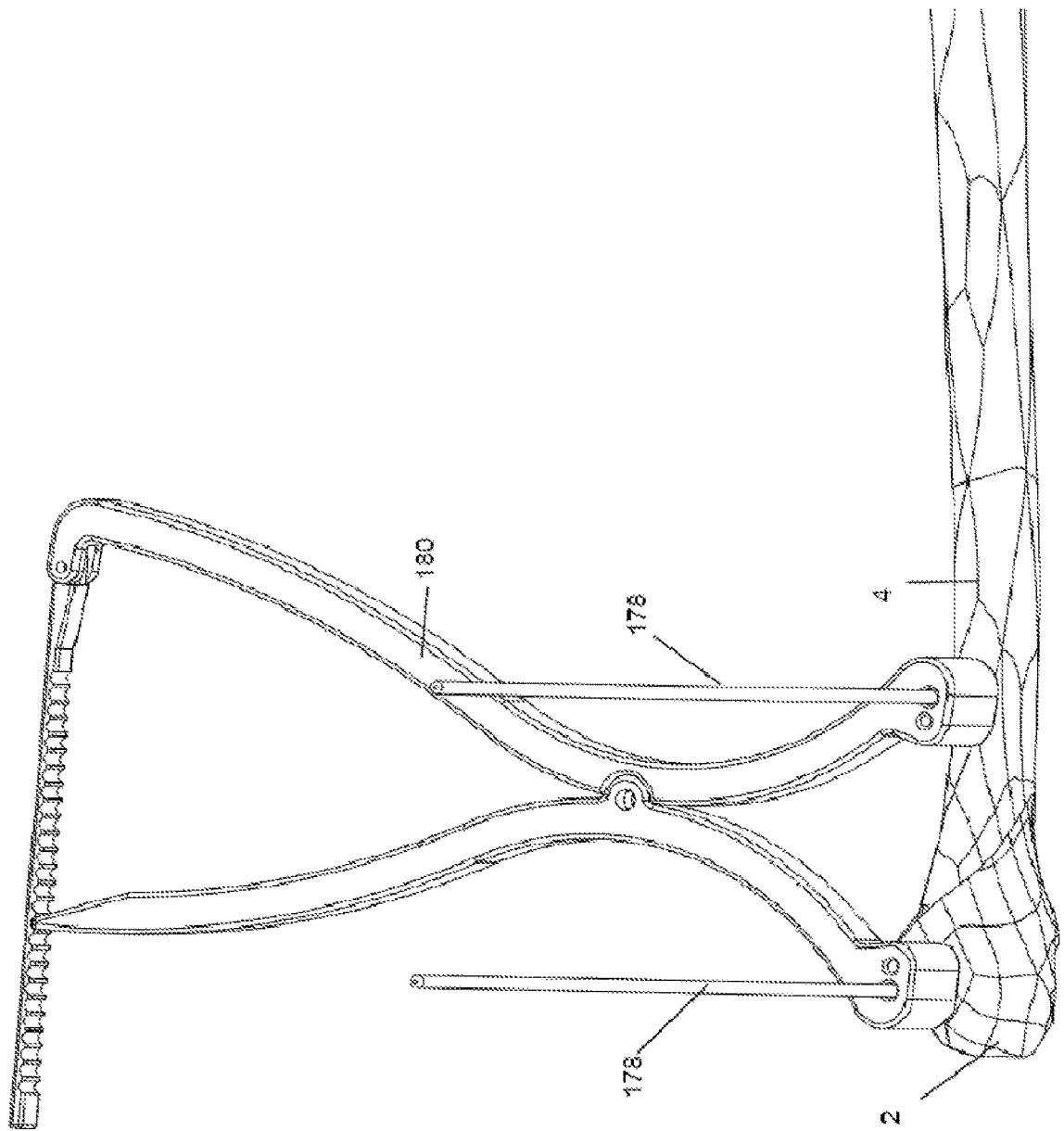

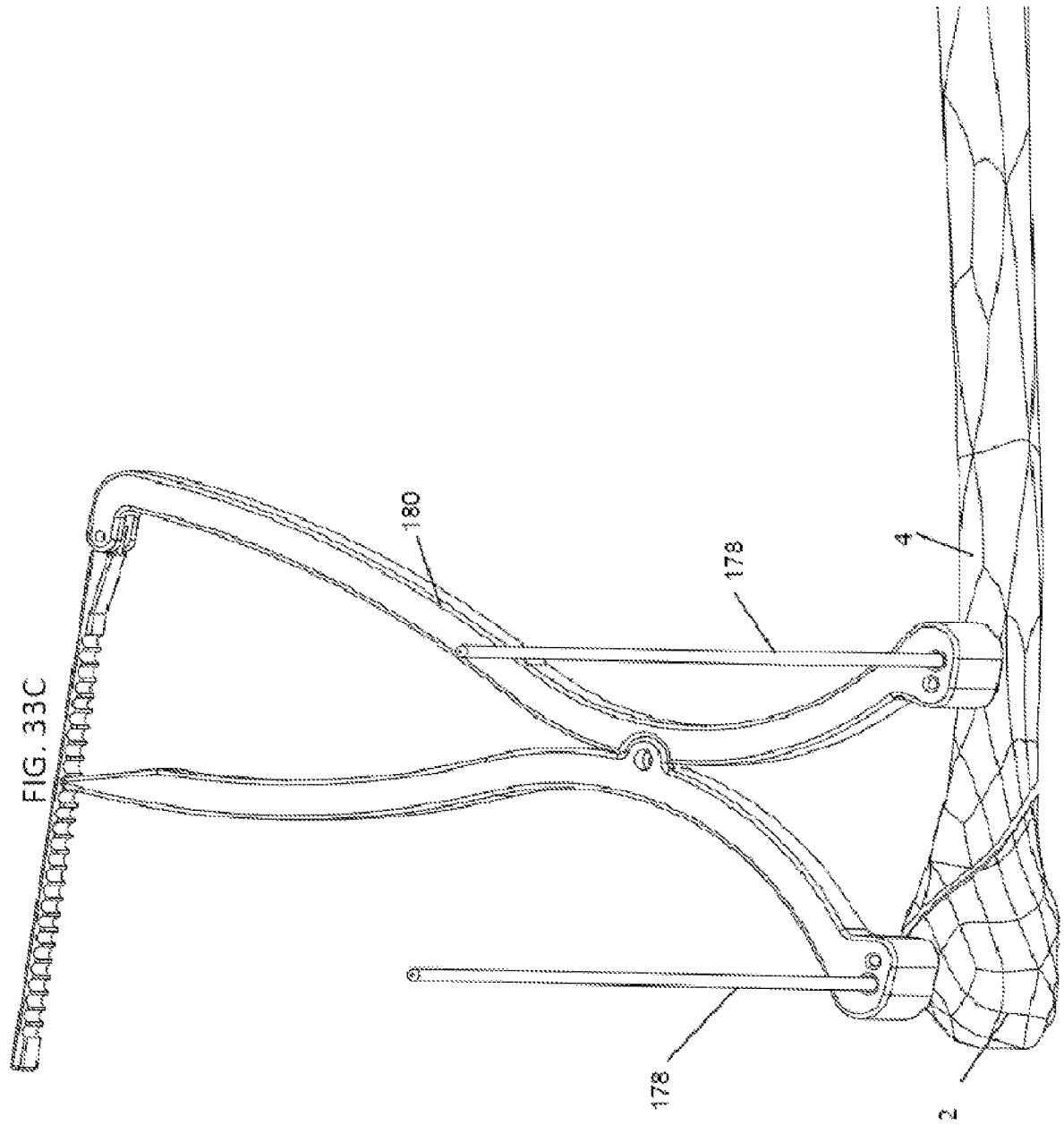

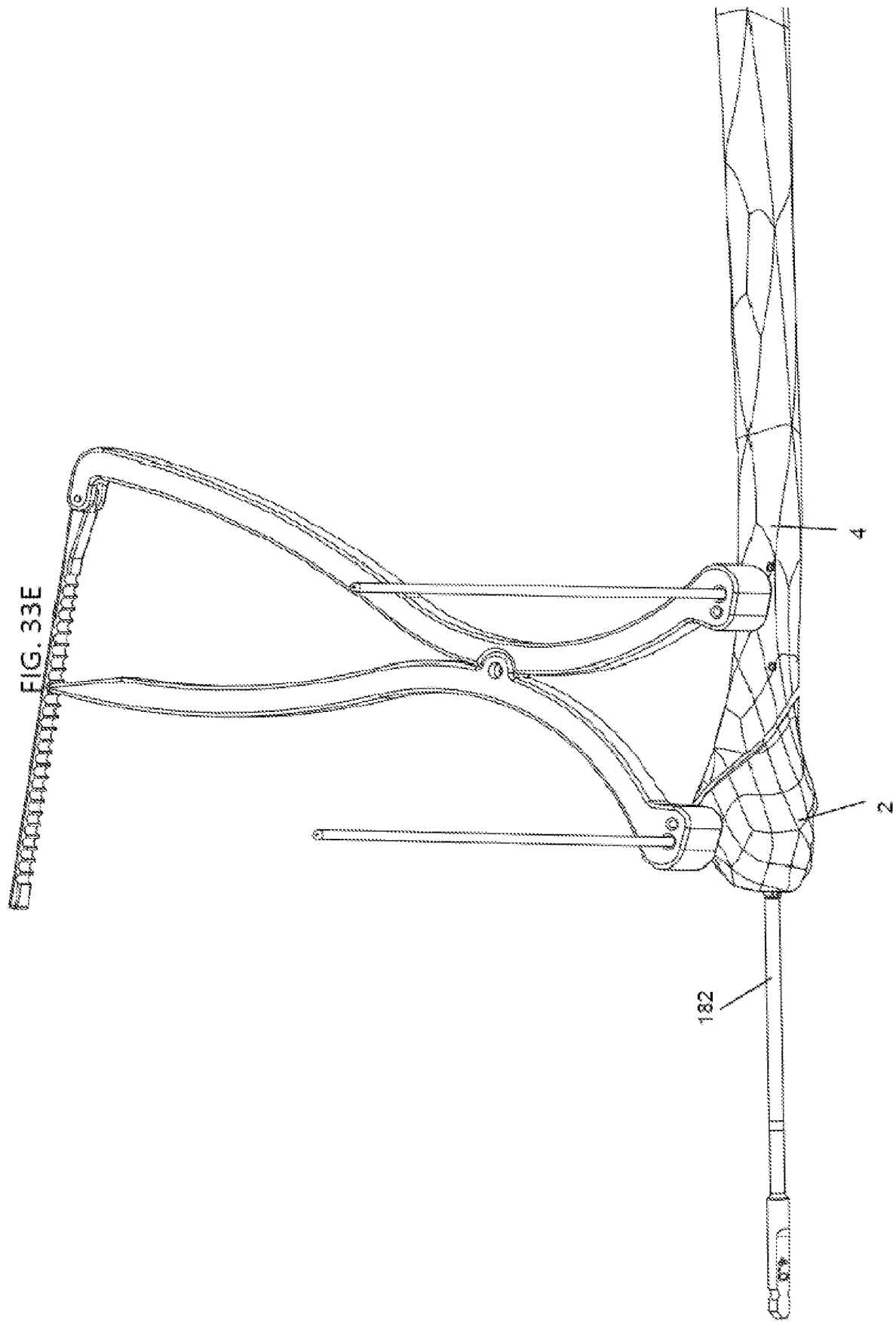

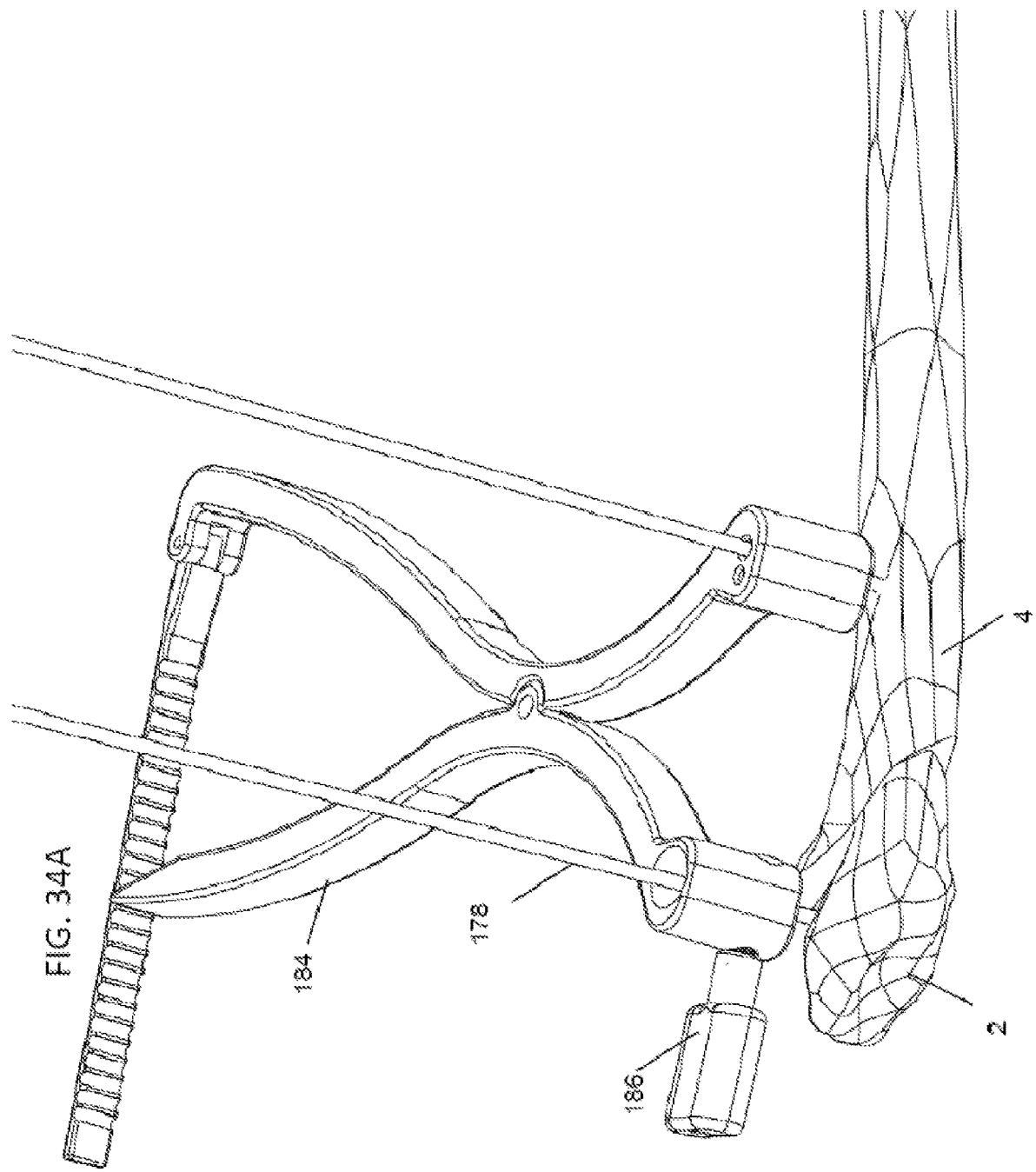

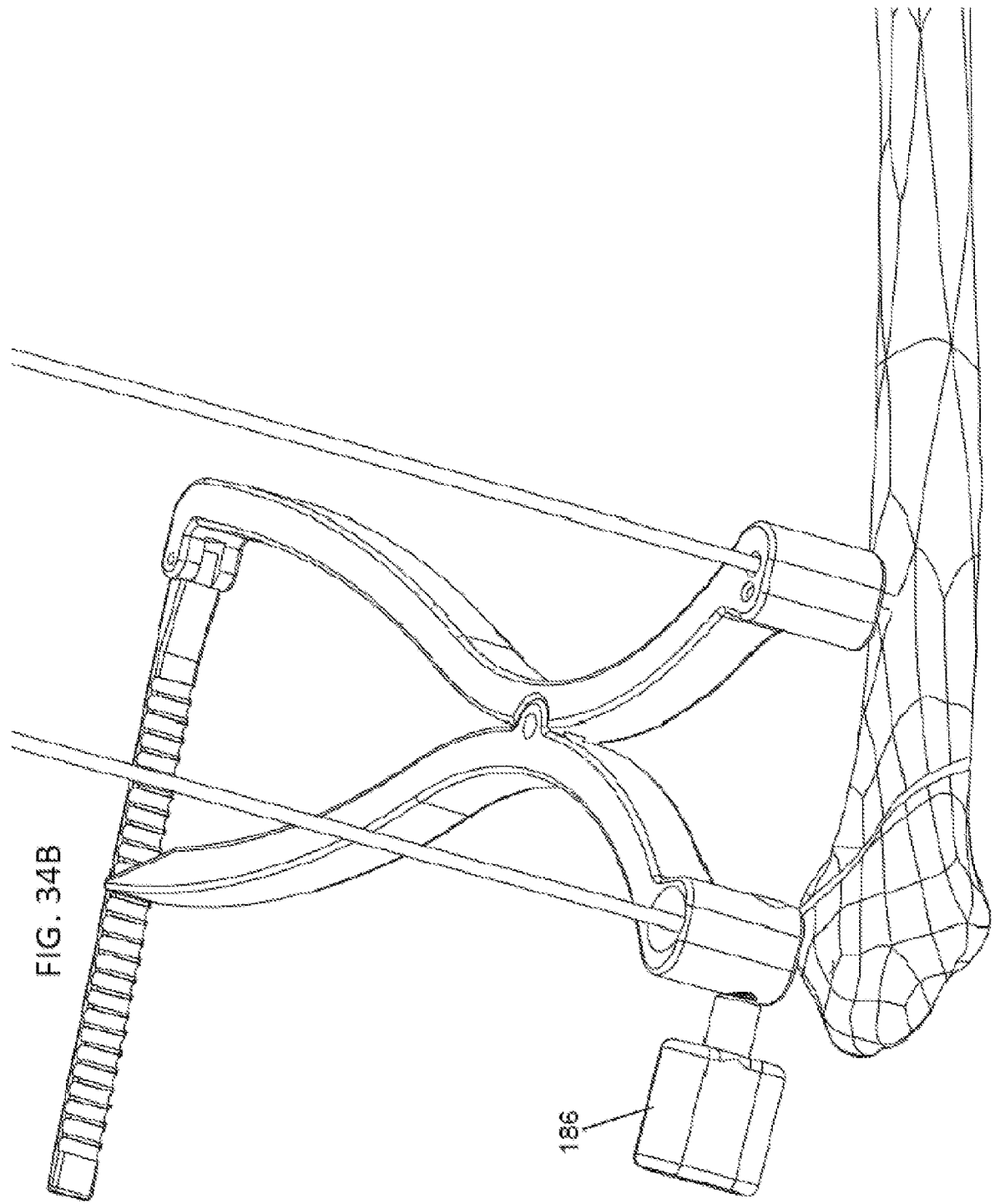

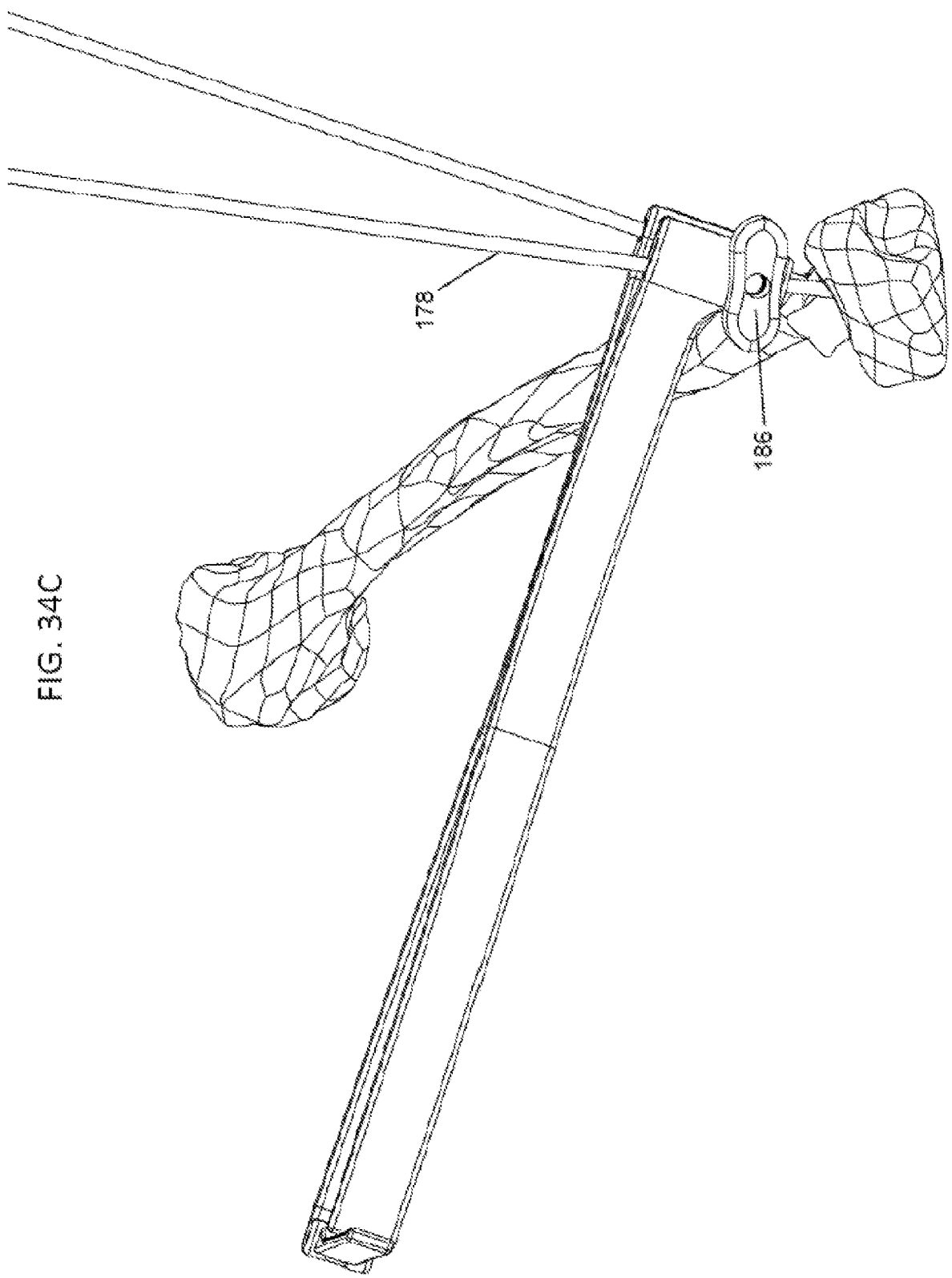

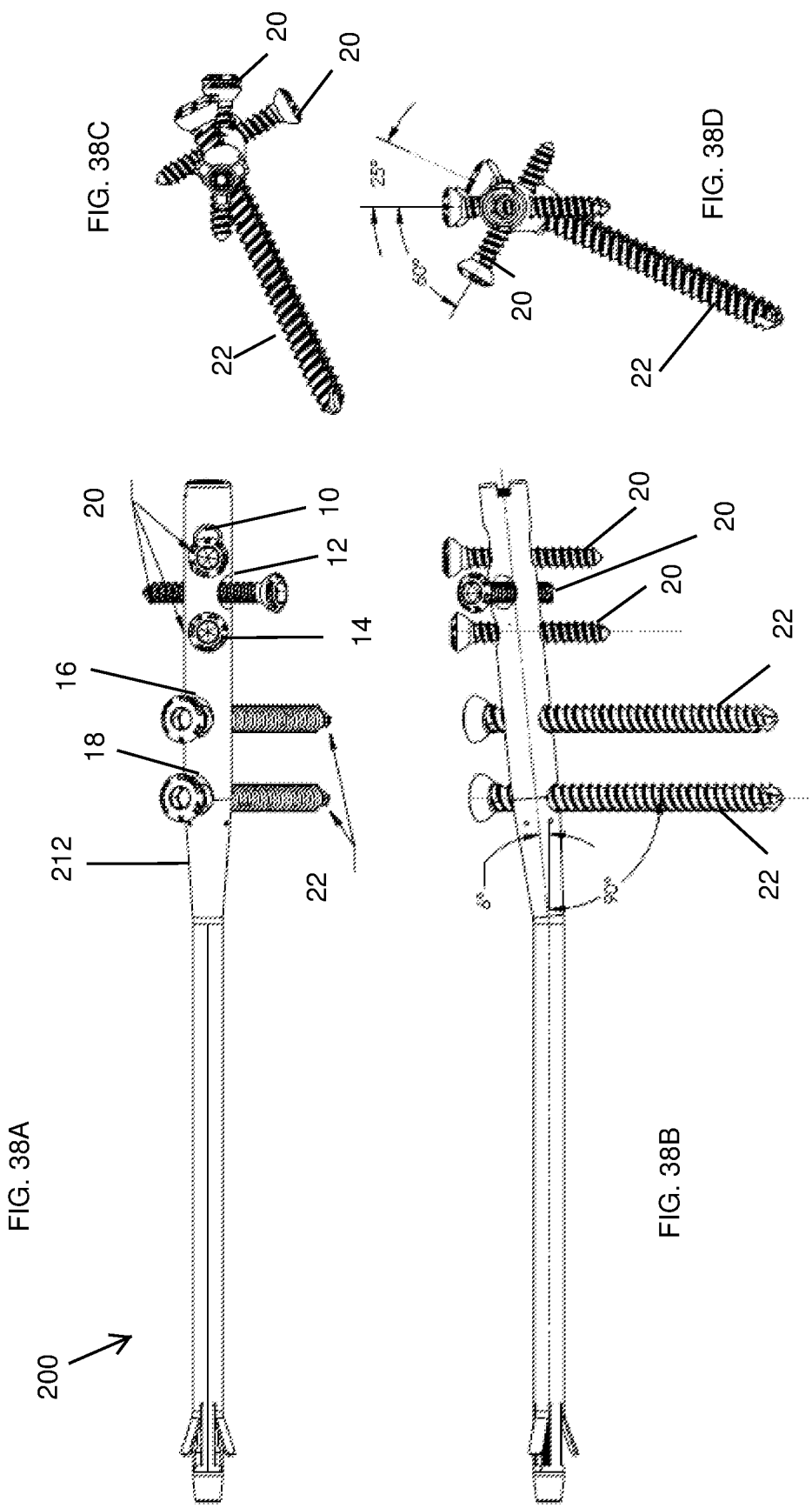

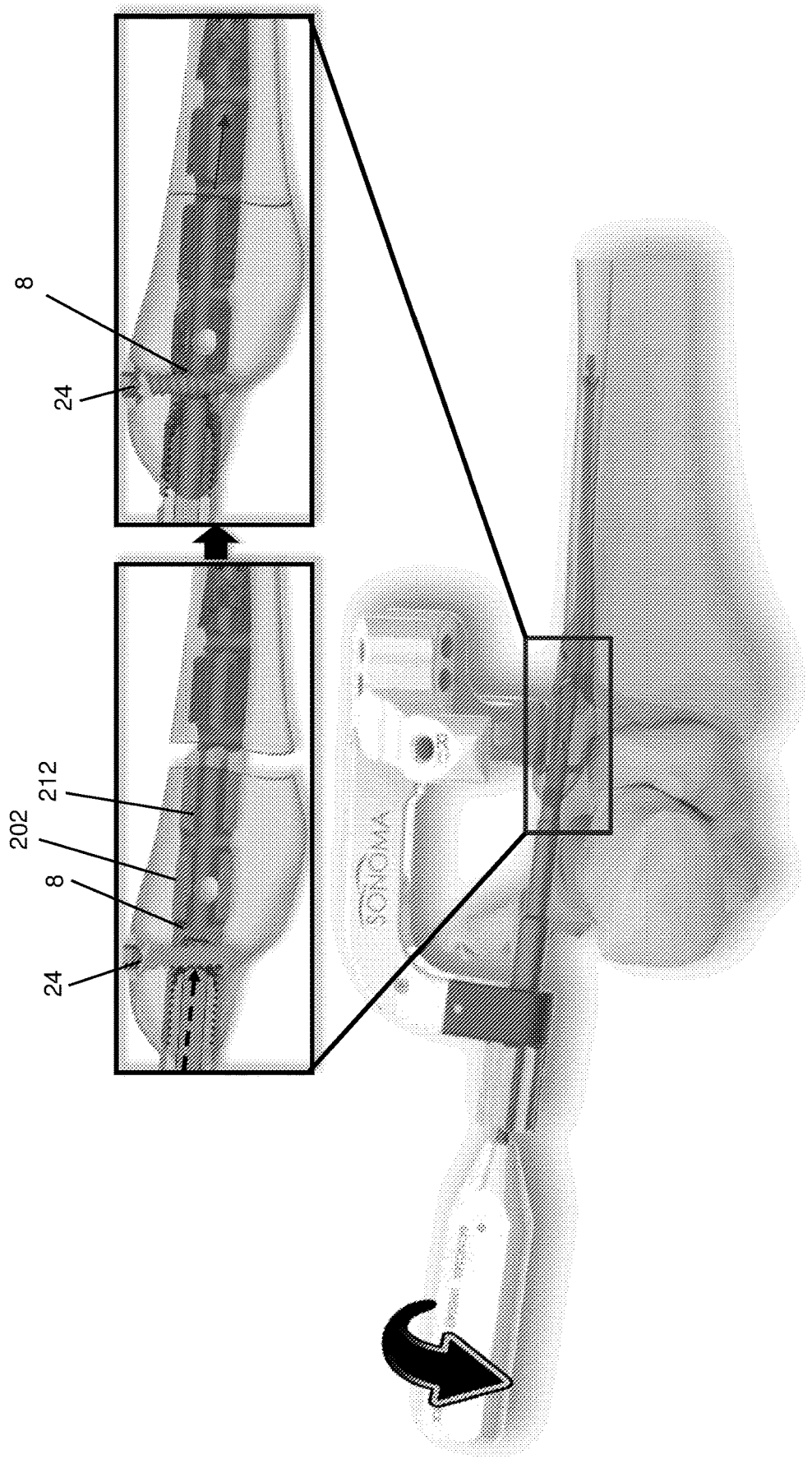

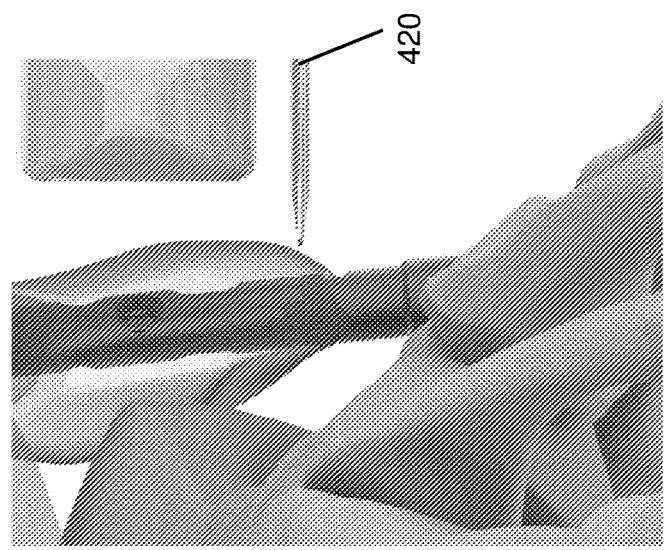
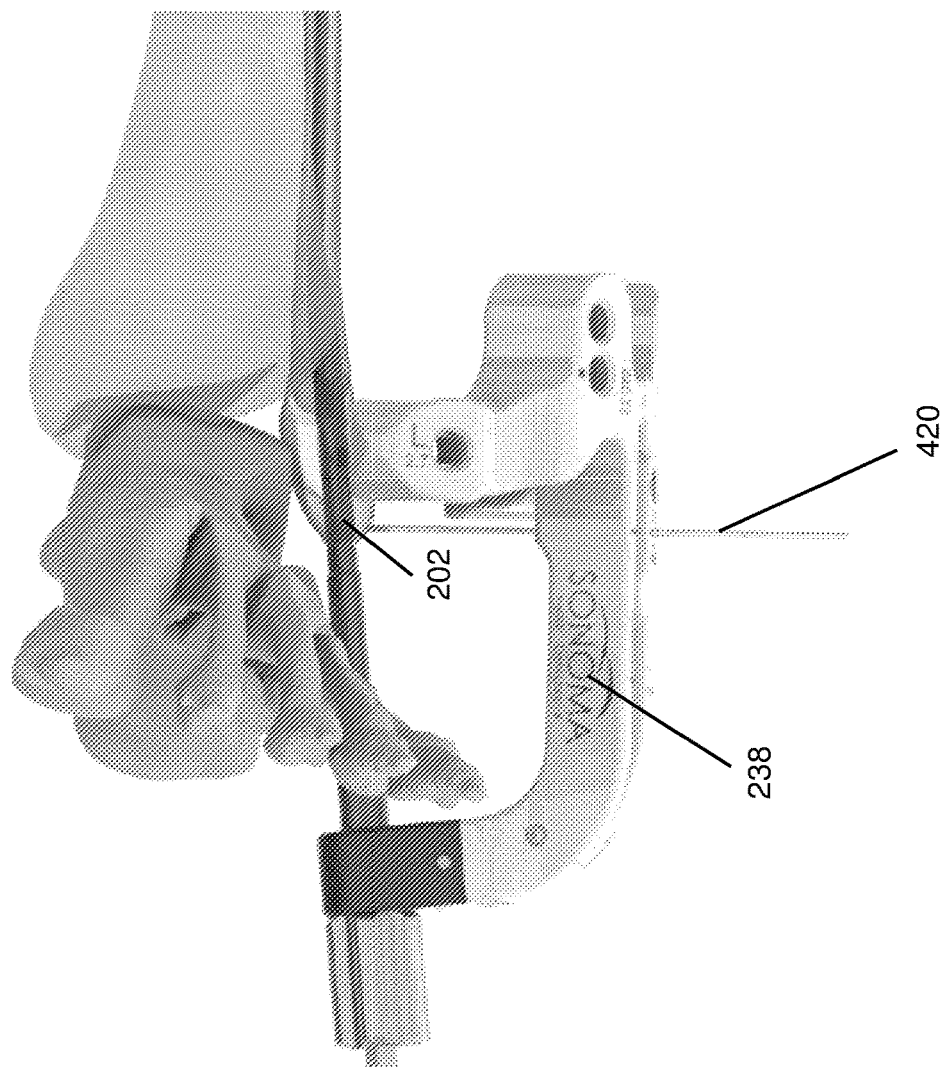
FIG. 44I

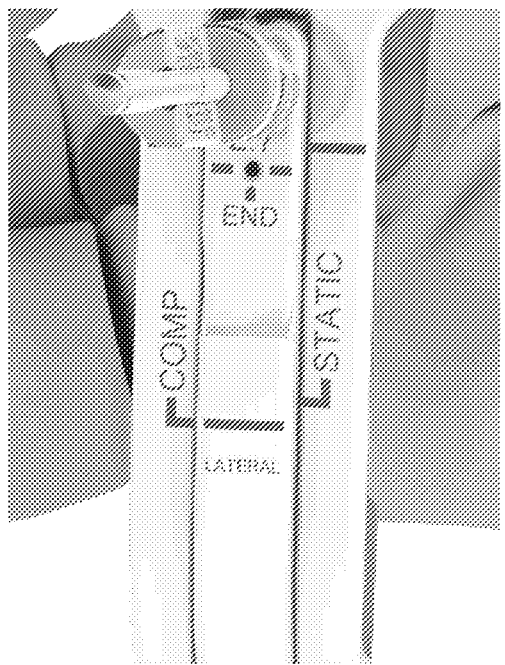
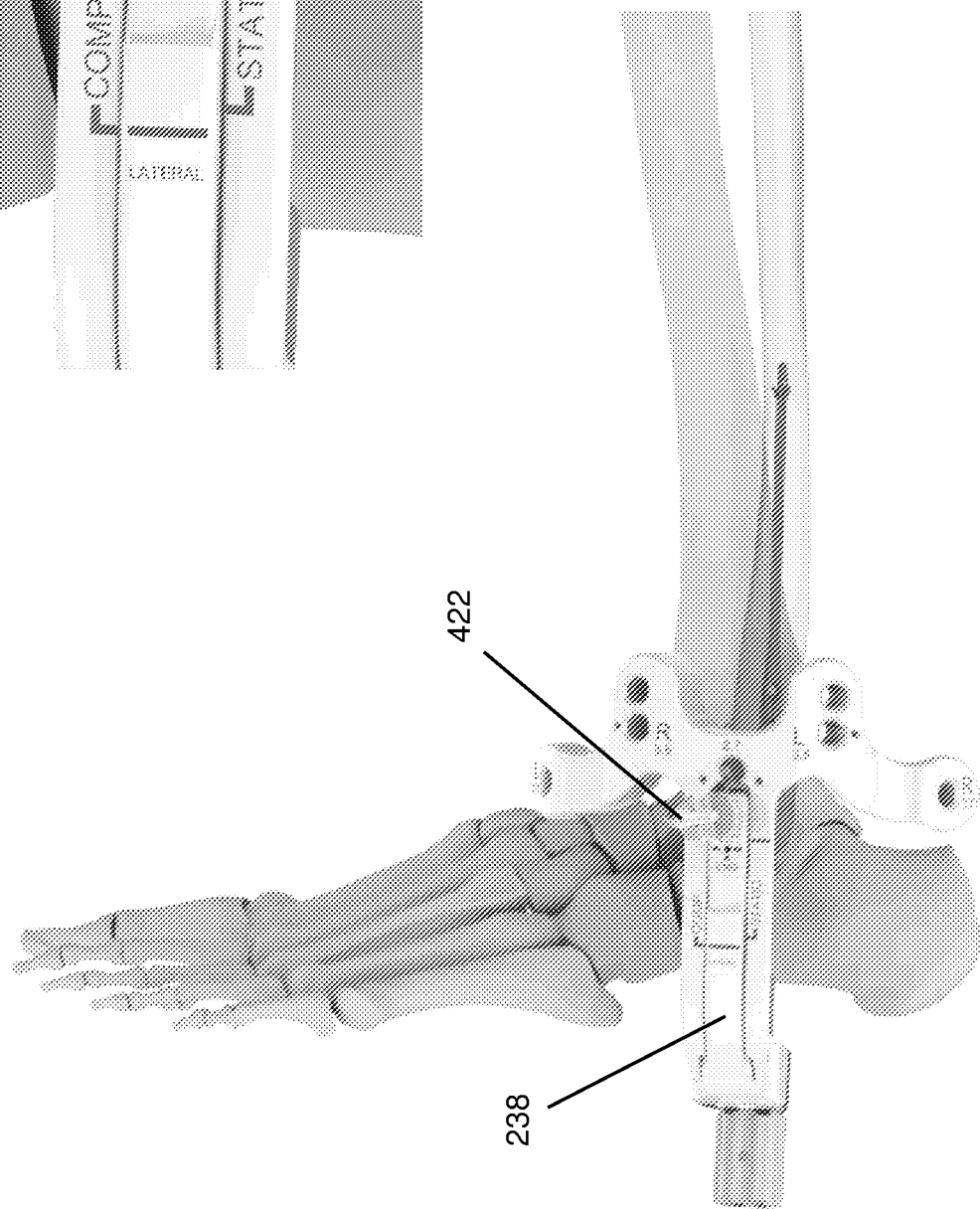
FIG. 44K

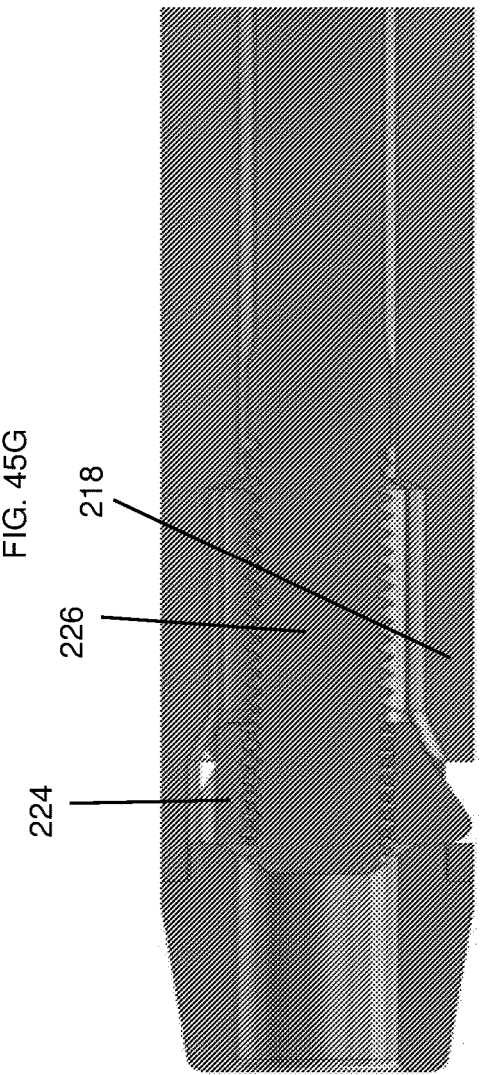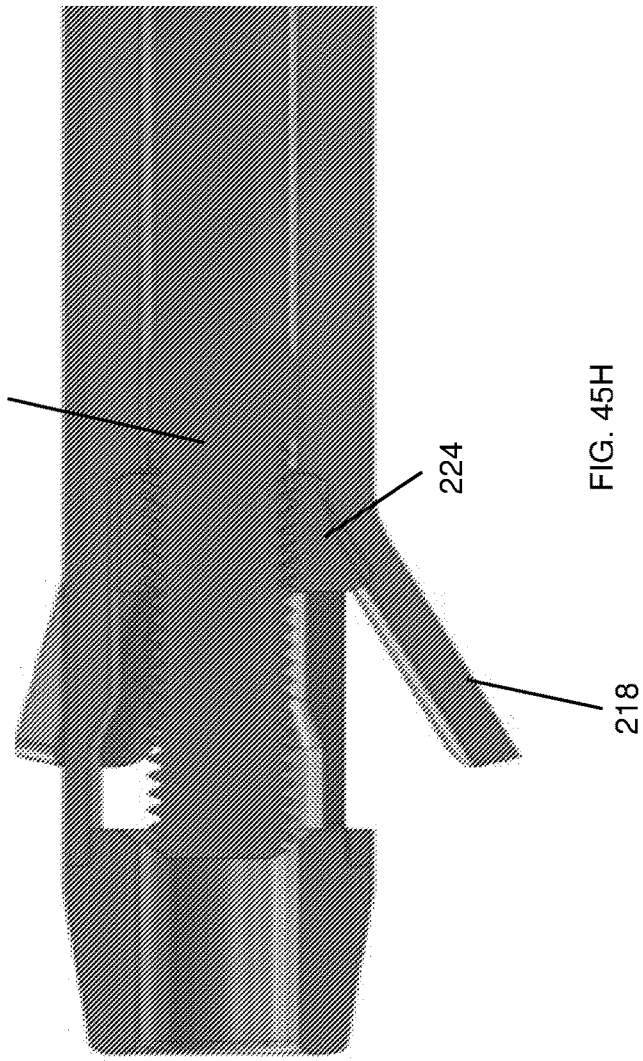

INTRAMEDULLARY FRACTURE FIXATION DEVICES AND METHODS

INCORPORATION BY REFERENCE

The present application is a divisional of prior U.S. application Ser. No. 14/861,355, filed Sep. 22, 2015. The '355 application claims priority under 35 U.S.C. § 119(e) to U.S. Provisional Application No. 62/057,913 filed on Sep. 30, 2014. The entirety of the disclosures of the '355 and '913 applications are incorporated by reference herein in its entirety. All publications and patent applications mentioned in this specification are herein incorporated by reference in their entirety to the same extent as if each individual publication or patent application was specifically and individually indicated to be incorporated by reference. For example, U.S. patent application Ser. No. 13/615,078, filed Sep. 13, 2012 is incorporated by reference in its entirety, including all applications to which it claims priority. For example, U.S. patent application Ser. No. 13/614,523, filed Sep. 13, 2012 is incorporated by reference in its entirety, including all applications to which it claims priority.

BACKGROUND OF THE INVENTION

Field of the Invention

Embodiments of the present invention relate to devices, tools and methods for providing reinforcement of bones. More specifically, the present invention relates to devices, tools and methods for providing reconstruction and reinforcement of bones, including diseased, osteoporotic and/or fractured bones.

Description of the Related Art

The number and diversity of sports and work related fractures are being driven by several sociological factors. The diversity of high energy sports has increased and the participation in these sports has followed the general trend of affluence and the resultant amount of time for leisure. High energy sports include skiing, motorcycle riding, snow mobile riding, snowboarding, mountain biking, road biking, kayaking, and all terrain vehicle (ATV) riding. As the general affluence of the economically developed countries has increased the number (or amount) and age of people participating in these activities has increased. Lastly, the acceptance and ubiquitous application of passive restraint systems, airbags, in automobiles has created greater numbers of non-life threatening fractures. In the past, a person that might expire from a serious automobile accident now survives with multiple traumas and resultant fractures.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM (Nail), www.disc-o-tech.com. Placement of conventional IM rods are typically a "line of sight" and require access collinear with the center line of the IM canal. Invariably, this line of sight access violates, disrupts, and causes damage to important soft tissue structures such as ligaments, tendons, cartilage, fascia, and epidermis. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micro-motion between the bone and the IM nail may cause pain or necrosis of the bone. In still other cases, infection can occur. The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

In view of the foregoing, it would be desirable to have a device, system and method for providing effective and minimally invasive bone reinforcement and fracture fixation to treat fractured or diseased bones, while improving the ease of insertion, eliminating cross-screw incisions and minimizing trauma.

SUMMARY

As used herein, the term "aspect" may be used interchangeably with the term "embodiment." Aspects of the invention relate to embodiments of a bone fixation device and to methods for using such a device for repairing a bone fracture. The bone fixation device may include an elongate body with a longitudinal axis, and/or having a flexible state and a rigid state. The device further may include a plurality of grippers disposed at longitudinally-spaced locations along the elongate body, a rigid hub connected to the elongate body, and an actuator that is operably-connected to the grippers to deploy the grippers from a first shape to an expanded second shape. In various embodiments, the elongate body and the rigid hub may or may not be collinear or parallel.

In one embodiment, a bone fixation device is provided with an elongate body; an oblong aperture in the elongate body configured to accept a screw; an bone engaging mechanism disposed within the elongate body; an actuator operably connected to the bone engaging mechanism to actuate the bone engaging mechanism from a disengaged configuration to an engaged configuration, wherein the actuator comprises a ramped surface that is slideably coupled to an interior surface of the bone engaging mechanism, wherein proximally moving the ramped surface of the actuator causes the ramped surface to slideably engage the interior surface of the bone engaging mechanism at an angle thereby pivoting the bone engaging mechanism away from the elongate body to deploy the bone engaging mechanism into the engaged configuration; and wherein the screw is configured to be pushed from a first position within the oblong aperture to a second position within the oblong aperture to reduce a fracture.

A screw driver configured to engage with a corresponding hex socket, the screw driver is provided with a shaft having a proximal end and a distal end; the distal end having a hex tip comprising at least six flats and a slot bisecting at least two of the six flats; and wherein the hex tip is deformed outward to create an interference with the corresponding hex socket.

Methods of repairing a bone fracture are also disclosed. One such method comprises providing an elongate fixation device having a proximal end, a distal end, an oblong aperture, and a radially expandable gripper; extending the radially expandable gripper away from the elongate fixation device by moving a ramped surface of an actuator head toward the proximal end thereby engaging the radially expandable gripper with a surface of an intramedullary canal of a first bone segment; inserting a first screw into a second bone segment and through the oblong aperture; and translating the first screw to reduce a distance between the first bone segment and the second bone segment.

A system for installing a screw is provided including a bone fixation device having an elongate body; an oblong aperture in the elongate body configured to accept the screw, a bone engaging mechanism, and an actuator operably coupled to the bone engaging mechanism to actuate the bone engaging mechanism from a disengaged configuration to an engaged configuration; and a combination tool operably connected to the elongate body, wherein the combination tool comprises at least one bore configured to align with the oblong aperture in the elongate body.

Methods of repairing a bone fracture between a first bone segment and a second bone segment of a bone are also disclosed. One such method comprises providing an elongate body having an oblong aperture and a bone engaging mechanism; coupling the elongate body with a combination tool having a first bore configured to accept a K-wire; extending the elongate body into a canal of the bone of the first bone segment; extending the K-wire through the first bore and into the second bone segment; and manipulating the combination tool to reposition the first bone segment relative to the second bone segment. One such method comprises extending a first K-wire into the first bone segment and a second K-wire into the second bone segment; coupling the first K-wire and the second K-wire to a distractor; manipulating the distractor to reposition the first bone segment relative to the second bone segment; reaming a canal in the first bone segment and the second bone segment; coupling an elongate body having an oblong aperture with a combination tool; and inserting the elongate body into the canal.

A reamer configured to be used with bone is provided with a shaft having a proximal end and a distal end; the distal end having at least one spiral cutting edge having a first diameter; the proximal end having a handle; and wherein a portion of the shaft has a diameter less than the first diameter.

A method of using a bone fixation device is provided including the steps of providing an elongate body having a bone engaging mechanism; extending the elongate body into a canal of a bone; and actuating the bone engaging mechanism from a disengaged configuration to an engaged configuration, wherein in the engaged configuration, the bone engaging mechanism pivots away from the elongate body to deploy the bone engaging mechanism against the wall of the canal.

In some embodiments, a method of inserting a device is provided. The method can include the step of inserting a device within the intramedullary canal of a fibula, the device comprising one or more apertures. The method can include the step of inserting a first fastener through the device in a lateral-medial direction. The method can include the step of inserting a second fastener through the device, the second screw angled from the first screw by angle alpha. The method can include the step of inserting a third fastener through the device, the third screw angled from the first screw by angle beta, wherein the third screw extends into the tibia. The method can include the step of actuating a mechanism of the device to grip the intramedullary canal of a fibula.

In some embodiments, angle alpha is between 45-75 degrees. In some embodiments, angle beta is between 10-40 degrees. The method can include the step of translating the first fastener within an aperture of the device toward the mechanism. The method can include the step of rotating the first fastener, wherein the rotation of the first fastener causes translation of the first fastener within an aperture of the device toward the mechanism. In some embodiments, actuating the mechanism comprises deflecting three members towards the intramedullary canal. In some embodiments, the first fastener and the second fastener are contained within the fibula. In some embodiments, the third fastener is a screw. The method can include the step of passing at least one of the first fastener, the second fastener, and the third fastener through an aperture in a tool aligned with an aperture in the device. The method can include the step of inserting K-wires within bones portion near a fracture and rotating the bone portions using the K-wires. In some embodiments, rotating the bone portions further comprises rotating a knob of a distractor.

In some embodiments, a device is provided. The device can include an elongate body comprising at least a first aperture, a second aperture and a third aperture. In some embodiments, the elongate body sized to be inserted within the fibula. The device can include a first fastener configured to be inserted through the first aperture in a lateral-medial direction. The device can include a second fastener configured to be inserted through the second aperture. In some embodiments, the second aperture angled from the first aperture by angle alpha. The device can include a third fastener configured to be inserted through the third aperture. In some embodiments, the third aperture angled from the first screw by angle beta. In some embodiments, the third fastener has a longer length than the first fastener and the second fastener. The device can include an actuator configured to actuate a portion of the device to grip the intramedullary canal of a fibula.

In some embodiments, angle alpha is 60 degrees. In some embodiments, angle beta is 25 degrees. In some embodiments, the first aperture is oblong, wherein the first fastener is configured to translate within the first aperture toward the actuator. In some embodiments, the portion comprises three members configured to deflect towards the intramedullary canal. In some embodiments, the first fastener and the second fastener are sized to be contained within the fibula. In some embodiments, the third fastener is sized to extend into the tibia. In some embodiments, the third fastener is a screw. The device can include a tool comprising at least a fourth aperture aligned with the first aperture, a fifth aperture aligned with the second aperture and a sixth aperture aligned with the third aperture.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15 is a cross-sectional view of the distal end of the device shown in FIG. 12 shown in a deployed state.

FIG. 26 is cross-sectional view of the proximal end of the system shown in FIG. 22 shown in a deployed state after translation of the screw.

FIG. 27 is cross-sectional view of the proximal end of the system shown in FIG. 22 shown in a deployed state after insertion of a cap.

FIG. 28A is a perspective view of the device shown in FIG. 16A during insertion of the screw.

FIG. 30 is a perspective view of the distal end of the screw driver of FIG. 29.

FIGS. 31A-31I are various views of entry points of the tibia to implant the device of FIGS. 1-30.

FIGS. 32A-32J are various method steps to implant the device of FIGS. 1-30.

FIGS. 33A-33G are various steps of methods to implant the device of FIGS. 1-30.

FIGS. 34A-34D are various steps of methods to implant the device of FIGS. 1-30.

FIGS. 38A-38D are schematic views of the device shown in FIG. 35A.

FIG. 40 is a perspective view of the device shown in FIG. 35A during insertion of a compression screw.

DETAILED DESCRIPTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

Figure 1:
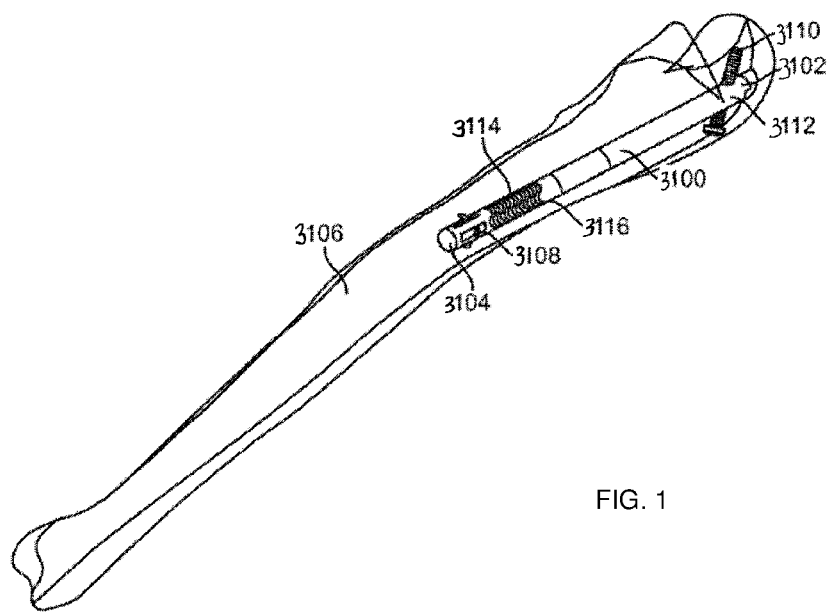
FIG. 1 is a perspective view of an embodiment of a bone fixation device implanted in a bone.
Figure 2:
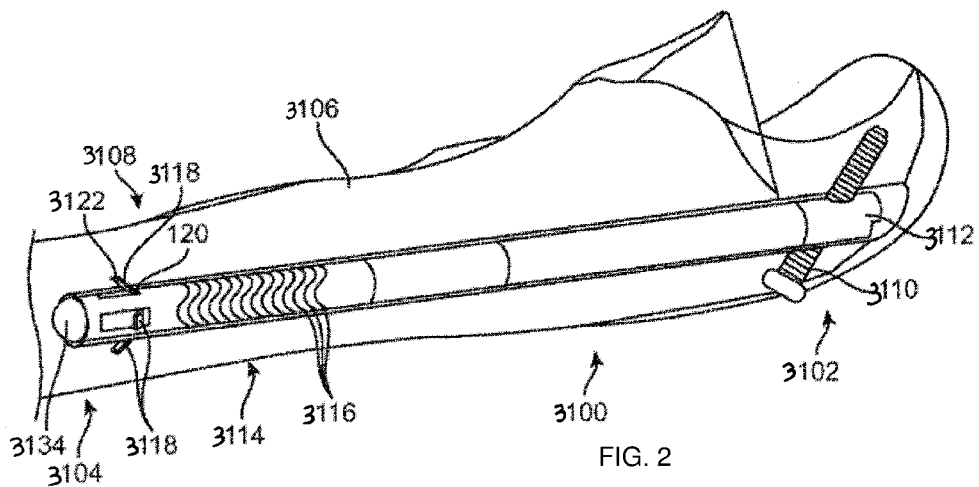
FIG. 2 is another perspective view of the implanted device of FIG. 1.

FIGS. 1 and 2 are perspective views of an embodiment of a bone fixation device 3100 having a proximal end 3102 (nearest the surgeon) and a distal end 3104 (further from surgeon) and positioned within the bone space of a patient according to the invention. In this example, device 3100 is shown implanted in the upper (or proximal) end of an ulna 3106. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 3100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 3100 may be implanted or attached through the skin so that a pulling force (traction may be applied to the skeletal system).

Figure 3:
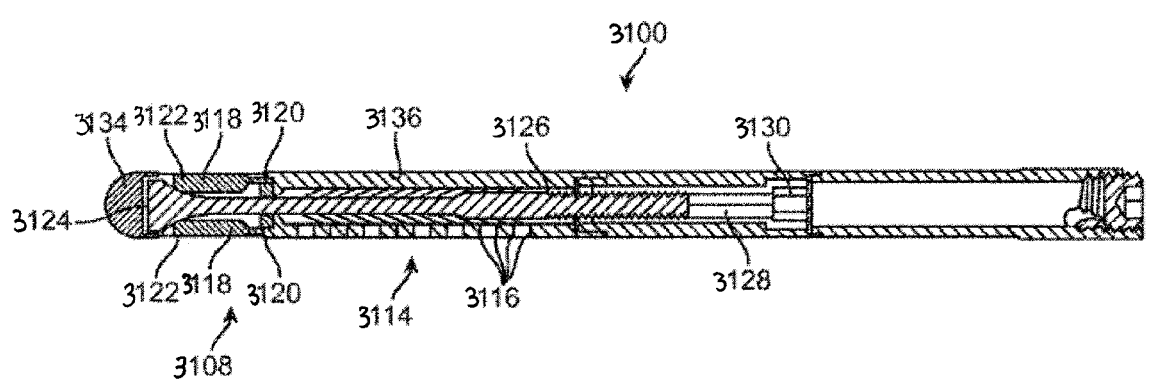
FIG. 3 is a longitudinal cross-section view of the bone fixation device of FIG. 1 in a non-deployed state.

In the embodiment shown in FIG. 1, the design of the metaphyseal fixation device 3100 depicted is adapted to provide a bone engaging mechanism or gripper 3108 adapted to engage target bone of a patient from the inside of the bone. As configured for this anatomical application, the device is designed to facilitate bone healing when placed in the intramedullary space within a post fractured bone. This device 3100 has a gripper 3108 positioned distally and shown deployed radially outward against the wall of the intramedullary cavity. On entry into the cavity, gripper 3108 is flat and retracted (FIG. 3). Upon deployment, gripper 3108 pivots radially outward and grips the diaphyseal bone from the inside of the bone. One or more screws 3110 placed through apertures through the hub 3112 lock the device 3100 to the metaphyseal bone. Hence, the metaphysis and the diaphysis are joined. A flexible-to-rigid body portion 3114 may also be provided, and in this embodiment is positioned between gripper 3108 and hub 3112. It may be provided with wavy spiral cuts 3116 for that purpose, as will be described in more detail below.

FIG. 3 shows a longitudinal cross-section of device 3100 in a non-deployed configuration. In this embodiment, gripper 3108 includes two pairs of opposing bendable gripping members 3118. Two of the bendable gripping members 3118 are shown in FIG. 3, while the other two (not shown in FIG. 3) are located at the same axial location but offset by 90 degrees. Each bendable gripping member 3118 has a thinned portion 3120 that permits bending as the opposite distal end 3122 of member 3118 is urged radially outward, such that member 3118 pivots about thinned portion 3120. When extended, distal ends 3122 of bendable members 3118 contact the inside of the bone to anchor the distal portion of device 3100 to the bone. In alternative embodiments (not shown), the gripper may comprise 1, 2, 3, 4, 5, 6 or more bendable members similar to members 3118 shown.

During actuation, bendable members 3118 of gripper 3108 are urged radially outward by a ramped surface on actuator head 3124. Actuator head 3124 is formed on the distal end of actuator 3126. The proximal end of actuator 3126 is threaded to engage a threaded bore of drive member 3128. The proximal end of drive member 3128 is provided with a keyed socket 3130 for receiving the tip of a rotary driver tool 3132 (shown in FIG. 5) through the proximal bore of device 3100. As rotary driver tool 3132 turns drive member 3128, actuator 3126 is drawn in a proximal direction to outwardly actuate gripper members 3118.

A hemispherical tip cover 3134 may be provided at the distal end of the device as shown to act as a blunt obturator. This arrangement facilitates penetration of bone (e.g. an intramedullary space) by device 3100 while keeping the tip of device 3100 from digging into bone during insertion.

As previously mentioned, device 3100 may include one or more flexible-to-rigid body portions 3114. This feature is flexible upon entry into bone and rigid upon application of compressive axial force provided by tensioning actuator 3126. Various embodiments of a flexible-to-rigid portion may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures.

The design of the flexible-to-rigid tubular body portion 3114 allows a single-piece design to maximize the transformation of the same body from a very flexible member that minimizes strength in bending to a rigid body that maximizes strength in bending and torsion. The flexible member transforms to a rigid member when compressive forces are applied in the axial direction at each end, such as by an actuator similar to 3126. The body portion 3114 is made, for example, by a near-helical cut 3116 on a tubular member at an angle of incidence to the axis somewhere between 0 and 180 degrees from the longitudinal axis of the tubular body portion 3114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap or interdigitate with the segment on either side of it, thus increasing the bending strength when the body is in compression. Additionally, the cuts can be altered in depth and distance between the cuts on the longitudinal axis along the length of body portion 3114 to variably alter the flexible-to-rigid characteristics of the tubular body along its length.

The cuts 3116 in body portion 3114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, wound flexible cable, or actuator 3126 as shown will transform the body from flexible to rigid and vice versa.

Figure 9:
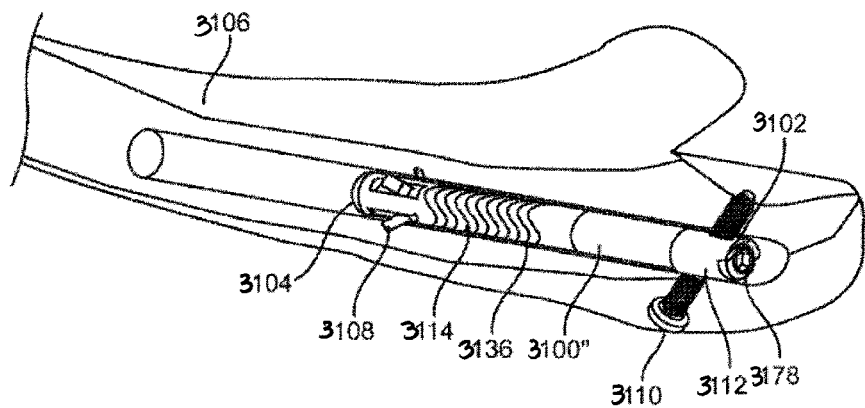
FIG. 9 is a perspective view of another alternative embodiment of the implanted device of FIG. 1.

In operation, as actuator 3126 is tightened, gripper members 3118 are extended radially outwardly. Once the distal ends of gripper members 3118 contact bone and stop moving outward, continued rotation of actuator 3126 draws the proximal end 3102 and the distal end 3104 of device 3100 closer together until cuts 3116 are substantially closed. In one embodiment, as this happens, body portion 3114 changes from being flexible to rigid to better secure the bone fracture. Rotating drive member 3128 in the opposite direction causes body portion 3114 to change from a rigid to a flexible state, such as for removing device 3100 if needed in the initial procedure or during a subsequent procedure after the bone fracture(s) have partially or completely healed. Body portion 3114 may be provided with a solid longitudinal portion 3136 (as seen in FIGS. 3 and 9) such that cuts 3116 are a series of individual cuts each traversing less than 360 degrees in circumference, rather than a single, continuous helical cut. This solid portion 3136 can aid in removal of device 3100 by keeping body portion 3114 from extending axially like a spring.

Figure 4:
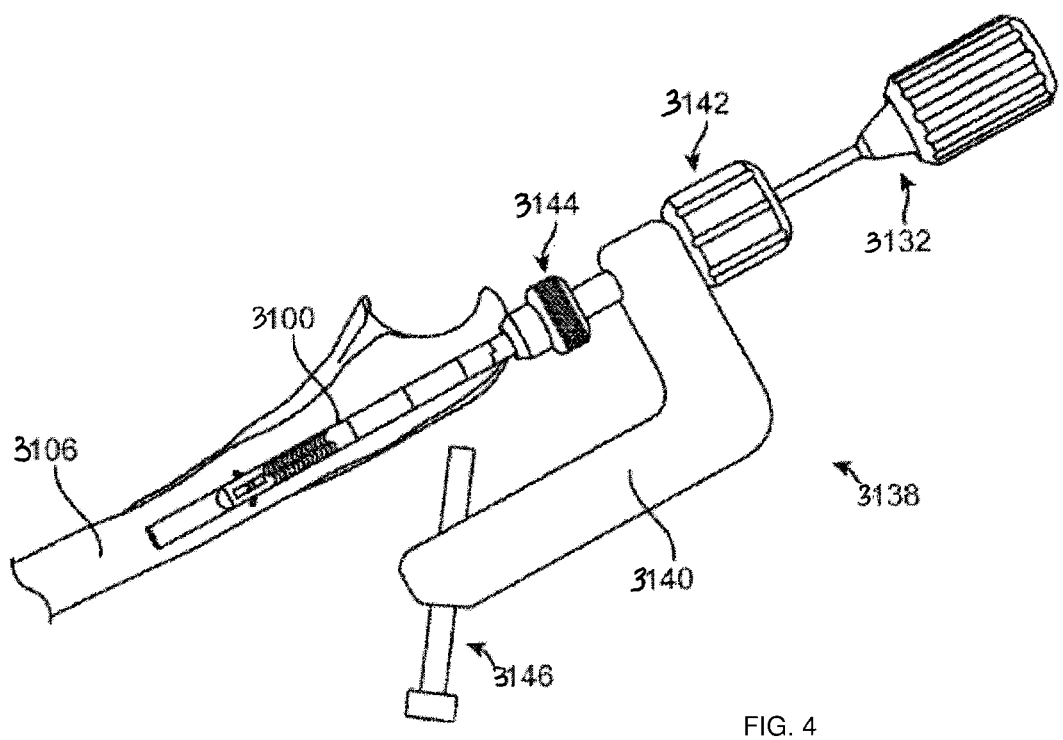
FIG. 4 is a plan view of a combination deployment tool that may be used with the bone fixation device of FIG. 1.

FIG. 4 illustrates a combination tool 3138 useful for inserting device 3100, actuating gripper 3108, compressing flexible-to-rigid body portion 3114, approximating the fracture in bone 3106, aligning anchor screw(s) 3110, and removing device 3100, if desired. In this exemplary embodiment, tool 3138 includes an L-shaped body 3140 that mounts the other components of the tool and also serves as a handle. The main components of tool 3138 are a device attachment portion 3142, a rotary driver 3132, an approximating driver 3144, and a screw alignment portion 3146.

Figure 5:
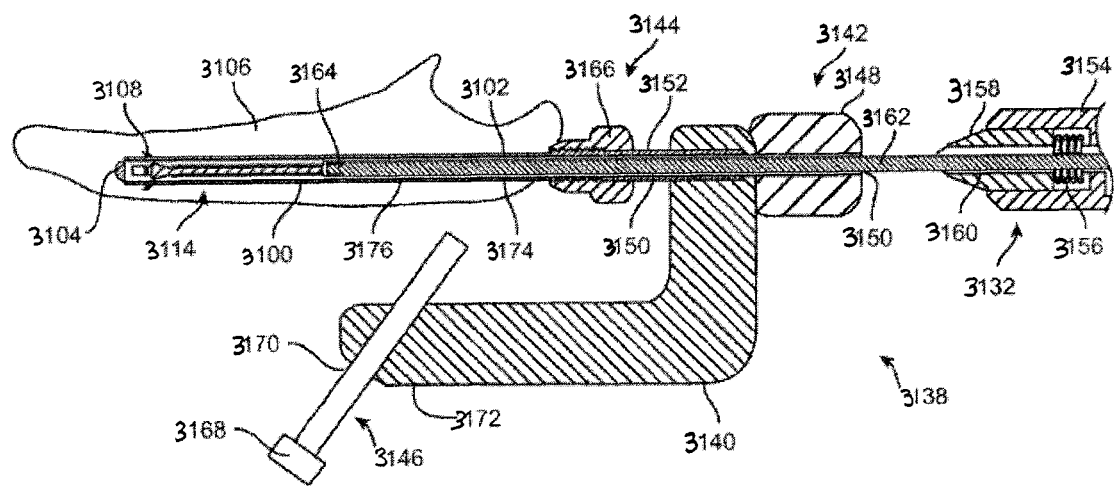
FIG. 5 is a cross-section view of the tool and device shown in FIG. 4.

FIG. 5 shows a cross-section of the tool 3138 and device 3100 illustrated in FIG. 4. As shown, device attachment portion 3142 includes a knob 3148 rigidly coupled to a tube 3150 which is rotatably mounted within sleeve 3152. Sleeve 3152 in turn is fixedly mounted to tool body 3140. The distal end of tube 3150 is provided with external threads for engaging the internal threads on the proximal end of device 3100. As seen in FIG. 4, both the distal end of sleeve 3152 and the proximal end of device 3100 may be provided with semicircular steps that inter-engage to prevent device 3100 from rotating with respect to sleeve 3152. With this arrangement, device 3100 can be prevented from rotating when it is secured to tool 3138 by tube 3150 of device attachment portion 3142. The mating semicircular steps also serve to position device 3100 in a particular axial and angular orientation with respect to tool 3138 for aligning screws with screw holes, as will be later described.

Rotary driver 3132 may be used to actuate gripper 3108 and compress flexible-to-rigid body portion 3114 after device 3100 is inserted into bone 3106. Driver 3132 may also be used to allow body portion 3114 to decompress and gripper 3108 to retract if removal of device 3100 from bone 3106 is desired. In the embodiment shown, driver 3132 includes knob 3154, torsion spring 3156, hub 3158, bushing 3160 and shaft 3162. The distal end of shaft 3162 is provided with a mating tip 3164, such as one having a hex-key shape, for engaging with keyed socket 3130 of device 3100 (seen in FIG. 3), such that turning driver shaft 3162 turns drive member 3128 and axially actuates actuator 3126, as described above.

The proximal end of shaft 3162 may be fitted with a bushing 3160, such as with a press-fit. Hub 3158 may be secured over bushing 3160, such as with a pin through bushing 3160 and shaft 3162. In this embodiment, knob 3154 is rotatably mounted over hub 3158 and bushing 3160 such that knob 3154 can rotate independently from shaft 3162. A torsion spring 3156 may be used to couple knob 3154 to hub 3158 as shown to create a torque limiting and/or torque measuring driver. With this indirect coupling arrangement, as knob 3154 is rotated about shaft 3162, spring 3156 urges hub 3158 and shaft 3162 to rotate in the same direction. Rotational resistance applied by device 3100 to shaft tip 3164 will increase in this embodiment as gripper 3108 engages bone 3106, and flexible-to-rigid body portion 3114 compresses. As more torque is applied to knob 3154, it will advance rotationally with respect to hub 3158 as torsion spring 3156 undergoes more stress. Markings may be provided on knob 3154 and hub 3158 to indicate the torque being applied. In this manner, a surgeon can use driver 3132 to apply torque to device 3100 in a predetermined range. This can help ensure that gripper 3108 is adequately set in bone 3106, body portion 3114 is sufficiently compressed, and excessive torque is not being applied that might damage device 3100, bone 3106 or cause slippage therebetween. A slip clutch or other mechanism may be provided to allow the applied torque to be limited or indicated. For example, driver 3132 may be configured to "click" into or out of a detent position when a desired torque is reached, thus allowing the surgeon to apply a desired torque without needing to observe any indicia on the driver. In alternative embodiments, the driver knob may be selectably or permanently coupled to shaft 3162 directly.

After device 3100 is inserted in bone 3106 and deployed with tool 3138 as described above, the approximating driver portion 3144 of tool 3138 may be used to compress one or more fractures in bone 3106. Approximating driver 3144 includes knob 3166 located on sleeve 3152. Knob 3166 may be knurled on an outer circumference, and have threads on at least a portion of its axial bore. The internal threads of knob 3166 engage with mating external threads on sleeve 3152 such that when knob 3166 is rotated it advances axially with respect to sleeve 3152. When device 3100 is anchored in bone 3106, sleeve 3152 is prevented from moving away from the bone. Accordingly, as knob 3166 is advanced axially toward bone 3106, it serves to approximate bone fractures located between gripper 3108 and knob 3166. Suitable thread pitch and knob circumference may be selected to allow a surgeon to supply a desired approximating force to bone 3106 by using a reasonable rotation force on knob 3166. In alternative embodiments (not shown), a torque indicating and/or torque limiting mechanism as described above may be incorporated into approximating driver 3144.

As previously indicated, tool 3138 may also include a screw alignment portion 3146. In the embodiment depicted in the figures, alignment portion 3146 includes a removable alignment tube 3168 and two bores 3170 and 3172 through tool body 3140. In alternative embodiments (not shown), a single bore or more than two bores may be used, with or without the use of separate alignment tube(s).

In operation, alignment tube 3168 is first received in bore 3170 as shown. In this position, tube 3168 is in axial alignment with angled hole 3174 at the distal end 3102 of device 3100. As described above, the mating semicircular steps of device 3100 and sleeve 3152 position angled hole 3174 in its desired orientation. With this arrangement, a drill bit, screw driver, screw and/or other fastening device or tool may be inserted through the bore of tube 3168 such that the device(s) are properly aligned with hole 3174. The outward end of alignment tube 3168 may also serve as a depth guide to stop a drill bit, screw and/or other fastener from penetrating bone 3106 beyond a predetermined depth.

Alignment tube 3168 may be withdrawn from bore 3170 as shown, and inserted in bore 3172. In this position, tube 3168 aligns with hole 3176 of device 3100. As described above, a drill bit, screw driver, screw and/or other fastening device may be inserted through the bore of tube 3168 such that the device(s) are properly aligned with hole 3176.

Figure 6:
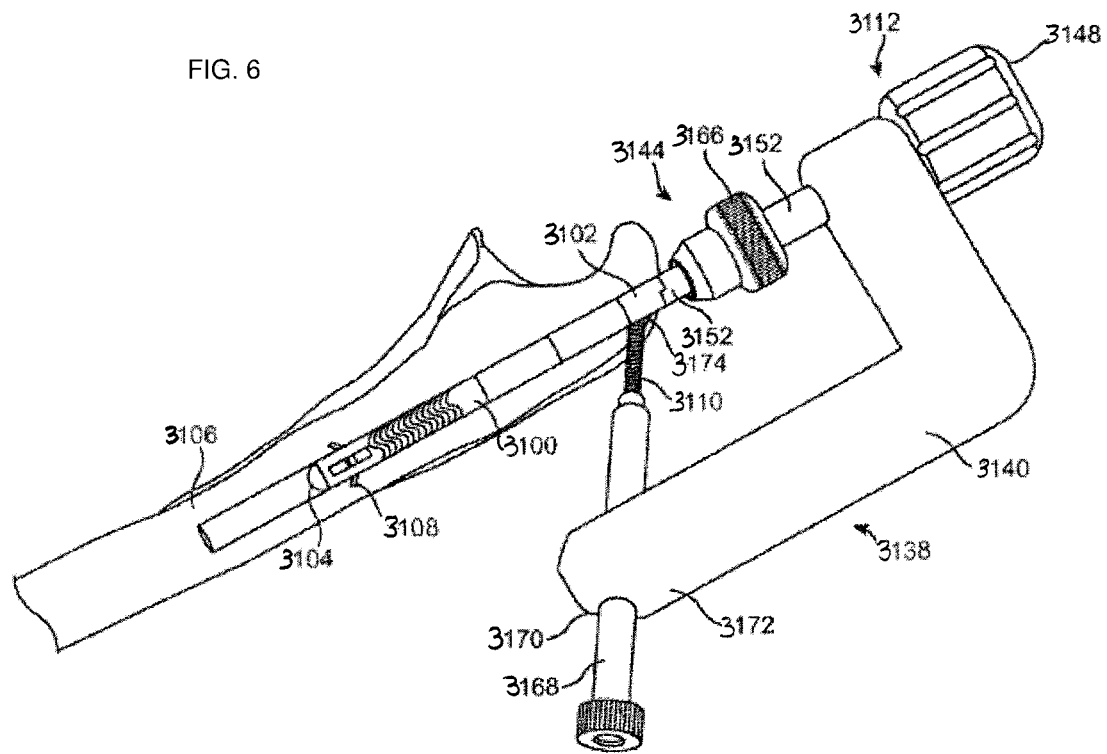
FIG. 6 is a perspective view of the tool and device shown in FIG. 4.

FIG. 6 shows alignment tube 3168 of tool 3138 aligning screw 3110 with angled hole 3174 at the distal end of device 3100, as described above.

Figure 7A:
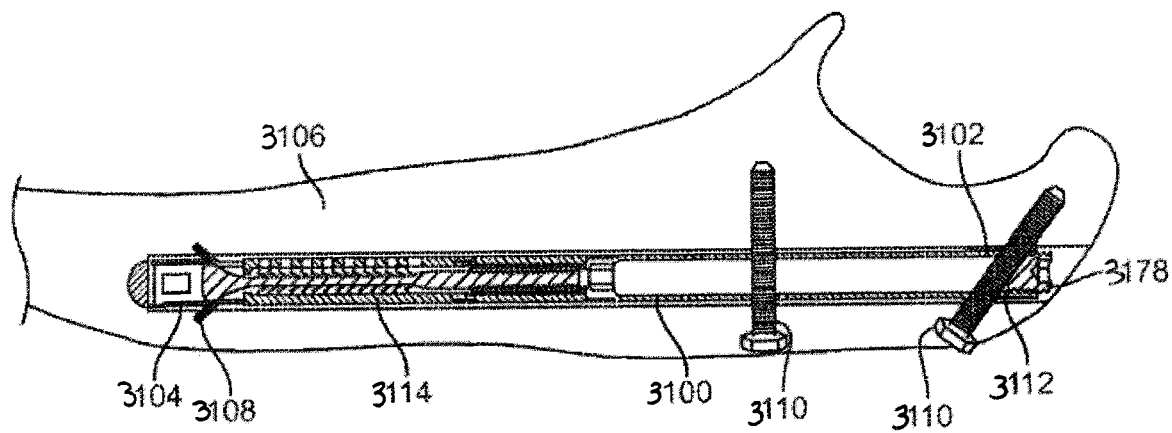
FIG. 7A is a cross-section view of the implanted device of FIG. 1.

FIG. 7A shows a first screw 3110 received through angled hole 3174 and a second screw 3110 received through hole 3176 in device 3100 and into bone 3106. Screws 3110 may be installed manually or with the aid of tool 3138 as described above. The heads of screws 3110 may be configured to be self-countersinking such that they remain substantially beneath the outer surface of the bone when installed, as shown, so as to not interfere with adjacent tissue. In this embodiment, the proximal end 3102 of device 3100 is secured to bone 3106 with two screws 3110, and the distal end 3104 is secured by gripper 3108. In this manner, any bone fractures located between the proximal screw 3110 and distal gripper 3108 may be approximated and rigidly held together by device 3100. In alternative embodiments (not shown), more than one gripper may be used, or only screws or other fasteners without grippers may be used to secure device 3100 within bone 3106. For example, the device shown in FIG. 1 could be configured with a second gripper located between screw 3110 and the middle of the device if the fracture is located more at the mid-shaft of the bone. Similarly, more than two screws or other fasteners may be used, or only grippers without fasteners may be used. In various embodiments, holes such as 3174 and 3176 as shown and described above can be preformed in the implantable device. In other embodiments, some or all of the holes can be drilled or otherwise formed in situ after the device is implanted in the bone.

Once device 3100 is secured within bone 3106, combination tool 3138 may be removed by turning knob 3148 to disengage threads of tube 3150 from threads within the proximal end 3102 of device 3100. An end plug 3178 may be threaded into the proximal end 3102 of device 3100 to preventing growth of tissue into implanted device 3100. Device 3100 may be left in bone 3106 permanently, or it may be removed by performing the above described steps in reverse. In particular, plug 3178 is removed, tool 3138 is attached, screws 3110 are removed, gripper 3108 is retracted, and device 3100 is pulled out using tool 3138.

Figure 7B:
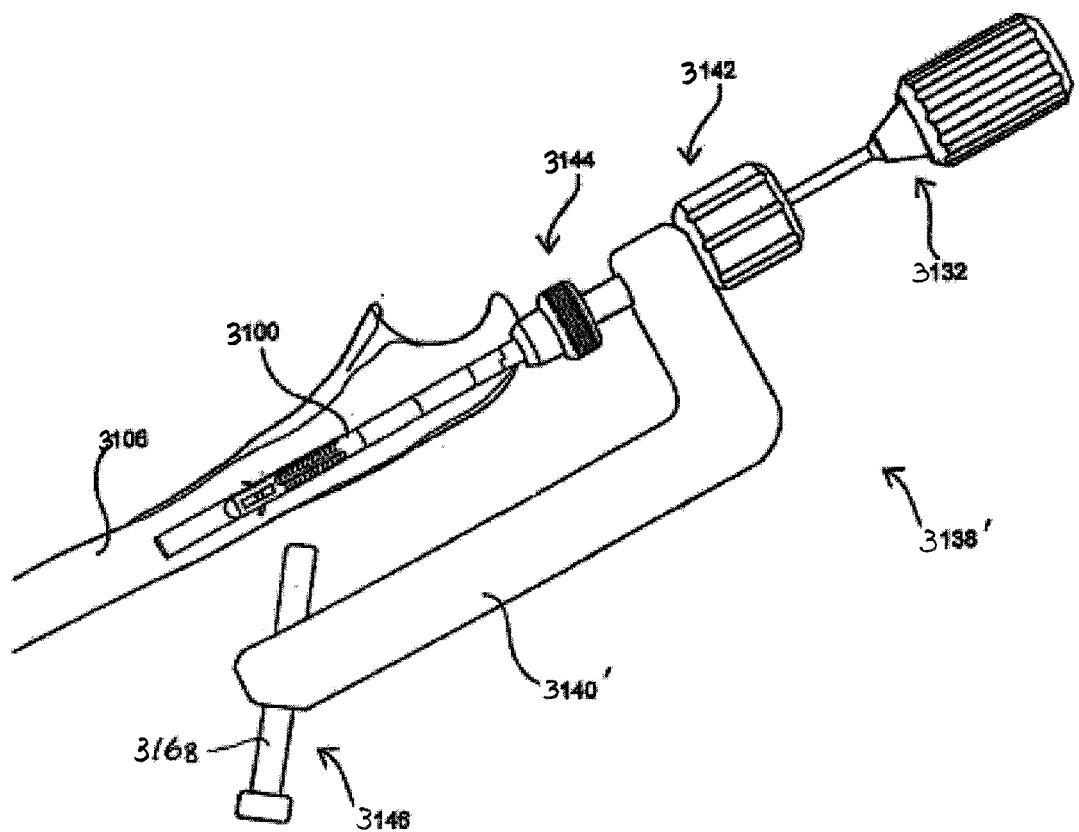
FIG. 7B is a plan view of an alternative combination deployment tool that may be used with the bone fixation device of FIG. 1.

FIG. 7B shows an alternative embodiment of a combination tool 3138' useful for inserting device 3100, actuating gripper 3108, compressing flexible-to-rigid body portion 3114, approximating the fracture in bone 3106, aligning anchor screw(s) 3110, and removing device 3100, if desired. Like tool 3138 described above, exemplary tool 3138' includes an L-shaped body 3140' that mounts the other components of the tool and also serves as a handle. The main components of tool 3138' are a device attachment portion 3142, a rotary driver 3132, an approximating driver 3144, and a screw alignment portion 3146. These components are constructed and function in a similar fashion to the components of tool 3138 described above. Tool 3138' is constructed to allow one or more screw holes to be formed in vivo, and/or allow screw(s) to be aligned with such screw holes or preformed screw holes, through flexible-to-rigid body portion 3114 of device 3100. Tool 3138' may be configured to allow the screw hole(s) may be formed at an angle through body portion 3114, and/or formed perpendicularly to the longitudinal axis of device 3100. Tool 3138' may also include the capability to form screw holes or align screws for insertion in the proximal hub portion of device 3100 as described above.

Tool 3138' may be used to form screw hole(s) in flexible-to-rigid body portion 3114 by guiding a drill bit with alignment tube 3168. Screw hole(s) may also be formed directly in body portion 3114 without pre-forming or drilling holes in vivo, but by placing a screw directly into body portion 3114, such as with a self-tapping screw guided with alignment tube 3168.

Internal components within device 3100, such as actuator 3126, may be configured such that screw(s) pass though it or pass around it. For example, in some embodiments the actuator comprises one or more cables, leaving enough room within body portion 3114 so that a screw can avoid the actuator(s), or move it/them out of the way when passing into or through body portion 3114. In some embodiments, the one or more actuators are large enough to allow one or more screws to pass through it/them without impeding the operation of the actuator(s). In some embodiments, the screw(s) only enter one wall of tubular body portion 3114 without entering the interior space of the body portion.

Figure 8:
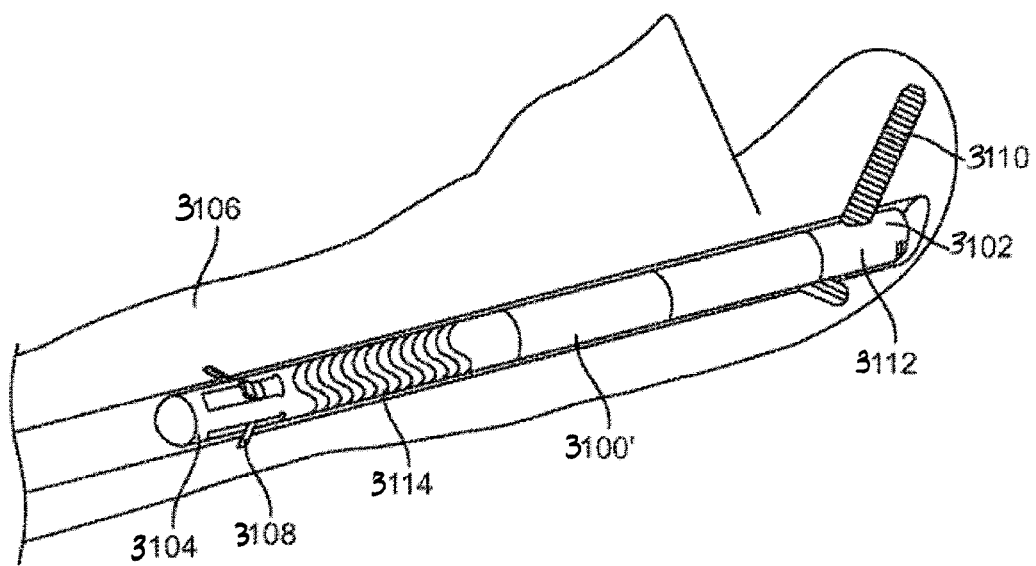
FIG. 8 is a perspective view of an alternative embodiment of the implanted device of FIG. 1.

FIGS. 8 and 9 show alternative embodiments similar to device 3100 described above. Device 3100' shown in FIG. 8 is essentially identical to device 3100 described above but is shorter in length and utilizes a single anchor screw 3110 at its proximal end 3102. Device 3100" shown in FIG. 9 is similar to device 3100', but is shorter still. In various embodiments, the devices may be configured to have a nominal diameter of 3 mm, 4 mm, 5 mm or 6 mm. It is envisioned that all three device designs 3100, 3100' and 3100" may each be provided in all three diameters such that the chosen device is suited for the particular fracture(s) and anatomy in which it is implanted.

Figure 10A:
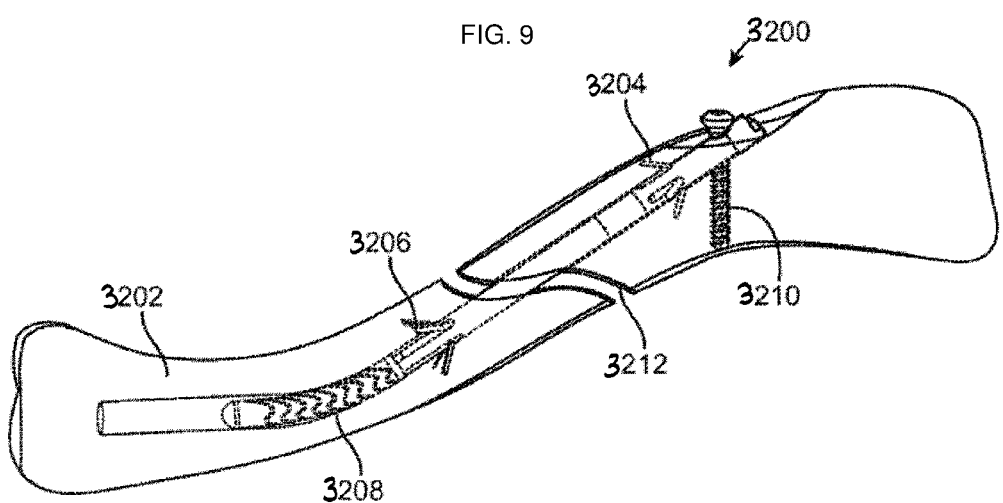
FIG. 10A is a perspective view of another embodiment of a bone fixation device shown deployed in a fractured clavicle.

FIGS. 10A-10I show another embodiment of a bone fixation device constructed according to aspects of the invention. FIG. 10A is a perspective view showing the exemplary device 3200 deployed in a fractured clavicle 3202. Device 3200 is similar to device 3100 described above and shown in FIGS. 1-7A, but has a gripper 3204 located near its proximal end, another gripper 3206 located at a more distal location, and a flexible-to-rigid body portion 3208 located near the distal end of the device. A bone screw 3210 and gripper 3204 are configured to secure device 3200 inside bone 3202 on the proximal side of fracture 3212, while gripper 3206 and flexible-to-rigid body portion 3208 are configured to secure device 3200 on the distal side of fracture 3212. In other respects, construction and operation of device 3200 is much like that of device 3100 described above.

Figure 10B:
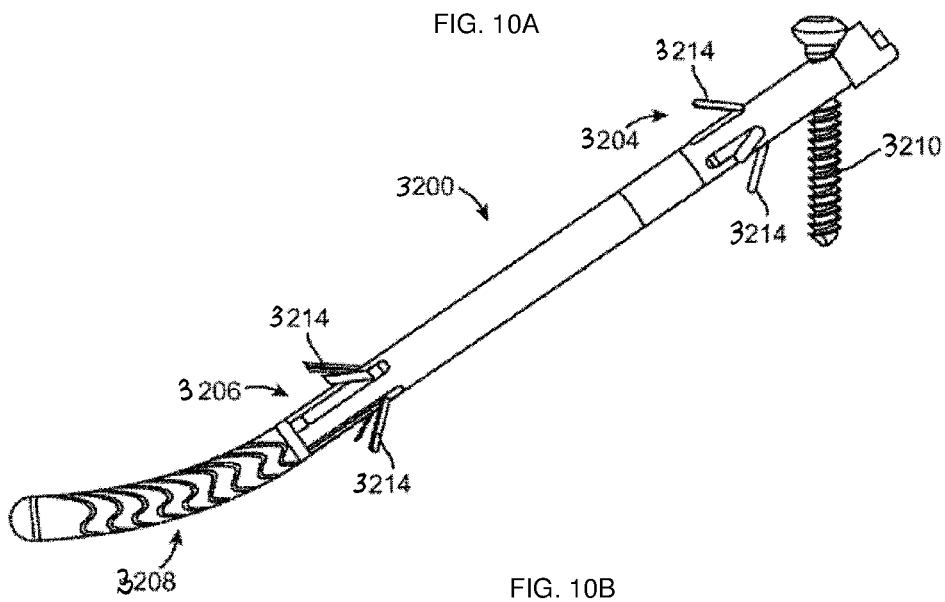
FIG. 10B is perspective view of the device shown in FIG. 10A shown in a deployed state.
Figure 10C:
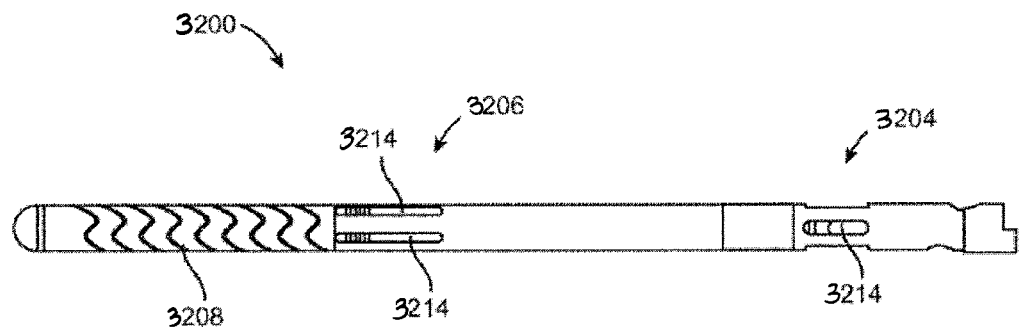
FIG. 10C is a side elevation view of the device shown in FIG. 10A shown in a retracted or undeployed state.
Figure 10D:
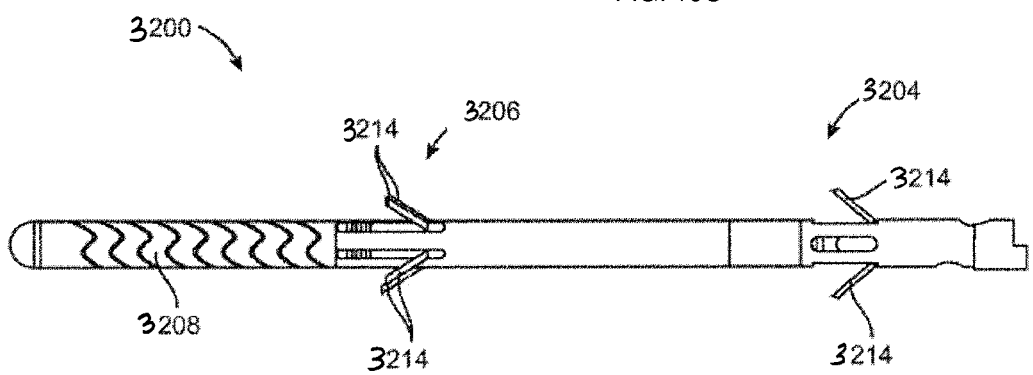
FIG. 10D is a side elevation view of the device shown in FIG. 10A shown in a deployed state.
Figure 10E:
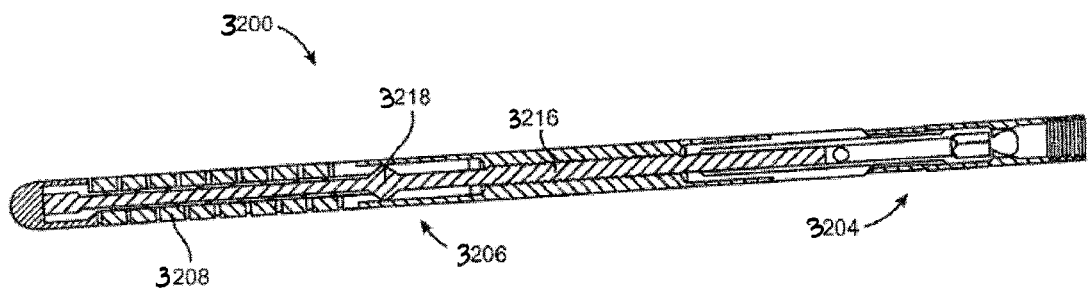
FIG. 10E is a cross-sectional view of the device shown in FIG. 10A shown in a retracted or undeployed state.
Figure 10F:
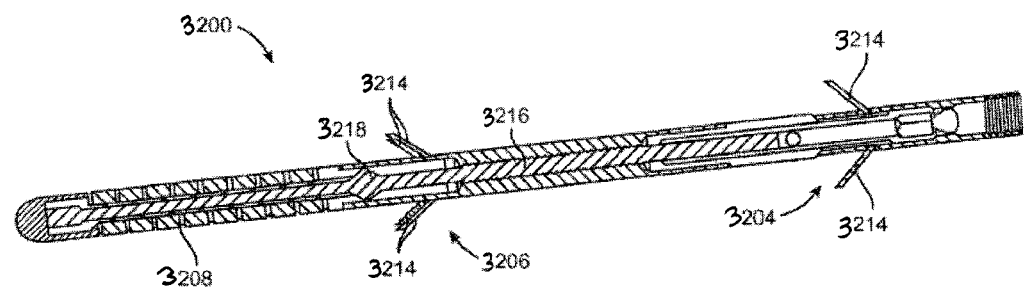
FIG. 10F is a cross-sectional view of the device shown in FIG. 10A shown in a deployed state.

In this exemplary embodiment, each of the two grippers 3204 and 3206 has four outwardly expanding arms 3214. These arms are spaced at 90 degree intervals around the circumference of the device body. The arms 3214 of gripper 3204 may be offset by 45 degrees from arms 3214 of gripper 3206 as shown in the figures to distribute the forces applied by grippers 3204 and 3206 on the bone 3202. As shown in FIGS. 10E and 10F, a single actuator 3216 may be used to deploy both grippers 3204 and 3206. Actuator 3216 may also be used to axially compress flexible-to-rigid body portion 3208 to make it substantially rigid. At least a portion of actuator 3216 may be flexible to allow flexible-to-rigid body portion 3208 to assume a curved shape, as seen in FIGS. 10A and 10B. Alternatively, it may be desirable in some embodiments to have flexible-to-rigid body portion 3208 maintain a straight or a curved configuration regardless of whether it is in a flexible or rigid state. In these embodiments, the actuator may be rigid and faulted with the desired straight and/or curved shape to match the flexible-to-rigid body portion. In some embodiments, it may also be desirable to design at least a portion of the actuator with a high degree of axial elasticity to allow the actuator to continue to expand some gripper(s) and/or compress some flexible-to-rigid body portion(s) after other gripper(s) and/or flexible-to-rigid body portion(s) have already been fully deployed.

Figure 10G:
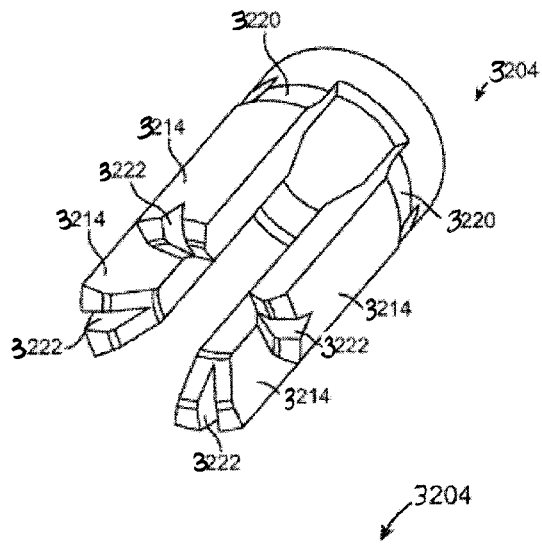
FIG. 10G is a perspective view of a gripper of the device shown in FIG. 10A shown in a retracted or undeployed state.
Figure 10H:
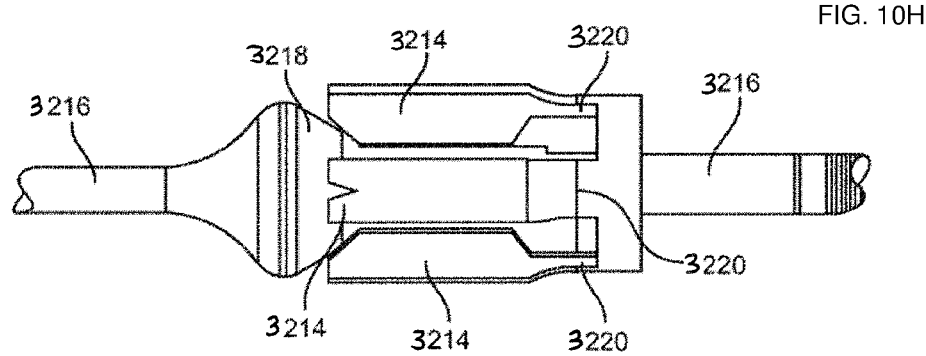
FIG. 10H is a side elevation view of a gripper and actuator of the device shown in FIG. 10A shown in a retracted or undeployed state.
Figure 10I:
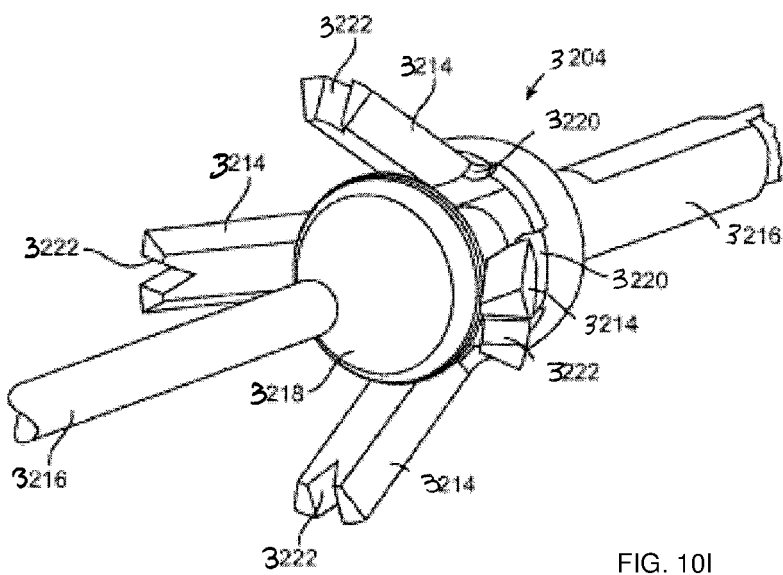
FIG. 10I is a perspective view of a gripper and actuator of the device shown in FIG. 10A shown in a deployed state.

Referring to FIGS. 10G-10I, further details of an exemplary gripper 3204 are shown. FIGS. 10G and 10H show gripper 3204 with bendable arms 3214 in a retracted state. As cam 3218 of actuator 3216 is driven axially into the distal ramped ends of arms 3214, arms 3214 bend at thinned portions 3220 to move radially outward toward the deployed position shown in FIG. 10I. Notches 3222 may be provided in the distal ends of arms 3214 as shown to allow arms 3214 to better grip interior bone surfaces. Without departing from the scope of the invention, one, two, three, or more bendable arms may be used.

Figure 11:
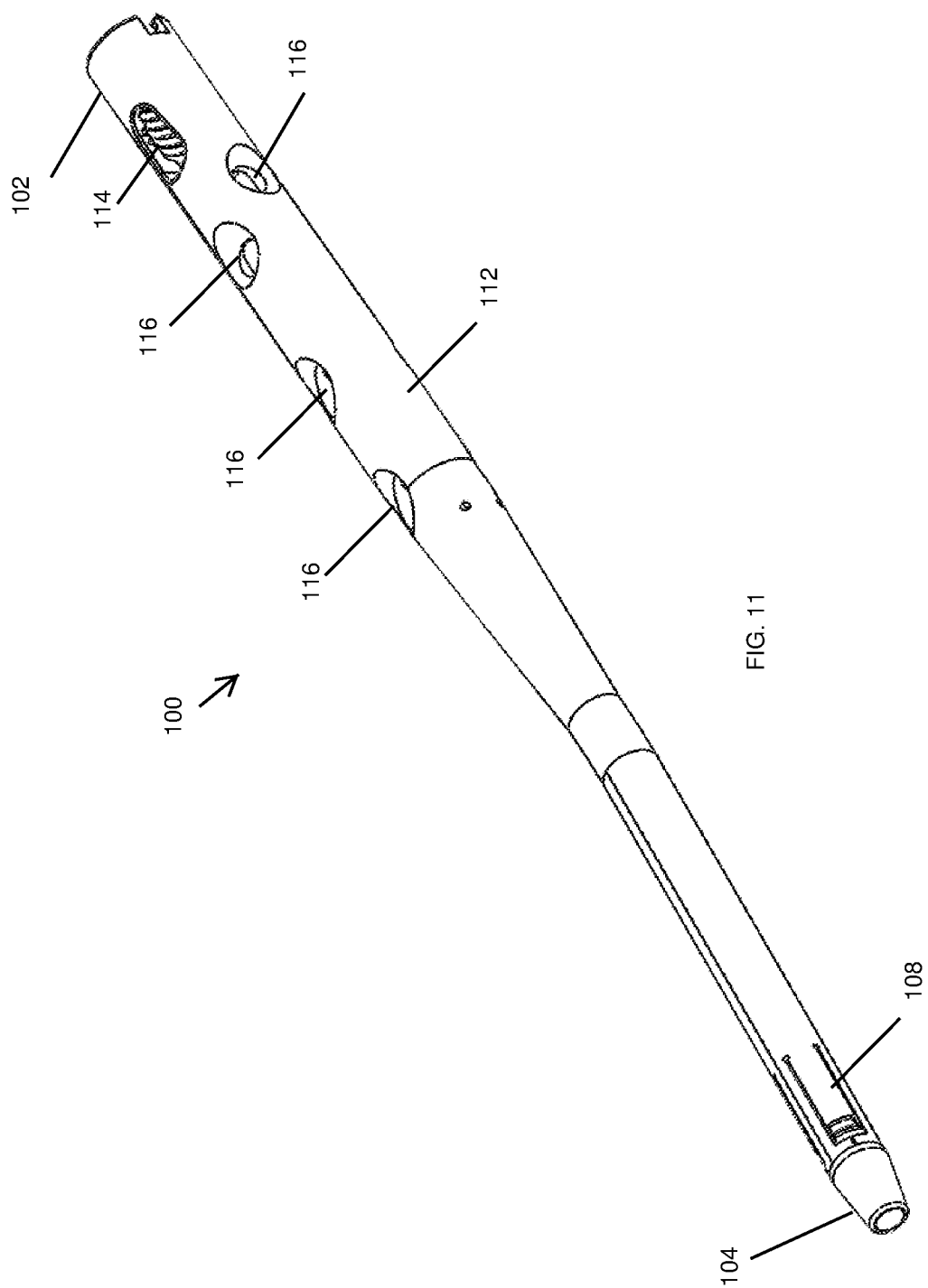
FIG. 11 is perspective view of another embodiment of a bone fixation device shown in a retracted or undeployed state.
Figure 12:
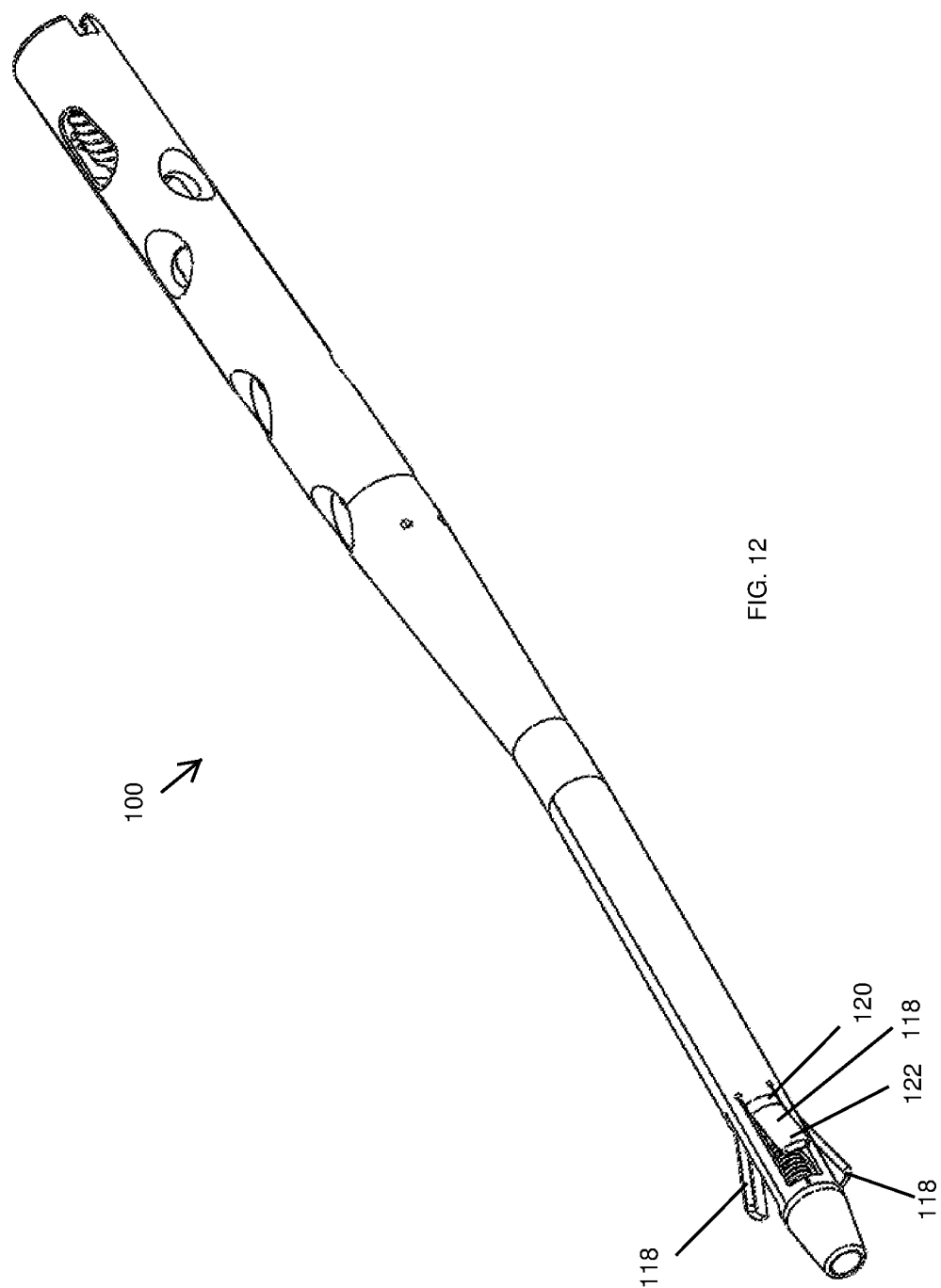
FIG. 12 is perspective view of the device shown in FIG. 11 shown in a deployed state.

FIGS. 11 and 12 are perspective views of an embodiment of a bone fixation device 100 having a proximal end 102 (nearest the surgeon) and a distal end 104 (further from surgeon) and positioned within the bone space of a patient according to the invention. In this example, device 100 is configured to be implanted in the fibula, but other configurations for other bony segments are contemplated. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 100 is used for fixation of fractures of the proximal or distal end of long bones such as intracapsular, intertrochanteric, intercervical, supracondular, or condular fractures of the fibula; for fusion of a joint; or for surgical procedures that involve cutting a bone. The devices 100 may be implanted or attached through the skin so that a pulling force (traction may be applied to the skeletal system).

In the embodiment shown in FIG. 11, the design of the fixation device 100 depicted is adapted to provide a bone engaging mechanism or gripper 108 adapted to engage target bone of a patient from the inside of the bone. As configured for this anatomical application, the device 100 is designed to facilitate bone healing when placed in the intramedullary space within a post fractured bone. This device 100 has a gripper 108 positioned distally and shown deployed radially outward against the wall of the intramedullary cavity. On entry into the cavity, gripper 108 is flat and retracted (FIG. 11). Upon deployment, gripper 108 pivots radially outward and grips the diaphyseal bone from the inside of the bone. The device 100 can include a hub 112 comprising one or more aperture 114, 116. One or more screws 110 placed through apertures 114, 116 through the hub 112 lock the device 100 to the bone, as described below. Hence, the metaphysis and the diaphysis are joined.

Figure 13:
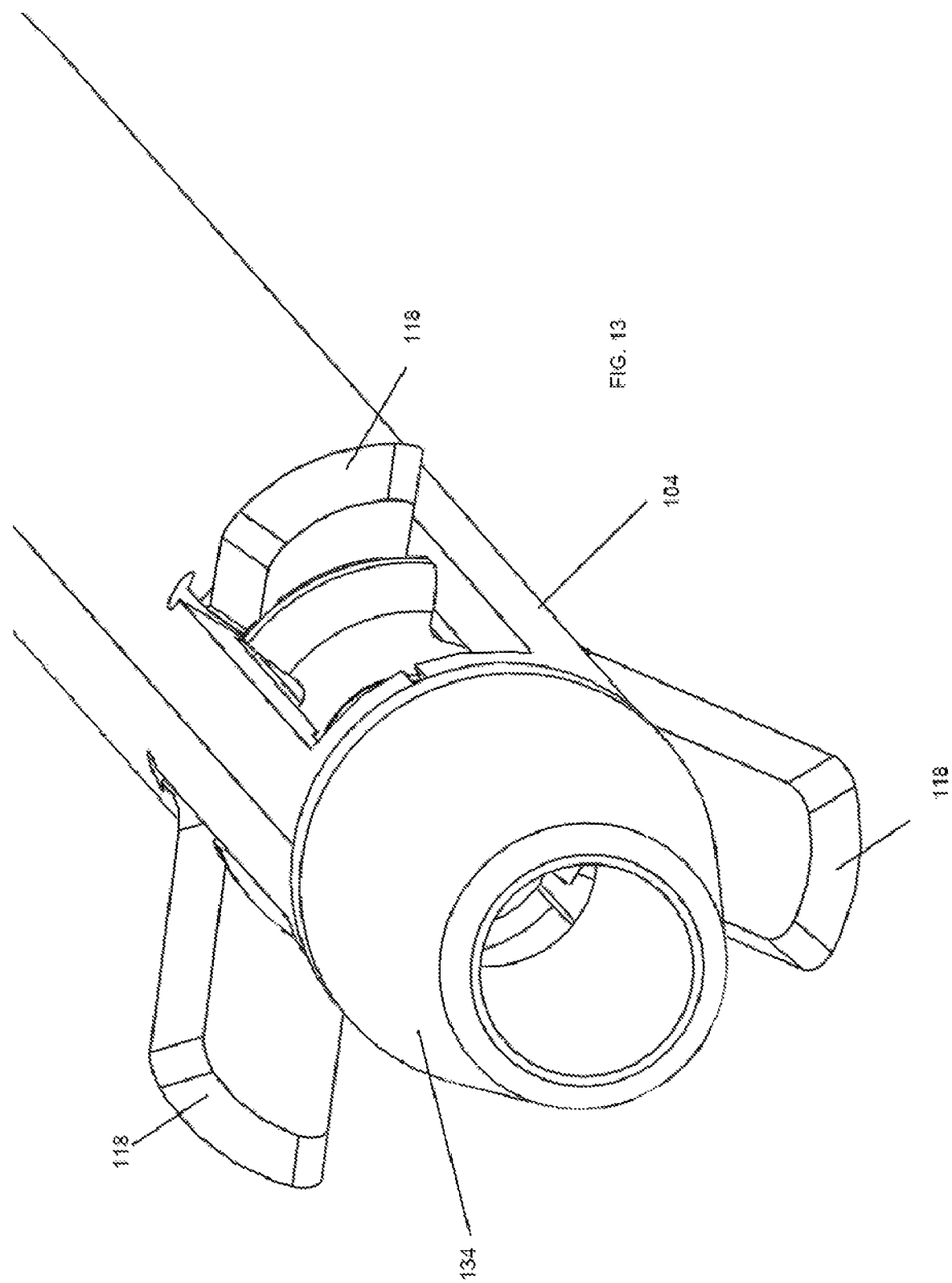
FIG. 13 is perspective view of the distal end of the device shown in FIG. 12 shown in a deployed state.

FIGS. 12-13 shows a perspective view of the device 100 in a deployed configuration. In this embodiment, gripper 108 includes three opposing bendable gripping members 118. Three bendable gripping members 118 are shown in FIG. 12, each located at the same axial location but offset by 120 degrees. Each bendable gripping member 118 has a thinned portion 120 that permits bending as the opposite distal end 122 of bendable gripping member 118 is urged radially outward, such that bendable gripping member 118 pivots about thinned portion 120. When extended, distal ends 122 of bendable members 118 contact the inside of the bone to anchor the distal portion of device 100 to the bone. In alternative embodiments (not shown), the gripper may comprise 1, 2, 3, 4, 5, 6 or more bendable gripping members similar to bendable gripping members 118 shown.

FIG. 13 shows a hemispherical tip cover 134 may be provided at the distal end 104 of the device 100 to act as a blunt obturator. This arrangement facilitates penetration of bone (e.g. an intramedullary space) by device 100 while keeping the tip of device 100 from digging into bone during insertion.

Figure 14:
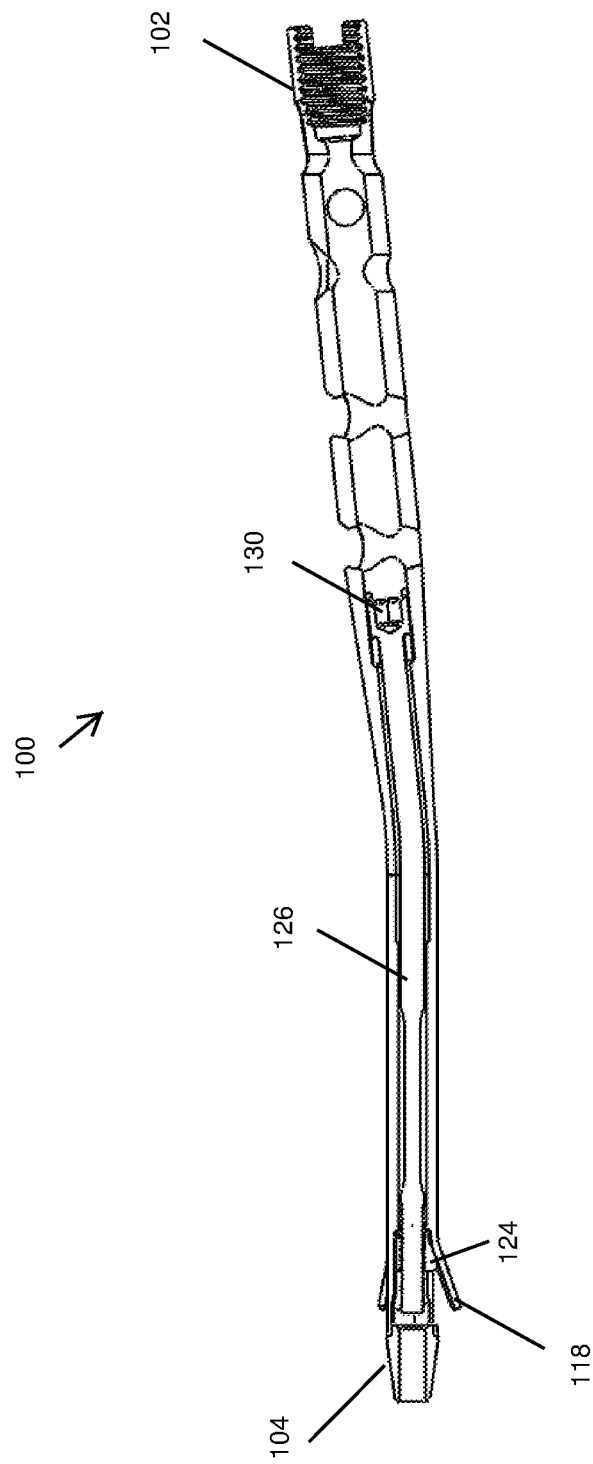
FIG. 14 is a cross-sectional view of the device shown in FIG. 12 shown in a deployed state.

FIG. 14 shows a longitudinal cross-sectional view of the device 100 in a deployed configuration. FIG. 15 shows the distal end of the device 100. During actuation, bendable gripping members 118 of gripper 108 are urged radially outward by a ramped surface on actuator head 124. Actuator head 124 is threaded onto the distal end of actuator 126. The proximal end of actuator 126 has a keyed socket 130 for receiving the tip of the tip of a screw driver through the proximal bore of device 100. In some embodiments, the keyed socket 130 is hex shaped. As screw driver turns actuator 126, a threaded surface of the actuator 126 rotates in relation to the actuator head 124. This causes the actuator head 124 to be drawn in a proximal direction toward the proximal end 102 of the device 100 as the actuator head 124 traverses the threaded surface of the actuator 126. The ramped surface on the actuator head 124 outwardly actuates bendable gripping members 118. The device 100 may include a stop to prevent translation of the actuator 126. The actuator 126 may include one or more bends to match the shape of the device 100. The actuator may 126 may be flexible or have a flexible portion between the keyed socket 130 and the threaded surface. In other embodiments, the actuator 126 is integrally formed with the actuator head 124. As a tool pulls the actuator 126, the actuator head 124 is drawn in a proximal direction toward the proximal end 102 of the device 100. The ramped surface on the actuator head 124 outwardly actuates bendable gripping members 118.

Figure 16A:
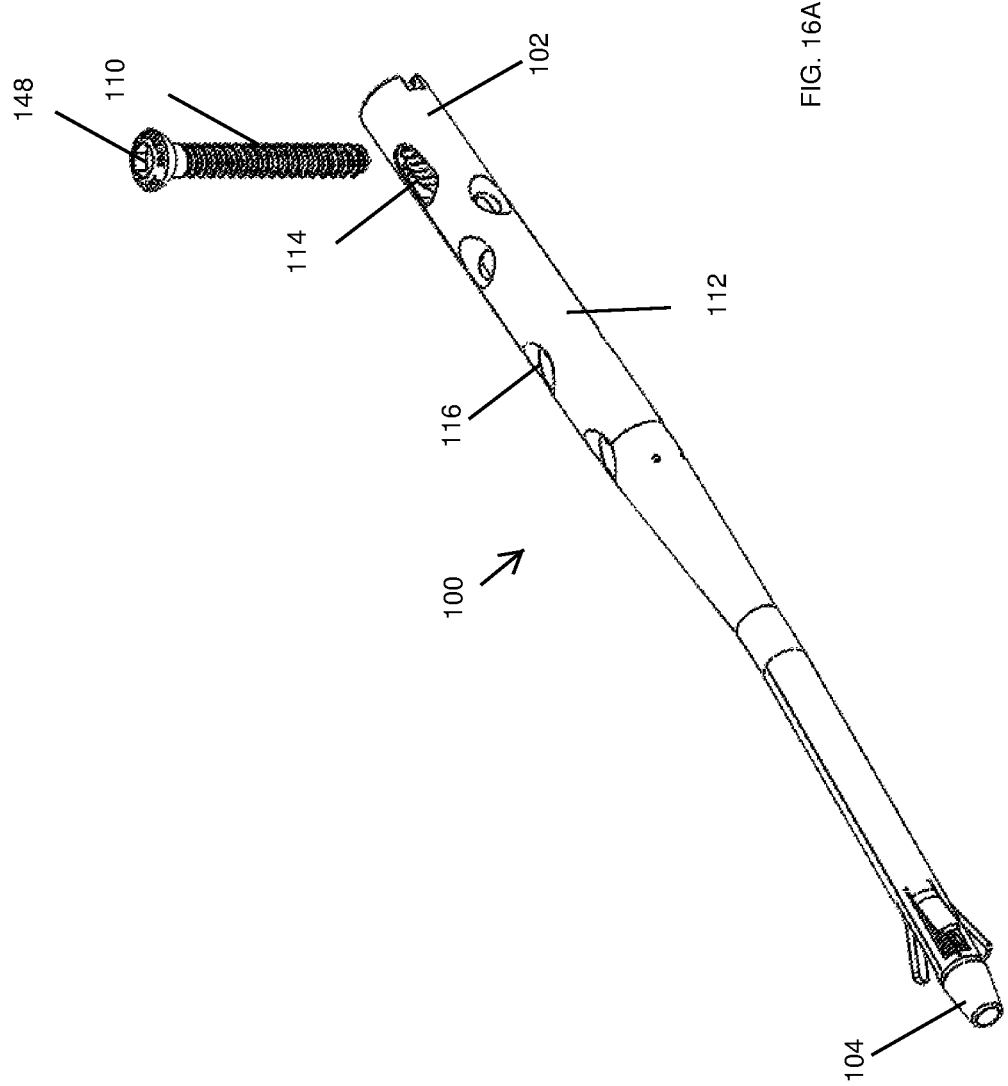
FIG. 16A is perspective view of the device shown in FIG. 12 shown in a deployed state prior to insertion of a screw.
Figure 16B:
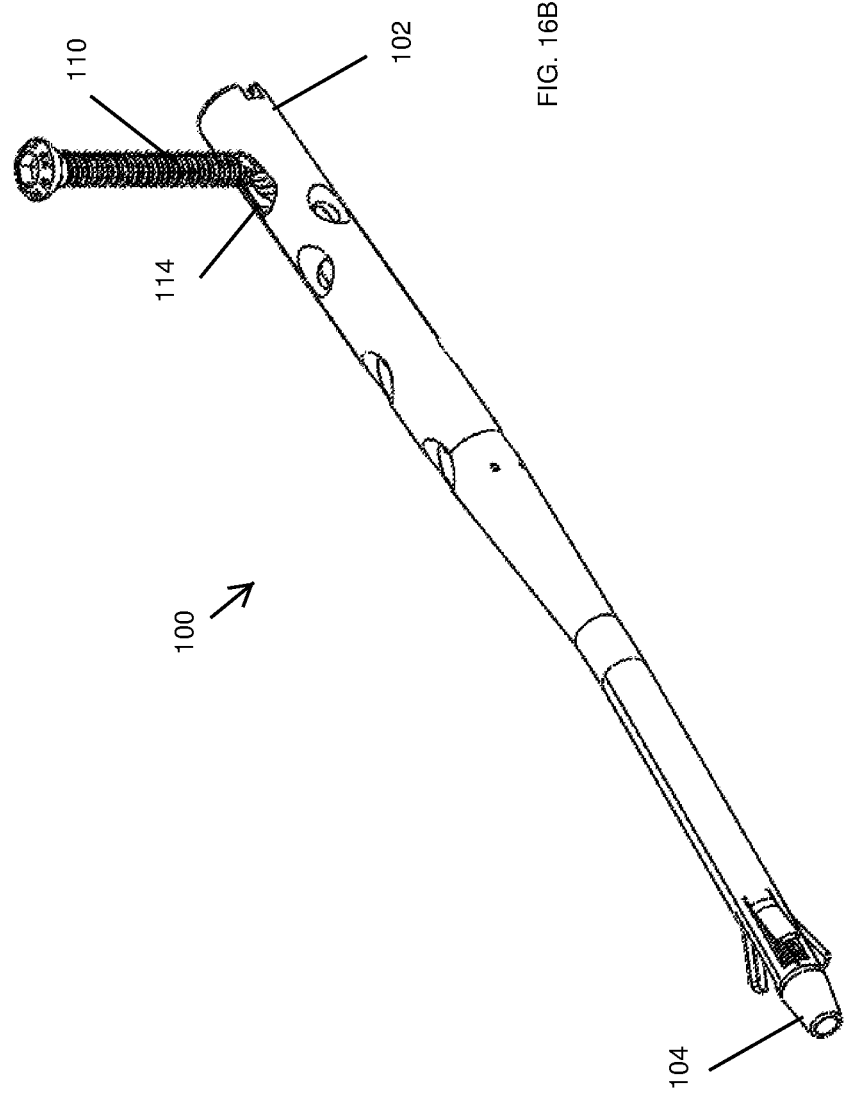
FIG. 16B is perspective view of the device shown in FIG. 16A shown in a deployed state during insertion of the screw.
Figure 16C:
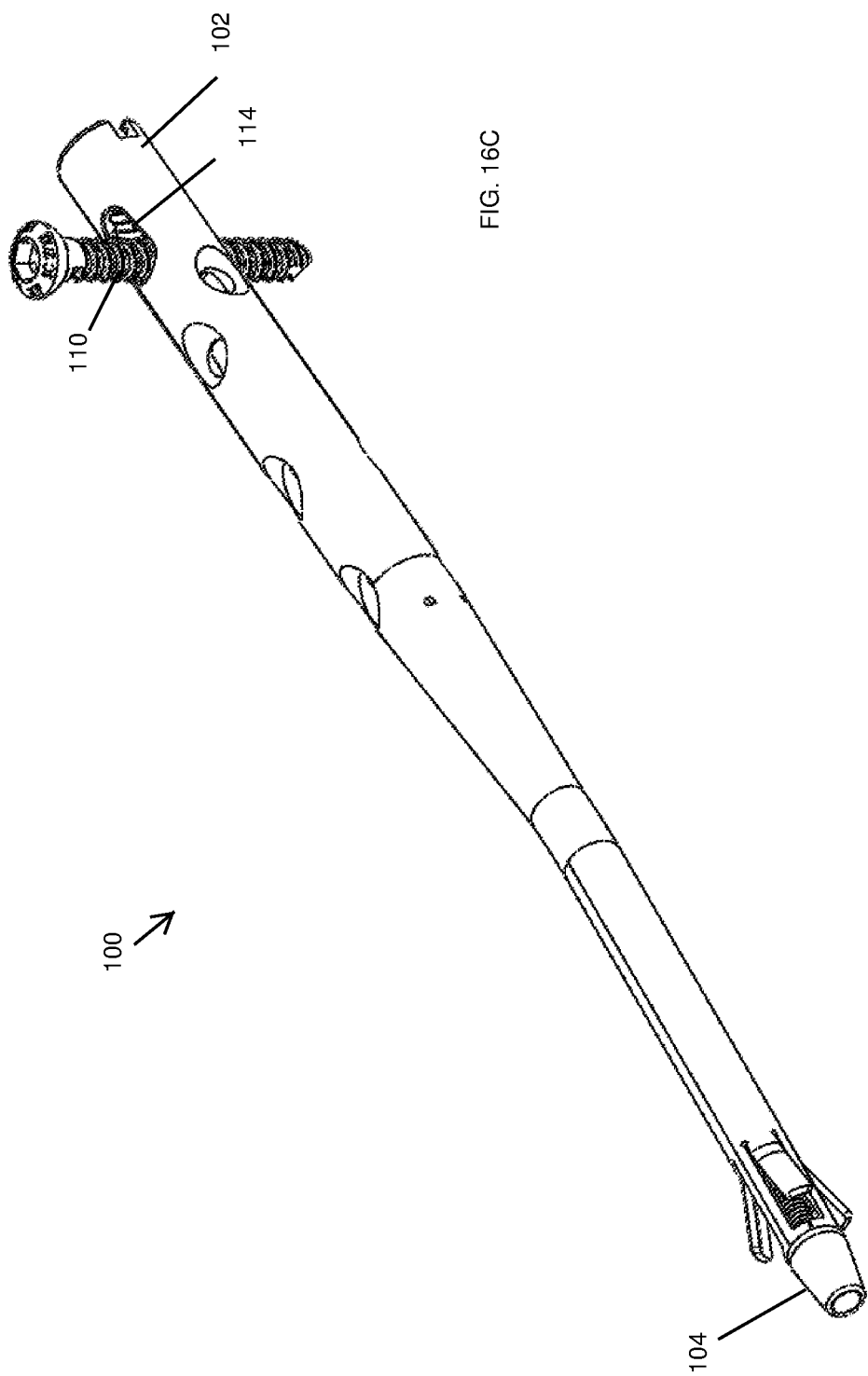
FIG. 16C is perspective view of the device shown in FIG. 16A shown in a deployed state after translation of the screw.

FIG. 16A-C illustrates a method of inserting the screw 110 into the aperture 114. The screw 110 can be inserted with a combination tool, described herein. The screw 110 is aligned with the aperture 114. In some embodiments, the screw 110 is oriented perpendicular to the longitudinal axis of the hub 112. The aperture 114 has at least one dimension greater that the diameter of the screw 110. The at least one dimension can be aligned with the longitudinal axis of the hub 112 and/or the longitudinal axis of the device 100. The aperture 114 can be generally oblong, elliptical or tear shaped. The shape of the aperture 114 allows the screw 110 to translate within the aperture 114. The screw 110 can be inserted into the aperture 114 near the proximal end 102 of the device 100. The screw can be translated toward the distal end 104 of the device 100 while within the aperture 114. FIG. 16B shows the screw 110 inserted in the aperture 114 near the proximal end 102 of the device 100. FIG. 16C shows the screw 110 translated within the aperture 114 toward the distal end 104 of the device 100.

Figure 17:
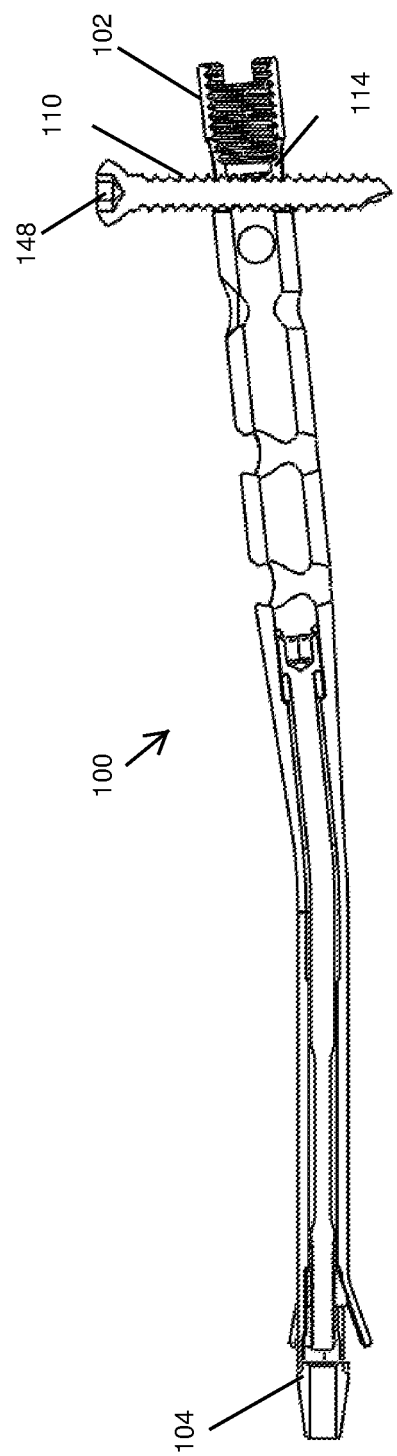
FIG. 17 is a cross-sectional view of the device shown in FIG. 16C shown in a deployed state after translation of the screw.
Figure 18:
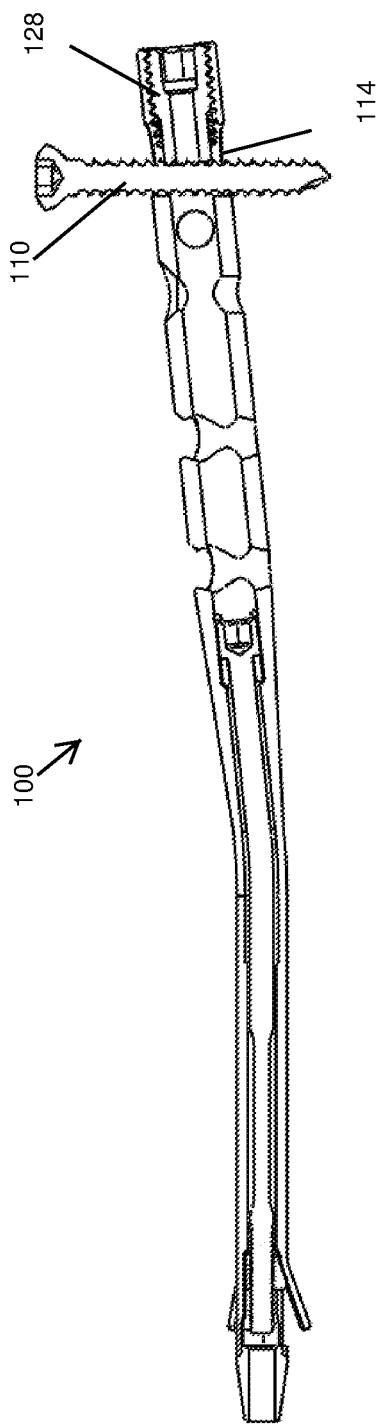
FIG. 18 is a cross-sectional view of the device shown in FIG. 16C shown in a deployed state after insertion of a cap.
Figure 19:
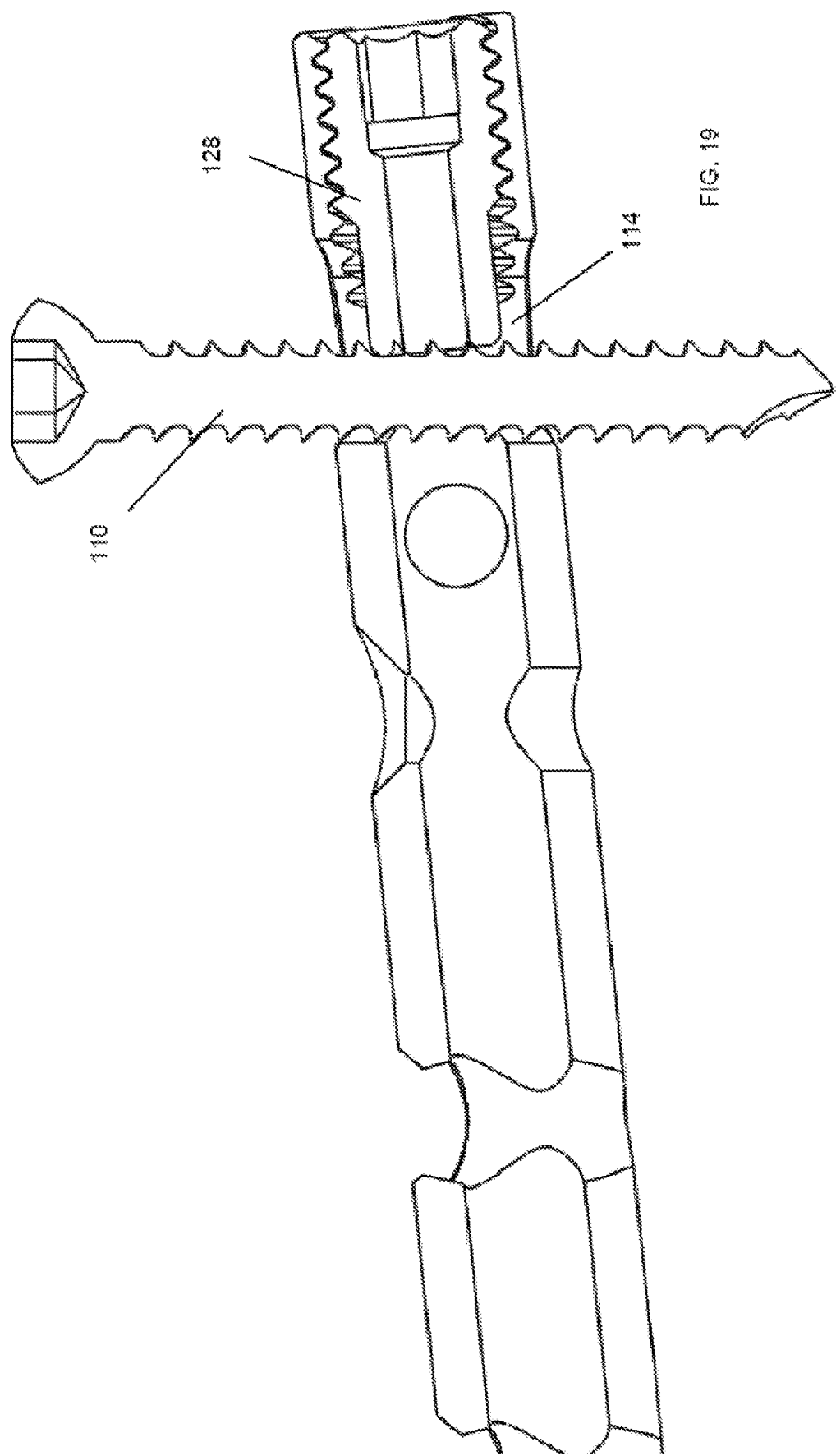
FIG. 19 is a cross-sectional view of the proximal end of the device shown in FIG. 18 shown in a deployed state after insertion of a cap.

FIGS. 17-19 shows a longitudinal cross-sectional view of the device 100 of FIG. 16C after the screw 110 has been translated. A cap 128 can be provided to maintain the position of the screw 110. The cap 128 can prevent the screw 110 from translating within the aperture 114 toward the proximal end 102 of the device 100. The cap 128 can be inserted within the proximal bore of the device 100 until the distal end of the cap abuts the screw 110. The proximal bore can be threaded and the cap 128 can include complementary threads. Other configurations of caps 128 are contemplated.

Figure 20:
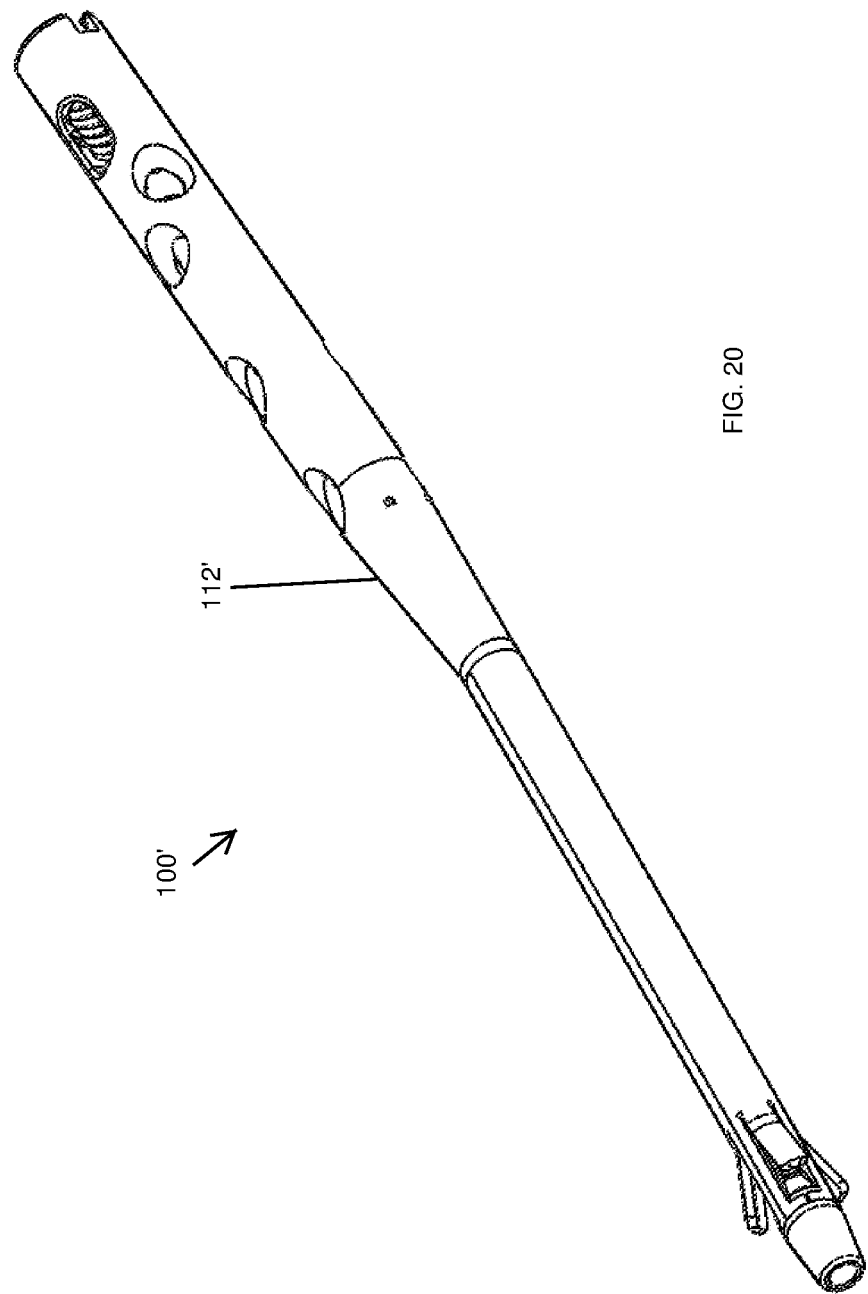
FIG. 20 is a perspective view of the another embodiment of a bone fixation device shown in a deployed state

FIG. 20 shows a perspective view of the device 100'. Device 100' is substantially similar to device 100 described above. The shape of the body of the device 100' has a different taper near the distal end of the hub 112'

Figure 21:
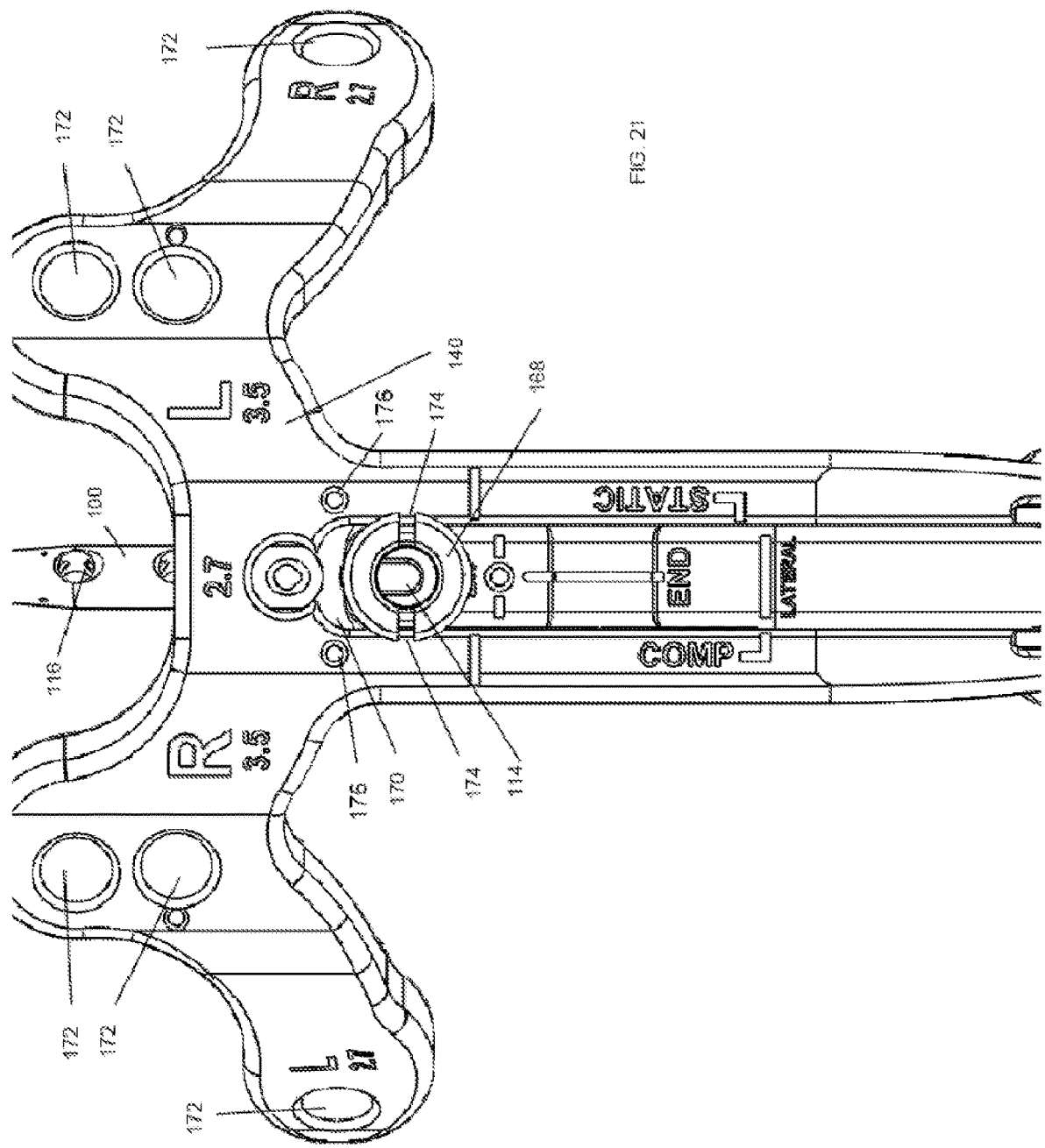
FIG. 21 is a perspective view of an embodiment of a tool.
Figure 22:
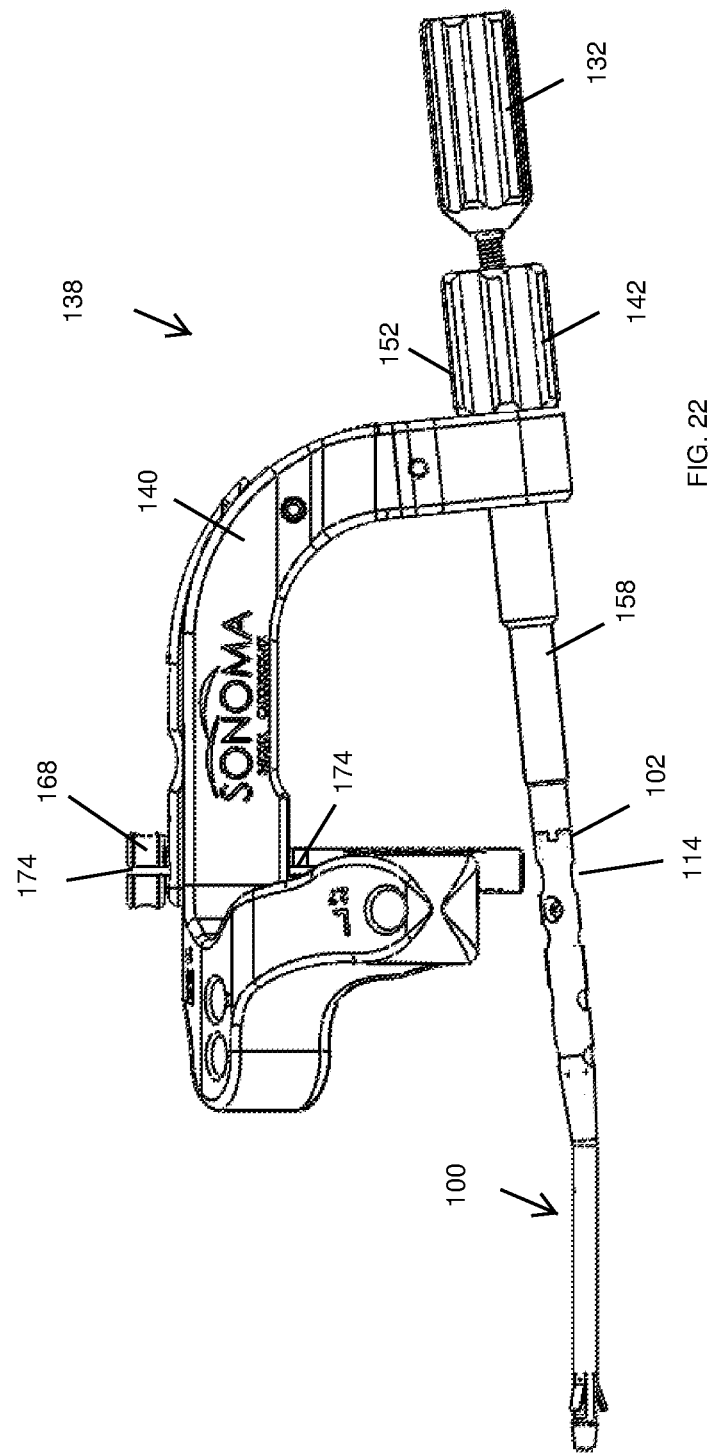
FIG. 22 is a perspective view the tool shown in FIG. 21 coupled to the bone fixation device of FIG. 12

FIGS. 21-22 shows a top and a side view of a combination tool 138 useful for inserting device 100, actuating gripper 108, approximating the fracture in bone, aligning one or more anchor screw(s) 110, and/or removing device 100, if desired. The main components of tool 138 are a hub 158, a T-shaped body 140, a device attachment portion 142, a rotary driver 132, and an alignment tube 168. The combination tool 138 can be assembled as follows.

Hub 158 is configured to abut the proximal end 102 of the device 100 (seen in FIG. 22). In the embodiment shown, the proximal end 102 includes a notch and the hub 158 includes a protrusion. Other mating configurations are contemplated. Hub 158 is coupled to the T-shaped body 140. In some embodiments, the hub 158 is integrally formed with the T-shaped body 140. In the embodiment shown, hub 158 is coupled to the T-shaped body 140 with a lock (shown in FIG. 24). In this exemplary embodiment, T-shaped body 140 couples with the hub 158 and can also serves as a handle.

Device attachment portion 142 prevents removal of the hub 158 and the T-shaped body from the device 100. Device attachment portion 142 includes a knob 152 connected with a tube 160 (seen in FIG. 25-26). In the embodiment shown, the distal end of the tube 160 has a mating configuration 166 to engage the proximal bore of the device 100 (shown in FIG. 26). In the illustrated embodiments, the mating configuration 166 is threads that engaging the threaded proximal bore of the device 100. The knob 152 facilitates rotation of the tube 160. The tube 160 of the device attachment portion 142 is inserted into the hub 158 until the mating configuration 166 of the tube 160 engages the proximal bore of the device 100. The tube 160 is partially inserted within proximal bore of the device 100 prior to inserting the screw 110. The tube 160 does not obstruct the aperture 114 prior to inserting the screw 110. Further rotation of the knob 152 causes the knob 152 to abut the T-shaped body 140. The knob 152 of the device attachment portion 142 rigidly couples the hub 158 and the T-shaped body 140 with the device 100.

The rotary driver 132 can be partially inserted within the device attachment portion 142 prior to inserting the screw 110. The rotary driver 132 can be inserted within the device attachment portion 142 after inserting the screw 110. In some embodiments, the device attachment portion 142 has a lock that prevents translation of the rotary driver 132 prior to inserting the screw 110. The lock can be released by rotating the lock within the device attachment portion 142 until the lock no longer prevents translation of the shaft 162. The lock can ensure that the shaft 162 is not obstructing the aperture 114 prior to inserting the screw 110.

Figure 23:
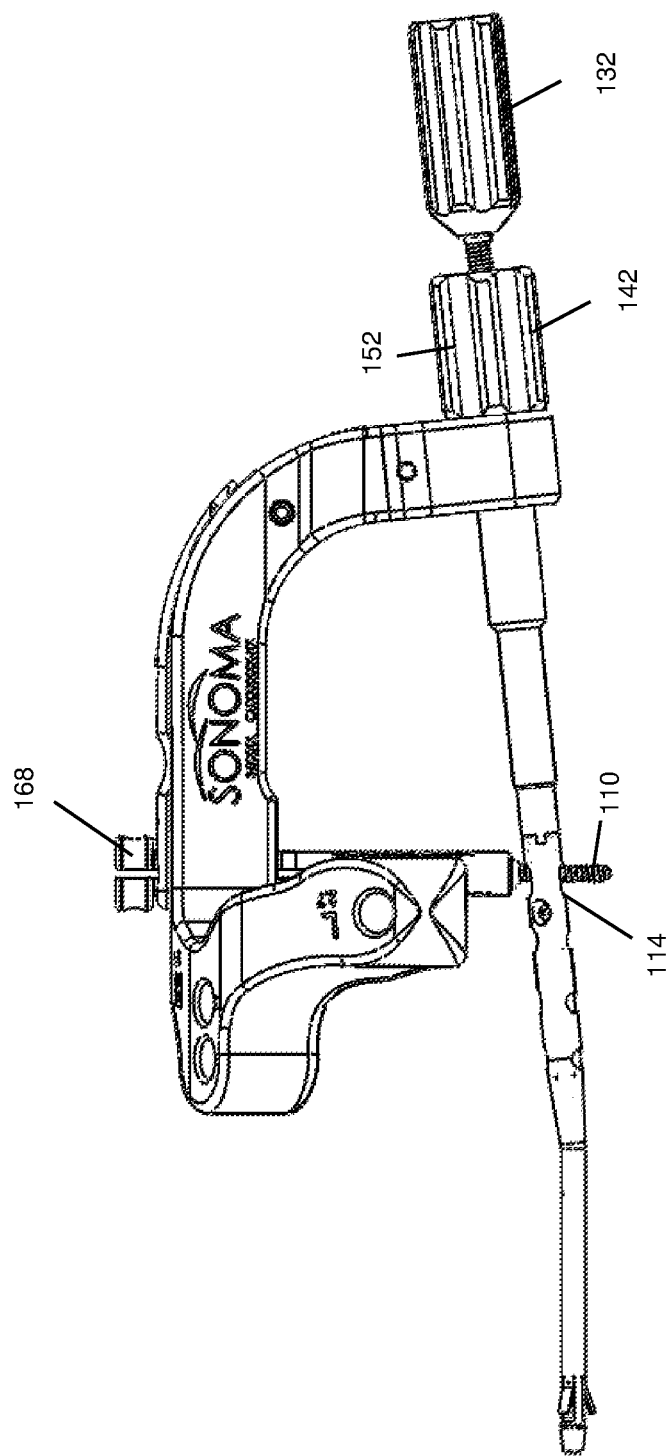
FIG. 23 is a perspective view of the system shown in FIG. 22 shown in a deployed state during insertion of the screw.

The alignment tube 168 is shown in FIGS. 21-23. The alignment tube 168 can be coupled to the T-shaped body 140. The combination tool 138 is in place when the device attachment portion 142 rigidly couples the hub 158 and the T-shaped body 140 to the device 100. In this configuration, the removable alignment tube 168 aligns with the proximal end of the aperture 114. In the embodiment depicted in the figures, the T-shaped body 140 includes a plurality of bores 170, 172. In alternative embodiments (not shown), a single bore or more than two bores may be used, with or without the use of separate alignment tube(s). the alignment tube 168 may include one or more slots. In the illustrated embodiment, the alignment tube 168 includes two longitudinally extending slots 174. The alignment tube 168 can be oversized to create an interference between the alignment tube 168 and the bore 170. The slots 174 allow the alignment tube 168 to compress to fit within the bore 170. The design of the alignment tube 168 allows the alignment tube 168 to be retained within the T-shaped body 140 and be held rigidly in place.

In operation, alignment tube 168 is first received in bore 170 (seen in FIG. 21). In this position, alignment tube 168 is in axial alignment with aperture 114 at the proximal end 102 of device 100. As described above, the mating configuration of device 100 and hub 158 position aperture 114 in its desired orientation. With this arrangement, a drill bit, screw driver, screw and/or other fastening device or tool may be inserted through the bore of alignment tube 168 such that the device(s) are properly aligned with aperture 114. The outward end of alignment tube 168 may also serve as a depth guide to stop a drill bit, screw and/or other fastener from penetrating bone beyond a predetermined depth. FIG. 22 shows alignment tube 168 with aperture 114 at the distal end of device 100, as described above. Inserting the screw 110 through the alignment tube 168 ensures that the screw 110 will have the placement as shown in FIG. 16B. The alignment tube 168 allows proper placement of the screw 110 even if the aperture 114 or other portions of the device 100 are obstructed from the view of the surgeon.

The T-shaped body 140 includes other bores 172 that align with apertures 116. Alignment tube 168 may be withdrawn from bore 170 as shown, and inserted in another bore 172. The alignment tube 168 can be inserted within these bores 172 to align and insert other screws 110 into apertures 116. In this position, alignment tube 168 aligns with aperture 116 of device 100. As described above, a drill bit, screw driver, screw and/or other fastening device may be inserted through the bore of alignment tube 168 such that the device(s) are properly aligned with aperture 116.

Figure 24:
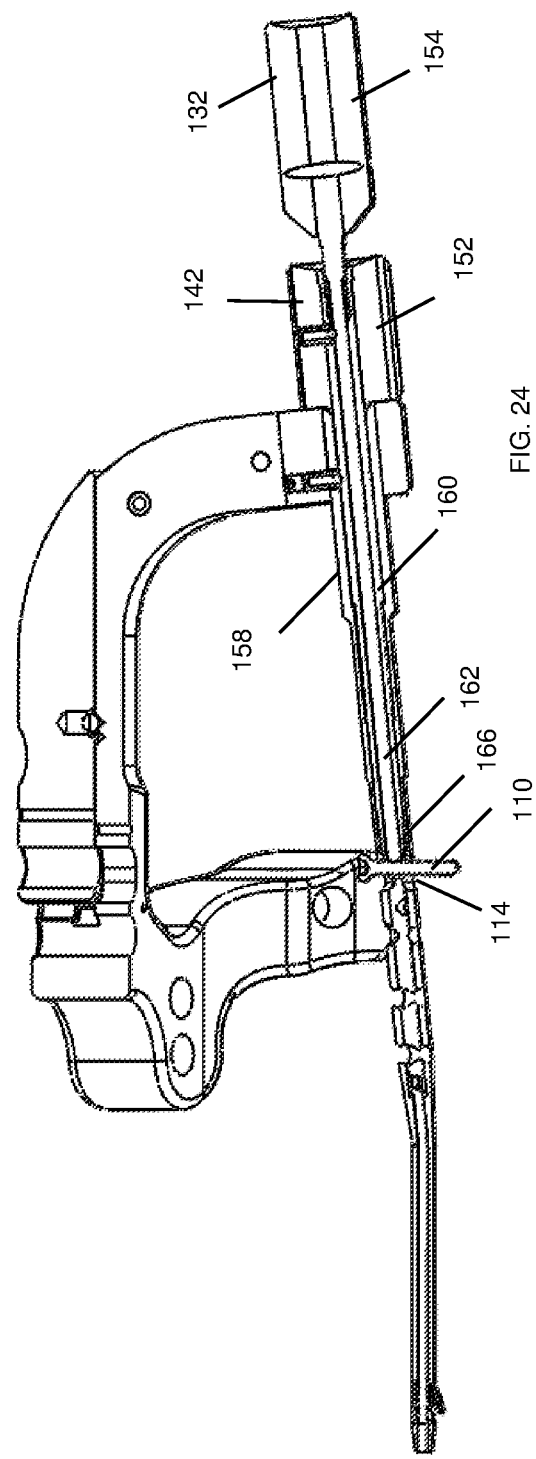
FIG. 24 is cross-sectional view of the system shown in FIG. 22 shown in a deployed state during insertion of the screw.

FIGS. 23-24 show a screw 110 received through aperture 114. Screws 110 may be installed manually or with the aid of tool 138 as described above. The heads of screws 110 may be configured to be self-countersinking such that they remain substantially beneath the outer surface of the bone when installed, as shown, so as to not interfere with adjacent tissue. The rotatory driver 132 remains stationary during insertion of the screw 110. The rotatory driver 132 does not obstruct the aperture 114.

Figure 25:
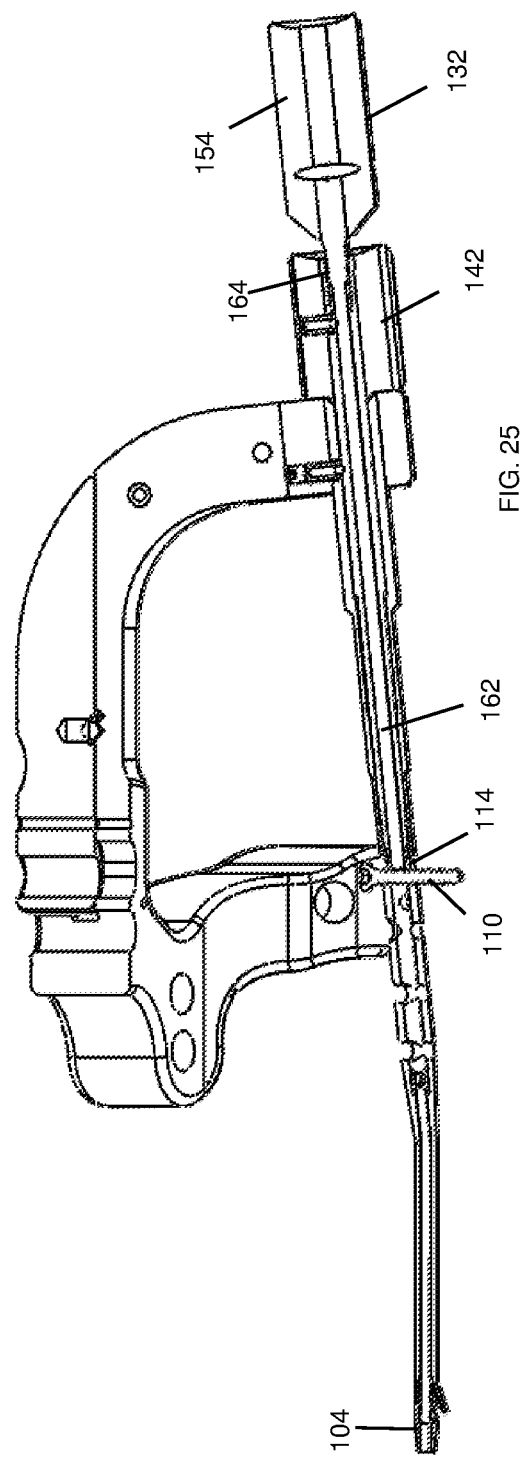
FIG. 25 is cross-sectional view of the system shown in FIG. 22 shown in a deployed state after translation of the screw.

FIG. 25-26 show the rotatory driver 132 may be used to translate the screw 110 within the aperture 114. In the embodiment shown, rotatory driver 132 includes knob 154 and shaft 162. The distal end of shaft 162 is provided with a mating configuration 164, such as threads, for engaging with device attachment portion 142. The mating configuration can prevent disengagement between the device attachment portion 142 and the rotatory driver 132. Suitable thread pitch and knob circumference may be selected to allow a surgeon to supply a desired force to the screw 100 by using a reasonable rotation force on knob 154. In some embodiments, the threads are removed. The knob 154 can be translated toward the distal end 104 of the device 100 instead of rotating the knob 154. The device attachment portion 142 can act as a bearing to align the shaft 126 with the proximal bore of the device 100. In alternative embodiments (not shown), a torque indicating and/or torque limiting mechanism as described above may be incorporated into the device attachment portion 142 and/or rotatory driver 132.

Turning the knob 154 causes the shaft 162 to rotate and thereby translate within the device attachment portion 142. Rotation of the rotatory drive 132 causes the shaft 162 to translate toward the distal end 104 of the device 100 toward the screw 110. Further translation of the shaft 162 will push the screw 110 toward the distal end 104 of the device 100 while the screw 110 is within the aperture 114. Further rotation of the rotary driver 132 causes the screw 110 to translate within the aperture 114. The tool 138 is removed and the cap 128 is inserted within the proximal bore of the device 100. FIG. 16 shows the position of the screw 110 after translation within the aperture 114.

Figure 28B:
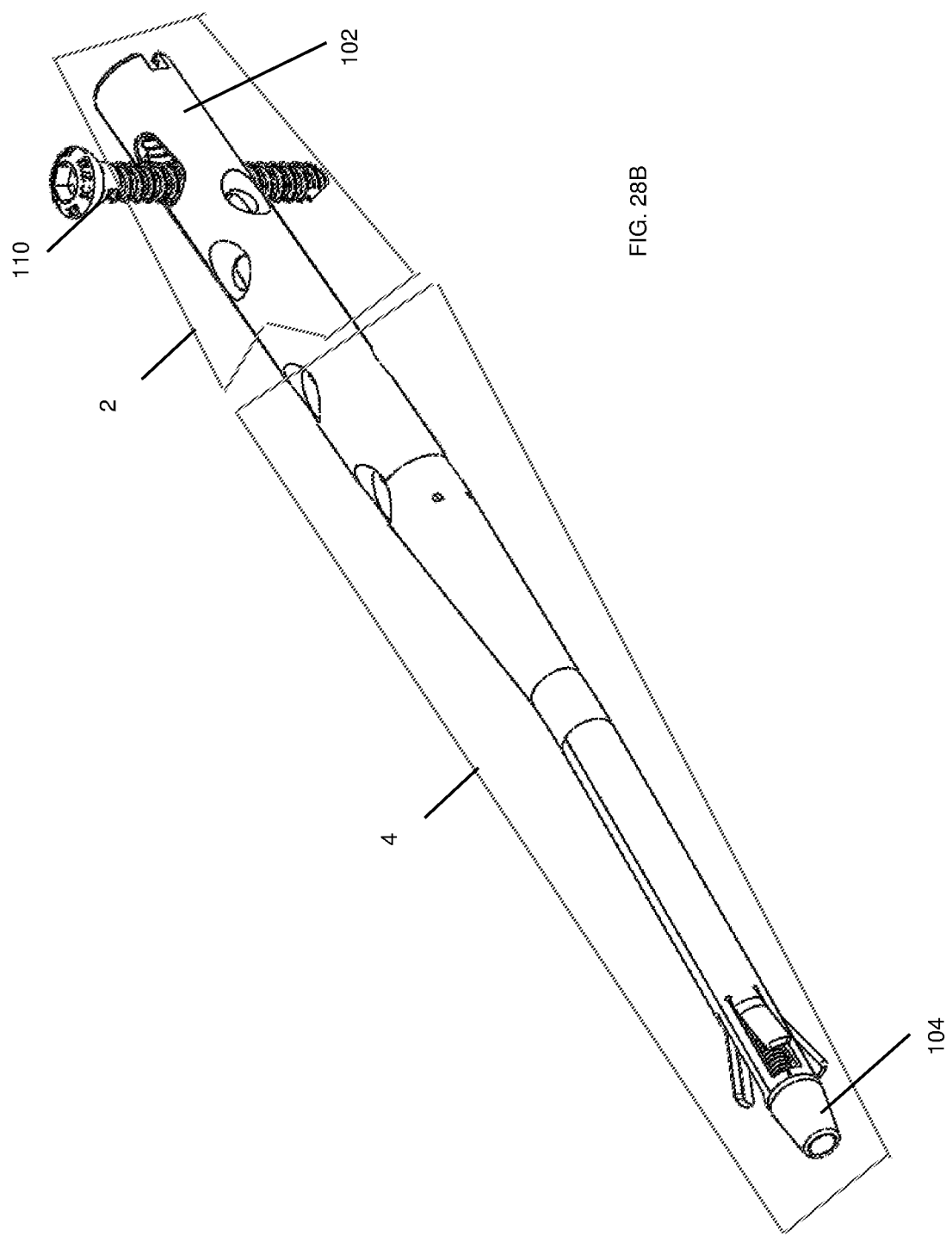
FIG. 28B is a perspective view of the device shown in FIG. 16A shown in a deployed state after translation of the screw.

The translation of the screw 110 may be used to compress one or more fractures in bone. FIG. 28A-28B illustrates a method of inserting the screw 110 into the aperture 114 in relation to bone segments 2 and 4. Bone segment 2 is near the proximal end 102 of the device 100. Bone segment 4 is near the distal end 104 of the device 100. The bone segment 4 is held in place gripper 108 adapted to engage bone segment 4 from the inside of the bone. This device 100 has a gripper 108 positioned distally and shown deployed radially outward against the wall of the intramedullary cavity. Upon deployment, gripper 108 pivots radially outward and grips the diaphyseal bone from the inside of the bone. The proximal bore of the device 100 is not obstructed by the bone screw 110 allowing a screw driver to actuate the actuator 126 thereby translating the actuator head 124 (seen in FIG. 15). In the illustrated method, the gripper 108 engages bone segment 204 prior to insertion of the screw 110. In other methods, the gripper 108 engages bone segment 204 after insertion of the screw 110 but prior to translation of the bone screw.

The screw 110 can be inserted with a combination tool 138. The screw 110 is aligned with the aperture 114. In some embodiments, the screw 110 is oriented perpendicular to the longitudinal axis of bone. The screw 110 penetrates bone segment 2. The screw 110 extends past the device 100 to rigidly fix the screw 110 to the bone segment 2. The aperture 114 has at least one dimension greater that the diameter of the screw 110. The at least one dimension can be aligned with the longitudinal axis of the bone and/or the longitudinal axis of the device 100.

The screw 110 can be translated with respect to the aperture 114. The shape of the aperture 114 allows the screw 110 to translate within the aperture 114. The screw 110 can be inserted into the aperture 114 near the proximal end 102 of the device 100. The screw can be translated toward the distal end 104 of the device 100 while within the aperture 114. FIG. 28B shows the screw 110 translated within the aperture 114 toward the distal end 104 of the device 100. The bone segment 2 translates with the screw 110. With the bone segment 4 held in place by the gripper 108, the translation of the screw 110 and the bone segment 2 reduces the fractures and/or aligns the bone segments 4, 2. As screw 110 is advanced axially toward bone segment 4, the screw 110 serves to approximate bone fractures located between gripper 108 and screw 110.

Referring back to FIG. 23, additional screws (not shown) can be inserted into the bores 172 and through the bone segments 2, 4 after translation of the screw 110 within the aperture 114. The bores 172 are aligned with the other apertures 116 before and after the translation of the screw 110 within the aperture 114. In the illustrated embodiment, the apertures 116 are substantially circular and do not permit the additional screws to translate within the apertures 116. In the illustrated embodiments, the additional screws are inserted after the screw 110 in translated within the aperture 114. In other embodiments (not shown), the apertures 116 are oblong and allow the additional screws to translate therewithin. The bone segment 2 in this embodiment would have multiple points of fixation between screws and the bone segments 2, 4 prior to translation.

In the illustrated embodiments, the distal end 104 is secured by gripper 108. In this manner, any bone fractures located between the proximal screw 110 and distal gripper 108 may be approximated and rigidly held together by device 100. In alternative embodiments (not shown), more than one gripper may be used. For example, the device shown in FIGS. 28A-28B could be configured with a second gripper located between gripper 108 and the middle of the device if the fracture is located more at the mid-shaft of the bone. In alternative embodiments (not shown), screws or other fasteners may be used to secure the distal end 104 of the device 100 to the bone. Similarly, more than two screws or other fasteners may be used, or only grippers without fasteners may be used.

Once device 100 is secured within bone 106, combination tool 138 may be removed by turning device attachment portion 142 to disengage threads of tube 160 from threads within the proximal bore of device 100. The hub 158 can be disengaged from the proximal end 102 of the device 100. The cap 128 may be threaded into the proximal end 102 of device 100 to preventing growth of tissue into implanted device 100. Device 100 may be left in bone permanently, or it may be removed by performing the above described steps in reverse. In particular, cap 128 is removed, tool 138 is attached, one or more screws 110 are removed, gripper 108 is retracted, and device 100 is pulled out using tool 138.

Figure 29:
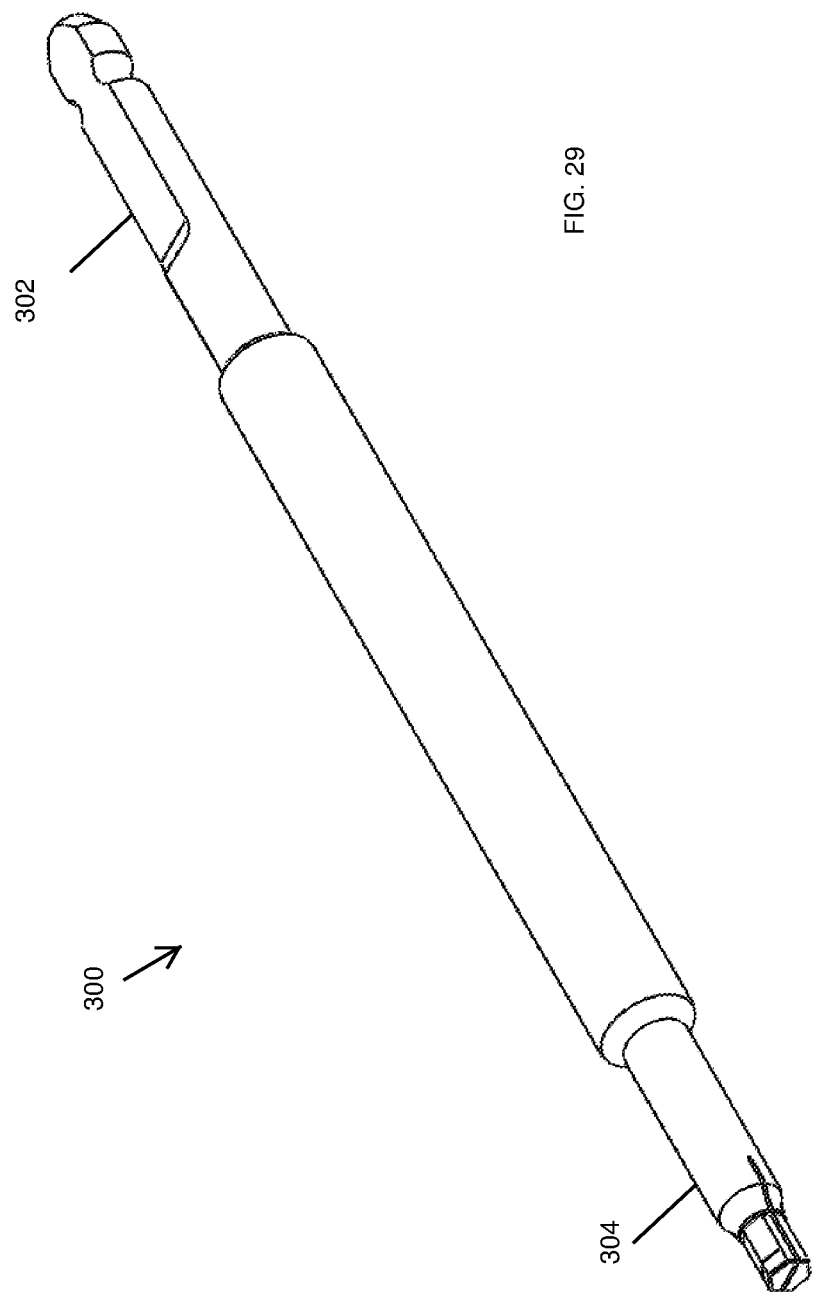
FIG. 29 is a perspective view of an embodiment of a screw driver.
Figure 31A:
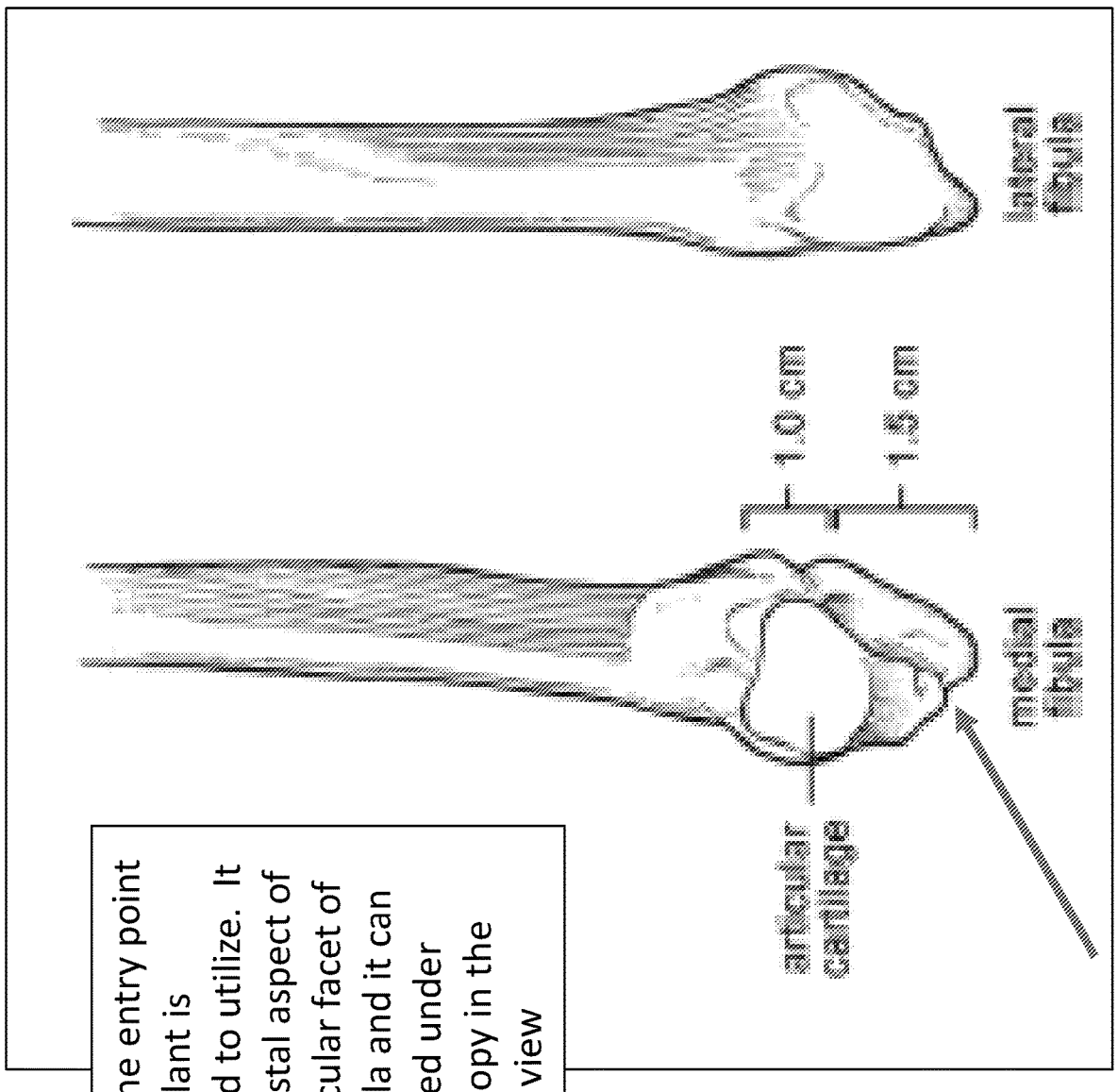

FIG. 29 shows a perspective view of an embodiment of a screw driver 300. The screw driver 300 may be configured to engage the keyed socket 130 of the actuator 126 (seen in FIG. 14). The screw driver 300 may be configured to engage the keyed socket 148 of the screw 110 (seen in FIG. 16A).

The screw driver 300 includes a proximal end 302 and a distal end 304. The proximal end 302 can have a mating configuration such as a flattened surface. The mating surface can engage a knob to facilitate rotation. The mating surface can engage a power source such a drill. The mating configuration can be a hand grip. The screw driver 300 can be sized and shaped to fit within the proximal bore of the device 100. The screw driver 300 can be sized and shaped to fit within the alignment tube 168.

The distal end 304 includes a hex tip 306. All the hex flats 308 are sized to fit a female hex of the corresponding keyed socket 130, 148. In the illustrated embodiment, each flat 308 is 2.5 mm but other sizes are contemplated. The hex tip 306 includes a slot 310 across one pair of flats 308. In the illustrated embodiment, the slot 310 bisects the pair of flats 308. In the illustrated embodiment, the slot 310 extends into the screw driver 300, beyond the hex tip 306. The depth and width of the slot 310 depends on the retaining force with the actuator 126 or with the screw 110.

The hex tip 306 is then deformed outward to create an interference between the screw driver 300 and the keyed socket 130, 148. In the illustrated embodiment, the interference is on the order of 0.003" (e.g., 0.002", 003", 0.004", 0.005", between 0.002" and 0.005", etc.). The material of the screw driver 300 is selected maintain the deformed state. One suitable material is heat treated stainless steel. The configuration of the screw driver 300 prevents stripping of the keyed socket 130, 148. In some embodiments (not shown), an elastomer could be inserted into the slot 310 to provide additional spring back if needed.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculoskeletal systems.

Further, the reinforcement device may, in one embodiment, be osteo incorporating, such that the reinforcement device may be integrated into the bone. In a further embodiment, there is provided a low weight to volume device deployed in conjunction with other suitable materials to form a composite structure in-situ. Examples of such suitable materials may include, but are not limited to, bone cement, high density polyethylene, Kapton™, polyetheretherketone (PEEK), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

FIGS. 31A-31H show the anatomy of the fibula. The fibula is a leg bone located below the knee. The fibula is connected to the tibia and is the slenderest of the long bones in the human body. The arrow shows the entry point of the device within the patient. The distal end 104 would extend toward the knee in the intramedullary canal. The proximal end 102 would be toward the ankle.

FIGS. 32A-32J are various method steps to implant the device of FIGS. 1-30. FIGS. 32A-32J shows the device 100 and the tool 138, but any of the devices described herein can be inserted using one or more of the following method steps.

Figure 32A:
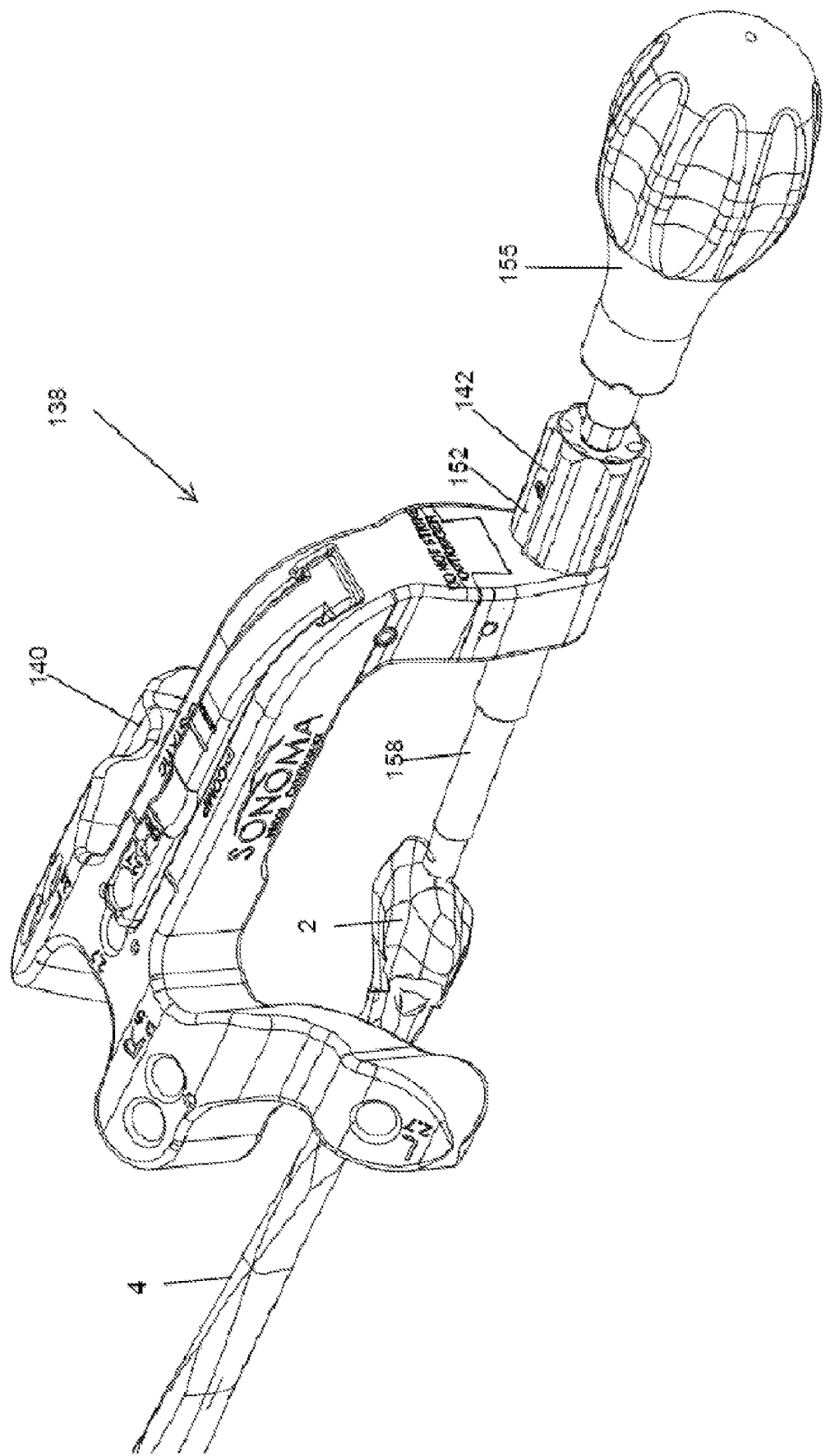

FIG. 32A shows the assembled tool 138 useful for inserting device 100 (not shown) into bone. Hub 158 is configured to abut the proximal end 102 of the device 100. Hub 158 is coupled to the T-shaped body 140. Device attachment portion 142 prevents removal of the hub 158 and the T-shaped body from the device 100. Device attachment portion 142 includes a knob 152 that abut the T-shaped body 140. The knob 152 of the device attachment portion 142 rigidly couples the hub 158 and the T-shaped body 140 with the device 100. Screwdriver 155 can be inserted into the knob 152 of the device attachment portion 142. The assembled tool 138 is shown removed from the bone in FIG. 22.

Figure 32B:
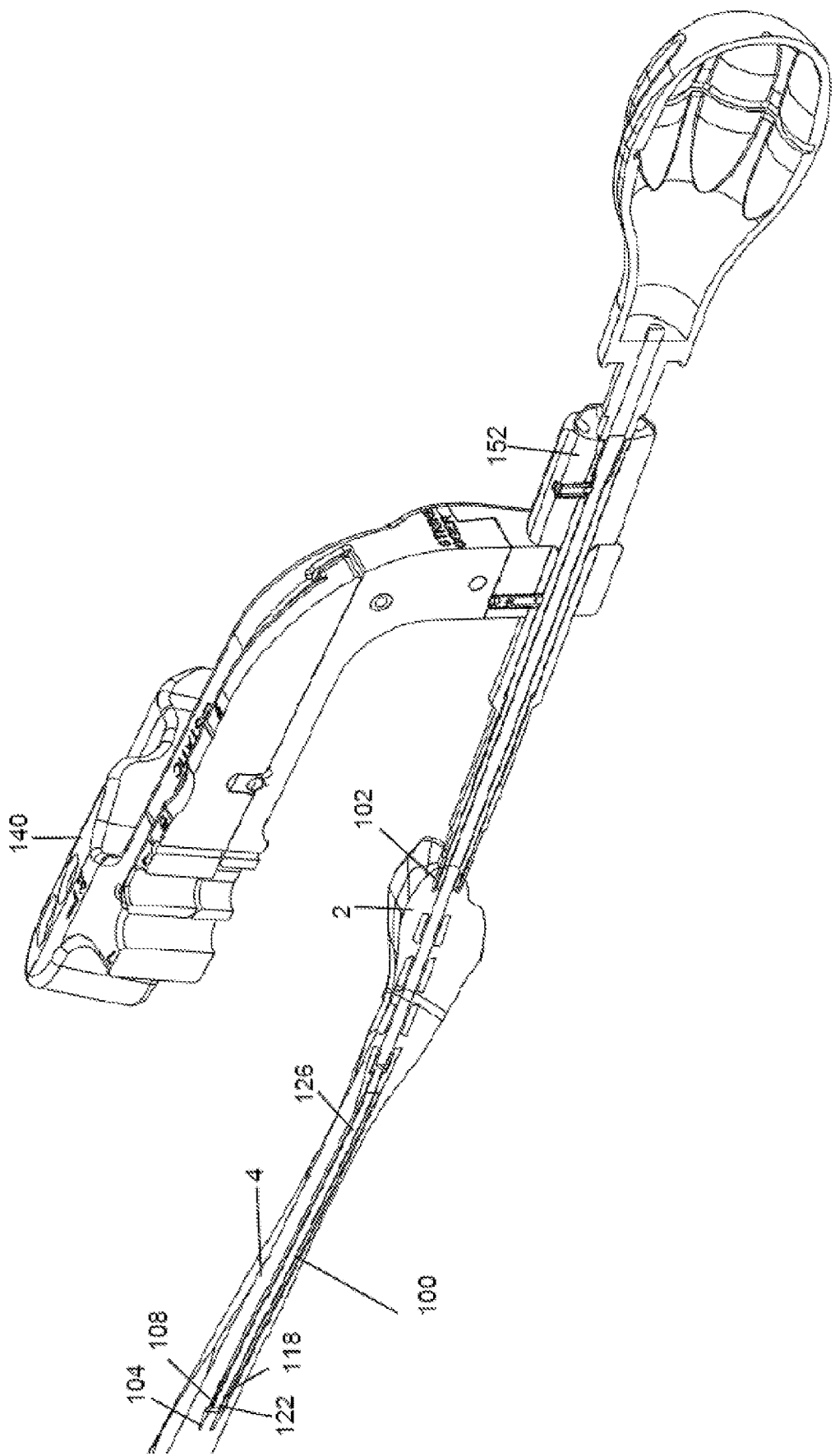

FIG. 32B shows a cross-sectional view of the inserted device 100. The device 100 is inserted into the fibula. In some methods, T-shaped body 140 can serve as a handle to facilitate insertion of the device 100. In other methods, knob 152, knob 154 (not shown) and or screwdriver 155 are used to facilitate insertion of the device 100.

Distal end 104 of device 100 can be inserted into the bone before the proximal end 102 of the device 100. Device 100 is inserted into bone segments 2 and 4. Bone segment 2 is near the proximal end 102 of the device 100 and bone segment 4 is near the distal end 104 of the device 100.

Device 100 is in the undeployed state during insertion. In the undeployed state, gripper 108 is not actuated by actuator 126. Distal ends 122 of bendable gripping members 118 do not contact the inside of the bone to anchor the distal portion 104 of device 100 to the bone. Device 100 can remain in the undeployed state until the fracture is reduced. The device 100 is inserted into the bone until the device 100 is inserted into both bone segments 2, 4 and therefore spans the fracture.

In the illustrated embodiment, the bone is a fibula. Bone segment 2 is the distal portion of the fibula and bone segment 4 is a proximal segment of the fibula. In other methods, bone segment 2 is the proximal portion of the fibula and bone segment 4 is a distal segment of the fibula. The method described herein can be used with other bones, such as the femur, humerus, tibia, radius, ulna, and clavicle.

In some methods, the insertion of the device 100 does not align the fracture. For instance, one fragment of the bone (e.g., bone segment 2) may not be aligned with another fragment of the bone (e.g., bone segment 204). Further manipulation of the bone segment 2 and/or the bone segment 204 may be necessary. In some factures, the bone segments 2, 4 may be misaligned posteriorly or anteriorly, as those terms are commonly understood anatomically. In some factures, the bone segments 2, 4 may be misaligned distally or proximally, as those terms are commonly understood anatomically.

FIG. 32C shows the use of K-wires 178 to reduce the fracture. K-wires 178 can be inserted into bone segment 2. T-shaped body 140 includes bores 176 sized to accept K-wires 178. Bores 176 are also shown in FIG. 21. K-wires 178 are inserted through bores 176 and into the bone segment 2. In the illustrated embodiment, bone segment 2 is the distal portion of the fibula. In other methods, the K-wires may be inserted into bone segment 4. K-wires may be inserted one or more bone segments (bone segment 2, bone segment 4, additional bone segments). In the illustrated method, two K-wires 178 are inserted into bone segment 2, but any number of K-wires 178 can be used (e.g., one, two, three, four, five, six, etc.). In the illustrated method, K-wires 178 are substantially parallel, but other configures are possible. K-wires 178 may be coaxial, coplanar, parallel, perpendicular, skewed, or any other configuration.

Bores 176 and thus K-wires 178 inserted through bores 176 are positioned on either side of a proximal-distal line. K-wires 178 pass through the bone segment 2 on either side of the device 100. In some methods, one or more K-wires 178 pass on the anterior side of the device 100. In some methods, one or more K-wires 178 pass on the posterior side of the device 100. The location and number of K-wires will depend on the nature of the fracture.

FIG. 32D shows the insertion of the K-wires 178 into the bone segment 2. Movement of K-wires 178 can cause movement of bone segment 2. In some methods, T-shaped body 140 can also serve as a handle to facilitate movement of K-wires 178. In other methods, knob 152 is used to facilitate movement of K-wires 178. In some methods, K-wires 178 and bone segment 2 are pulled away from the bone segment 4 to increase the gap between bone segments 2, 4. In some methods, K-wires 178 and bone segment 2 are pushed toward the bone segment 4 to decrease the gap between bone segments 2, 4. In some methods, K-wires 178 and bone segment 2 are rotated relative to the bone segment 4 to alter the gap between bone segments 2, 4. In some methods, the device 100 remains positioned with bone segments 2, 4 during this motion to align bone segments 2, 4. FIGS. 32E-32F show the fracture is reduced. By manipulating (e.g., pulling, pushing, twisting) the K-wires 178, the fracture can be manually reduced.

In some methods it is desirable to maintain the position of the bone segments 2, 4. In some methods, one or more K-wires 178 are driven through the bone segment 2. K-wires 178 can be driven into the talus (not shown) to maintain the position of the bone segment 2. K-wires 178 can be driven into any stable surface to maintain the position.

FIG. 32G shows that in some methods, the gripper 108 is deployed to maintain the position of one or more the bone segments 2, 4. In some methods, gripper 108 can be deployed to maintain the position of bone segment 4. In some methods, the gripper 108 is not deployed until the fracture is reduced by manipulating the K-wires 178. In some methods, the gripper 108 is deployed prior to manipulating the K-wires 178. In some methods, the gripper 108 is deployed during manipulation of the K-wires 178.

Figure 32H:
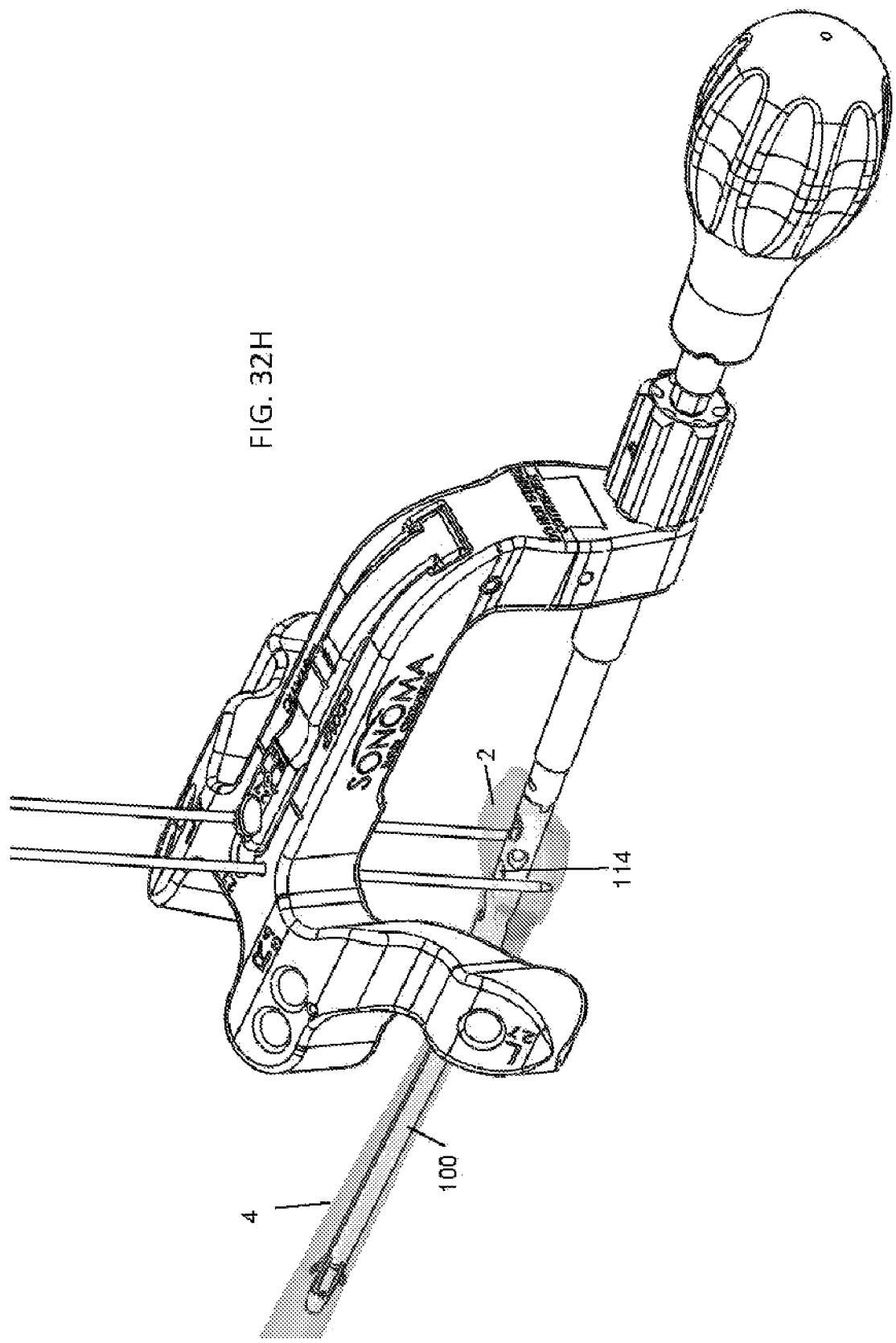

During actuation, bendable gripping members 118 of gripper 108 are urged radially outward by a ramped surface on actuator head 124. Actuator head 124 is threaded onto the distal end of actuator 126. As screw driver 155 turns actuator 126, a threaded surface of the actuator 126 rotates in relation to the actuator head 124. This causes the actuator head 124 to be drawn in a proximal direction toward the proximal end 102 of the device 100 as the actuator head 124 traverses the threaded surface of the actuator 126. The ramped surface on the actuator head 124 outwardly actuates gripper members 118. The device 100 may include a stop to prevent translation of the actuator 126. Gripper 108 is deployed in the bone segment 4 to lock the position of the device 100. FIG. 32G shows the method of immobilizing both bone segments 2, 4. Gripper 108 prohibits movement of the bone segment 4. K-wires 178 prohibit movement of bone segment 2. FIGS. 32H-32J show various views of the bone with the device 100.

In some methods, screw 110 (not shown) is inserted into aperture 114 of device 100. Screw 110 may be guided by removable alignment tube 168 as shown in FIG. 23. Screw 110 can be coupled to the bone segment 2 during insertion of screw 110. In the illustrated embodiments, screw 110 will extend transverse to the device 100. In some methods, one or more K-wires 178 remain in place while the screw 110 is inserted. Screw 110 can be located within the aperture 114 and coupled to the bone segment 2.

The bone segments 2, 4 have been previously aligned by manipulating K-wires 178. In some methods, shaft 162 (FIG. 26) is translated toward the distal end 104 of the device 100 toward the screw 110. Further translation of shaft 162 will push screw 110 and bone segment 2. Further rotation of the rotary driver 132 causes the screw 110 to translate within the aperture 114. Screw 110 and bone segment 2 can be pushed toward the distal end 104 of the device 100. As screw 110 is advanced toward bone segment 4, screw 110 functions to approximate the bone fracture. In some methods, K-wires 178 translate when the screw 110 is translated. In some methods, T-shaped body 140 and K-wires 178 translate when the screw 110 is translated.

Figure 33A:
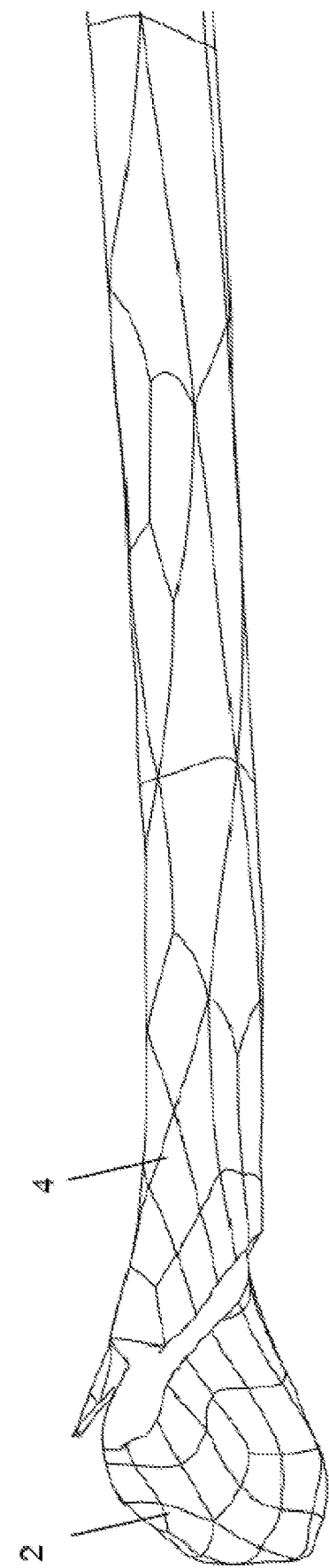

FIGS. 33A-33G are various method steps to implant the device of FIGS. 1-30. FIGS. 33A-33G shows the device 100, but any of the devices described herein can be inserted using one or more of the following method steps. FIG. 33A shows a fibula fracture. Typical fibula fractures result in a compressed and rotated bone fragments. Bone segment 2 is the distal fragment of the fibula and bone segment 4 is the proximal fragment of the fibula. In other methods, bone segment 2 is the proximal fragment of the fibula and bone segment 4 is a distal fragment of the fibula.

FIG. 33B shows a Hintermann style distractor 180. The Hintermann style distractor 180 can separate the compressed bone segments 2, 4 by actuating the handles. The Hintermann style distractor 180 can rotate the bone segments 2, 4 by deforming the K-wires 178 relative to each other. K-wires 178 inserted through the Hintermann style distractor 180 are position on either side of a proximal-distal line. K-wires 178 pass through the bone segments 2, 4 on either side of the device 100. In some methods, one or more K-wires 178 pass on the anterior side of the device 100. In some methods, one or more K-wires 178 pass on the posterior side of the device 100. The location and number of K-wires will depend on the nature of the fracture. FIG. 33C shows the fracture is reduced by distracting the bone segments 2, 4 and if necessary rotating the bone segments 2, 4 relative to each other.

Figure 33D:
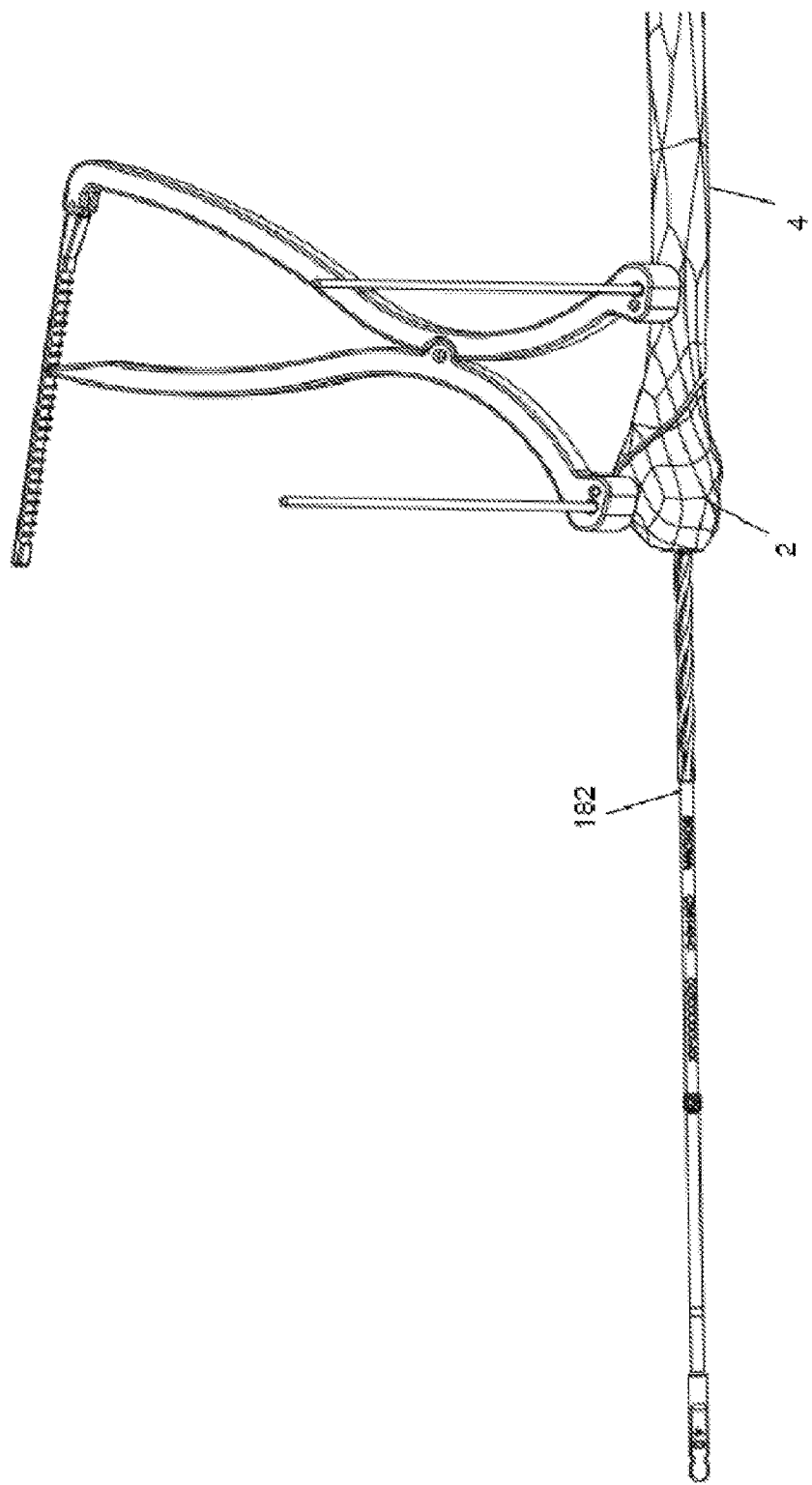

In some methods it is desirable prepare the bone segments 2, 4 for the device 100. FIGS. 33D-33E shows the insertion of a reamer 182 to prepare the bone segments 2, 4. In one embodiment, a reamer is a drill. In some methods, a reamer 182 is driven through the bone segments 2, 4. Strategic placement of the K-wires 178 allows the reamer 182 to pass through the bone segments 2, 4 without interfering with the K-wires 178.

Figure 33F:
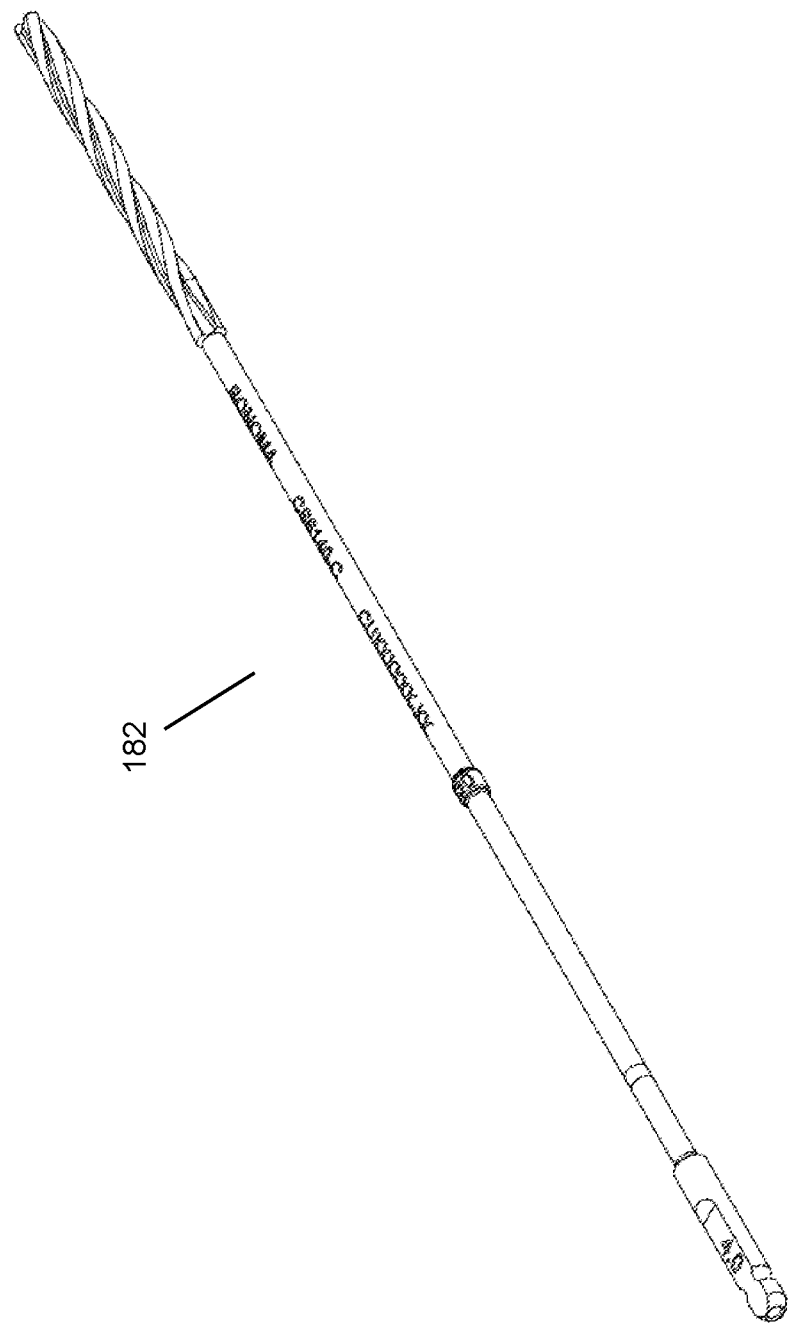

FIG. 33F shows an embodiment of the reamer 182. The reamer 182 has a proximal end and a distal end. The distal end can include at least one spiral cutting edge having a first diameter. The proximal end can include a handle. In some embodiments, the handle can be manipulated by a user. In some embodiments, the handle can be coupled to a power tool. A portion of the shaft of the reamer 182 has a diameter less than the first diameter (e.g., an area of reduced diameter). In some embodiments, the reamer 182 includes a through lumen. The through lumen of the reamer 182 can be inserted over a guiding wire. The shank of the reamer 182 can have a reduced diameter to increase the flexibility. In some embodiments, a radiographic depth indicator on the shank indicates when the proper drilling depth is achieved.

Figure 33G:
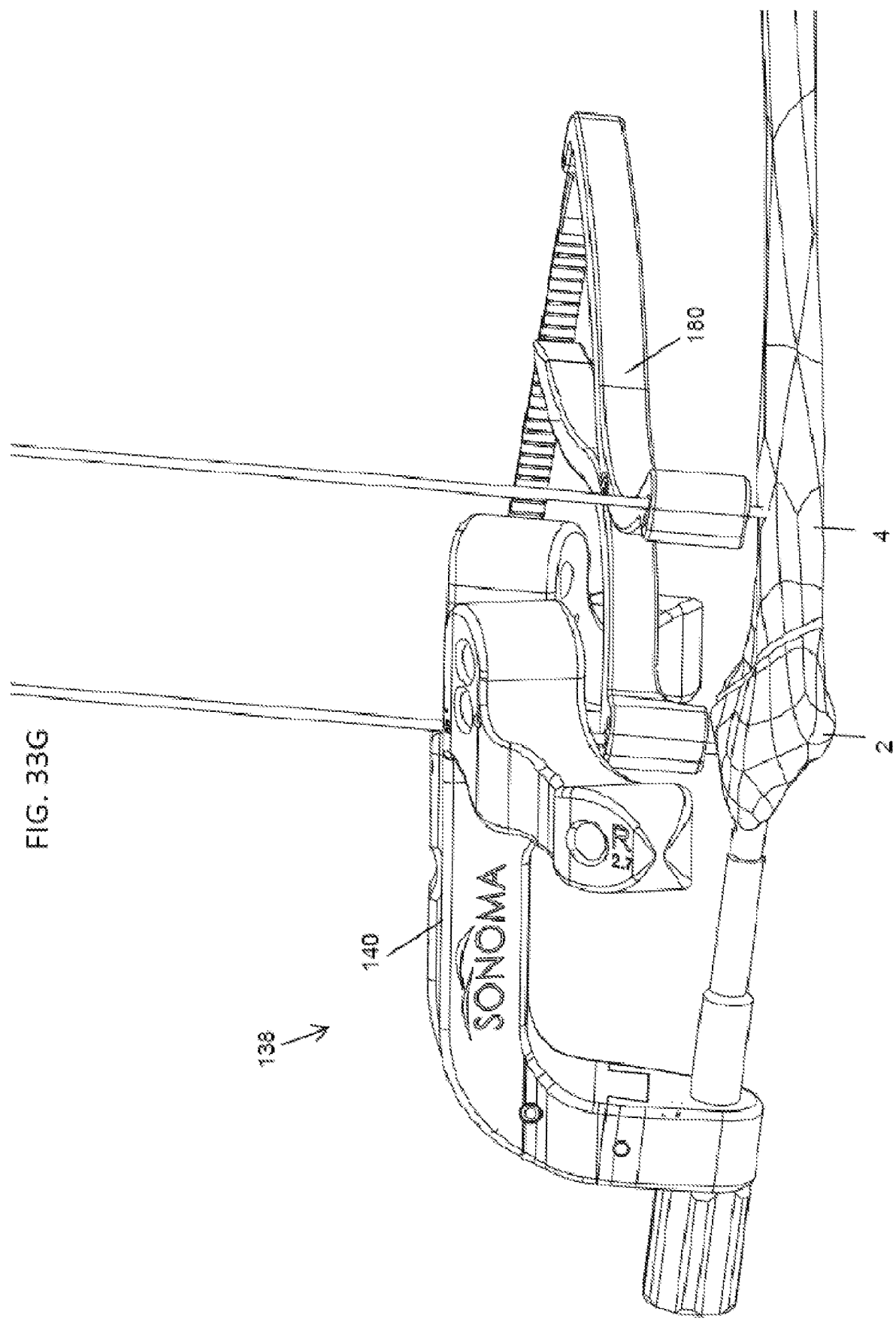

FIG. 33G shows the implant 100 (not shown) can be inserted with the combination tool 138 while maintaining the reduction with the Hintermann style distractor 180. In some methods, T-shaped body 140 can also serve as a handle to facilitate insertion of the device 100. Grippers 108 can be deployed (as shown in FIGS. 32G-32I). Screw 110 may be guided through the device 100. In some methods, shaft 162 (FIG. 26) is translated toward the distal end 104 of the device 100 toward the screw 110, as described herein.

Figure 34D:
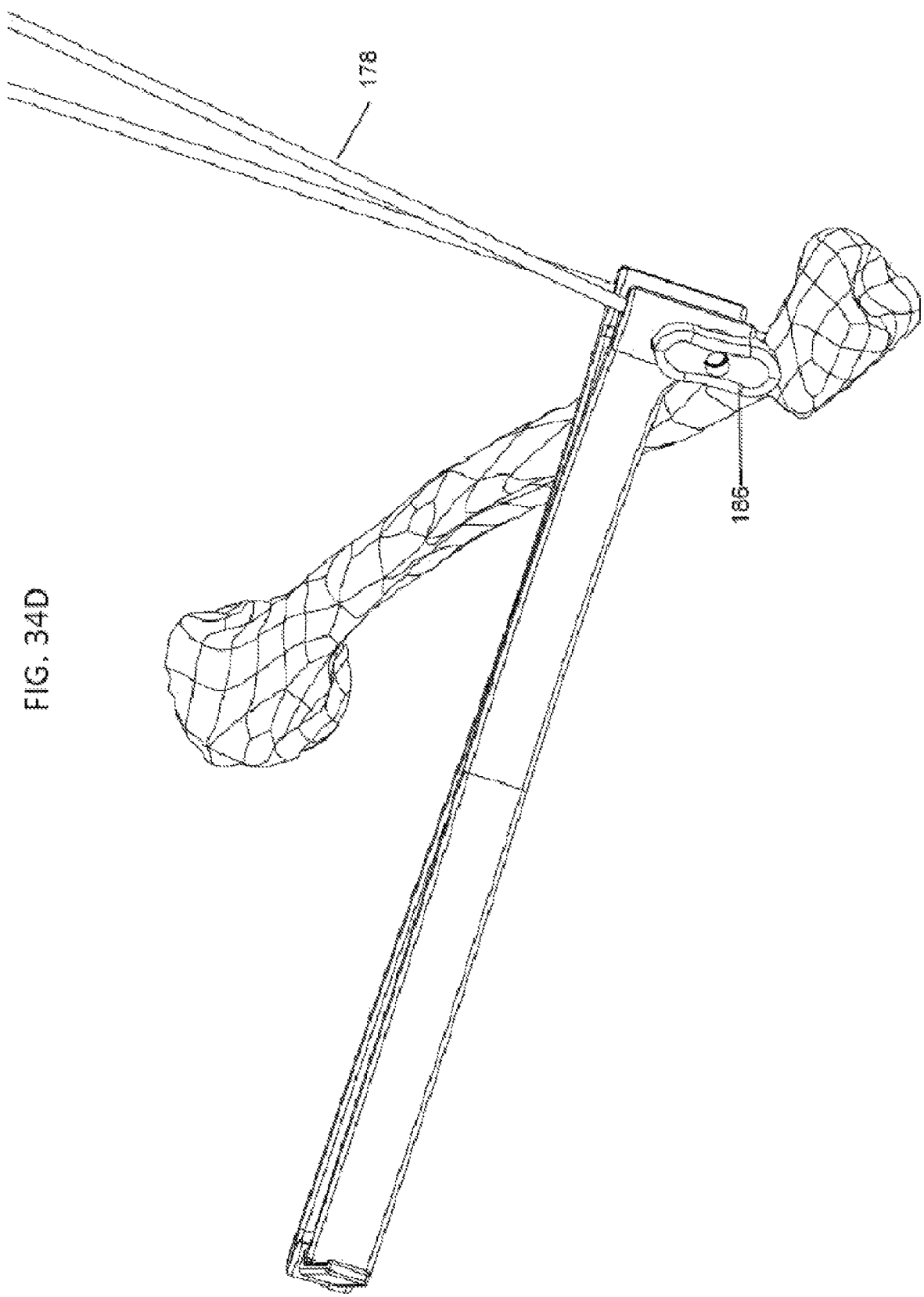

FIGS. 34A-34D are various method steps to implant the device of FIGS. 1-30. FIGS. 34A-34D shows the device 100, but any of the devices described herein can be inserted using one or more of the following method steps. FIG. 34A shows an alternative style distractor 184. This distractor 184 can allow rotation of the bone segment 2 without requiring wire deformation of one or more K-wires 178. FIGS. 34A and 34C show a compressed and rotated bone segment 2. Knob 186 of distractor 184 can be rotated to rotate the bone segment 2. FIGS. 34A and 34C show the bone segment 2 in the original position. FIGS. 34B and 34D show the bone segment 2 rotated to a new position.

Figure 35A:
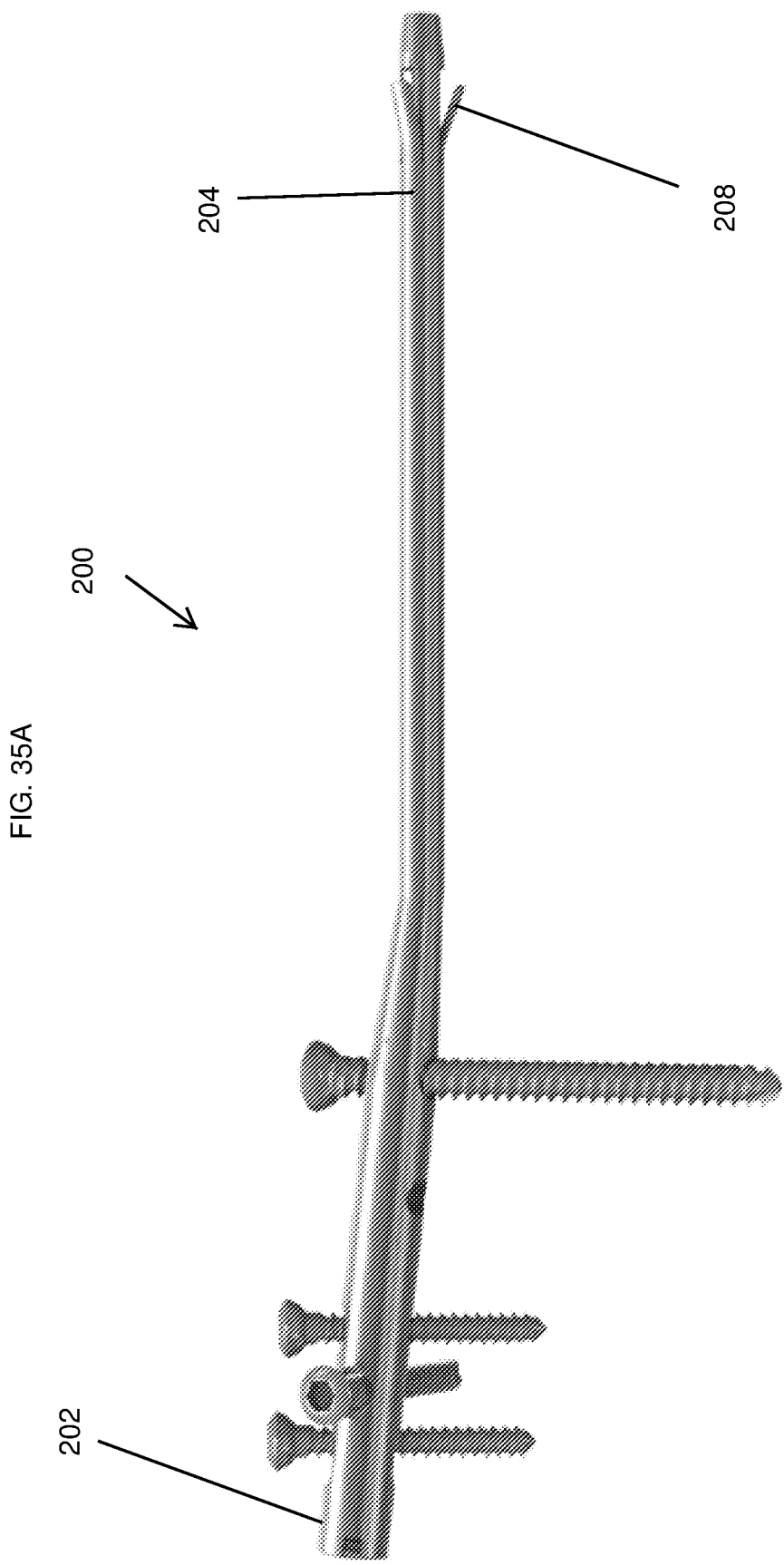
FIGS. 35A-35B are perspective views of another embodiment of a bone fixation device shown in a deployed state.
Figure 35B:
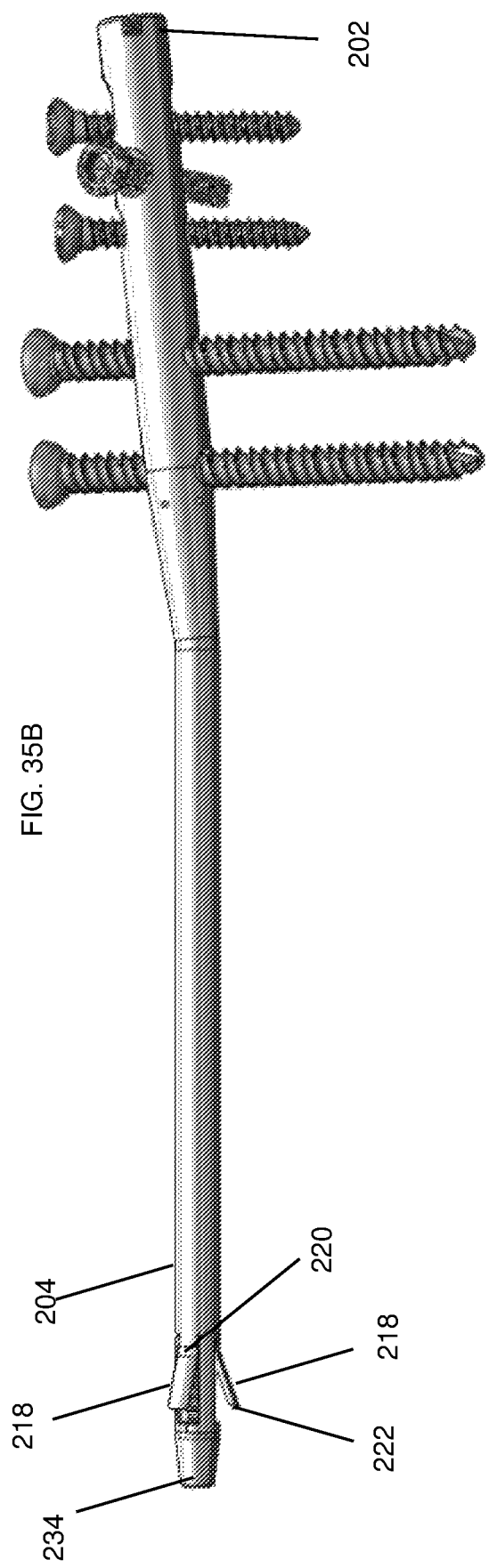

FIGS. 35A and 35B are perspective views of an embodiment of a bone fixation device 200 having a proximal end 202 (nearest the surgeon) and a distal end 204 (further from surgeon) and positioned within the bone space of a patient according to the invention. The bone fixation device 200 can be similar to bone fixation device 100, and can include any feature or combination of features described herein. In this example, device 200 is configured to be implanted in the fibula, but other configurations for other bony segments are contemplated. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 200 is used for fixation of fractures of the proximal or distal end of long bones such as intracapsular, intertrochanteric, intercervical, supracondular, or condular fractures of the fibula; for fusion of a joint; or for surgical procedures that involve cutting a bone. The devices 200 may be implanted or attached through the skin so that a pulling force (traction may be applied to the skeletal system).

The design of the fixation device 200 depicted is adapted to provide a bone engaging mechanism or gripper 208 adapted to engage target bone of a patient from the inside of the bone. As configured for this anatomical application, the device 200 is designed to facilitate bone healing when placed in the intramedullary space within a post fractured bone. This device 200 has a gripper 208 positioned distally and shown deployed radially outward against the wall of the intramedullary cavity in FIG. 36. On entry into the cavity, gripper 208 is flat and retracted, as described herein. Upon deployment, gripper 208 pivots radially outward and grips the diaphyseal bone from the inside of the bone.

Figure 36:
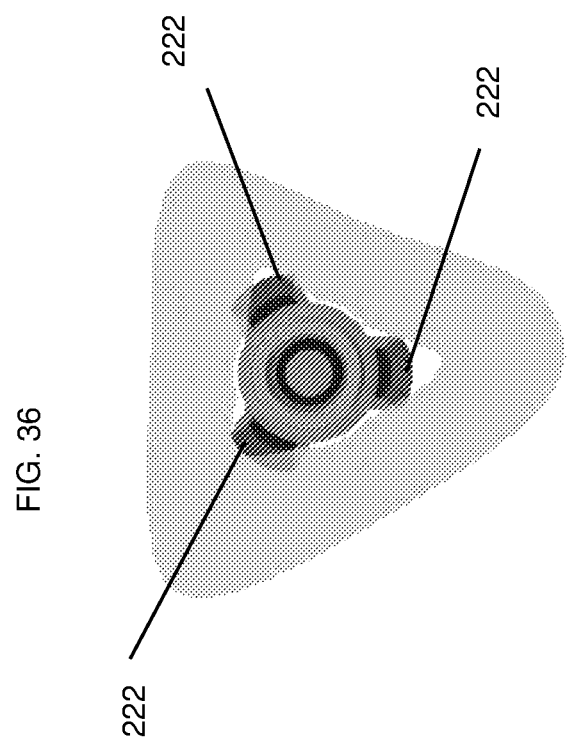
FIG. 36 is a perspective view of the distal end of the device shown in FIG. 35A in a deployed state.

FIG. 35B shows a perspective view of the device 200 in a deployed configuration. In this embodiment, gripper 208 includes opposing bendable gripping members 218. The bendable gripping members 218 can be referred to as talons. Three bendable gripping members 218 are shown in FIG. 36, but other configurations are contemplated. Each bendable gripping member 218 is located at the same axial location but offset by 120 degrees. Each bendable gripping member 218 has a thinned portion 220 that permits bending as the opposite distal end 222 of bendable gripping member 218 is urged radially outward, such that bendable gripping member 218 pivots about thinned portion 220. When extended, distal ends 222 of bendable members 218 contact the inside of the bone to anchor the distal portion of device 200 to the bone, as shown in FIG. 36. The device 200 has triangular bendable gripping members 218 which are ideal for fixation in the triangular fibula canal. The bone canal can be any shape including circular, non-circular or triangular. The gripper 208 can have any shape gripping members 218 to correspond with the anatomical canal. In alternative embodiments (not shown), the gripper may comprise 1, 2, 3, 4, 5, 6 or more bendable gripping members similar to bendable gripping members 218 shown.

FIG. 35B shows a hemispherical tip cover 234 may be provided at the distal end 204 of the device 200 to act as a blunt obturator. This arrangement facilitates penetration of bone (e.g. an intramedullary space) by device 200 while keeping the tip of device 200 from digging into bone during insertion.

Figure 37:
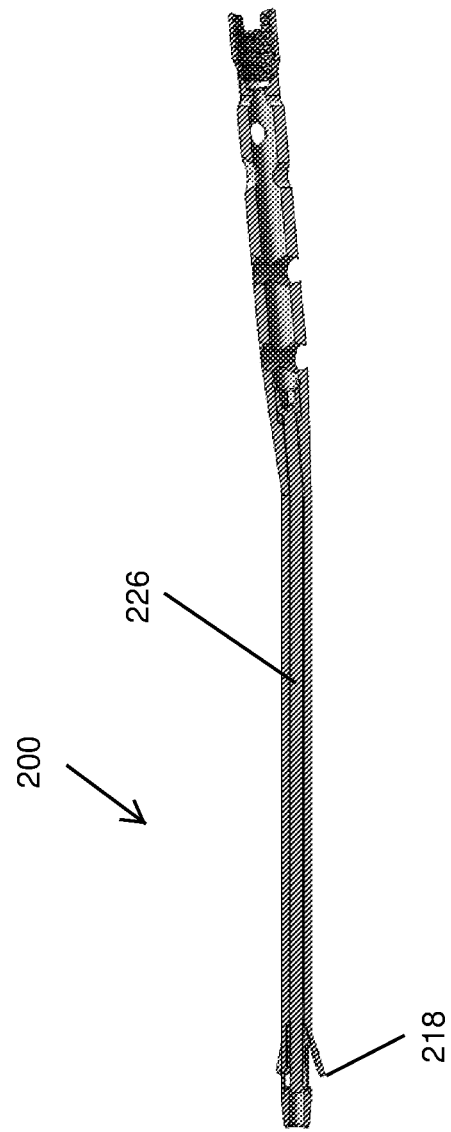
FIG. 37 is a longitudinal cross-section view of the bone fixation device of FIG. 35A in a deployed state

FIG. 37 shows a longitudinal cross-section of device 200 in a deployed configuration. The device 200 includes an actuator 226 to deploy the device 200 from a un-deployed configuration to the deployed configuration. The actuator 226 interacts with the bendable gripping members 218 to splay the bendable gripping members 218 outward from the device 200.

FIGS. 38A-38D show various views of the device 200. The device 200 can include a hub 212 comprising one or more aperture 10, 12, 14, 16, 18. Each aperture 10, 12, 14, 16, 18 has an angle corresponding to the anatomy of the patient. Some apertures accept one type or length of screw. Some apertures accept another type or length of screw. One or more screws 20, 22 are placed through apertures 10, 12, 14, 16, 18 through the hub 212 to lock the device 200 to the bone, as described below. Hence, the metaphysis and the diaphysis are joined.

The screws 20 are distal screws. The screws 20 have a length between 12 mm and 20 mm. The screws 20 have a diameter of 2.7 mm. The screws 20 are locking screws. The screws 20 engage cortical bone. The screws 20 are multi-planar. The screws 20 are locking screws which can resist back-out. Multi-planar screws 20 are stronger in pull out, torsions, tension and compression. Two screws 20 can have the same orientation. Aperture 10 and 14 can have the same orientation. Apertures 10 and 14 can position screws 20 in the lateral-medial directions, as described herein. One screws 20 can have a different orientation. Aperture 12 can have a different orientation than apertures 10 and 14. Apertures 12 can position screw 20 in the anterior-posterior direction. The aperture 12 is externally rotated in relation to the transepicondylar axis. The aperture 12 is rotated anteriorly from the coronal plane. The screw 20 through aperture 12 is placed obliquely an angle alpha. The angle alpha is approximately 60 degrees from anteromedial to posterolateral in the transverse plane. The aperture 12 is oriented 60 degree anteriorly.

In alternative embodiments (not shown), the device may comprise a 40 degree, 45 degree, 50 degree, 55 degree, 60 degree, 65 degree, 70 degree, 75 degree, 80 degree, or different anterior angle similar to angle of the aperture 12 shown. The aperture 12, may form an anterior angle of, for example, approximately 30 degrees, approximately 35 degrees, approximately 40 degrees, approximately 45 degrees, approximately 50 degrees, approximately 55 degrees, approximately 60 degrees, approximately 65 degrees, approximately 70 degrees, approximately 75 degrees, approximately 80 degrees, approximately 85 degrees, approximately 90 degrees etc. The aperture 12, may form an angle of, for example, between 50-60 degrees, between 55-65 degrees, between 60-70 degrees, between 65-75 degrees, etc. The aperture 12, may form an angle of, for example, between 40-60 degrees, between 45-65 degrees, between 50-70 degrees, between 55-75 degrees, between 60-80 degrees, between 65-85 degrees etc. The aperture 12, may form an angle of, for example, between 50-70 degrees, between 45-75 degrees, or between 40-80 degrees, etc.

The screws 22 are syndesmotic screws. The screws 22 have a length between 40 mm and 70 mm. The screws 22 have a diameter of 3.5 mm. The screws 22 are non-locking screws. The screws 22 engage cortical bone. The screws 22 are double-lead threads, which rotate twice as fast to engage bone. FIG. 38A shows three screws 20 and two screws 22, but other configurations are contemplated. In alternative embodiments (not shown), the device may comprise 1, 2, 3, 4, 5, 6 or more screws similar to screw 20 shown. In alternative embodiments (not shown), the device may comprise 1, 2, 3, 4, 5, 6 or more screws similar to screw 22 shown. Aperture 16 and 18 can have the same orientation. Apertures 16 and 18 can position screws 22, as described herein. The apertures 16 and 18 are externally rotated in relation to the transepicondylar axis. The apertures 16 and 18 are rotated posteriorly from the coronal plane. The aperture 12 can position the screw 20 in an opposite direction from the coronal plane than the apertures 16 and 18. The screws 22 are placed obliquely an angle beta. The angle is approximately 25 degrees from posterolateral to anteromedial in the transverse plane. The apertures 16 and 18 are oriented 25 degree posteriorly.

In alternative embodiments (not shown), the device may comprise 10 degree, 15 degree, 20 degree, 25 degree, 30 degree, 35 degree, 40 degree, 45 degree, 50 degree, or different degree posteriorangle similar to angle of the apertures 16 and 18 shown. The apertures 16 and 18, may form a posterior angle of, for example, approximately 10 degrees, approximately 15 degrees, approximately 20 degrees, approximately 25 degrees, approximately 30 degrees, approximately 35 degrees, approximately 40 degrees, approximately 45 degrees, approximately 50 degrees, etc. The apertures 16 and 18, may form a posterior angle of, for example, between 15-25 degrees, between 20-30 degrees, between 25-35 degrees, between 30-40 degrees, etc. The apertures 16 and 18, may form a posterior angle of, for example, between 5-25 degrees, between 10-30 degrees, between 15-35 degrees, between 20-40 degrees, between 25-45 degrees, or between 30-50 degrees, etc. The apertures 16 and 18, may form a posterior angle of, for example, between 20-30 degrees, between 15-35 degrees, between 10-40 degrees, or between 5-45 degrees, etc.

The device 200 has a 6 degree bend between the hub 212 and the distal end 204 as shown in FIG. 38B. In alternative embodiments (not shown), the device may comprise 1 degree, 2 degree, 3 degree, 4 degree, 5 degree, 6 degree, 7 degree, 8 degree, 9 degree, 10 degree, 11 degree, 12 degree, 13 degree, 14 degree, 15 degree, or different degree bend similar to bend shown. The device 200 has a left configuration and a right configuration. For two proximal diameters (3 mm, 3.8 mm) and lengths (130 mm, 180 mm), there are many possible configurations (e.g., 3 mm×130 mm left and right, 3.8 mm×130 mm left and right, 3 mm×180 mm left and right, 3.8 mm×180 mm left and right).

Figure 39B:
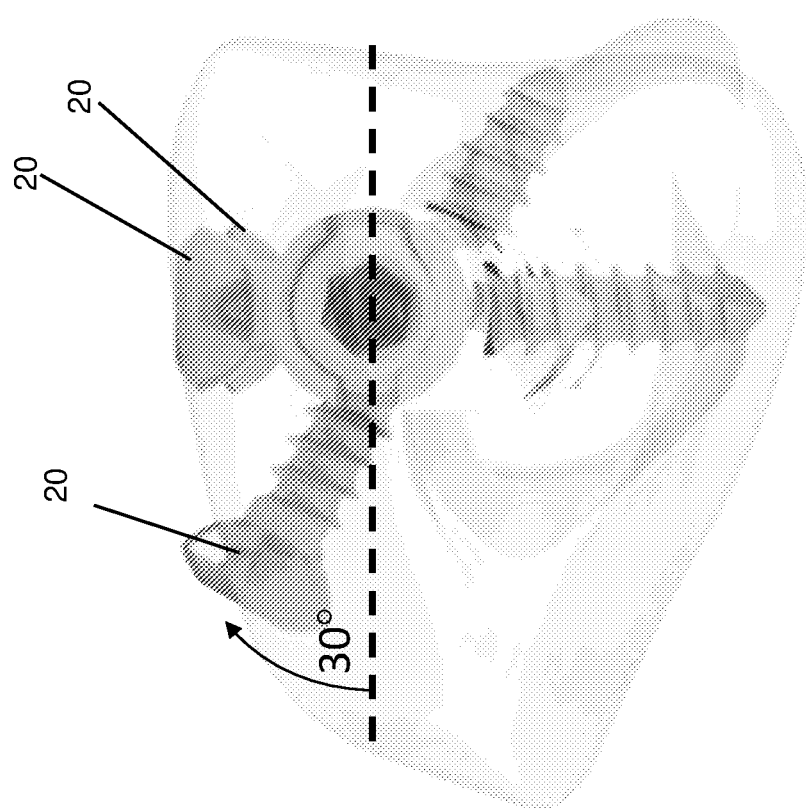
FIGS. 39A-39B are perspective views of the proximal end of the device shown in FIG. 35A.
Figure 39A:
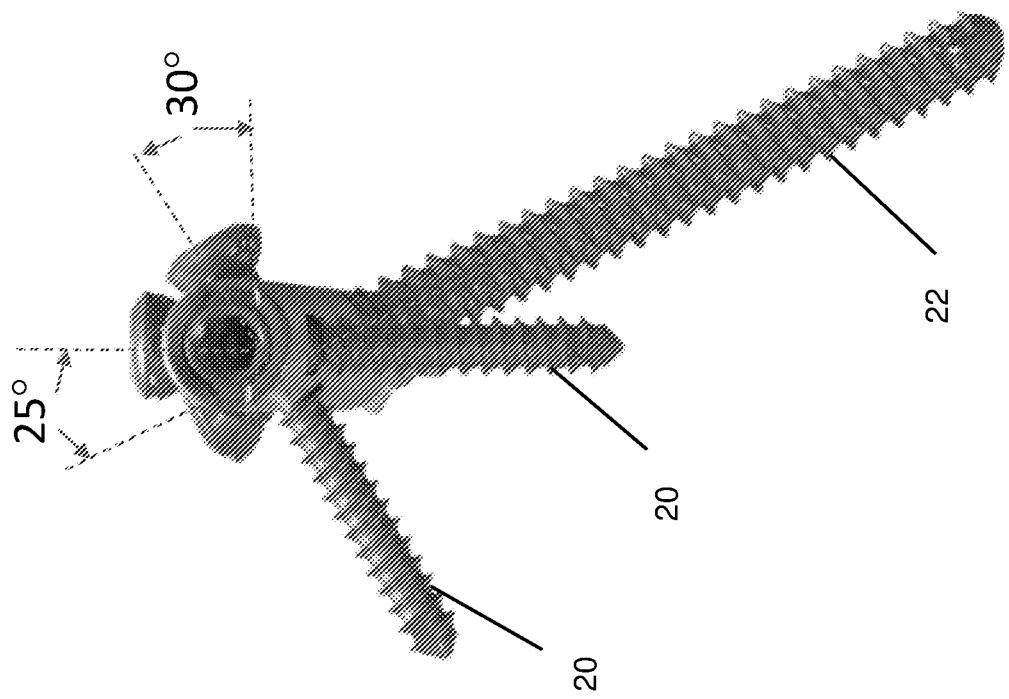

FIGS. 39A-39B show other views of the screws 20, 22. The apertures 16 and 18 are 25 degree anteriorly. The aperture 12 has a 30 degree orientation from directly anterior.

FIG. 40 illustrates a method of inserting a compression screw 24 into an aperture 10. The compression screw 24 can be substantially similar or identical to screw 20. The screw 24 can be inserted with a combination tool, described herein. The screw 24 is aligned with the aperture 10. In some embodiments, the screw 24 is oriented perpendicular to the longitudinal axis of the hub 212. The aperture 10 has at least one dimension greater that the diameter of the screw 24. The at least one dimension can be aligned with the longitudinal axis of the hub 212 and/or the longitudinal axis of the device 200. The aperture 10 can be generally oblong, elliptical or tear shaped. The shape of the aperture 10 allows the screw 24 to translate within the aperture 8. The screw 24 can be inserted into the aperture 10 near the proximal end 202 of the device 200. The screw can be translated toward the distal end 204 of the device 200 while within the aperture 8. FIG. 40A shows the screw 24 inserted in the aperture 10 near the proximal end 202 of the device 200. FIG. 40 shows the screw 24 translated within the aperture 10 toward the distal end 204 of the device 200. In alternative embodiments (not shown), the screw 24 translates automatically due to the shape of the aperture 8. As the screw 24 is rotated, the screw 24 encounters resistance of the aperture 8. In order to continue to rotate, the screw 24 translates itself within the aperture 10 toward the distal end 204 of the device 200.

Figure 41B:
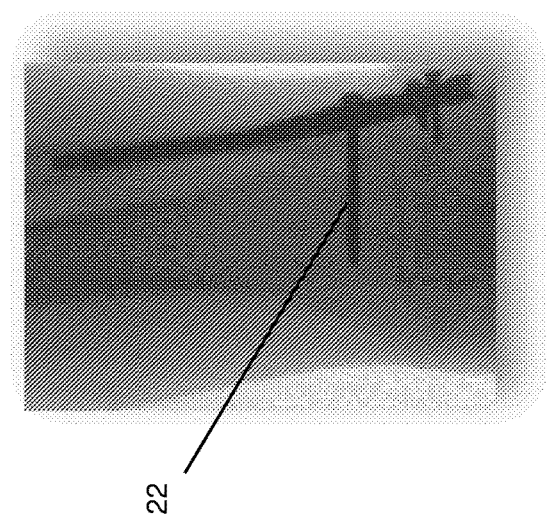
FIGS. 41A-41B are perspective views of the device shown in FIG. 35A shown in a deployed state during syndesmosis fixation.
Figure 41A:
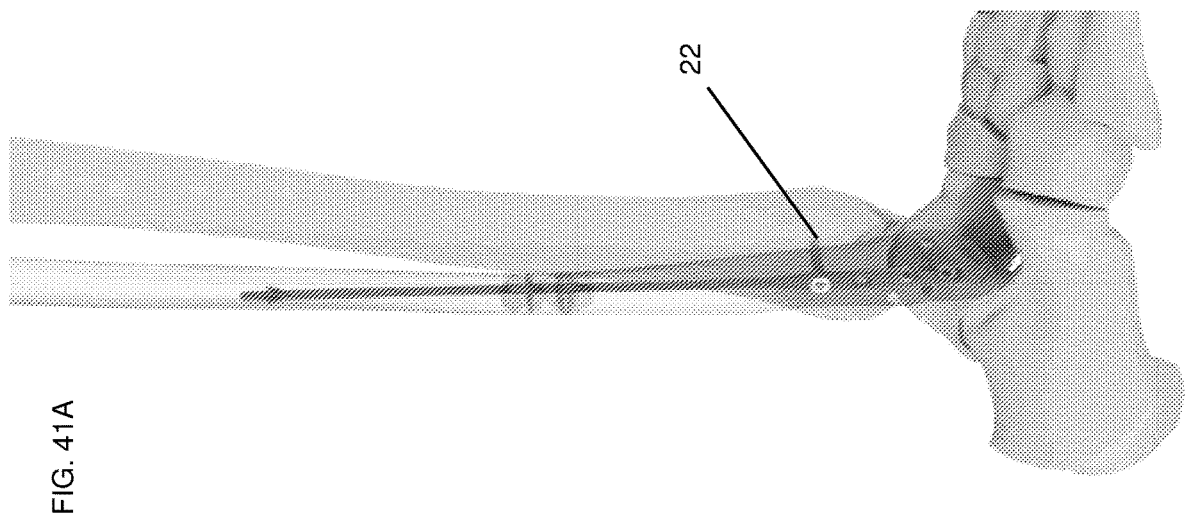
Figure 42:
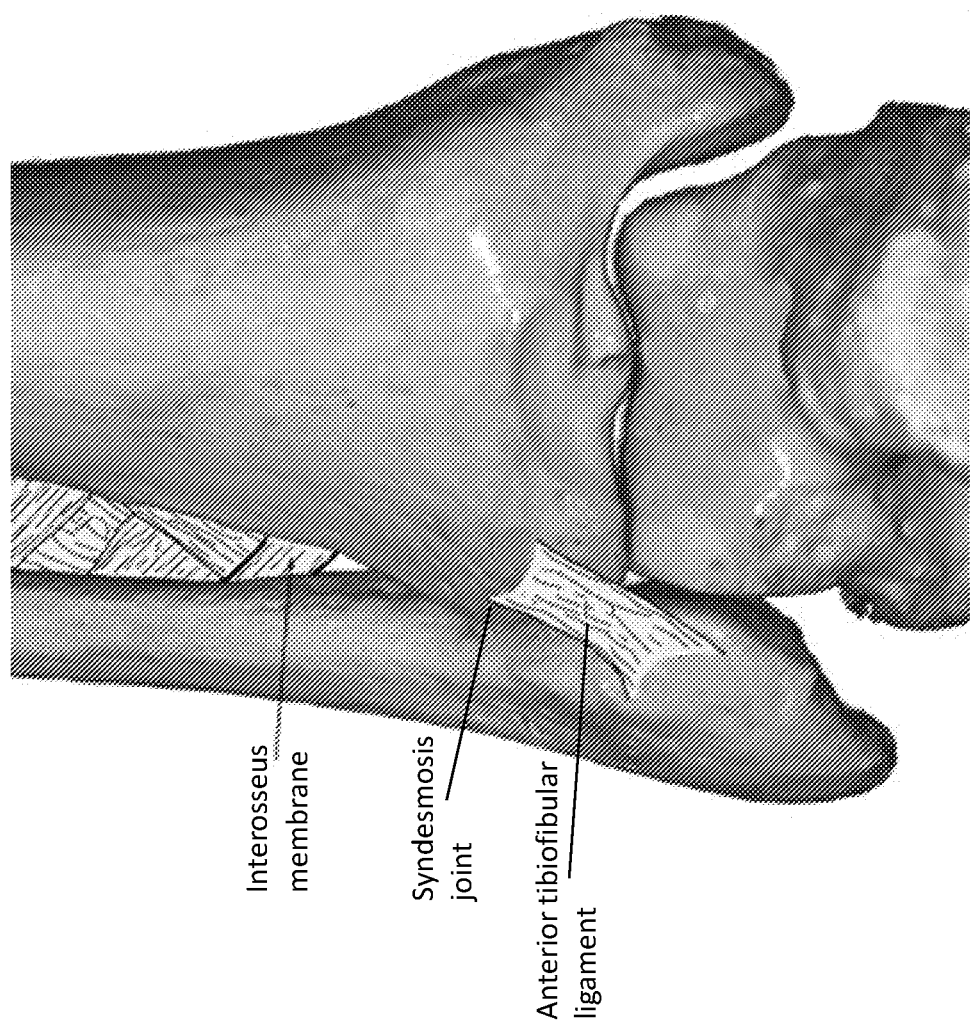
FIG. 42 is a view of the anatomy.

FIGS. 41A-41B show syndesmosis fixation. The screws 22 are syndesmotic screws, as described herein. The screws 22 are parallel to the ankle joint. The screws 22 are anatomically oriented 25 degrees anteriorly. The screws 22 are anatomically oriented. FIG. 42 shows the anatomical joint. The fibula sits posterior to the tibia. The fibula is connected to the tibia by the syndesmosis ligament. The syndesmosis ligament is comprised of the anterior tibiofibular ligament, the posterior tibiofibular ligament and the interosseous membrane. The syndesmosis joint is where the fibular incisura notch in the tibia meets the fibular. Referring back to FIGS. 41A-41B, the angle of the screws 22 reduces syndesmotic injury anatomically.

Figure 43B:
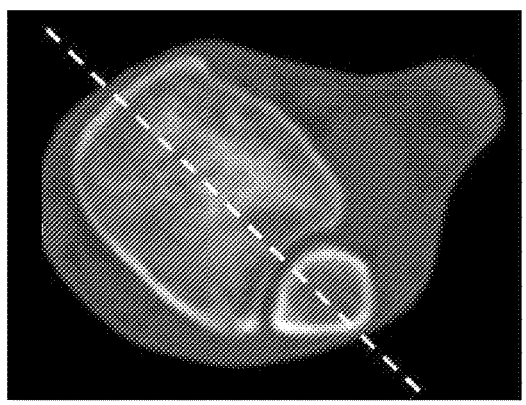
FIGS. 43A-43C are views of the anatomy.
Figure 43A:
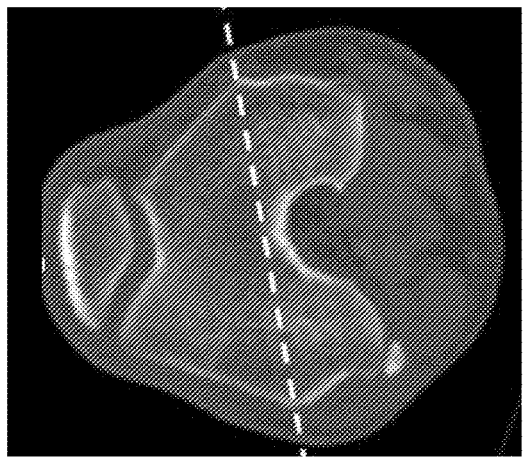
Figure 43C:
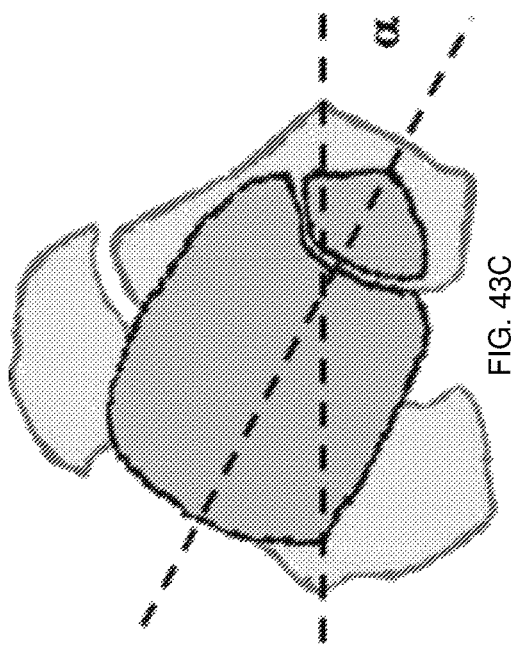

FIGS. 43A-43B shows data from a study. In some methods of use, transsyndesmotic screws are placed obliquely 30° from posterolateral to anteromedial in the transverse plane. Thirty-eight CT scans of the relevant anatomy were used to examine the rotational profile of the axis of the syndesmotic joint in relation to the transepicondylar axis. FIG. 43A shows a line drawn between the femoral epicondyles. FIG. 43B shows the rotation of the syndesmosis 10 mm superior to the ankle joint. FIG. 43C shows syndesmosis rotation superimposed on the transepicondylar axis. The average angle was 32°±6°. In other words, the axis of the distal tibiofibular joint was 32°±6° externally rotated in relation to the transepicondylar axis. This study demonstrates that the axis of the uninjured distal tibiofibular joint is approximately 30° externally rotated in relation to the transepicondylar axis.

Figure 44A:
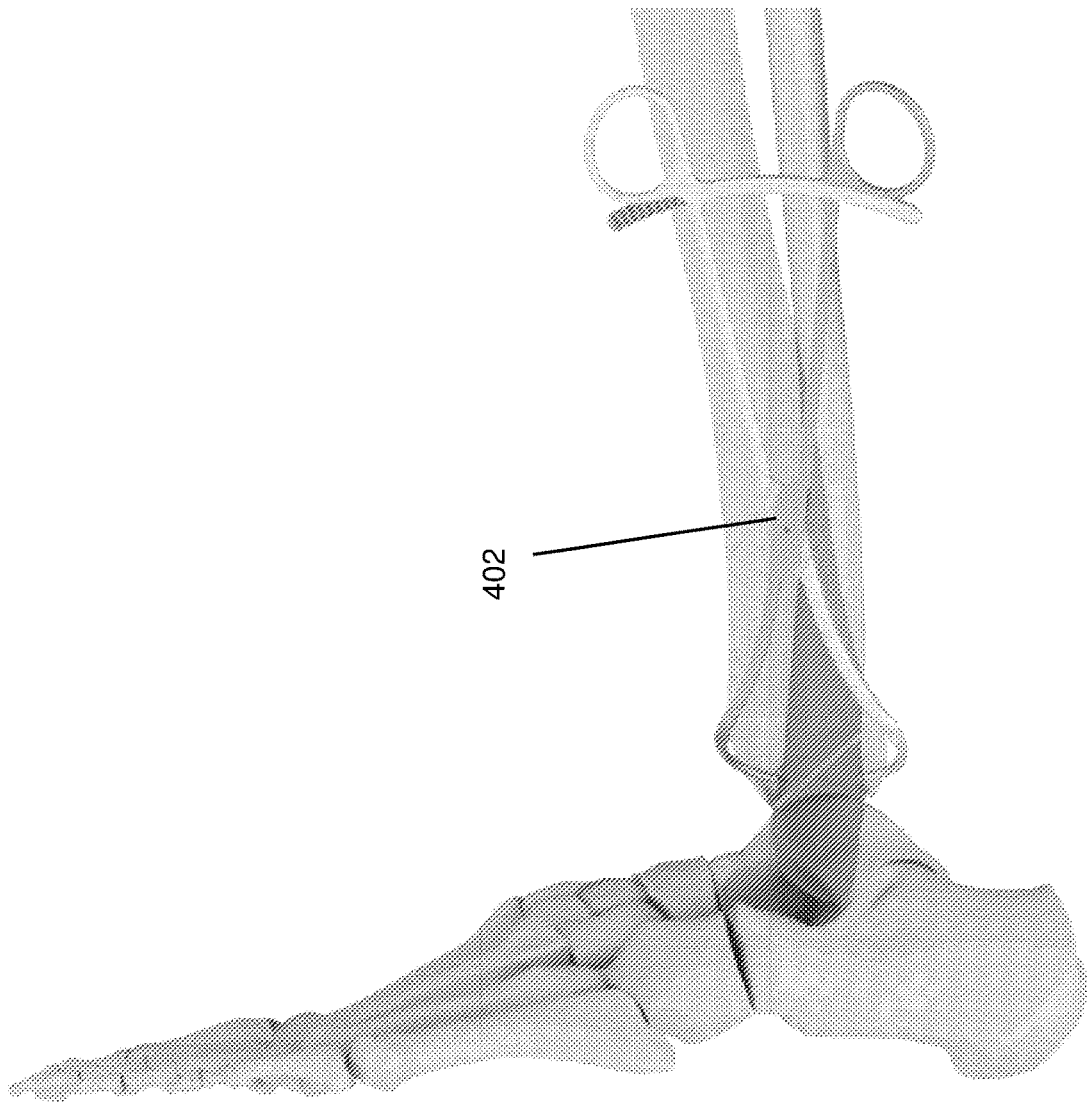
FIGS. 44A-44S are various method steps to implant the device of FIGS. 35-41B.
Figure 44B:
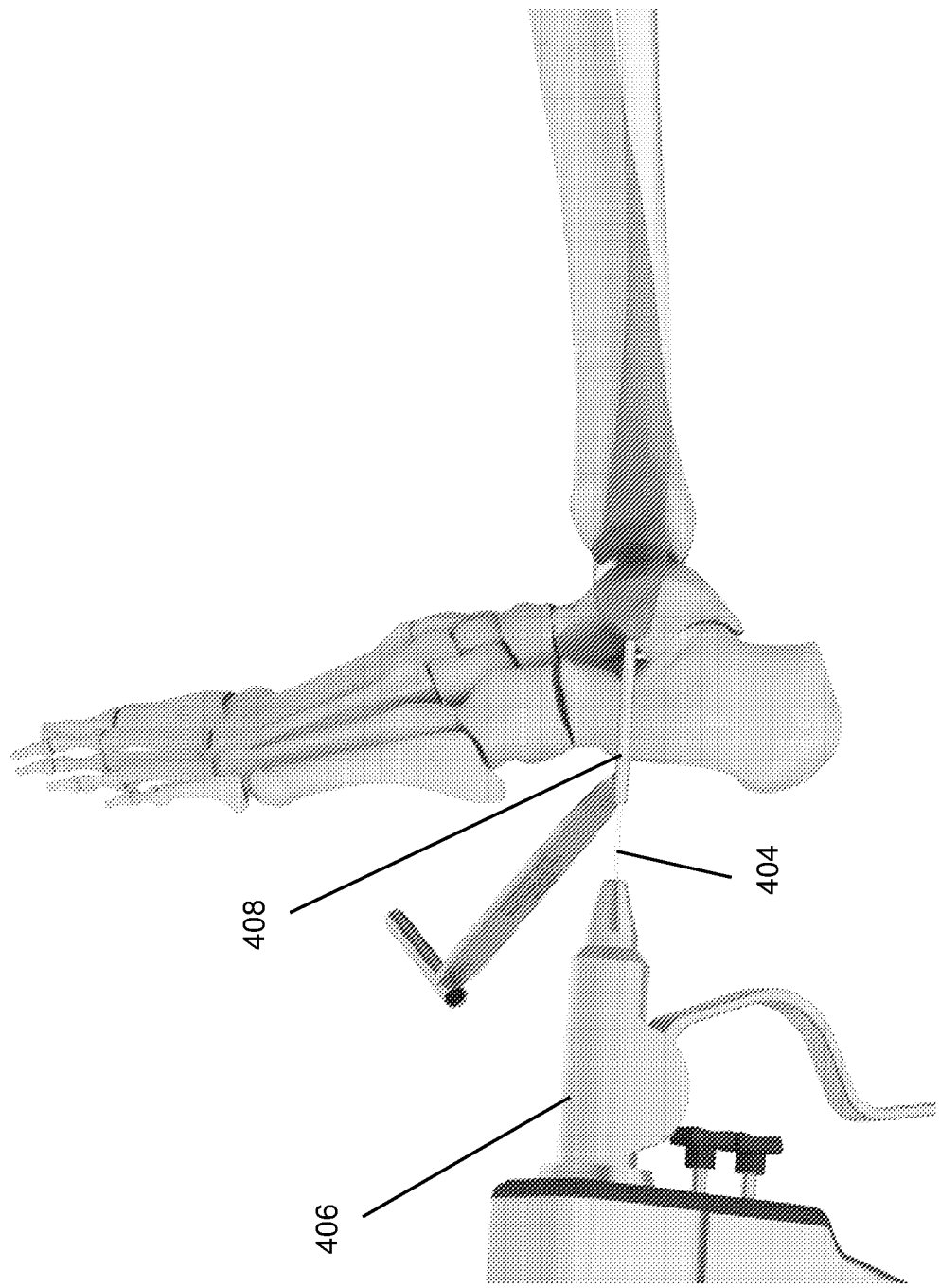
Figure 44C:
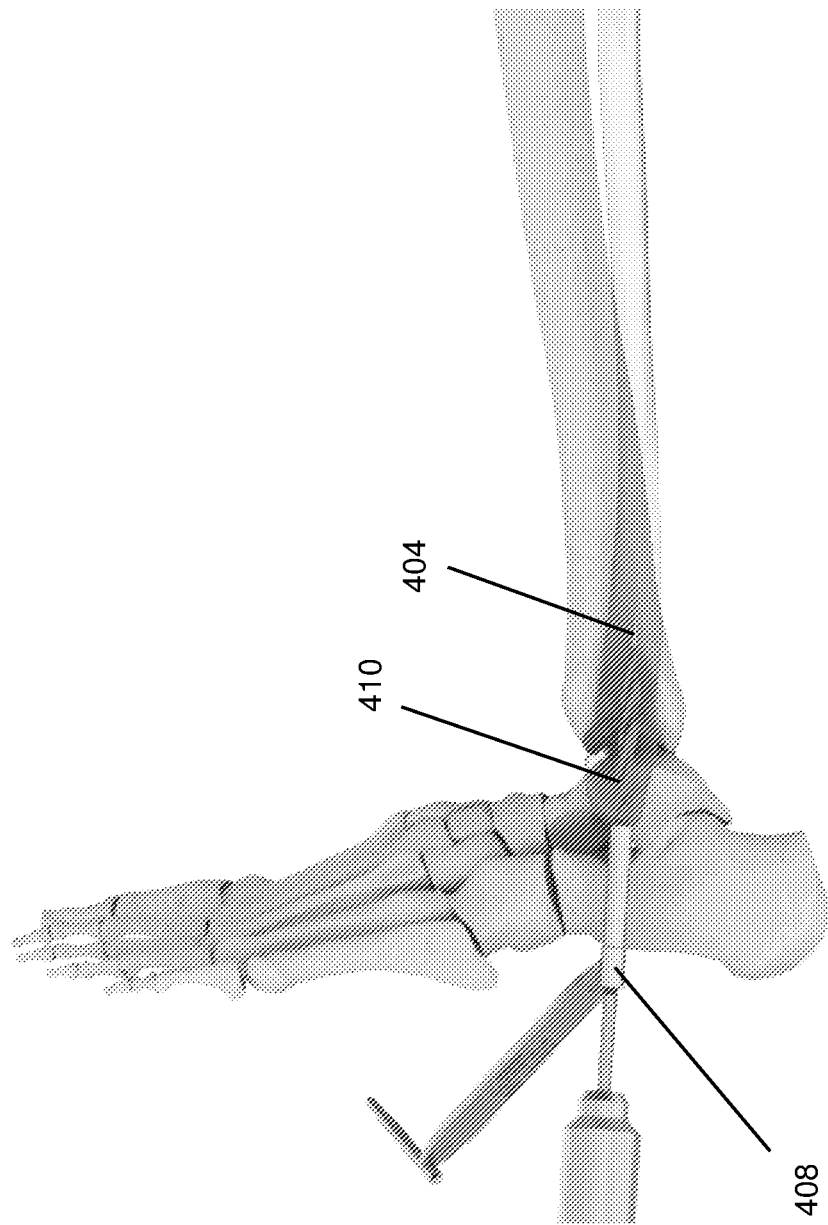
Figure 44D:
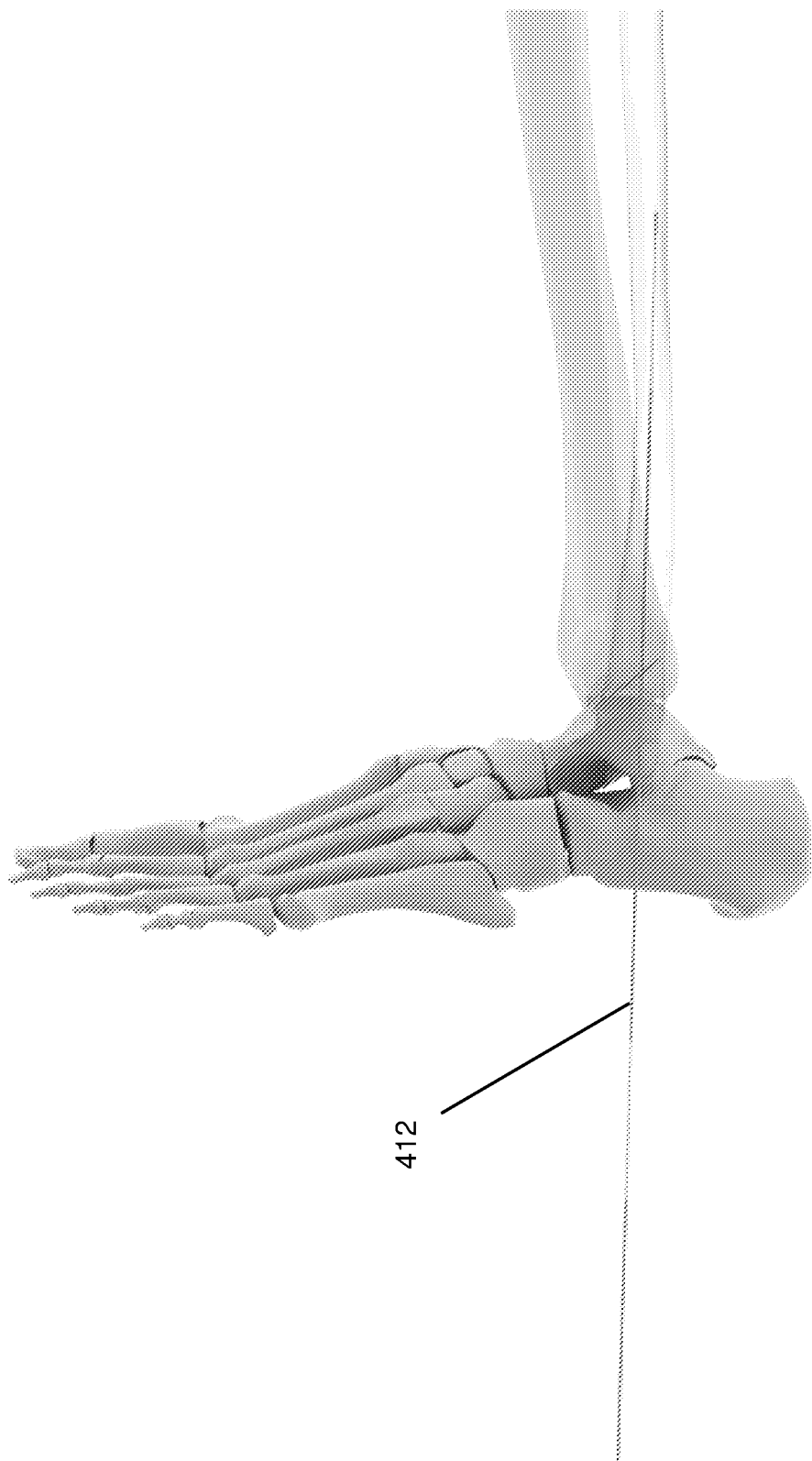
Figure 44E:
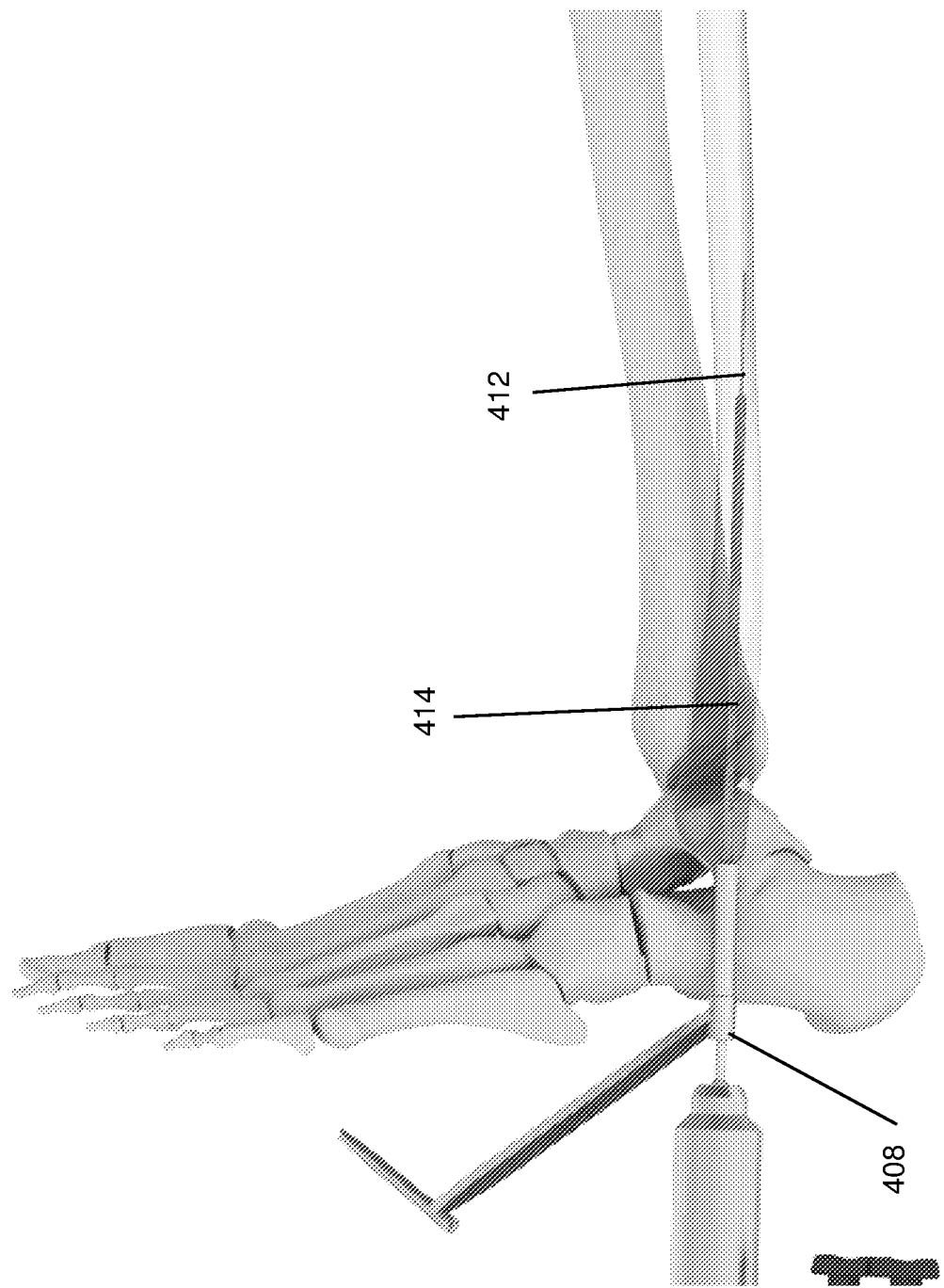
Figure 44F:
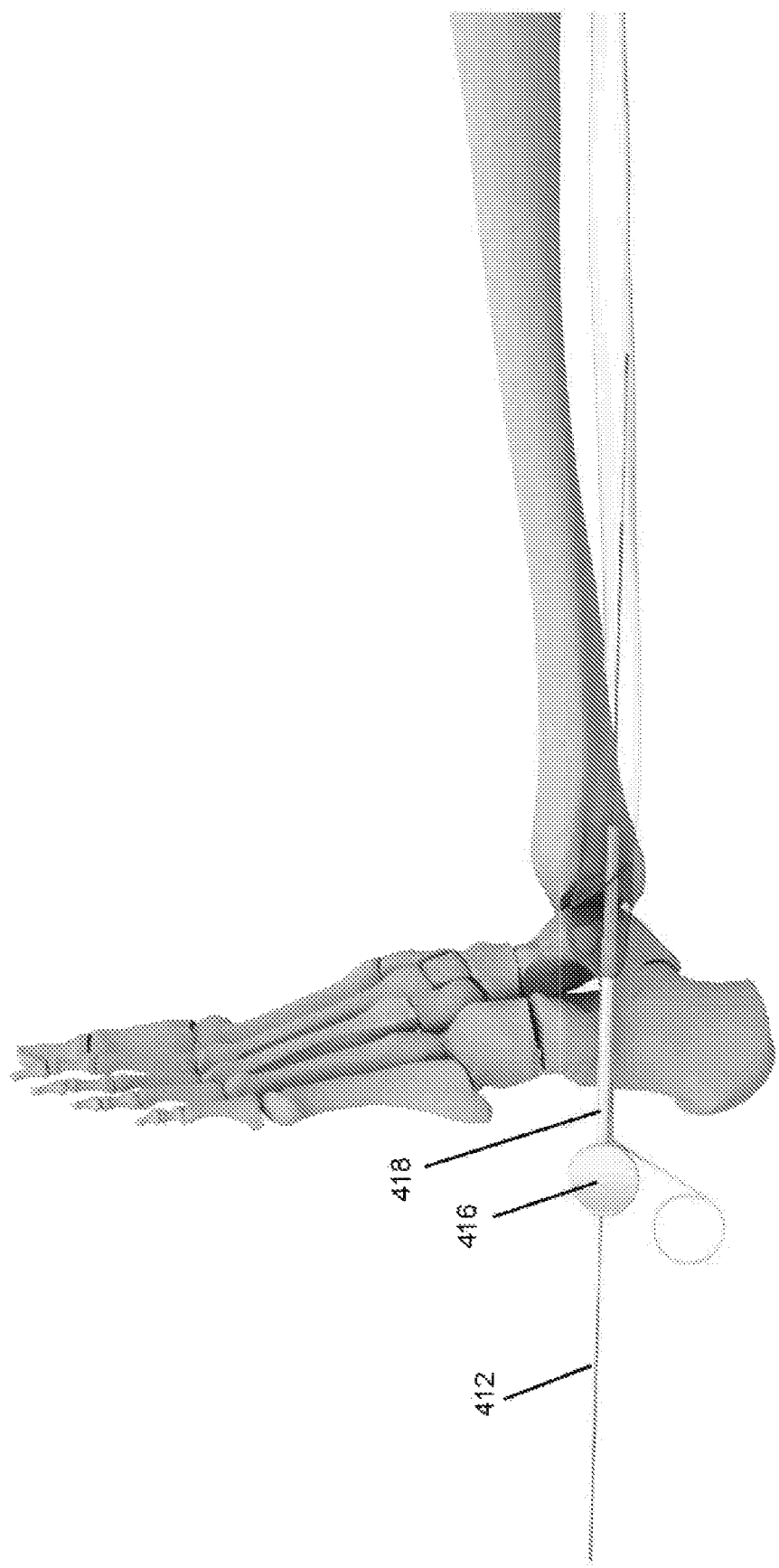
Figure 44G:
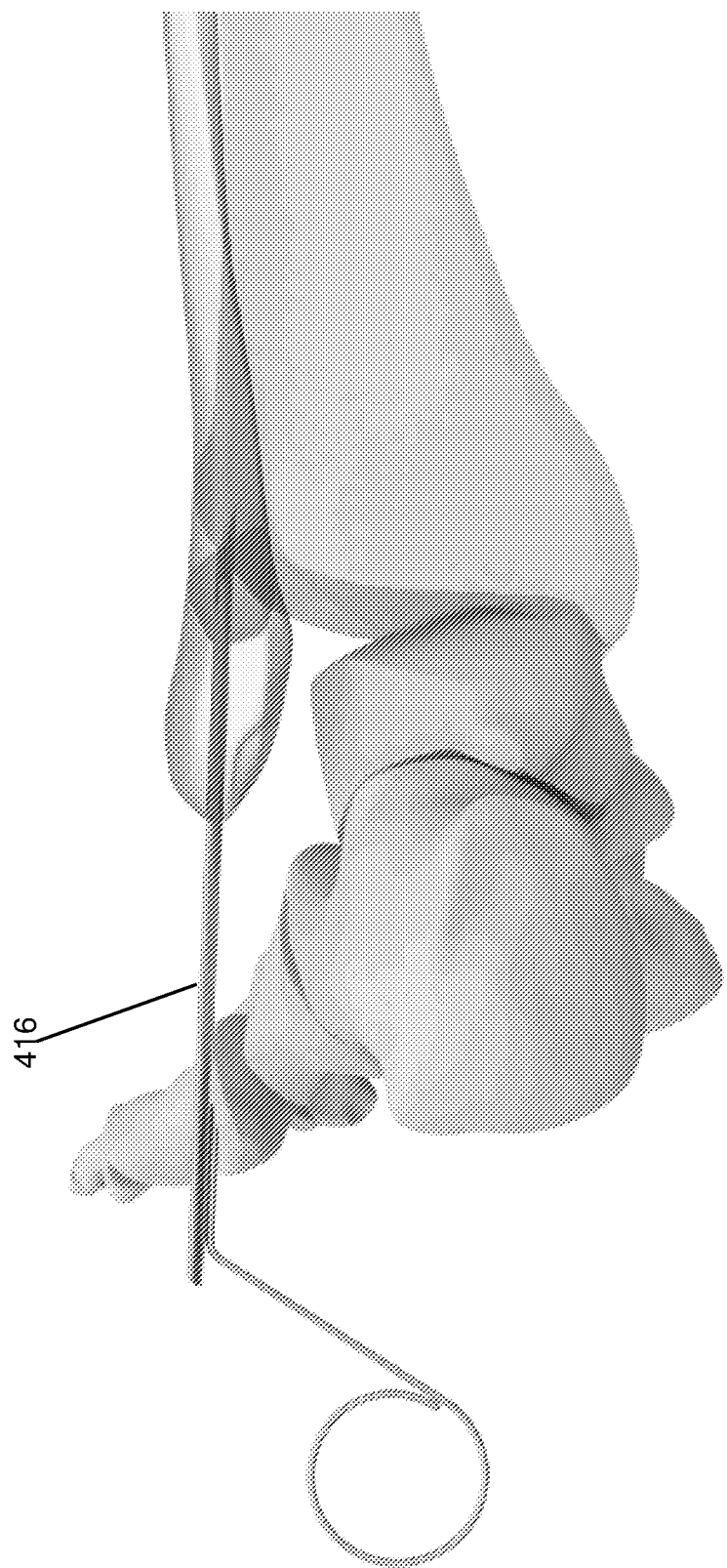
Figure 44H:
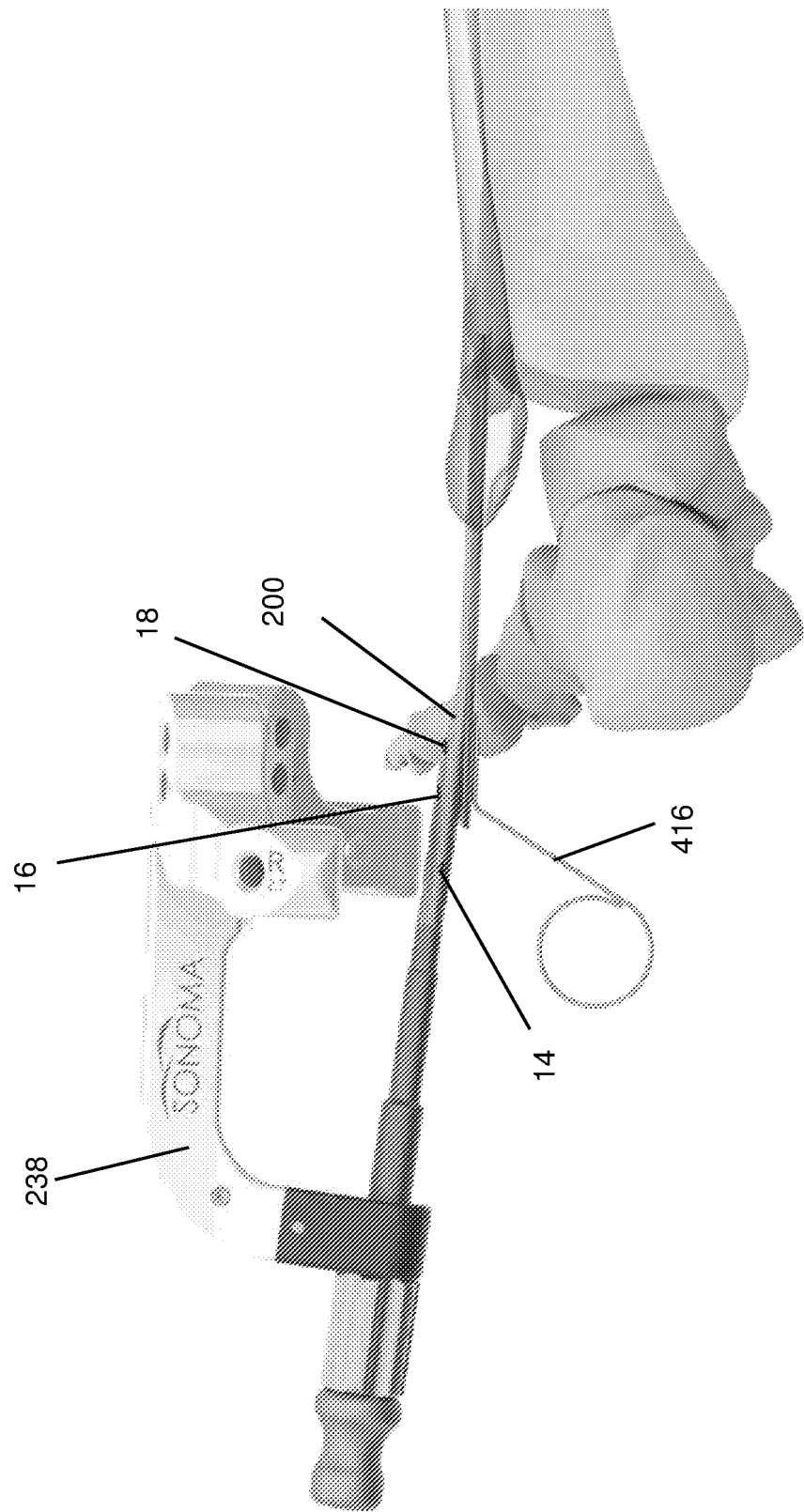
Figure 44J:
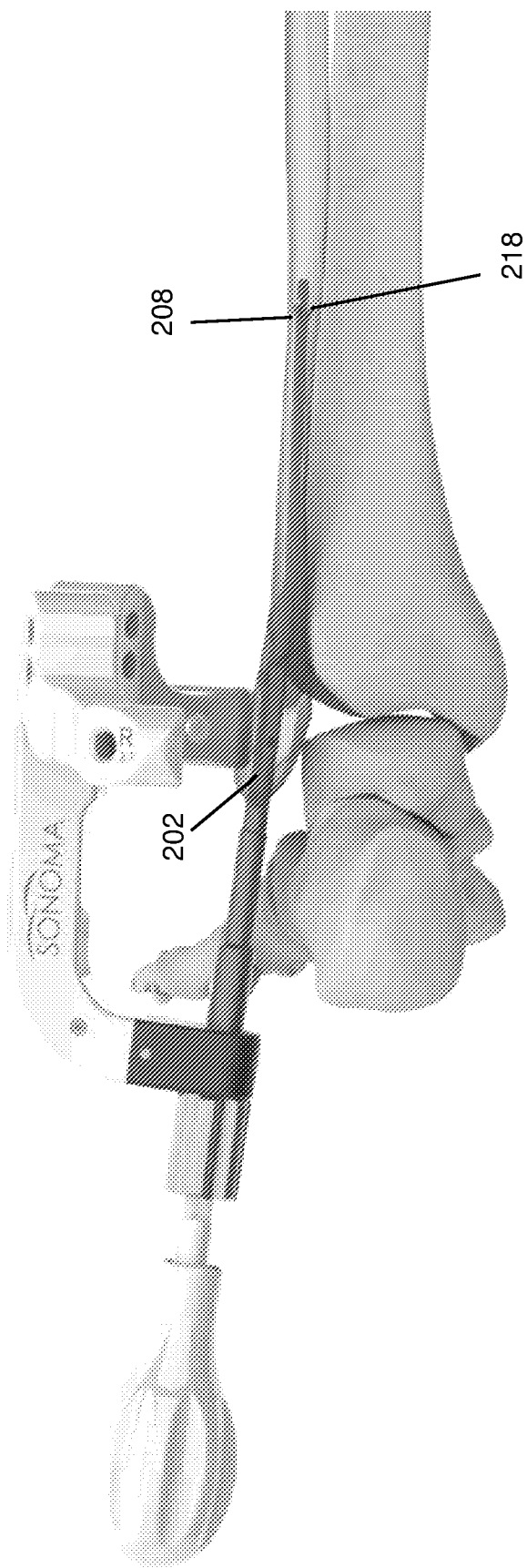
Figure 44L:
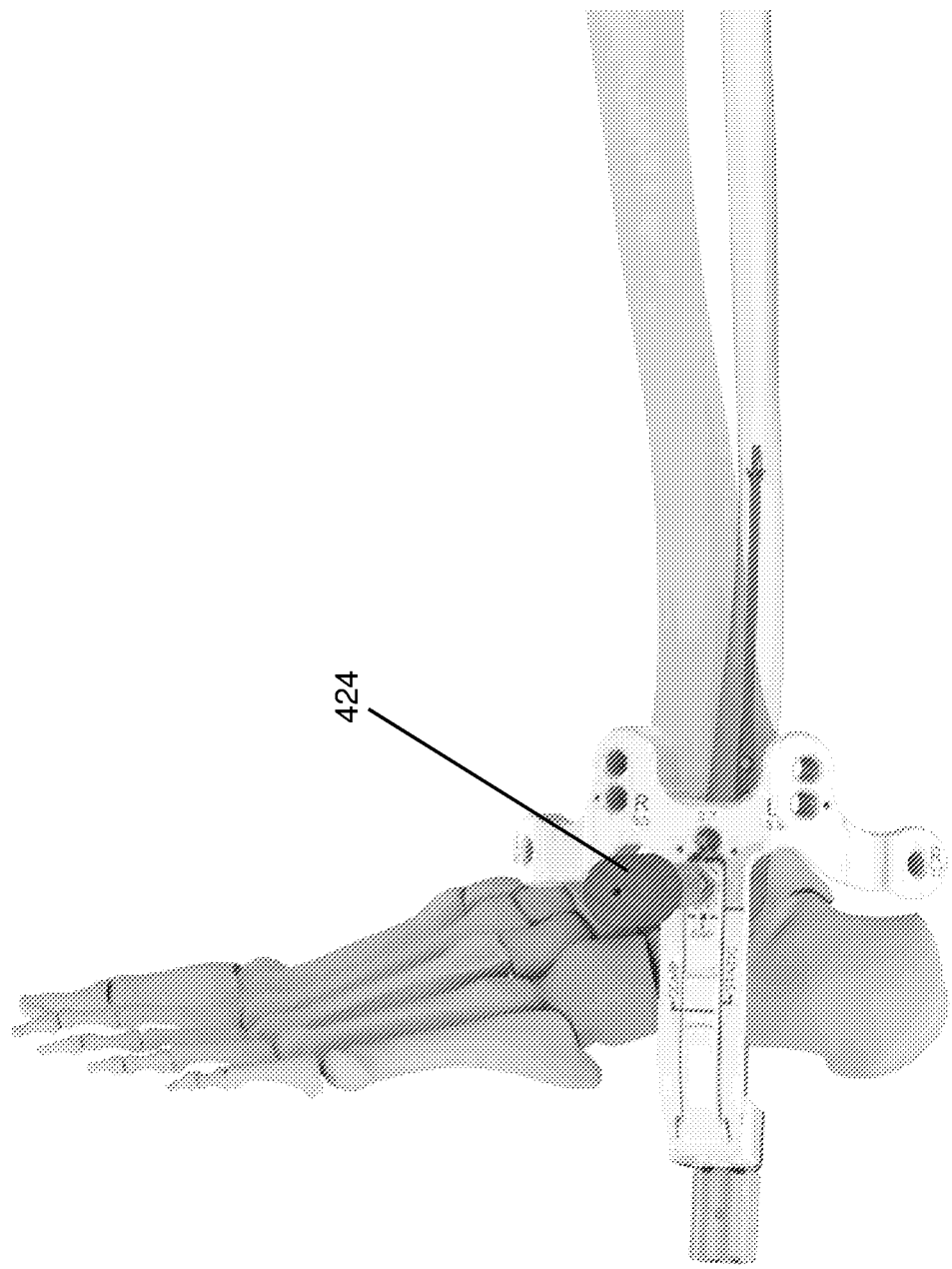
Figure 44M:
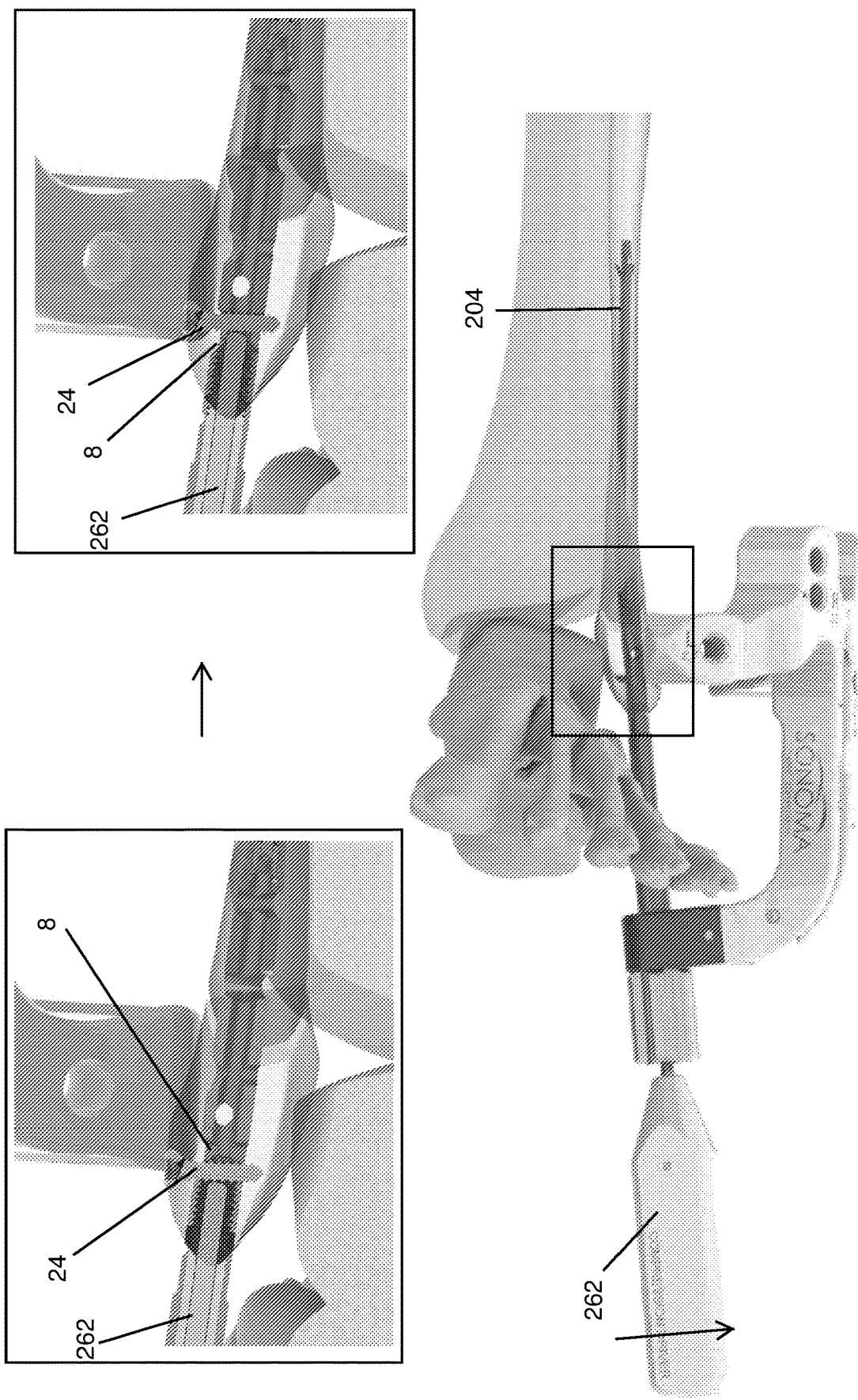
Figure 44N:
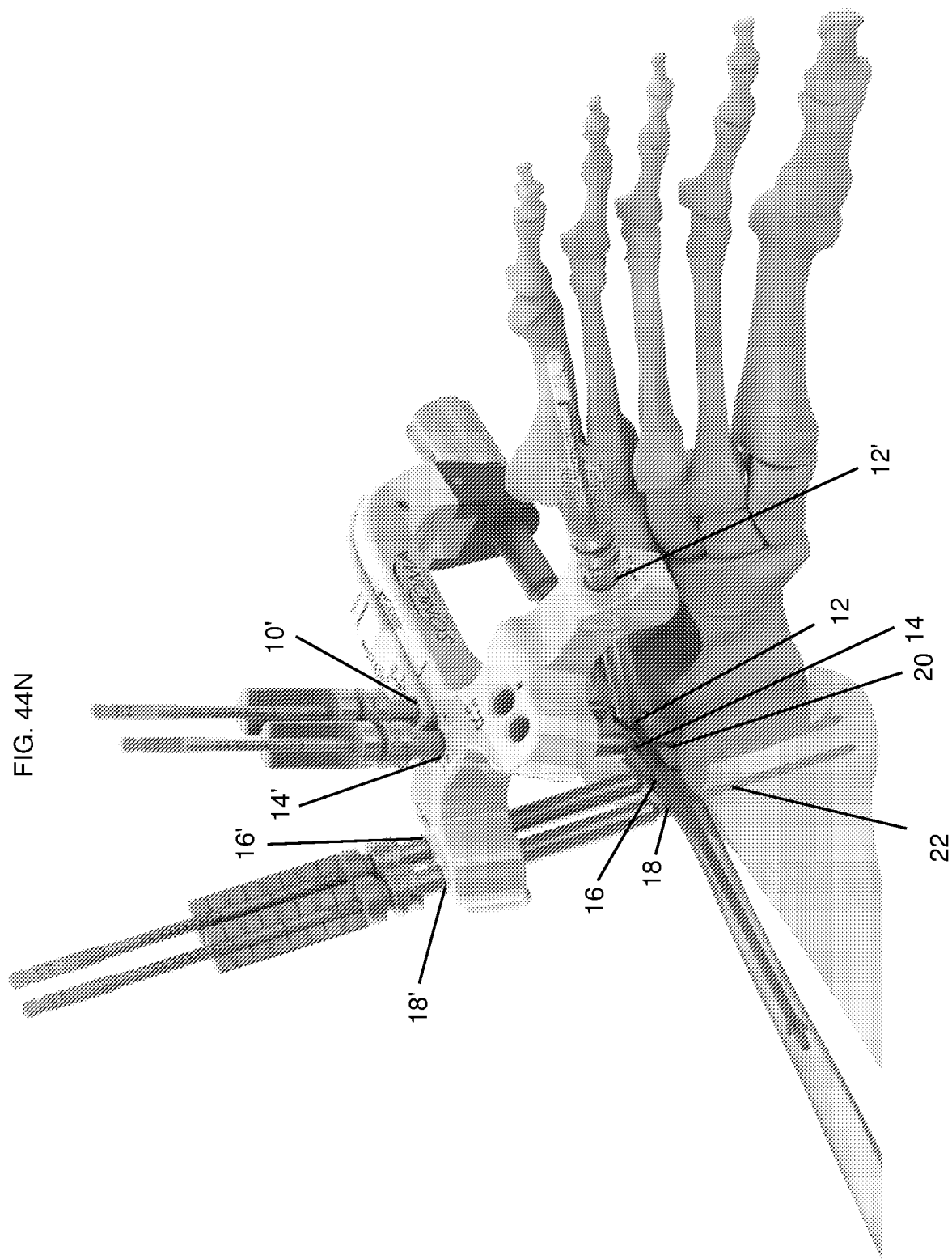
Figure 44O:
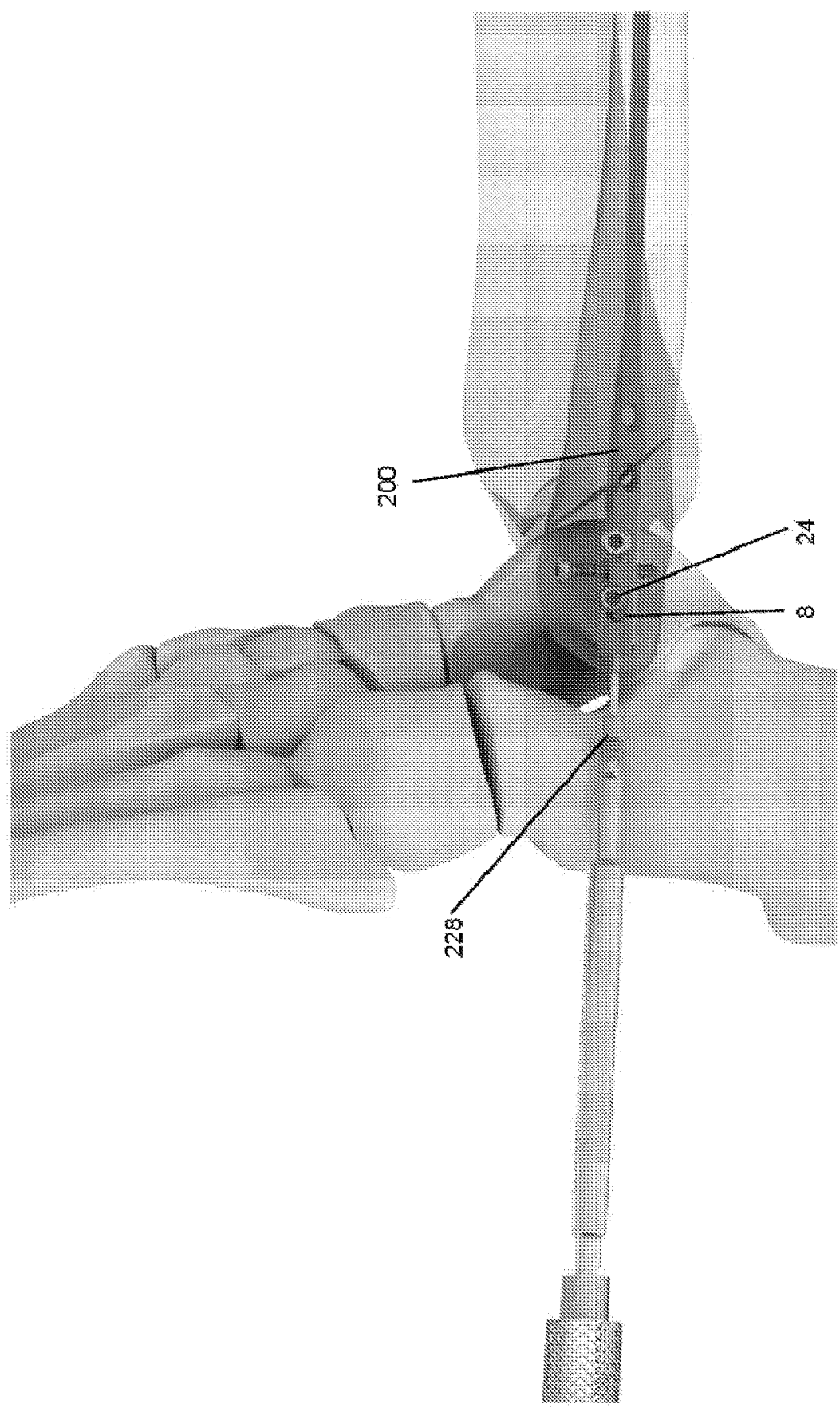
Figure 44P:
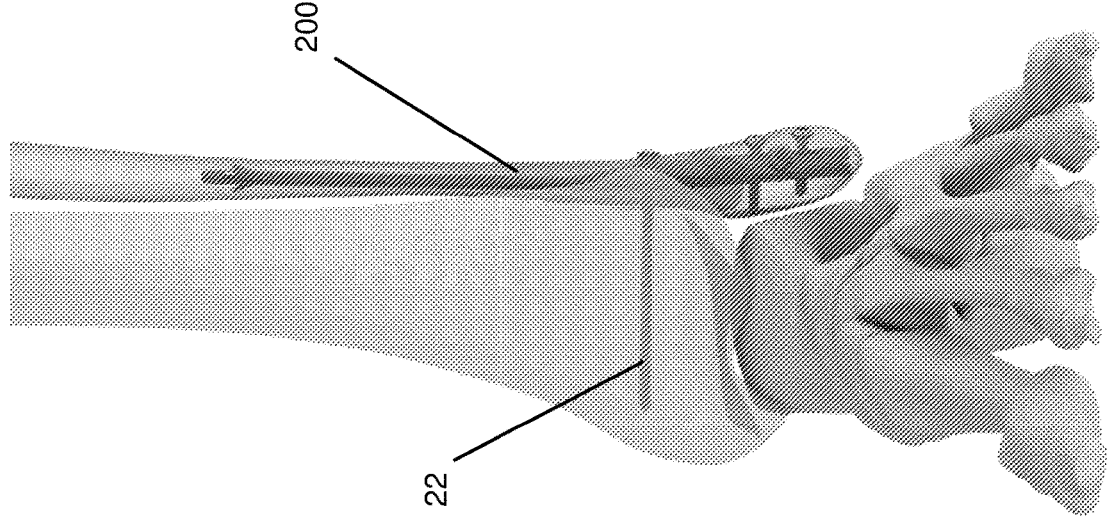
Figure 44Q:
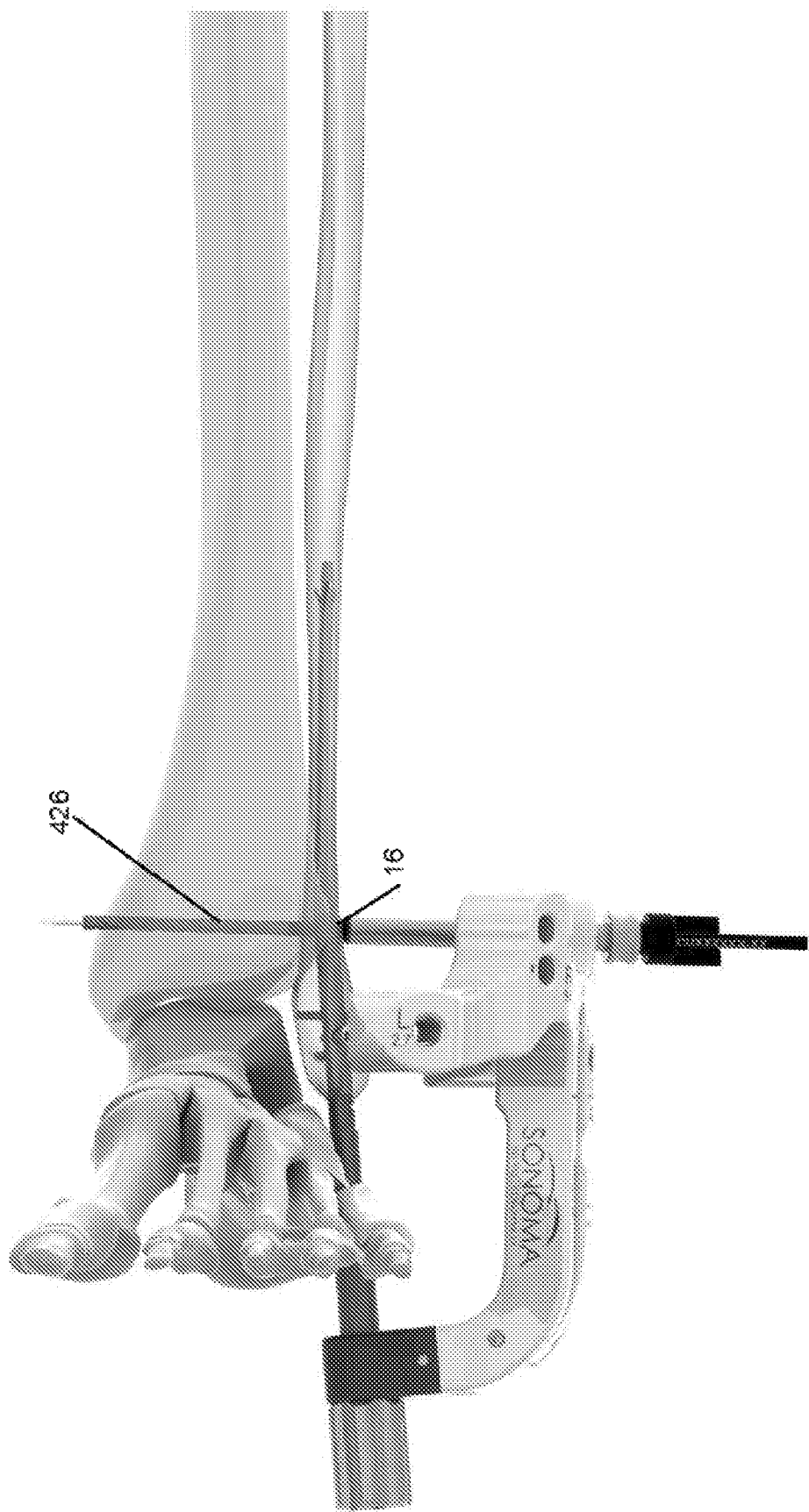
Figure 44R:
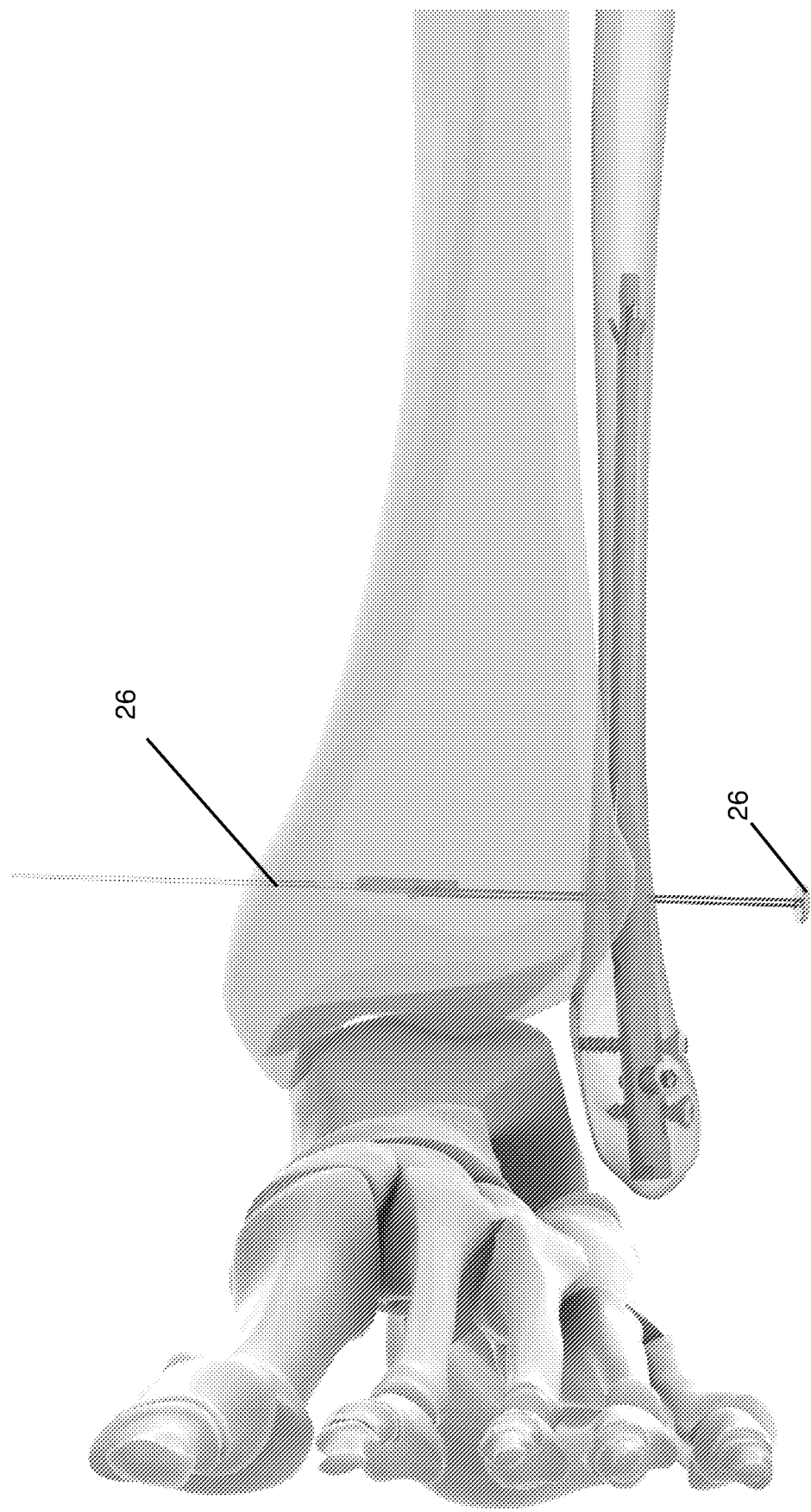
Figure 44S:
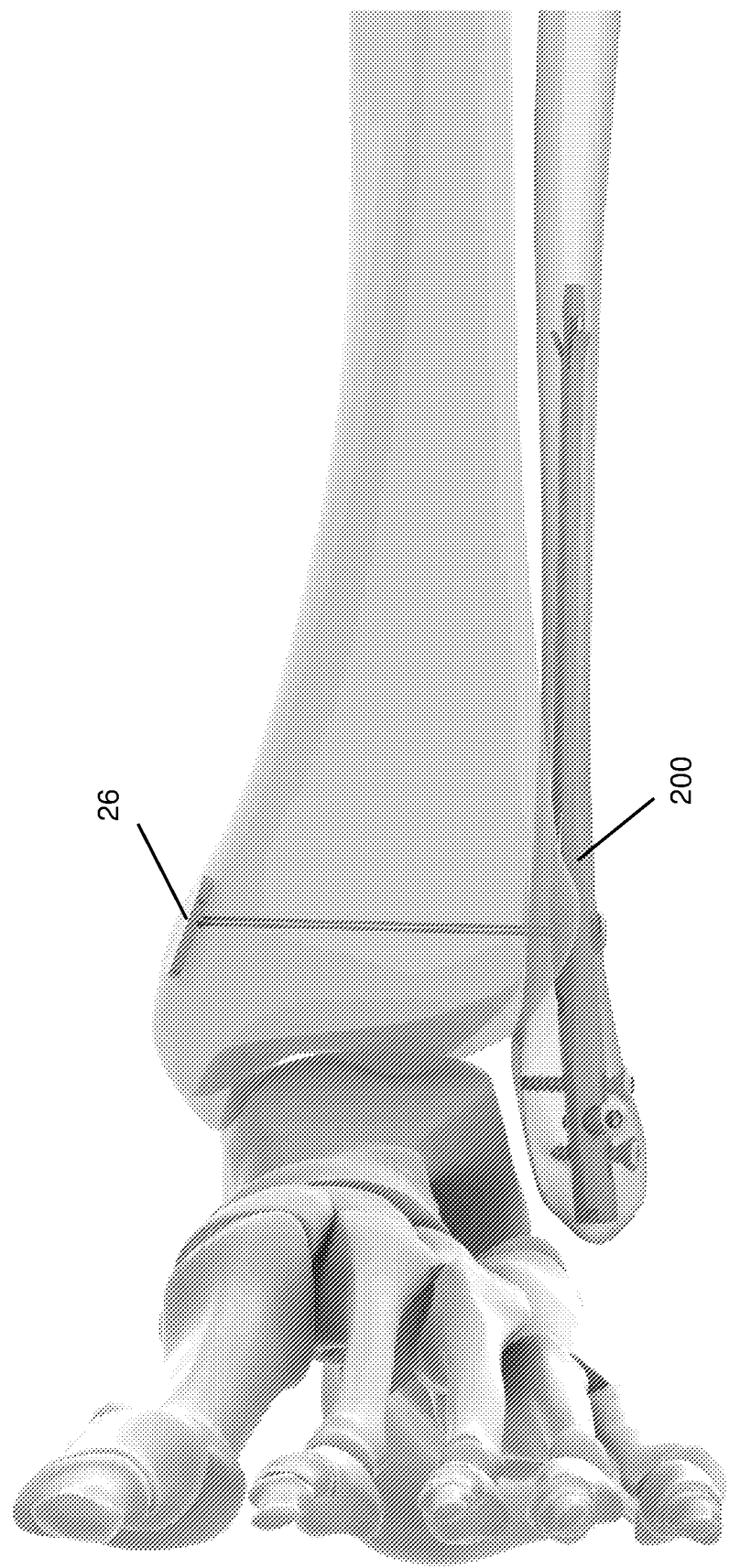

FIGS. 44A-44S are various method steps to implant the device 200 of FIGS. 35-41B. FIGS. 44A-44S shows the device 200, but any of the devices described herein can be inserted using one or more of the following method steps.

FIG. 44A shows the method step of reducing the fracture. The lateral malleolus are reduced percutaneously before reaming. A tool 402 such as the clamp shown in FIG. 44A is used to reduce the fracture. Other commercially available tools can be utilized to reposition and/or hold the fracture.

FIG. 44B shows the method step of establishing an entry point. The surgeon can align the entry point with the long axis of the fibula in the lateral view. The surgeon can aim for the canal center in the anterior/posterior view. A K-wire 404 is driven across the fracture line. A tool 406 such as the inserter shown in FIG. 44B and/or the cannula 408 is used to position the K-wire. Other commercially available tools can be utilized to insert a K-wire across the fracture line.

FIG. 44C shows the method step of preparing the fibula. The surgeon can drive a tapered reamer 410 over the K-wire 404. The reamer 410 can be placed through the cannula 408. The diameter of the reamer is 6.2 mm. Other commercially available tools can be utilized to ream the distal portion of the fibula. The surgeon can drive a flexible guide wire 412 through the reamer into the proximal fibula. FIG. 44D shows the inserted guide wire 412.

FIG. 44E shows the method step of preparing the fibula. The surgeon can sequentially ream the proximal fibula. The surgeon can use one or more proximal reamers 414. The proximal reamers 414 can be driven over the guide wire 412. The proximal reamer 414 can be placed through the cannula 408. The proximal reamer 414 can be flexible. Other commercially available tools can be utilized to ream the fibula.

FIG. 44F shows the method step of inserting an insertion guide 416. The insertion guide 416 can be driven over the guide wire 412. The insertion guide 416 has an inner cannula 418. Other commercially available tools can be utilized to insert the implant. FIG. 44G shows the method step of removing the inner cannula 418 of the insertion guide 416. The guide wire 412 is also removed. The insertion guide 416 can be a portion of a circular cross-section.

FIG. 44H shows the method step of inserting the bone fixation device 200 through the insertion guide 416. Other commercially available tools can be utilized to insert the device 200. The insertion guide 416 can support and guide the bone fixation device 200. The insertion guide 416 can surround a portion of the bone fixation device 200 during insertion. The tool 238 can be coupled to the bone fixation device 200 during insertion. The tool 238 can include apertures aligned with apertures 10, 12, 14, 16, 18 as described herein.

FIG. 44I shows the method step of confirming the depth of insertion of the bone fixation device 200. The stylet 420 is inserted through the tool 238. The stylet 420 can be inserted toward the proximal end 202 of the bone fixation device 200. The stylet 420 can confirm the location of the most proximal edge of the bone fixation device 200.

FIG. 44J shows the method step of actuating the gripper 208 as described herein. During actuation, bendable gripping members 218 of gripper 208 are urged radially outward by an actuator 226 (not shown). The actuator 226 is drawn in a proximal direction toward the proximal end 202 of the bone fixation device 200. The ramped surface on the actuator 226 outwardly actuates gripper members 218. Gripper 208 is deployed in the bone to lock the position of the bone fixation device 200.

FIGS. 44K-44M shows the methods steps of placing the compression screw 24 as described herein. In some methods, a drill 422 is inserted into an aperture in the tool 238 as shown in FIG. 44K. The drill 422 prepares a pilot hole in the bone and/or through the aperture 10 (see FIG. 44M). The screw 24 is inserted into aperture 10 of device 200 (see FIG. 44M). Screw 24 may be guided by a tool such as a screwdriver 424 as shown in FIG. 44L. In the illustrated embodiments, screw 24 will extend transverse to the device 200. Screw 24 can be located within the aperture 10 and coupled to the bone segment, as shown in FIG. 44M. The fracture may have been previously aligned. In some methods, shaft 262 is translated toward the distal end 204 of the device 200 toward the screw 24. Further translation of shaft 262 will push screw 24 and the bone segment connected to the screw 24. The screw 24 translates within the aperture 8. Screw 24 and the attached bone segment can be pushed toward the distal end 204 of the device 200. As screw 24 is advanced toward the distal end 204, screw 24 functions to approximate the bone fracture.

FIG. 44N show the methods step of placing the screws 20, 22 as described herein. The tool 238 can include apertures 10' 12', 14', 16', 18' aligned with apertures 10, 12, 14, 16, 18. Screw 20, 24 is inserted within aperture 10. Screw 20 is inserted within aperture 12. Screw 20 is inserted within aperture 14. Screw 22 is inserted within aperture 16. Screw 22 is inserted within aperture 18. The screws 20, 22, 24 can be inserted sequentially. One or more screws 20, 22, 24 can be inserted simultaneously. The surgeon can inserted the screws 20, 22 in the order best suited for the surgical procedure. The surgeon can insert the screws 22 in either a right orientation or a left orientation depending on the leg being operated on. The surgeon can insert the screw 20, 24 in aperture 12 in either a right orientation or a left orientation depending on the leg being operated on. The screws 20, 24 in apertures 10, 14 may be universally located for both the right leg and the left leg.

FIG. 44O show the methods step of placing the endcap 228. The endcap 228 can prevent encroachment of tissue and/or bone in the lumen of the device 200. The cap 228 can be provided to maintain the position of the screw 24, similar to the endcap 128 shown in FIG. 27. The cap 228 can prevent the screw 24 from translating within the aperture 10 toward the proximal end 202 of the device 200. The cap 228 can be inserted within the proximal bore of the device 200 until the distal end of the cap abuts the screw 24. The proximal bore can be threaded and the cap 228 can include complementary threads. Other configurations of caps 228 are contemplated.

FIG. 44P shows the orientation of the device 200 within the bone. While only one screw 22 is shown, more screws 22 can be positioned within the bone.

FIGS. 44Q-44S show the method step of utilizing other fasteners for securing the syndesmosis. FIG. 44Q shows the method step of forming a hole. The reamer 426 can pass through aperture 16 or 18 of the device. The reamer can form a hole through bone aligned with aperture 16 or 18. The diameter of the hole is 3.5 mm. FIG. 44R shows the method step of passing a suture bundle through the hole. The suture bundle can guide the fastener 26. The fastener 26 can be similar to commercially available fasteners. FIG. 44S shows the orientation of the device 200 with the fastener 26. While only one fastener 26 is shown, more fasteners can be positioned within the bone.

Figure 45A:
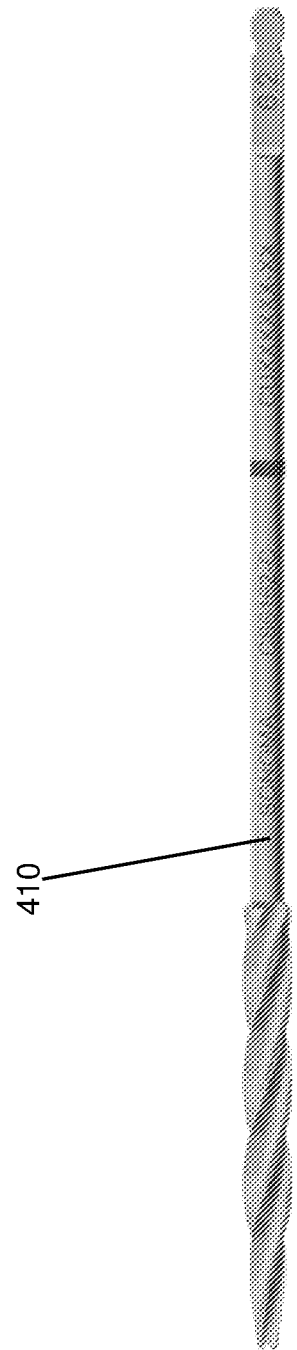
FIGS. 45A-45O are various tools to implant the device of FIGS. 35-41B.
Figure 45B:

FIG. 45A show the reamer 410. The reamer 410 shown in FIG. 45A is used to perform method step shown in 44C. The reamer 410 is tapered. The reamer 410 can have a central lumen (not shown) to accept a K-wire or flexible guide wire. The diameter of the reamer 410 is 6.2 mm.

FIG. 44B show the reamer 414. The reamer 414 shown in FIG. 44B is used to perform method step shown in FIG. 44E. The reamer 414 can have a central lumen (not shown) to accept a guide wire. The proximal reamer 414 can be flexible.

Figure 45C:
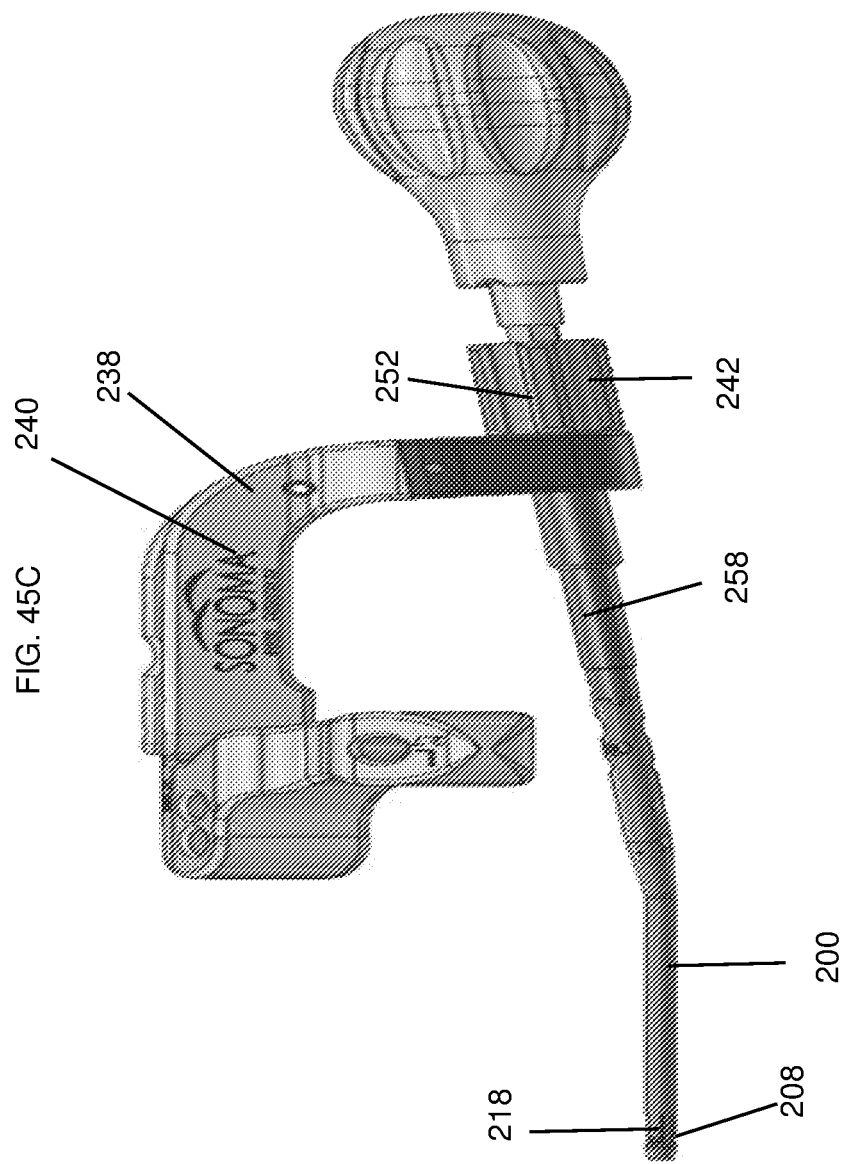
Figure 45D:
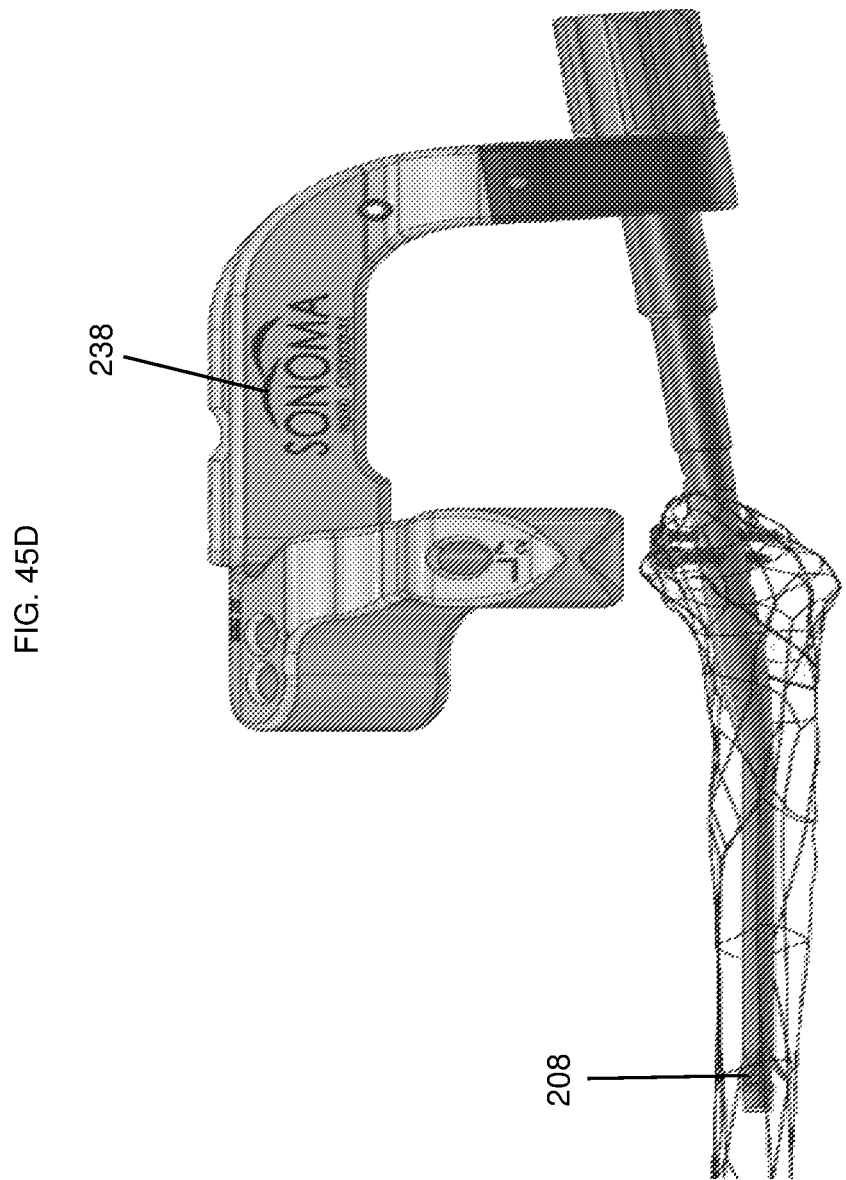
Figure 45E:
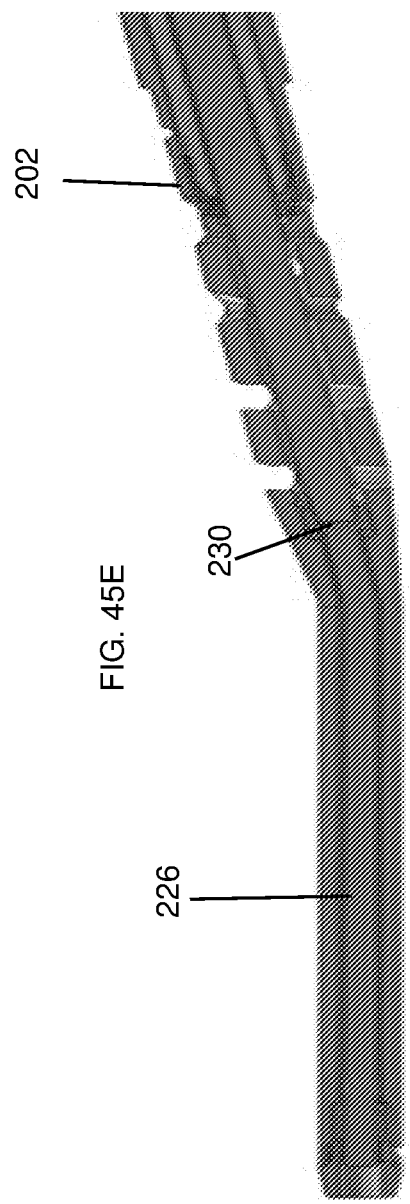
Figure 45F:
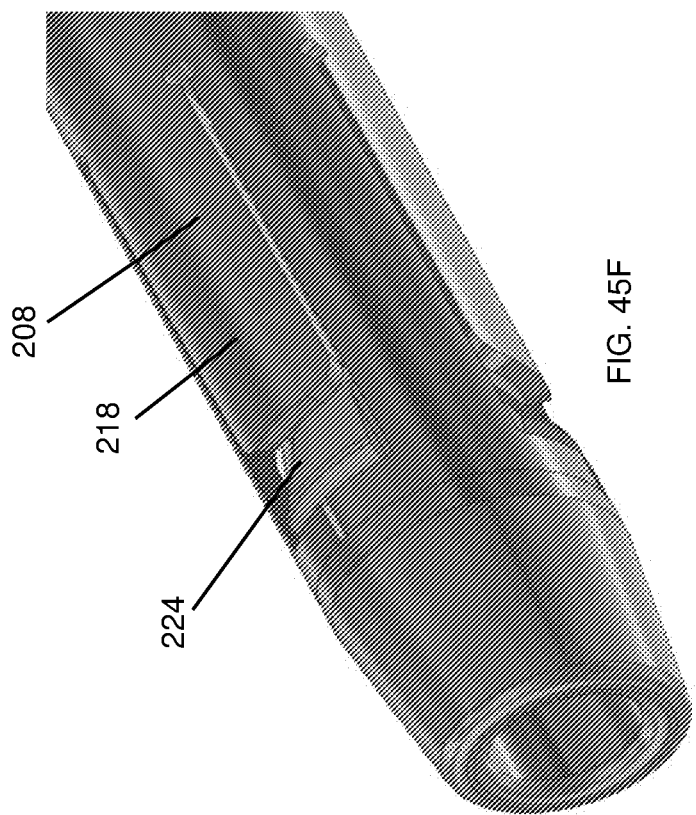

FIGS. 45C-45D show the assembled tool 238 useful for inserting device 200 into bone. Hub 258 is configured to abut the proximal end 202 of the device 200. Hub 258 is coupled to the T-shaped body 240. Device attachment portion 242 prevents removal of the hub 258 and the T-shaped body from the device 200. Device attachment portion 242 includes a knob 252 that abut the T-shaped body 240. The knob 252 of the device attachment portion 242 rigidly couples the hub 258 and the T-shaped body 240 with the device 200. The assembled tool 238 is shown removed from the bone in FIG. 45C. FIG. 45D shows a view of the inserted device 200. The device 200 is inserted into the fibula. In some methods, T-shaped body 240 can serve as a handle to facilitate insertion of the device 200.

Distal end 204 of device 200 can be inserted into the bone before the proximal end 202 of the device 200. Device 200 is in the un-deployed state during insertion as shown in FIG. 45C. In the undeployed state, gripper 208 is not actuated by actuator 226. Distal ends 222 of bendable gripping members 218 do not contact the inside of the bone to anchor the distal portion 204 of device 200 to the bone. Device 200 can remain in the un-deployed state until the fracture is reduced. FIG. 45D shows that in some methods, the gripper 208 is deployed to maintain the position of one or more the bone segments. Typical fibula fractures result in a compressed and rotated bone fragments.

FIG. 45D shows the implant 200 can be inserted with the combination tool 138. In some methods, T-shaped body 240 can also serve as a handle to facilitate insertion of the device 200. Grippers 208 can be deployed (as shown in FIG. 45D). Screws 20 may be guided through the device 200. Screws 22 may be guided through the device 200.

FIGS. 45E-45H show an embodiment of the actuator 226. During actuation, bendable gripping members 218 of gripper 208 are urged radially outward by a ramped surface on actuator head 224. Actuator head 224 is threaded onto the distal end of actuator 226. The proximal end of actuator 226 has a keyed socket 230 for receiving the tip of the tip of a screw driver through the proximal bore of device 200. In some embodiments, the keyed socket 230 is hex shaped. As screw driver turns actuator 226, a threaded surface of the actuator 226 rotates in relation to the actuator head 224. This causes the actuator head 224 to be drawn in a proximal direction toward the proximal end 202 of the device 200 as the actuator head 224 traverses the threaded surface of the actuator 226. The ramped surface on the actuator head 224 outwardly actuates bendable gripping members 218. The device 200 may include a stop to prevent translation of the actuator 226. The actuator 226 may include one or more bends to match the shape of the device 200. The actuator 226 may be flexible or have a flexible portion between the keyed socket 230 and the threaded surface.

Figure 45I:
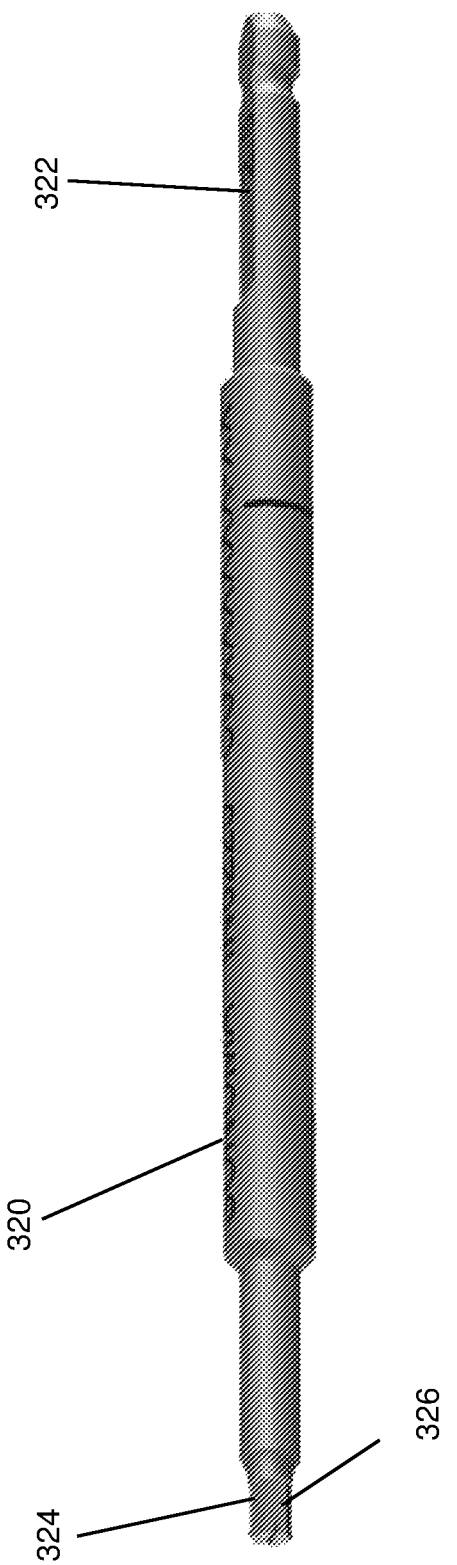
Figure 45J:
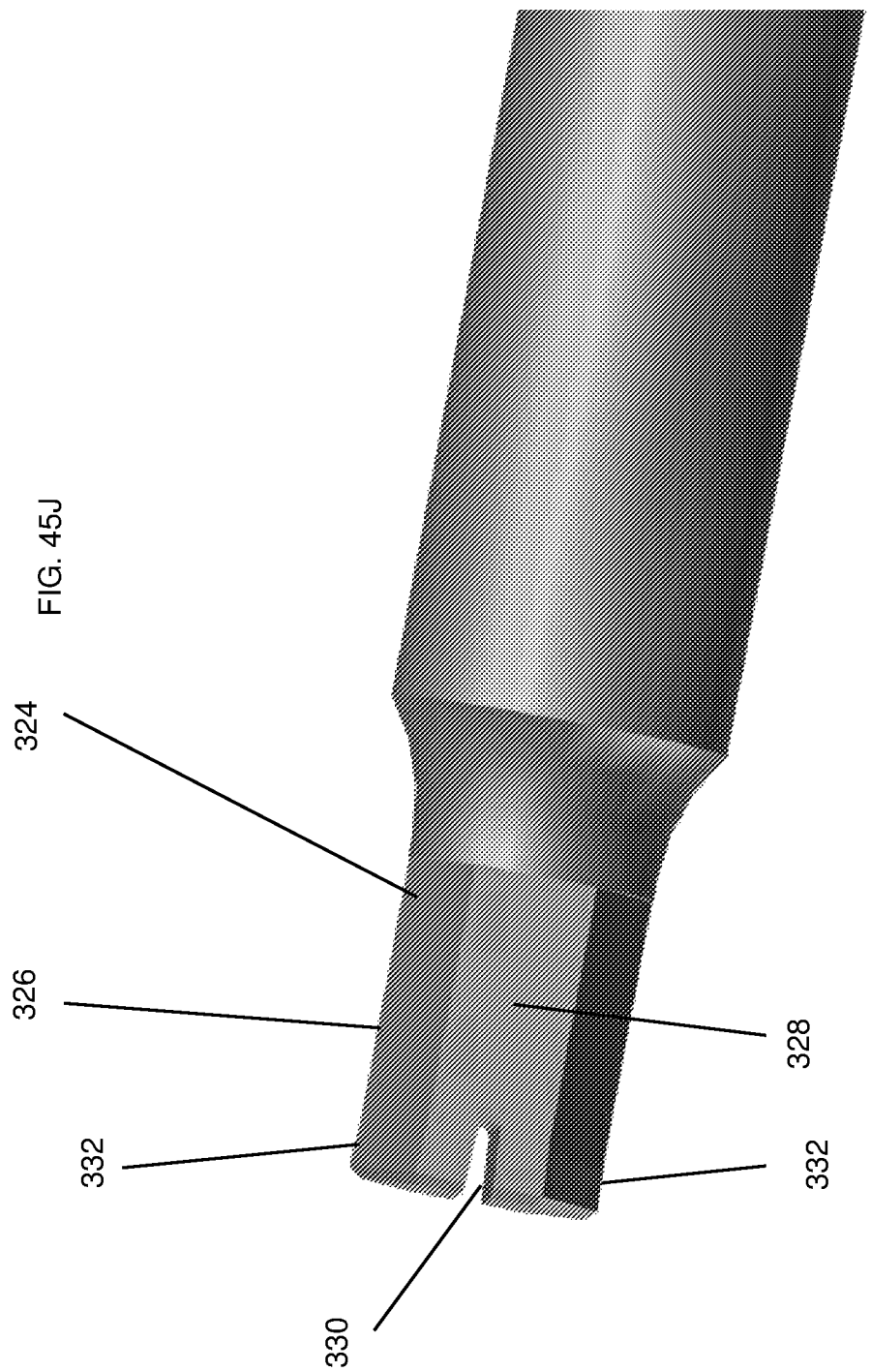

FIGS. 45I-45J show a perspective view of an embodiment of a screw driver 320. The screw driver 320 may be configured to engage the keyed socket 130 of the actuator 126 (shown in FIG. 14) or the keyed socket 230 of the actuator 226 (shown in FIG. 45E). The screw driver 320 may be configured to engage the keyed socket 148 of the screw 110 (shown in FIG. 16A).

The screw driver 320 includes a proximal end 322 and a distal end 324. The proximal end 322 can have a mating configuration such as a flattened surface. The mating surface can engage a knob to facilitate rotation. The mating surface can engage a power source such a drill. The mating configuration can be a hand grip. The screw driver 320 can be sized and shaped to fit within the proximal bore of the device 200. The screw driver 320 can be sized and shaped to fit within the alignment tube 168, 268, as described herein.

FIG. 45J shows the distal end 324. The distal end 324 includes a hex tip 326. All the flats 328 are sized to fit a female hex of the corresponding keyed socket 130, 148, 230. In the illustrated embodiment, each flat 328 is 2.5 mm but other sizes are contemplated. The hex tip 326 includes a slot 330 across one pair of flats 328. In the illustrated embodiment, the slot 330 bisects the pair of flats 328. In the illustrated embodiment, the slot 330 does not extend beyond the hex tip 326. The depth and width of the slot 330 depends on the retaining force with the actuator 126, 226 or with the screw 110. The slot can extend about 0.020" into the distal end 324.

The hex tip 326 is machined with a lip 332. The hex tip is manufactures such that the hex surface is larger than the corresponding socket. The lip 332 creates an interference between the screw driver 320 and the keyed socket 130, 148, 230. In the illustrated embodiment, the interference is on the order of 0.0002"–0.001" (e.g., 0.0002", 0003", 0.0004", 0.0005", 0.0006", 0.0007", 0.0008", 0.0009", 0.001", between 0.002" and 0.005", etc.). The material of the screw driver 320 is selected maintain the shape of the lip 322. One suitable material is heat treated stainless steel. The configuration of the screw driver 320 prevents stripping of the keyed socket 130, 148, 230. In some embodiments (not shown), an elastomer could be inserted into the slot 330 to provide additional spring back if needed.

Figure 45K:
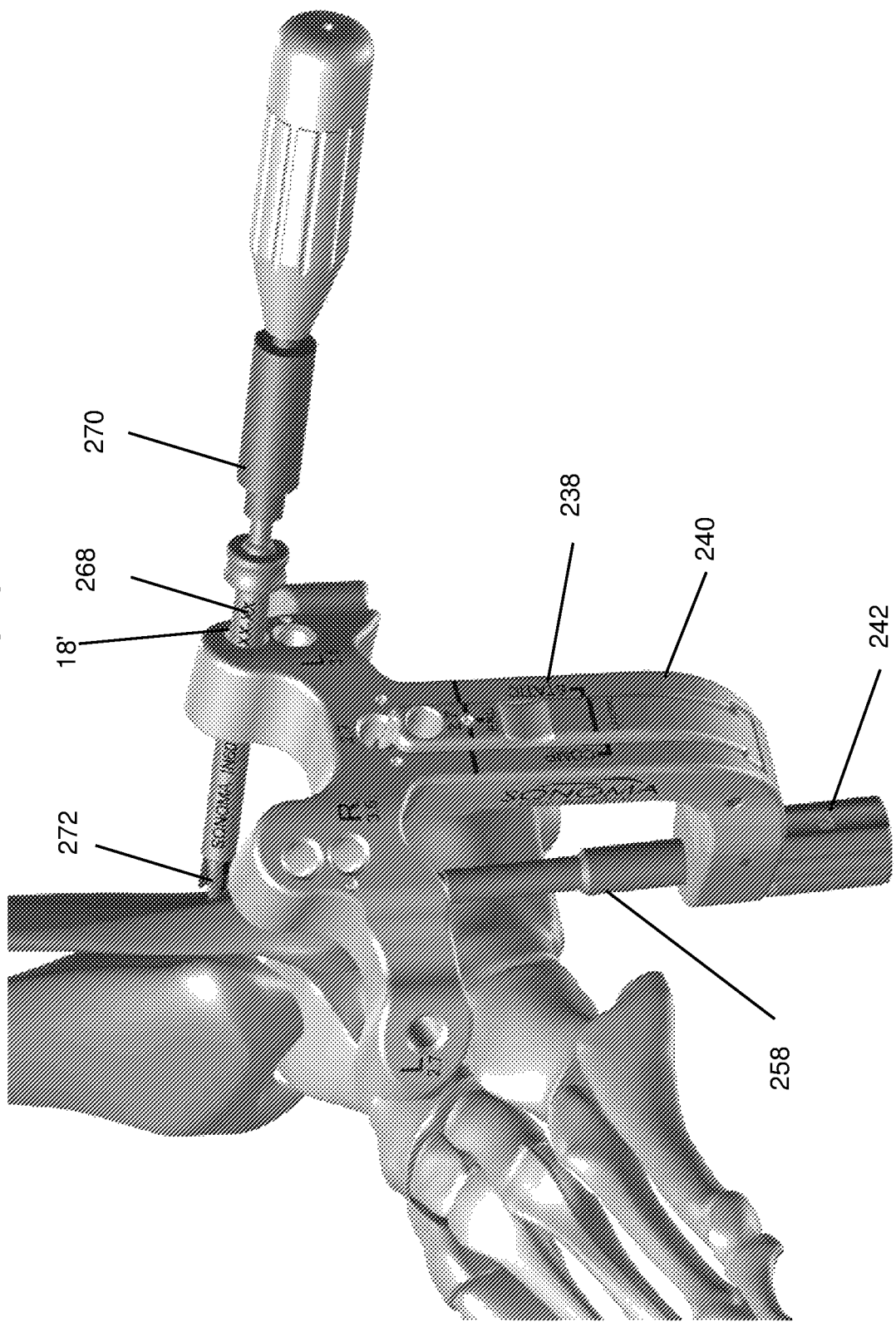
Figure 45L:
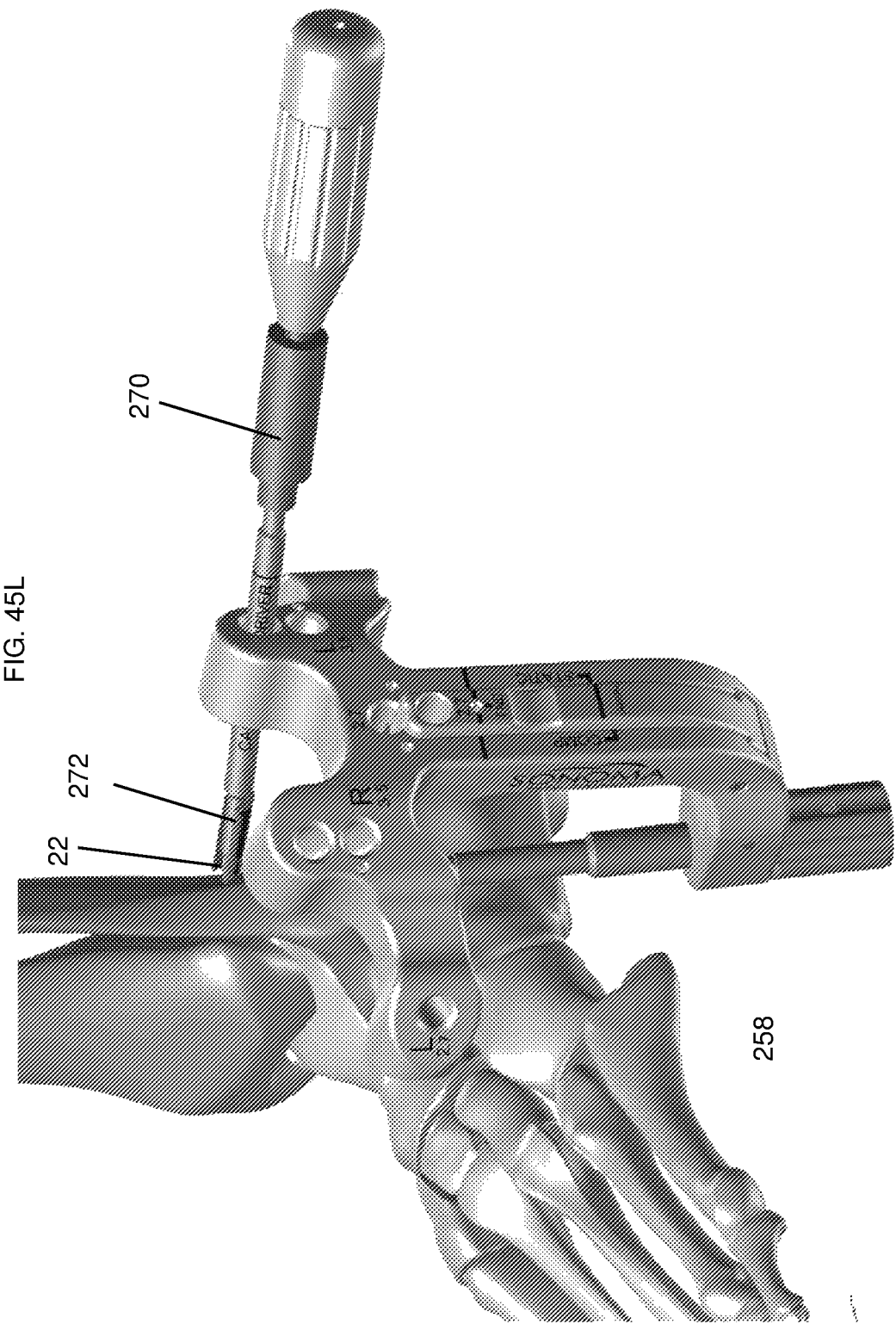

FIGS. 45K-45L show views of the combination tool 238 useful for inserting device 200, actuating gripper 208, approximating the fracture in bone, aligning one or more anchor screw(s) 20, 22, 24, and/or removing device 200, if desired. The main components of tool 238 are the hub 258, the T-shaped body 240, the device attachment portion 242, and the alignment tube 268.

The alignment tube 268 is shown in FIG. 45K. The alignment tube 268 can be coupled to the T-shaped body 240. The combination tool 238 is in place when the device attachment portion 242 rigidly couples the hub 258 and the T-shaped body 240 to the device 200. In this configuration, the removable alignment tube 268 aligns with the aperture 18 of the device 200. In the embodiment depicted in the figures, the T-shaped body 140 includes a plurality of apertures including aperture 18'.

Figure 45M:
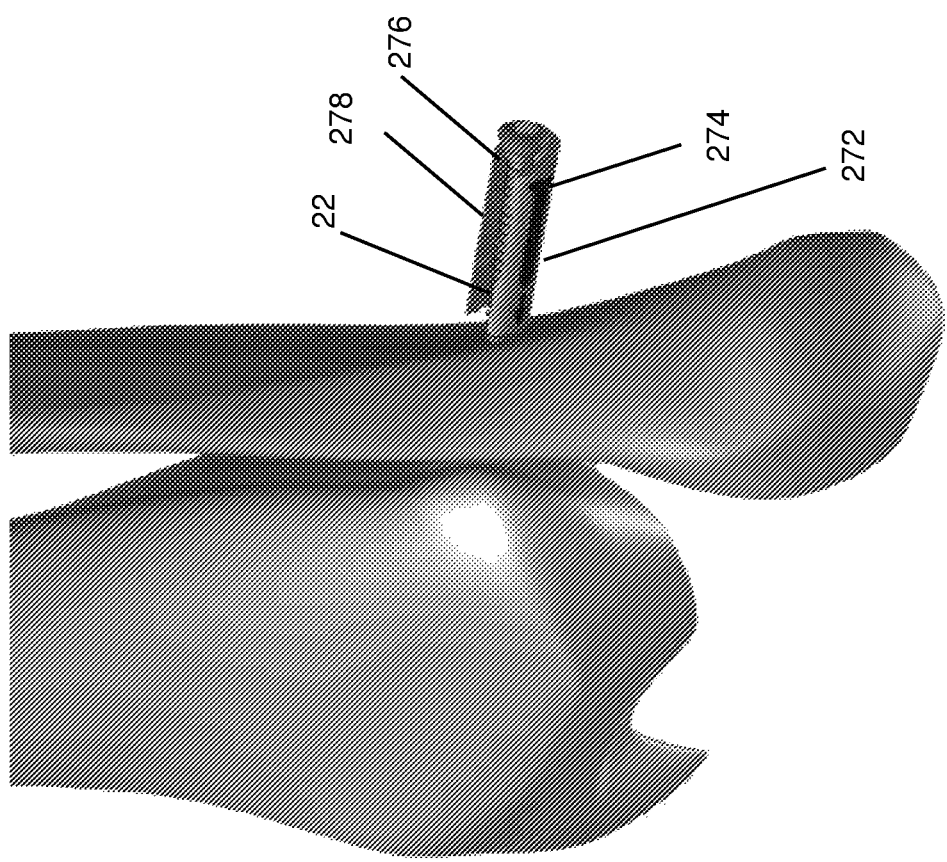

In operation, alignment tube 268 is first received in aperture 18'. In this position, alignment tube 268 is in axial alignment with aperture 18 of device 200. The mating configuration of device 200 and hub 258 positions aperture 18 in its desired orientation. With this arrangement, a drill bit, screw driver 270, screw 22 and/or other fastening device or tool may be inserted through the bore of alignment tube 268 such that the device(s) are properly aligned with aperture 18. While screw 22 is shown, the alignment tube 268 can be used with screw 20, 24 in the same manner. The outward end of alignment tube 268 may also serve as a depth guide to stop a drill bit, screw 22 and/or other fastener from penetrating bone beyond a predetermined depth. Inserting the screw 22 through the alignment tube 268 ensures that the screw 22 will have the placement as shown in FIG. 45M. The alignment tube 268 allows proper placement of the screw 22 even if the aperture 18 or other portions of the device 200 are obstructed from the view of the surgeon.

The T-shaped body 240 includes other apertures 10', 12', 14', 16' that align with apertures 10, 12, 14, 16, as described herein. Alignment tube 268 may be withdrawn from aperture 18' as shown, and inserted in another aperture 10', 12', 14', 16. The alignment tube 268 can be inserted within these apertures to align and insert other screws 20, 22.

The alignment tube 268 is removed in FIG. 45L. The screwdriver 270 is shown coupled to the end of the screw 22. The screwdriver 270 can be used to drive in other screw 20, 24 (not shown). A screw clip 272 surrounds a portion of the screwdriver 270 and a portion of the screw 22. The screw clip 272 can be used with screw 20, in the same manner as screw 22. The coupled combination of the screwdriver 270, the screw 22, and the screw clip 272 can be inserted into the alignment tube 268 and moved toward the fibula. The screwdriver 270 can rotate within the screw clip 272 to drive the screw 22 into the bone.

FIG. 45M shows the screw clip 272 and the screw 22. The screw clip 272 can include one or more markings 274. The markings 274 can indicate the proper orientation of the screw 22 into the screw clip 272. The screw clip 272 has a proximal edge 276 which is tapered. The proximal edge 276 interacts with the head of the screw 22. As the screw 22 is driven into the bone, the head of the screw 22 tilts the screw clip 272 away from the bone. The screw 22 can be removed from the screw clip 272 through enlarged slot 278.

Figure 45N:
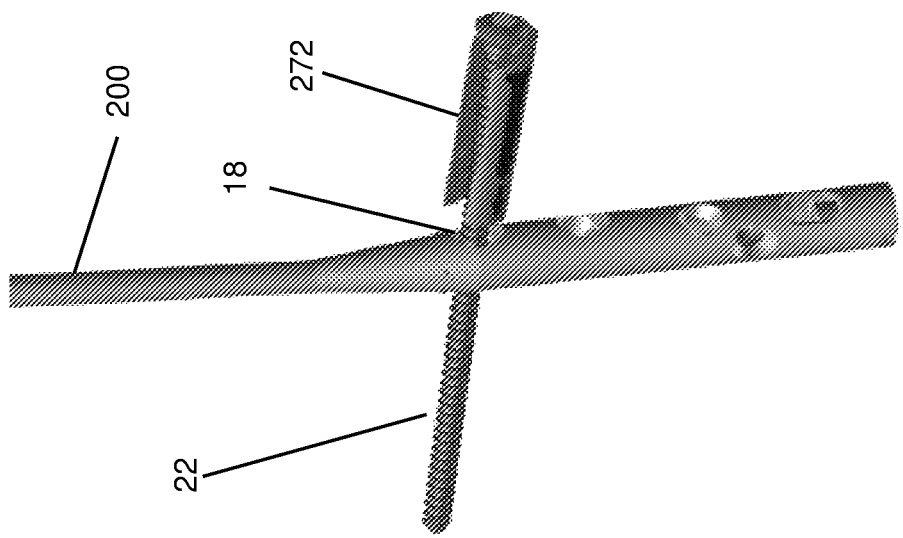
Figure 45O:
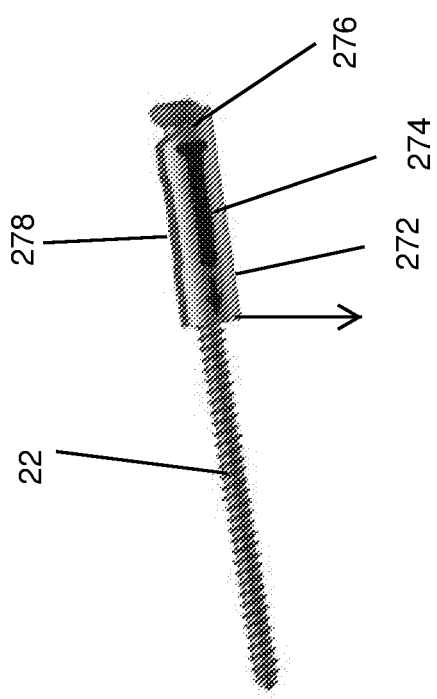

FIG. 45N shows the screw clip 272, the screw 22, and the device 200. The tool 238 ensure proper placement of the screw 22 through the aperture 18 in the device 200. FIG. 45O shows the screw clip 272 and the screw 22. As the screw 22 is driven into the bone, the head of the screw 22 tilts the screw clip 272 downward as shown by the arrow. The head of the screw 22 slides along the proximal edge 276 toward the top surface of the screw clip 22. As the screw 22 is driven further into the bone, the screw clip 272 falls away as the screw 22 passes through enlarged slot 278.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleolus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

While various embodiments of the present invention have been shown and described herein, it will be noted by those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. A method of inserting a device comprising:
inserting a device within an intramedullary canal of a fibula, the device comprising one or more apertures;
inserting a first fastener through the device in a lateral-medial direction;
inserting a second fastener through the device, the second fastener angled from the first fastener by angle alpha;
inserting a third fastener through the device, the third fastener angled from the first fastener by angle beta, wherein the third fastener extends into a tibia; and
actuating a mechanism of the device to grip the intramedullary canal of a fibula,
wherein actuating the mechanism comprises deflecting at least two members towards the intramedullary canal, wherein the mechanism includes an actuator extending through a central portion of the device, the actuator having a drive head adjacent a proximal end and an actuator head adjacent a distal end, wherein the actuator head engages the at least two members, and wherein the one or more apertures includes a first aperture for accepting the first fastener and the actuator head is located distal of the first aperture and the first aperture is located adjacent a proximal end of the device and separates the proximal end of the device from another one of the one or more apertures.

2. The method of claim 1, wherein angle alpha is between 45-75 degrees.

3. The method of claim 1, wherein angle beta is between 10-40 degrees.

4. The method of claim 1, further comprising translating the first fastener within an aperture of the device toward the mechanism.

5. The method of claim 4, wherein the aperture of the device is a first aperture and is elongated in a direction parallel to a longitudinal axis of the device.

6. The method of claim 5, further comprising translating the first fastener from a proximal side of the first aperture to a distal side of the first aperture.

7. The method of claim 6, further comprising engaging the first fastener with a cap to prevent the first fastener from translation through the first aperture.

8. The method of claim 7, wherein the cap includes external threads that engage internal threads on a proximal end of the device.

9. The method of claim 1, further comprising rotating the first fastener, wherein the rotation of the first fastener causes translation of the first fastener within an aperture of the device toward the mechanism.

10. The method of claim 1, wherein the first fastener and the second fastener are contained within the fibula.

11. The method of claim 1, wherein the third fastener is a screw.

12. The method of claim 1, further comprising passing at least one of the first fastener, the second fastener, and the third fastener through an aperture in a tool aligned with an aperture in the device.

13. The method of claim 1, further comprising inserting K-wires within bone portions near a fracture and rotating the bone portions using the K-wires.

14. The method of claim 13, wherein rotating the bone portions further comprises rotating a knob of a distractor.

15. The method of claim 1, wherein the device includes a hub portion at a proximal end and the one or more apertures are located in the hub.

16. The method of claim 15, wherein the hub portion extends along a hub portion central longitudinal axis and a distal end portion of the device extends along a distal end portion central longitudinal axis that is transverse to the hub portion central longitudinal axis.

17. The method of claim 16, wherein the hub portion is connected to the distal end portion through a connecting portion having a bend.

18. The method of claim 1, wherein the at least two members includes three members.

19. The method of claim 1, wherein the at least two members includes two, three, four, five, or six members.

* * * * *